(12) United States Patent
Grimm et al.

(10) Patent No.: US 12,234,281 B2
(45) Date of Patent: *Feb. 25, 2025

(54) ANTIBODY-BASED THERAPY OF TRANSTHYRETIN (TTR) AMYLOIDOSIS AND HUMAN-DERIVED ANTIBODIES THEREFOR

(71) Applicant: Neurimmune Holding AG, Schlieren (CH)

(72) Inventors: Jan Grimm, Dübendorf (CH); Aubin Michalon, Baden (CH)

(73) Assignee: Neurimmune Holding AG, Schlieren (CH)

( * ) Notice: Subject to any disclaimer, the term of this patent is extended or adjusted under 35 U.S.C. 154(b) by 291 days.

This patent is subject to a terminal disclaimer.

(21) Appl. No.: 17/532,292

(22) Filed: Nov. 22, 2021

(65) Prior Publication Data

US 2022/0144928 A1 May 12, 2022

Related U.S. Application Data

(62) Division of application No. 16/413,335, filed on May 15, 2019, now Pat. No. 11,180,545, which is a (Continued)

(30) Foreign Application Priority Data

Dec. 20, 2013 (EP) .................................. 13199251

(51) Int. Cl.
A61K 39/00 (2006.01)
A61K 39/395 (2006.01)
(Continued)

(52) U.S. Cl.
CPC ......... C07K 16/18 (2013.01); G01N 33/6896 (2013.01); A61K 2039/505 (2013.01); (Continued)

(58) Field of Classification Search
None
See application file for complete search history.

(56) References Cited

U.S. PATENT DOCUMENTS 10,344,080 B2 7/2019 Grimm et al.
11,180,545 B2 11/2021 Grimm et al.
(Continued)

FOREIGN PATENT DOCUMENTS

| CN | 102016059 A | 4/2011 |
|---|---|---|
| JP | 2010-195710 A | 9/2010 |

(Continued)

OTHER PUBLICATIONS

Ando et al., "Presence of autoantibody against ATTR Val30Met after sequential liver transplantation," Transplantation 73(5):751-755 (2002) (9 pages).

(Continued)

*Primary Examiner* — Aurora M Fontainhas
(74) *Attorney, Agent, or Firm* — Clark & Elbing LLP

(57) ABSTRACT

Provided are novel human-derived antibodies specific for transthyretin (TTR), preferably capable of binding misfolded, misassembled, and/or aggregated TTR species, as well as methods related thereto. In addition, methods of diagnosing and/or monitoring diseases and treatments thereof which are associated with TTR amyloidosis are provided. Assays and kits related to antibodies specific for TTR or TTR deposits and aggregates are also disclosed. The novel anti-TTR antibodies can be used in pharmaceutical and diagnostic compositions for TTR targeted immunotherapy and diagnostics.

13 Claims, 22 Drawing Sheets

Specification includes a Sequence Listing.

Related U.S. Application Data division of application No. 15/106,176, filed as application No. PCT/EP2014/079094 on Dec. 22, 2014, now Pat. No. 10,344,080.

(51) Int. Cl.
  *C07K 16/18* (2006.01)
  *G01N 33/68* (2006.01)

(52) U.S. Cl.
  CPC ...... *C07K 2317/21* (2013.01); *C07K 2317/33* (2013.01); *C07K 2317/34* (2013.01); *C07K 2317/52* (2013.01); *C07K 2317/565* (2013.01); *C07K 2317/92* (2013.01); *G01N 2800/28* (2013.01); *G01N 2800/7047* (2013.01)

(56) References Cited

U.S. PATENT DOCUMENTS

| | | | |
|---|---|---|---|
| 2008/0131907 | A1 | 6/2008 | Wang et al. |
| 2016/0347832 | A1 | 12/2016 | Hosoi et al. |
| 2016/0355576 | A1 | 12/2016 | Grimm et al. |
| 2019/0345237 | A1 | 11/2019 | Grimm et al. |

FOREIGN PATENT DOCUMENTS

| | | |
|---|---|---|
| WO | WO-2008/081008 A1 | 7/2008 |
| WO | WO-2009/007958 A2 | 1/2009 |
| WO | WO-2009/079585 A2 | 6/2009 |
| WO | WO-2009/086539 A2 | 7/2009 |
| WO | WO-2010/030203 A1 | 3/2010 |
| WO | WO-2010/040209 A1 | 4/2010 |
| WO | WO-2014/124334 A2 | 8/2014 |
| WO | WO-2015/115331 A1 | 8/2015 |

OTHER PUBLICATIONS

Ando, Y., "Liver Transplantation and Development of New Therapeutic Approaches for Familia Amyloidotic Polyneuropathy (FAP)," Annual Review, Shinkei 2011, Chugaiigakusha, 2011, 310-317 (English translation) (10 pages).

Bergstrom et al., "Surface exposed epitopes and structural heterogeneity of in vivo formed transthyretin amyloid fibrils," Biochem. Biophys. Res. Commun. 348:532-539 (2006).

Chen et al., Enhancement and destruction of antibody function by somatic mutation: unequal occurrence is controlled by V gene combinatorial associations, The EMBO Journal 14(12):2784-2794 (1995).

Edwards et al., "The remarkable flexibility of the human antibody repertoire; isolation of over one thousand different antibodies to a single protein, BLyS," J. Mol. Biol. 334(1):103-118 (2003).

English translation of JP-2010-195710 (2010) (14 pages).

English translation of Notice of Reasons for Refusal dated Oct. 2, 2018 for Japanese Patent Application No. 2016-541159 (11 pages).

Goldsteins et al., "Exposure of cryptic epitopes on transthyretin only in amyloid and in amyloidogenic mutants," Proc. Natl. Acad. Sci. U.S.A. 96:3108-3113 (1999).

International Preliminary Report on Patentability for International Patent Application No. PCT/EP2014/079094, dated Jun. 30, 2016 (8 pages).

International Search Report for International Patent Application No. PCT/EP2014/079094, dated Apr. 28, 2014 (4 pages).

Kussie et al., "A Single Engineered Amino Acid Substitution Changes Antibody Fine Specificity," J. Immunol. 152(1):146-152 (1994).

Lippow et al., "Computational Design of Antibody-Affinity Improvement Beyond in Vivo Maturation," available in PMC Jan. 7, 2010, published in final edited form as: Nat. Biotechnol. 25(10):1171-1176 (2007) (14 pages).

Michalon et al., "Characterization of conformation-specific, human-derived monoclonal antibodies against TTR aggregates with potential for diagnostic and therapeutic use," Orphanet. J. Rare Diseases 10(Suppl 1):39 (2015).

Obayashi et al., "Impact of antibodies against amyloidogenic transthyretin (ATTR) on phenotypes of patients with familial amyloidotic polyneuropathy (FAP) ATTR Valine30Methionine," Clin. Chim. Acta. 419:127-131 (2013).

Rajpal et al., "A General Method for Greatly Improving the Affinity of Antibodies by Using Combinatorial Libraries," Proc. Natl. Acad. Sci. U.S.A. 102(24):8466-8471 (2005).

Rudikoff et al., "Single amino acid substitution altering antigen-binding specificity," Proc. Natl. Acad. Sci. U.S.A. 79:1979-1983 (1982).

Suhr et al., "One mutation, two distinct disease variants: unravelling the impact of transthyretin amyloid fibril composition," J. Intern. Med. 281:337-347 (2017).

Terazaki et al., "Immunization in familiar amyloidotic polyneuropathy: counteracting deposition by immunization with a Y78F TTR mutant," Lab Invest. 86(1):23-31 (2006).

USCAFC "*Abbvie* v. *Janssen*," *Abbvie* v. *Janssen* 759 F.3d 1285 (Fed. Cir. 2014) (38 pages).

Vajdos et al., "Comprehensive Functional Maps of the Antigen-Binding Site of an anti-ErbB2 Antibody Obtained with Shotgun Scanning Mutagenesis," J. Mol. Biol. 320(2):415-428 (2002).

Gerasimova et al. "Protein Misfolding during Pregnancy: New Approaches to Preeclampsia Diagnostics," Int J Mol Sci. 20(24): 1-18 (Dec. 2019).

FIG. 1A   NI-301.59F1-VH (variable heavy chain)

```
FR1-----------------------------CDR1-FR2------------CDR2--------------FR3-
EVQLVESGGGLVQPGGSLRLSCVASGFTFSNYWMSWVRQAPGKGLEWVANINQDSEKYYVDSVKGRFA
                             (SEQ ID NO: 92)      (SEQ ID NO: 93)
------------------------------------CDR3--------------FR4----------
SRDNSKNSLYLQMNSLRVEDTGVYYCARDRYCSGGRCSRGNNWFDPWGQGTLVTVSS
(SEQ ID NO: 2)               (SEQ ID NO: 94)
```

NI-301.59F1-VL (variable kappa light chain)

```
FR1--------------------------CDR1-------FR2-------------CDR2---FR3----------
EIVLTQSPATLSLSPGERATLSCRASQSVRSNLAWYQQKPGQAPRLLIYGASTRATDIPARFSGSGSGT
                       (SEQ ID NO: 95)              (SEQ ID NO: 96)
--------------------CDR3------FR4--------
EFTLTISSLQSEDFAVYYCQQYNNWPPYTFGQGTKVDIK
(SEQ ID NO: 4)       (SEQ ID NO: 97)
```

FIG. 1B   NI-301.35G11-VH (variable heavy chain)

```
FR1-----------------------------CDR1-FR2------------CDR2--------------FR3
EVQLVESGGGLVQPGGSLRLSCVASGFTFSSYAMSWVRQVPGKGLEWVSSISGSGDTTKYTDSVKGRFT
                             (SEQ ID NO: 98)      (SEQ ID NO: 99)
--------------------------------CDR3---------FR4----------
ISRDNSKNTVFLQMSSLRAEDTALYYCVKDGSGRIDPFALWGQGTMVTVSS
(SEQ ID NO: 6)                 (SEQ ID NO: 100)
```

NI-301.35G11-VL (variable kappa light chain)

```
FR1--------------------------CDR1-----------FR2-------------CDR2---FR3------
EIVMTQSPLSLPVTLGQPASISCRSSRSLVYSDGNIYLNWFQQRPGQSPRRLIYKVSNRDSGVPDRFSG
                       (SEQ ID NO: 101)               (SEQ ID NO: 102)
------------------------CDR3------FR4--------
SGSDTDFTLRISRVEAEDVGVYYCMQGTHWPRTFGQGTKVEIK
(SEQ ID NO: 8)           (SEQ ID NO: 103)
```

FIG. 1C   NI-301.37F1-VH (variable heavy chain)

```
FR1-----------------------------CDR1-FR2-------------CDR2---------------
QVQLQESGPGLVKPSETLSLTCSVSGGSIISRSSYWGWIRQPPGKGLEWIGGIYHSGNTYDNPSLKSRL
                             (SEQ ID NO: 104)      (SEQ ID NO: 105)
--------------------------------CDR3-------FR4----------
TMSVDTSKNQFSLNLRSVTAADTAVYYCARIVPGGDAFDIWGQGTMVTVSS
(SEQ ID NO: 10)               (SEQ ID NO: 106)
```

NI-301.37F1-VL (variable kappa light chain)

```
FR1---------------------CDR1--------FR2-------------CDR2---FR3-----------
DIQMTQSPSSLSASVGDRVTIACRASQSVGTYLNWYQQKRGKAPKLLIFAASSLQSGVPSRFSGSGSGT
                       (SEQ ID NO: 107)             (SEQ ID NO: 108)
--------------------CDR3-----FR4--------
DFTLTISSLQPEDFATYYCQQSYSSPPTFGQGTKVEIK
(SEQ ID NO: 12)       (SEQ ID NO: 109)
```

FIG. 1D  NI-301.2F5-VH  (variable heavy chain)

```
FR1----------------------------------CDR1-FR2------------CDR2--------------FR3
EVQLVESGGGVVRSRRSLRLSCATSGFTFSNYAMHWVRQAPGKGLEWVAIISYDGNNKYYADSVRGRFT
                                 (SEQ ID NO: 110)       (SEQ ID NO: 111)
---------------------------CDR3--------FR4---------
VSRDNSKNTFYLQMNSLRIEDTAVYFCARGSGRAARHWFDPWGQGTLVTVSS
(SEQ ID NO: 14)                  (SEQ ID NO: 112)
```

NI-301.2F5-VL  (variable lambda light chain)

```
FR1------------CDR1----------FR2------------CDR2---FR3--------
QSALTQPASVSGSPGQSITISCTGTSSDVGGYNYVSWYQQYPGKAPKVMIFDVFNRPSGVSNRFSGSKS
                   (SEQ ID NO: 113)             (SEQ ID NO: 114)
---------------------CDR3--------FR4--------
GNTASLTISGLQAEDEADYYCSSYTSSVTPHWVFGGGTKLTVL
(SEQ ID NO: 16)       (SEQ ID NO: 115)
```

FIG. 1E  NI-301.28B3-VH  (variable heavy chain)

```
FR1-----------------------------CDR1----FR2------------CDR2------------FR
QLQLQESGPGLVKPSETLSLTCTVSGGSITSSNFYWGWIRQPPGKGLEWIGAIYSSGNTYYNPSLKSRV
                             (SEQ ID NO: 116)      (SEQ ID NO: 117)
3-------------------------CDR3--------------FR4----------
TISVDTSKKKFSLKLSSVTAADTAVYYCARHSCSSASCYPPGFWFDPWGQGTLVTVSS
(SEQ ID NO: 18)             (SEQ ID NO: 118)
```

NI-301.28B3-VL  (variable kappa light chain)

```
FR1-----------------CDR1--------FR2-------------CDR2---FR3-----------
EIVMTQSPATLSASPGERATLSCRASQTVSYNLAWYQQKPGQAPRLLIYGASTRATGIPGRFSGSGSGT
                    (SEQ ID NO: 119)             (SEQ ID NO: 120)
-------------------CDR3-------FR4--------
EFTLTISSLQSEDFAVYYCQQYNNWPPWTFGQGTKVEIK
(SEQ ID NO: 20)      (SEQ ID NO: 121)
```

FIG. 1F  NI-301.119C12-VH  (variable heavy chain)

```
FR1------------------------------CDR1----FR2------------CDR2----------------
QVQLQESGPRLVKPSQTLSLTCTVSGGSISSGVYYWSWIRQHPGKGLEWIGYISNTGNTYYNPSLKSRV
                             (SEQ ID NO: 122)      (SEQ ID NO: 123)
-----------------------CDR3--------------FR4----------
TISIDTSKNQFSLNLRSVTAADTADYFCAREYCSGGNCYSRFYYYMDVWGKGTTVTVSS
(SEQ ID NO: 22)              (SEQ ID NO: 124)
```

NI-301.119C12-VL  (variable lambda light chain)

```
FR1------------------CDR1----------FR2---------------CDR2----FR3---------
QSVLTQPPSVSGAPGQRVTISCTGSSSNIGAGYGVHWYQQLSGTPPKLLIYGDNNRPSGVPDRFSGSKS
                    (SEQ ID NO: 125)              (SEQ ID NO: 126)
-----------------------CDR3---------FR4--------
GTSASLAITGLQAEDEAHYYCQSYDTTLSGSRVFGGGTKLTVL
(SEQ ID NO: 24)        (SEQ ID NO: 127)
```

FIG. 1G  NI-301.5D8-VH (variable heavy chain)

```
FR1-----------------------------CDR1-FR2-----------CDR2------------FR3-
QVQLQQWGAGRLKPSETLSLTCAVYGGSFSAYYWNWIRQAPGKGLEWIGEVSHGGSSNYSPSLRGRVAI
                              (SEQ ID NO: 128)    (SEQ ID NO: 129)
---------------------------CDR3----------FR4---------
SLDTSKSQFSLRLNSVTAADTAVYYCARGSPVVLPGARFDPWGQGTLVTVSS
(SEQ ID NO: 26)            (SEQ ID NO: 130)
```

NI-301.5D8-VL (variable lambda light chain)

```
FR1------------------------------CDR1---FR2-------------CDR2----FR3---------
QSALTQPASVSGFPGQSITISCTGTSSDVGSYNLVSWYQQHPGKAPKLLIYEVNKRPSGVSTRFSGSKS
                               (SEQ ID NO: 131)       (SEQ ID NO: 132)
-----------------------CDR3-----FR4---------
GNTASLTISGLQTEDEADYYCCSYAGSTKVFGIGTKVTVL
(SEQ ID NO: 28)        (SEQ ID NO: 133)
```

FIG. 1H  NI-301.9D5-VH (variable heavy chain)

```
FR1-------------------------------CDR1----FR2--------------CDR2------------FR
QVQLQESGPGLVKPSETLSLTCIVSGVSIRSGGYYWSWIRQHPGKGLEWVGFIYYTGNTYYNPSLKSRA
                                (SEQ ID NO: 134)         (SEQ ID NO: 135)
3-------------------------CDR3----------FR4---------
TISVDTSKNQFSLRLTAVTAADTAVYYCARDCSGGSCPESYFDSWGRGTLVTVSS
(SEQ ID NO: 30)             (SEQ ID NO: 136)
```

NI-301.9D5-VL (variable kappa light chain)

```
FR1----------------------CDR1---------FR2-------------CDR2----FR3---------
EIVMTQSPATLSLSPGERATLSCRASQSVRSFLAWYQQKSGQAPRLLIYDASKRATGIPARFSDSGSGT
                       (SEQ ID NO: 137)             (SEQ ID NO: 138)
----------------------CDR3------FR4---------
DFTLTISRLETEDSAVYYCQQRTNWPPHLTFGGGTKVEIK
(SEQ ID NO: 32)        (SEQ ID NO: 139)
```

FIG. 1I  NI-301.104F5-VH (variable heavy chain)

```
FR1-----------------------------CDR1-FR2-------------CDR2--------------FR3
QVQLVESGGGVVQPERSLRLSCAASGFTFRSYGMHWVRQAPGKGLEWVAVIWFDGSNKYYADSVKGRFT
                              (SEQ ID NO: 140)     (SEQ ID NO: 141)
---------------------------CDR3------FR4---------
VSRDNSKNTLYLQMNSLRAEDTAVYYCARDGIAATYADYWGQGTLVTVSS
(SEQ ID NO: 34)            (SEQ ID NO: 142)
```

NI-301.104F5-VL (variable kappa light chain)

```
FR1-------------------------CDR1--------FR2-------------CDR2---FR3----------
EIVLTQSPATLSLSPGERATLSCRASQSVRSYLAWYQQKPGQAPRLLIYGASNRATGIPARFSGSGSGT
                         (SEQ ID NO: 143)              (SEQ ID NO: 144)
-----------------------CDR3------FR4---------
DFTLTISSLEPEDFAVYYCQQRSNWPITFGQGTRLEIK
(SEQ ID NO: 36)        (SEQ ID NO: 145)
```

FIG. 1J  NI-301.21F10-VH (variable heavy chain)

```
FR1----------------------------CDR1----FR2-----------CDR2-------------
QVQLVESGGGLVQPGGSLRLSCAVSGFTLSSLSSYYMSWVRQAPGKGLEWVATINPGGSEKSYVDSVKG
                              (SEQ ID NO: 146)      (SEQ ID NO: 147)
FR3-----------------------------CDR3---------FR4----------
RFTVSRDNARSSVYLQMDSLTVEDTAIYYCARPRYCTSGGCYFDNWGQGTLVTVSS
(SEQ ID NO: 38)                 (SEQ ID NO: 148)
```

NI-301.21F10-VL (variable lambda light chain)

```
FR1---------------------CDR1----------FR2-------------CDR2---FR3--------
QSALTQPRSVSGSPGQSVTISCTATNSDVGDYKSVSWYQQHPGKAPKLMIYDVGRRPSGVPDRFSGSKS
                      (SEQ ID NO: 149)               (SEQ ID NO: 150)
-----------------------CDR3------FR4----------
DNTAFLTISGLQTEDEADYFCCIYVGRSSVFGGGTKLTVL
(SEQ ID NO: 40)       (SEQ ID NO: 151)
```

FIG. 1K  NI-301.9G12-VH (variable heavy chain)

```
FR1------------------------------CDR1--FR2-----------CDR2------------FR3
QVQLQESGPGLVKPSETLSLTCAVSGFSISSGYYWGWIRQPPGTGLEWIGSMYHSGRTYYNPSLKSRVT
                              (SEQ ID NO: 152)     (SEQ ID NO: 153)
-----------------------------CDR3-----------FR4---------
ISVDTSKNQLSLKLSSVTAADTAVYYCARGFDTSGSHRPLSTDYWGQGTLVTVSS
(SEQ ID NO: 42)              (SEQ ID NO: 154)
```

NI-301.9G12-VL (variable lambda light chain)

```
FR1-------------------------CDR1----------FR2--------------CDR2----FR3---------
QSVLTQPPSVSAAPGQKVTISCSGSSSNIGNNYVSWYQQLPGTAPKLLIYDNNKRPSGIPDRISGSKSG
                     (SEQ ID NO: 155)                    (SEQ ID NO: 156)
-----------------------CDR3-------FR4---------
TSATLGITGLQTGDEADYYCGTWDSSLSAYVFGTGTKVTVL
(SEQ ID NO: 44)        (SEQ ID NO: 157)
```

FIG. 1L  NI-301.12D3-VH (variable heavy chain)

```
FR1-------------------------------CDR1-FR2-----------CDR2-------------FR3
EVQLVETGGGVVQPGRSLRLSCVASGFTFRNYGMHWVRRAPGRGLEWVAVIWSDGSDKYYADSVEGRFT
                             (SEQ ID NO: 158)       (SEQ ID NO: 159)
-----------------------------CDR3-------FR4----------
ISRDNSKNTVFLQMNSLRADDTAVYFCAREPSSTWAFDYWGQGTLVTVSS
(SEQ ID NO: 46)              (SEQ ID NO: 160)
```

NI-301.12D3-VL (variable lambda light chain)

```
FR1-------------------------CDR1----------FR2--------------CDR2---FR3---------
QSALTQPASVSGSPGQSITISCTGTSSDVGGYNLVSWYQQHPGKAPKLMIYEDIKGPSGVSNRFSGSKS
                     (SEQ ID NO: 161)                    (SEQ ID NO: 162)
-----------------------------CDR3-------FR4---------
GNTASLTISGLQAEDEADYFCCSYAGTGTLVFGGGTKLTVL
(SEQ ID NO: 48)              (SEQ ID NO: 163)
```

FIG. 1M NI-301.37F1-PIMC-VH (variable heavy chain)

```
FR1-------------------------------CDR1----FR2----------CDR2--------------
QLQLQESGPGLVKPSETLSLTCSVSGGSIISRSSYWGWIRQPPGKGLEWIGGIYHSGNTYDNPSLKSRL
                            (SEQ ID NO: 164)         (SEQ ID NO: 165)
FR3-------------------------------CDR3---------FR4---------
TMSVDTSKNQFSLNLRSVTAADTAVYYCARIVPGGDAFDIWGQGTMVTVSS
(SEQ ID NO: 53)              (SEQ ID NO: 166)
```

FIG. 1N NI-301.44E4-VH (variable heavy chain)

```
FR1-------------------------------CDR1--FR2-----------CDR2------------FR3
EVQLVESGGGLVQPGGSLRLSCAASGFTFSSYAMIWVRQAPGKGLEWVSGISGSGSTTYYADSVKGRFA
                              (SEQ ID NO: 167)        (SEQ ID NO: 168)
-------------------------------CDR3-------------FR4---------
ISRDKSKNTLSLQMNSLRAEDTAVYYCAKGAWEIPTYFDNWGQGTLVTVSS
(SEQ ID NO: 55)              (SEQ ID NO: 169)
```

NI-301.44E4-VK (variable lambda light chain)

```
FR1----------------------CDR1---------FR2-----------CDR2---FR3----------
EIVLTQSPATLSVSPGERATLSCRASQSIRNNLAWYQQKPGQAPRLLIYGASTRATGIPARFSGTGSGT
                       (SEQ ID NO: 170)           (SEQ ID NO: 171)
------------------------CDR3--------FR4---------
EFTLIVSSLQSEDFAVYYCQQYNNWPPTWTFGQGTKVEIK
(SEQ ID NO: 57)        (SEQ ID NO: 172)
```

FIG. 1O NI-301.18C4-VH (variable heavy chain)

```
FR1-------------------------------CDR1--FR2-----------CDR2------------FR3
EVQLVESGGTLVQPGGSLRLSCAASGFTFNIYAMTWVRLSPVRGLEWVSTITSGGVSIYYADSIKGRFT
                              (SEQ ID NO: 173)        (SEQ ID NO: 174)
-------------------------------CDR3-----------FR4---------
VSRDNAKNMVFLQLDNLTVDDTAIYYCGKDGNCDETSCYLRGMDVWGQGTTVTVSS
(SEQ ID NO: 62)              (SEQ ID NO: 175)
```

NI-301.18C4-VL (variable lambda light chain)

```
FR1----------------------CDR1----------FR2------------CDR2----FR3---------
QSVLTQPPSVSAAPGQKVTISCSGSRSDIGSKLVSWYQVIPGRAPRLVIFDTYKRPSGVPARFSASKSG
                       (SEQ ID NO: 176)             (SEQ ID NO: 177)
------------------------CDR3--------FR4---------
TSATLDIAGLQPGDEAEYFCGSWGNSENFYYVFGSGTRVTVL
(SEQ ID NO: 64)        (SEQ ID NO: 178)
```

FIG. 1P  NI-301.11A10-VH (variable heavy chain) (PIMC by default)

```
FR1--------------------------------CDR1-FR2--------------CDR2---------------
QLQLQESGPGLVKPSETLSLTCTVSGGSISSRSYYWGWMRQPPGKGLEWIGSIYYSGSTLYNPSLKSRV
                            (SEQ ID NO: 179)        (SEQ ID NO: 180)
FR3--------------------------------CDR3----FR4--------
TMSIVTSRNQFSLKLSSVTAADTAVYYCTRMGEGGRDYWGQGTLVTVSS
(SEQ ID NO: 66)                     (SEQ ID NO: 181)
```

NI-301.11A10-VK (variable kappa light chain) (PIMC by default)

```
FR1---------------------CDR1--------FR2--------------CDR2---FR3-----------
DIQMTQSPSTLSASVGDRVTITCRASQSISSWLAWYQQKPGKAPKVLIYDASSLERGVPSRFSGSGSGT
                       (SEQ ID NO: 182)           (SEQ ID NO: 183)
-----------------------CDR3-----FR4--------
EFTLTISSLQPDDSATYYCQHYNGYSRTFGRGTKVEIK
(SEQ ID NO: 68)        (SEQ ID NO: 184)
```

FIG. 1Q  NI-301.3C9-VH (variable heavy chain) (PIMC by default)

```
FR1-------------------------------CDR1----FR2--------------CDR2-------------FR
QVQLQESGPGLVKSSQTLSLTCTVSGASFTRGDFYWSWIRQVPGKGLEWIGYIYSTGDVYYNPSLKSRA
                             (SEQ ID NO: 185)         (SEQ ID NO: 186)
3-------------------------------CDR3----------FR4--------
NISVDTPKKQFFLKLTSLTAADTAVYFCAREGQYCSGGSCYPEYWGQGTLVTVSS
(SEQ ID NO: 70)                 (SEQ ID NO: 187)
```

NI-301.3C9-VL (variable lambda light chain)

```
FR1---------------------CDR1--------FR2--------------CDR2----FR3-------------
SYELTQPPSVSVSPGQTATITCSGDNLGHKFTCWYQQKPGQSPVLVIYQDHKRPSGIPERFSGSNSGDT
                      (SEQ ID NO: 188)             (SEQ ID NO: 189)
-----------------------CDR3-----FR4--------
ATLTISGTQAMDEAEYYCQAWAFPYVVFGGGTKLTVL
(SEQ ID NO: 72)        (SEQ ID NO: 190)
```

FIG. 1R  NI-301.14D8-VH (variable heavy chain)

```
FR1-------------------------------CDR1-FR2-------------CDR2---------------FR3
EVQLVETGGRLVQPGGSVRLSCIASGFPFRNYWMSWVRQPPGKGLEWVANIKEDGSDRYYVDSVKGRFT
                            (SEQ ID NO: 191)        (SEQ ID NO: 192)
-------------------------------CDR3----------FR4--------
IFRDNAKNFLSLQMNRLRAEDTAVYFCARIVGVIPSADPYYLDSWGQGTLVTVSS
(SEQ ID NO: 74)                (SEQ ID NO: 193)
```

NI-301.14D8-VL (variable lambda light chain) (PIMC by default)

```
FR1---------------------CDR1----------FR2--------------CDR2---FR3---------
QSALTQPASVSGFAGQSVTISCTGTSLNIGTYNLISWYQQHPGRAPRLIIFEGNRRPPGISNRFSASKS
                      (SEQ ID NO: 194)            (SEQ ID NO: 195)
-----------------------CDR3-------FR4--------
GNTASLTVSGLLAGDEADYYCCSFAGRVSLVFGGGTKLTVL
(SEQ ID NO: 76)        (SEQ ID NO: 196)
```

FIG. 1S  NI-301.9X4-VH  (variable heavy chain) (PIMC by default)

```
FR1----------------------------CDR1-FR2-----------CDR2----------------
QVQLQESGPGLVKPSETLSLTCSVSAGSISSHYWNWIRQPPGKGLEWIGSIYHSGSTNYNPSLKSRVTI
                            (SEQ ID NO: 197)        (SEQ ID NO: 198)
FR3--------------------------CDR3----FR4--------
SVDTSKNHVSLRLTSVTAADTAVYYCARDYYYYMDVWGKGTTVTVSS
(SEQ ID NO: 78)            (SEQ ID NO: 199)
```

NI-301.9X4-VL (variable lambda light chain) (PIMC by default)

```
FR1--------------------CDR1--------FR2-------------CDR2----FR3-----------
SYELTQPPSVSVSPGQTARITCSGDALPDKYAYWYQQKPGQAPMLVIYKDSERPSGIPERFSGSSLGTT
                      (SEQ ID NO: 200)            (SEQ ID NO: 201)
-------------------CDR3-------FR4--------
VMLTISGVQAEDEADYYCKSADSSGTYWVFGGGTKLTVL
(SEQ ID NO: 80)    (SEQ ID NO: 202)
```

FIG. 1T  NI-301.14C3-VH  (variable heavy chain) (PIMC by default)

```
FR1-------------------------------CDR1-FR2-------------CDR2--------------FR3-
EVQLVETGGGLIQPGGSLRLSCAASGFTVSSHYMSWVRQAPGKGLEWVSIIYSGGGTYYADSVKGRFTI
                              (SEQ ID NO: 203)        (SEQ ID NO: 204)
---------------------------CDR3---------FR4---------
SRDNSKNTLYLQMNSLRAEDTAVYYCAKIYRSGNTGYSYDYWGQGTLVTVSS
(SEQ ID NO: 82)            (SEQ ID NO: 205)
```

NI-301.14C3-VL (variable lambda light chain)

```
FR1------------------CDR1---------FR2-------------CDR2----FR3------------
SYELTQPPSVSVSPGQTASITCSGDKLGSKYACWYQQKPGQSPVLVIYEDKKRPSGIPERFSGSNSGNT
                    (SEQ ID NO: 206)             (SEQ ID NO: 207)
------------------------CDR3--------FR4--------
ATLTISGTQAMDEADYFCQAWDSSTSHVVFGGGTRLTVL
(SEQ ID NO: 84)      (SEQ ID NO: 208)
```

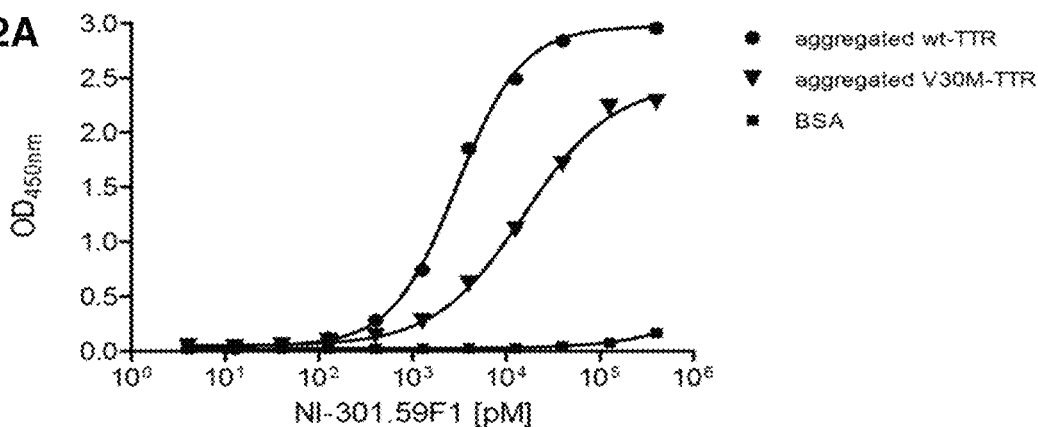
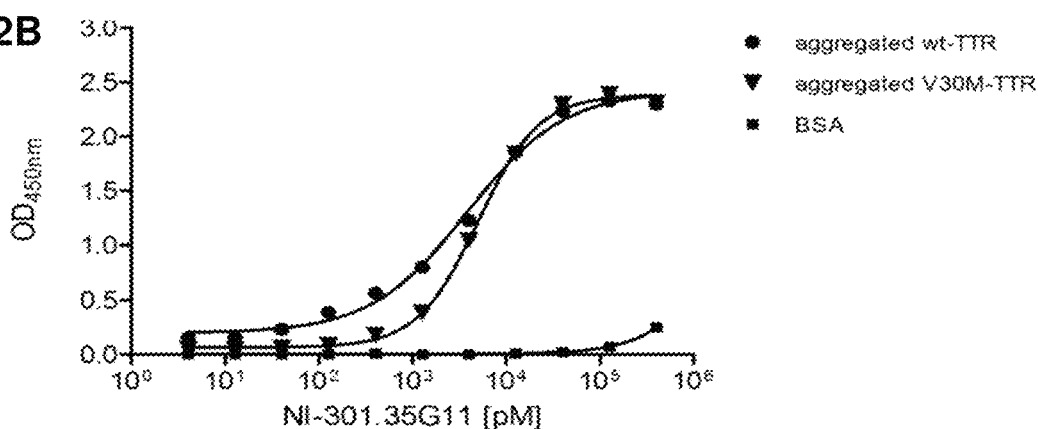
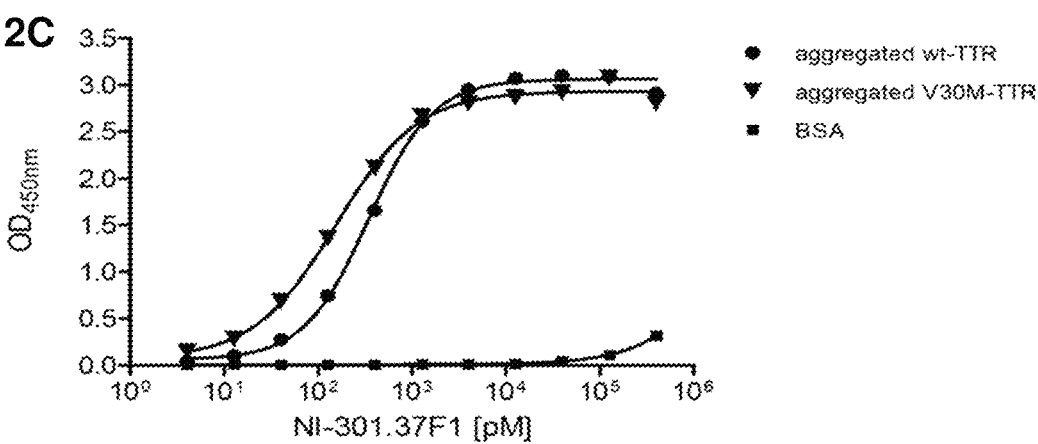

A: Dako 150 ng/ml
B: 59F1 50 nM
C: 35G11 50 nM
D: 37F1 50 nM

A: Dako 150 ng/ml
B: 59F1 50 nM
C: 35G11 50 nM
D: 37F1 50 nM

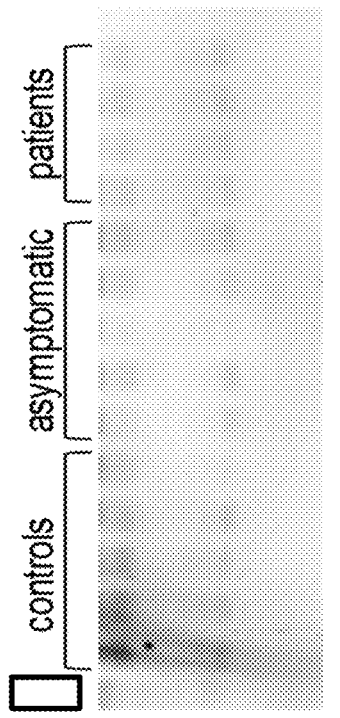
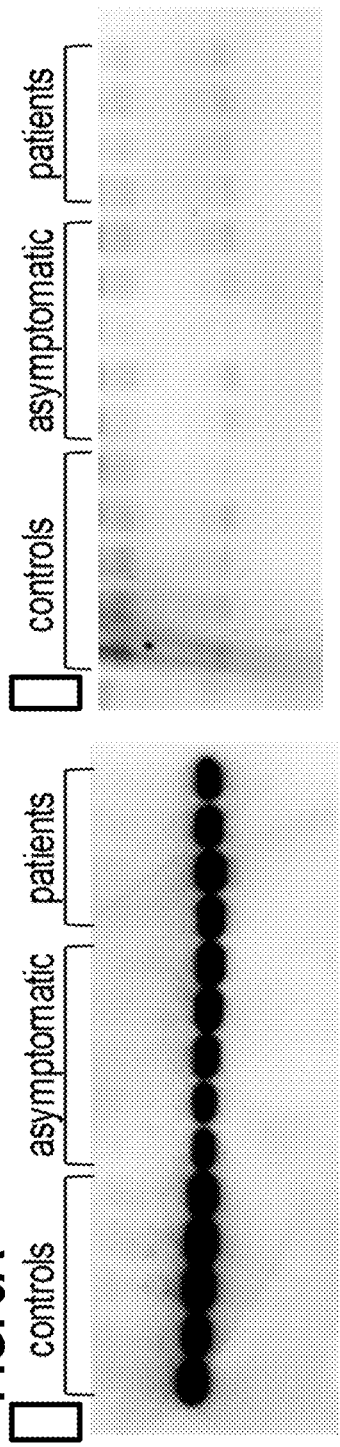
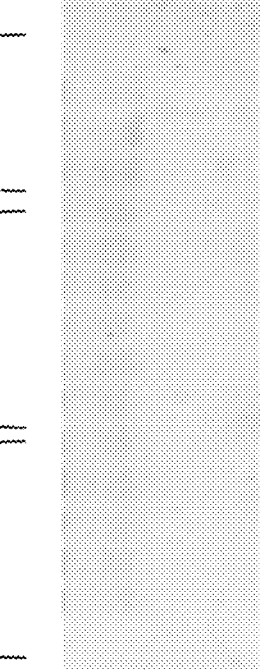
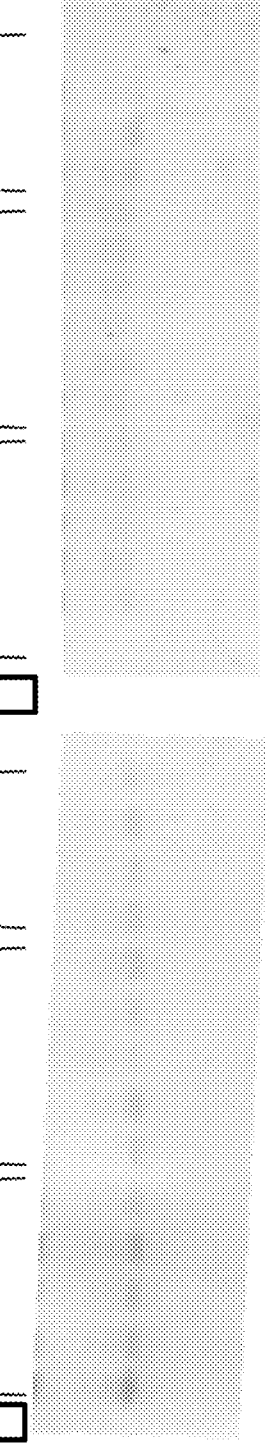

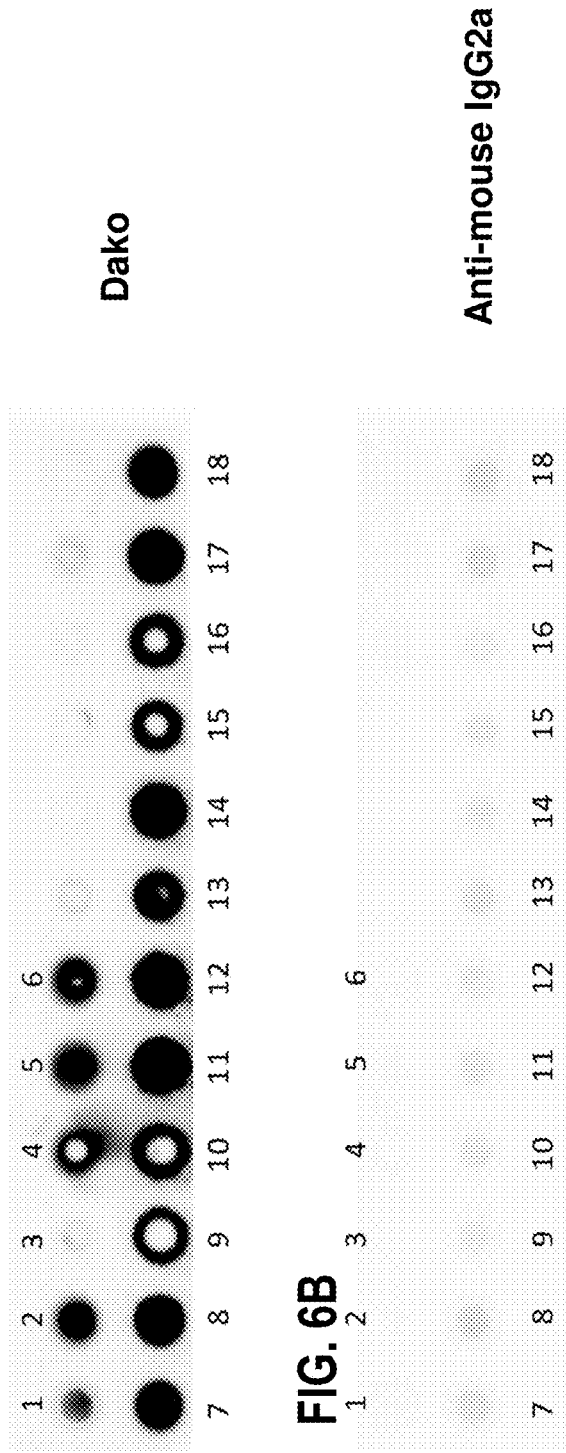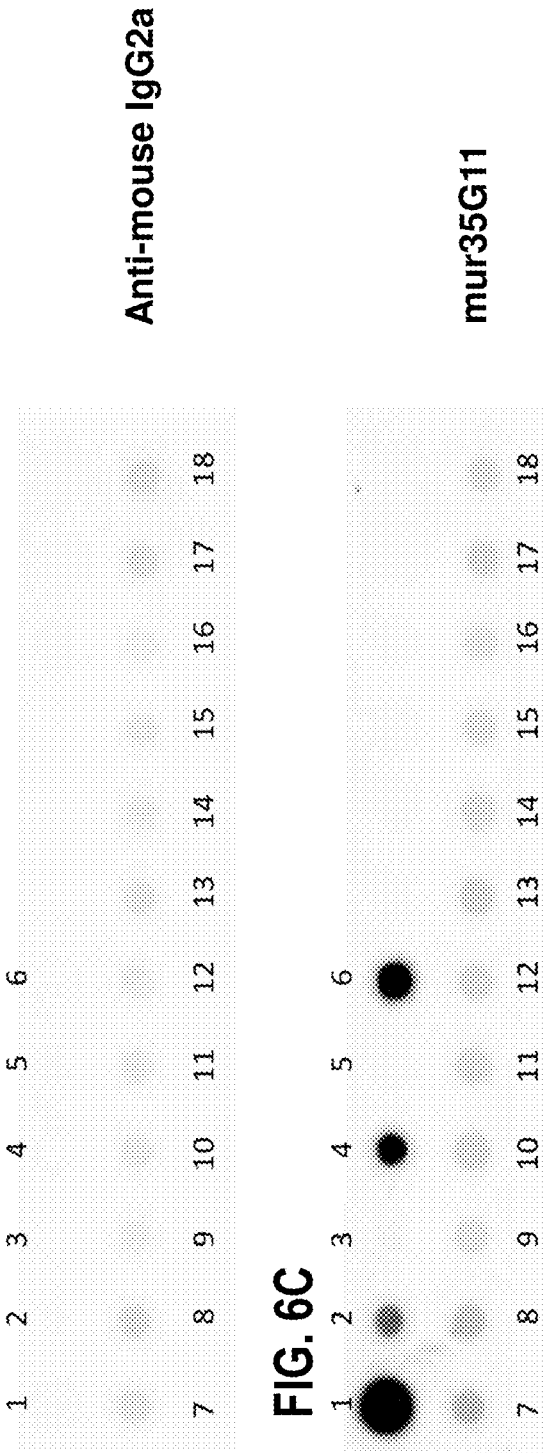

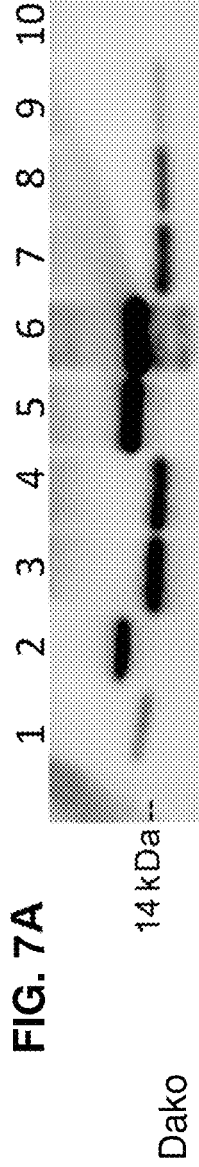
FIG. 7A Dako  14 kDa
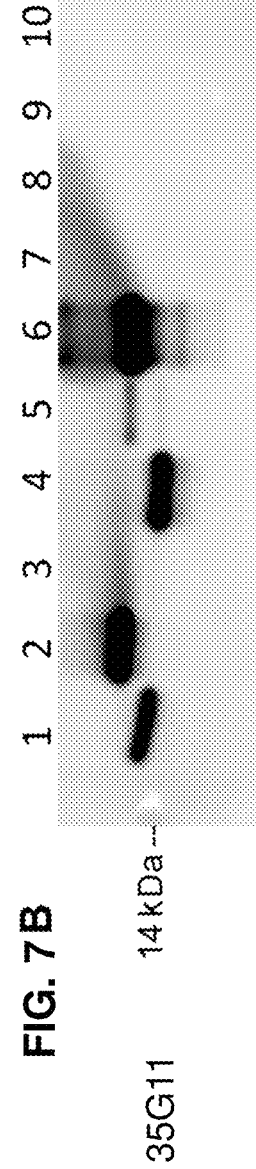
FIG. 7B 35G11  14 kDa
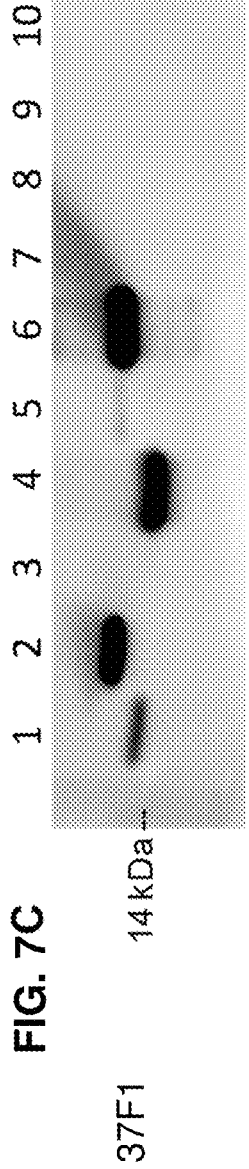
FIG. 7C 37F1  14 kDa

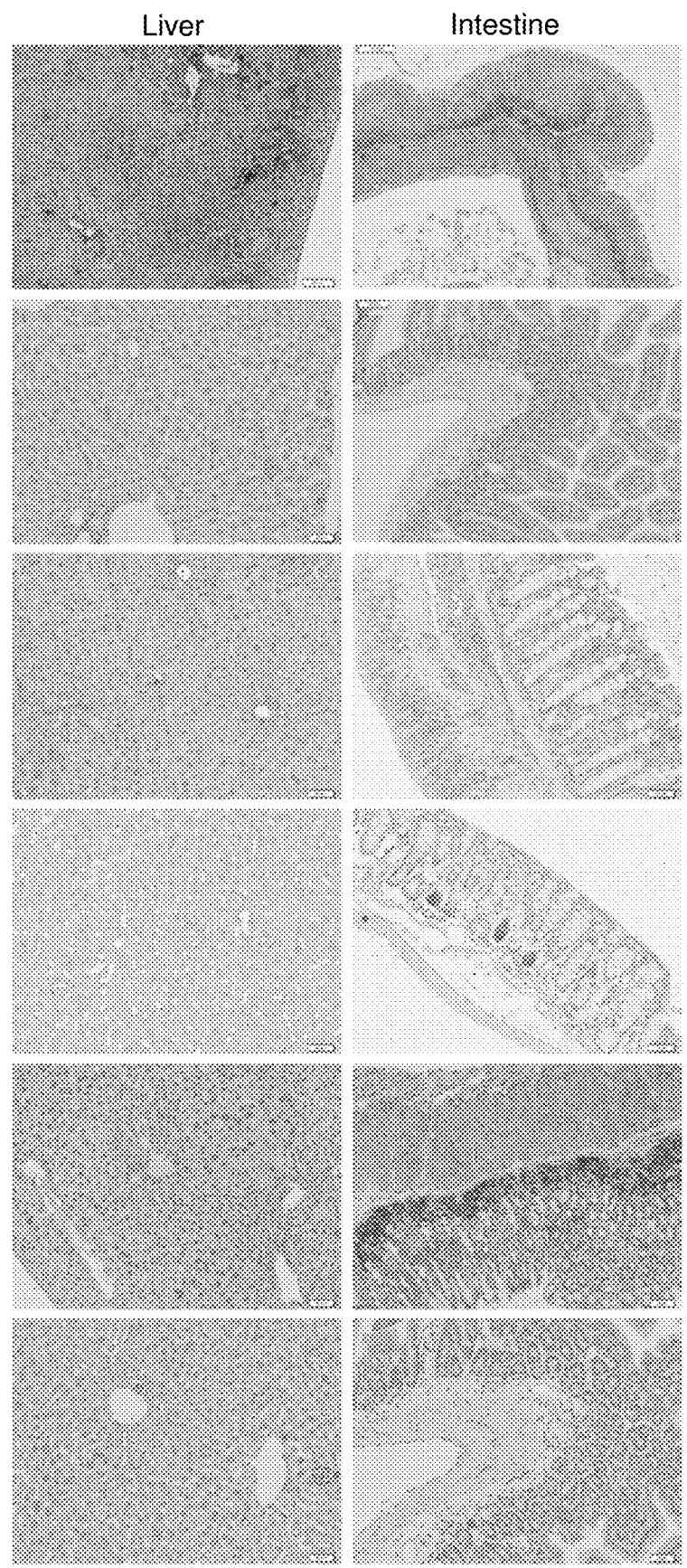

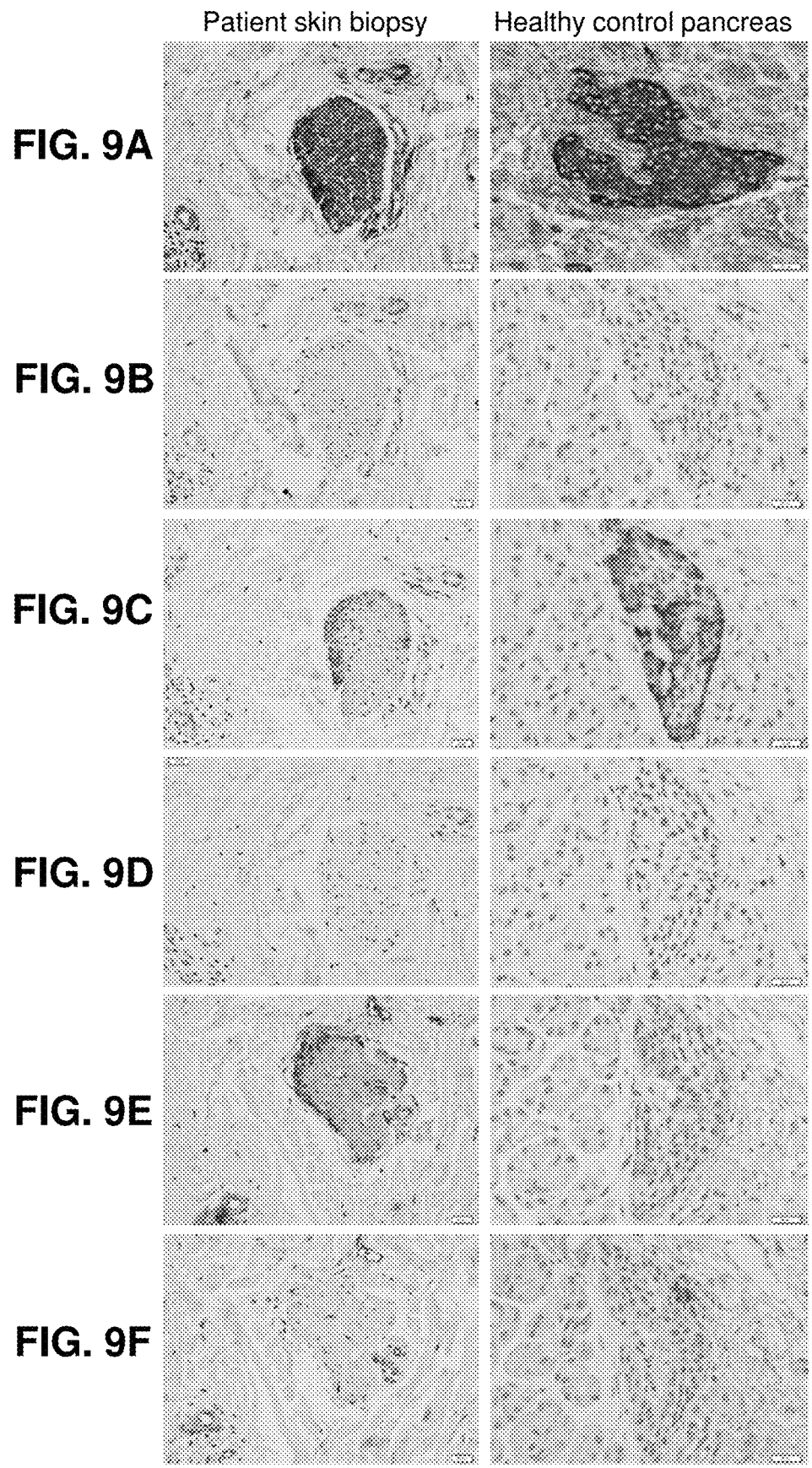

FIG. 10A
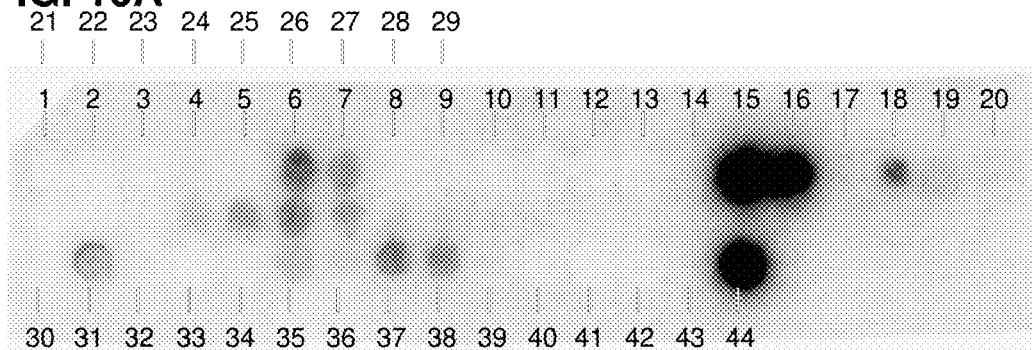
FIG. 10B
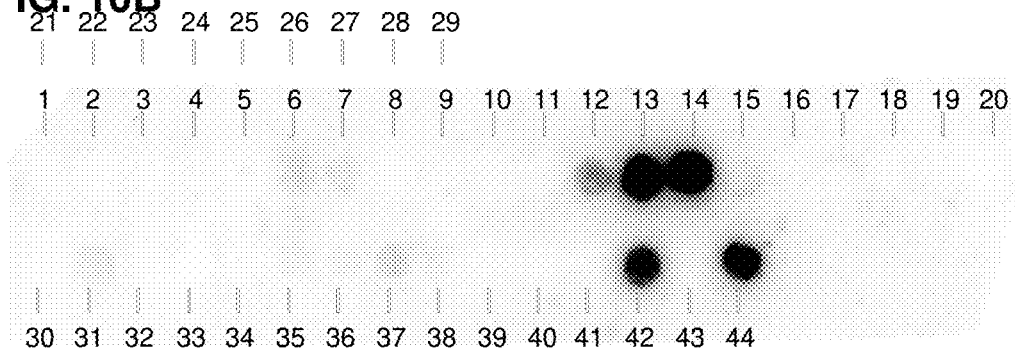
FIG. 10C
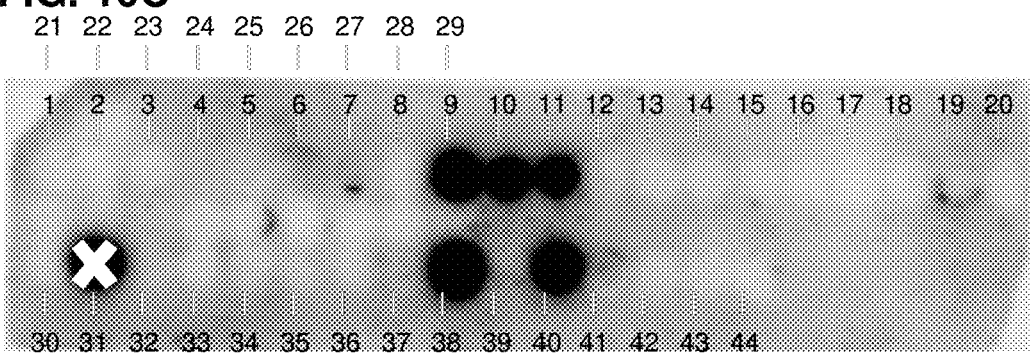
FIG. 10D
| Antibody | Binding epitope |
|---|---|
| NI-301.59F1 | 61-EEEFVEGIY-69 (SEQ ID NO: 49) |
| NI-301.35G11 | 53-GELHGLTTEEE-63 (SEQ ID NO: 50) |
| NI-301.37F1 | 41-WEPFA-45 (SEQ ID NO: 51) |

FIG. 10E
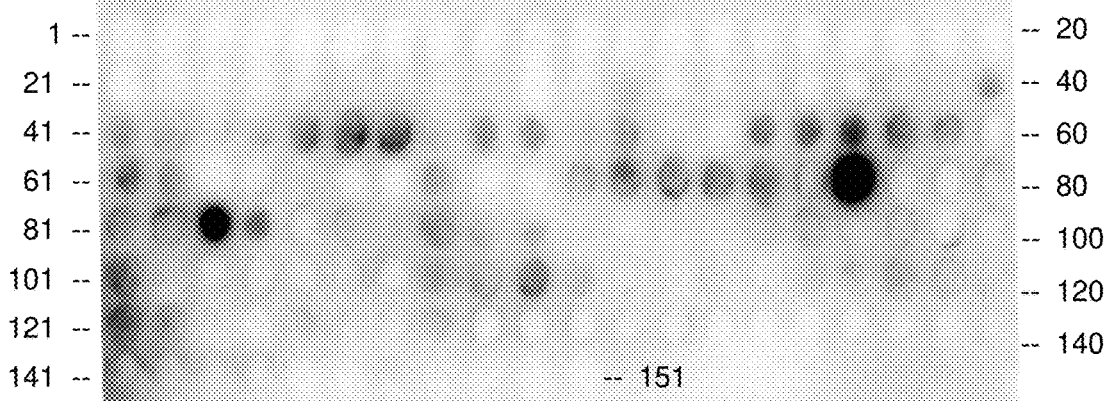
FIG. 10F
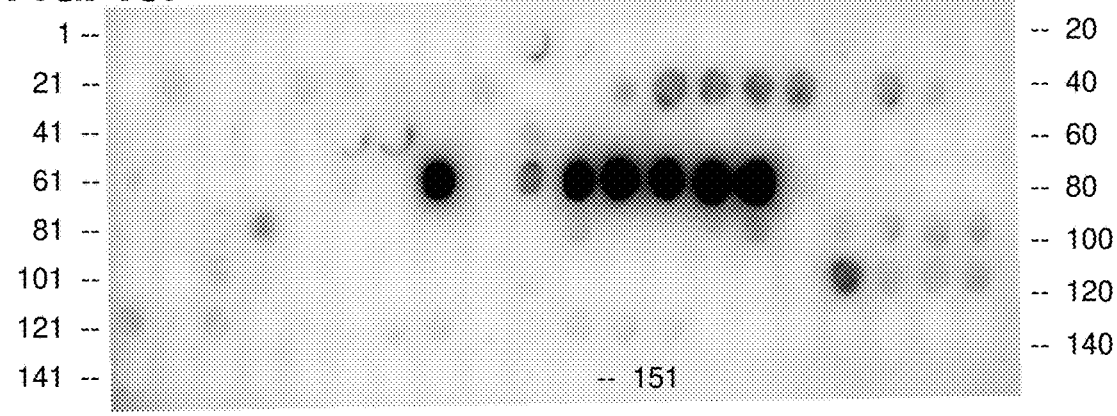
FIG. 10G
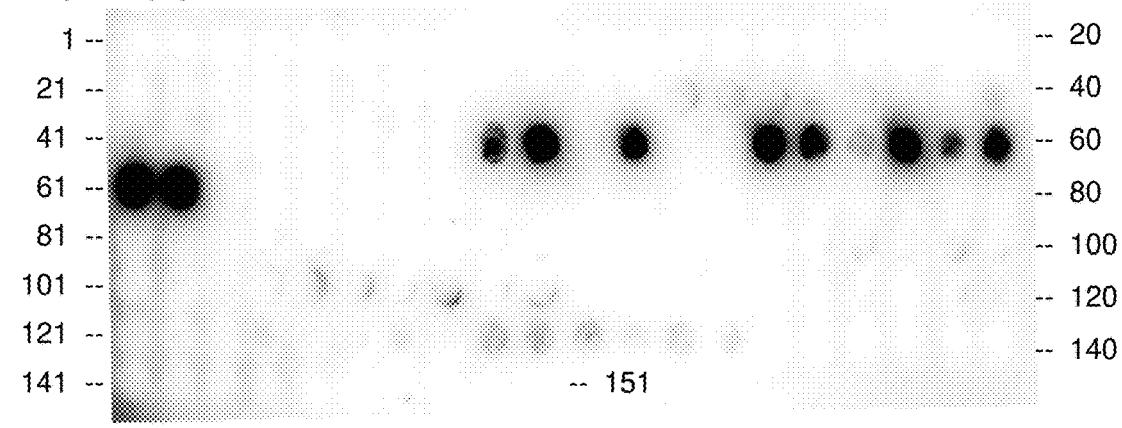
FIG. 10H
| Antibody | Binding epitope |
|---|---|
| NI-301.59F1 | 62-EEFXEGIY-69 (SEQ ID NO: 58) |
| NI-301.35G11 | 54-ELXGLTXE-61 (SEQ ID NO: 59) |
| NI-301.37F1 | 41-WEPFA-45 (SEQ ID NO: 60) |

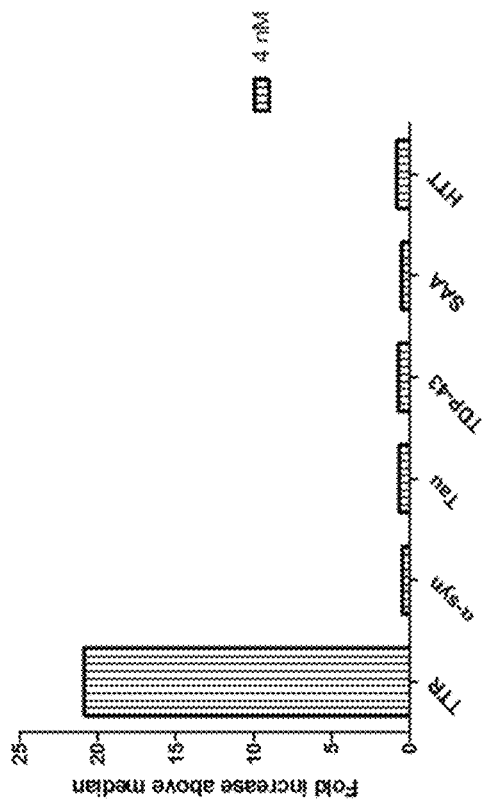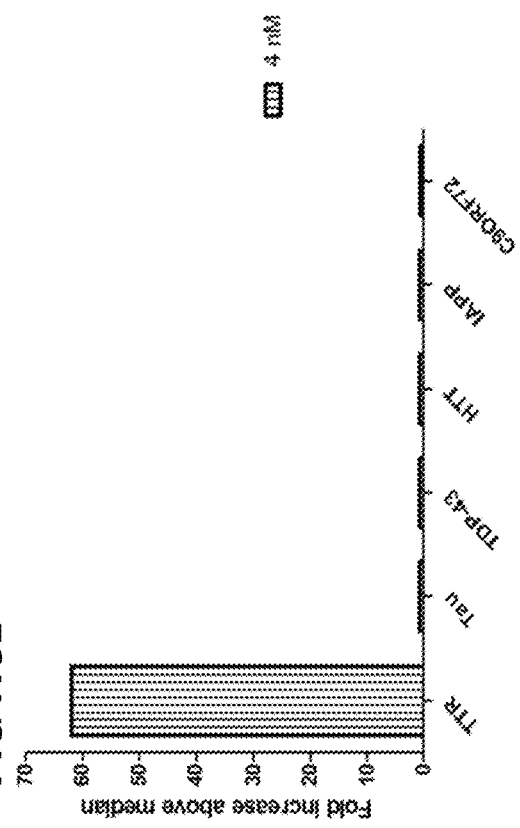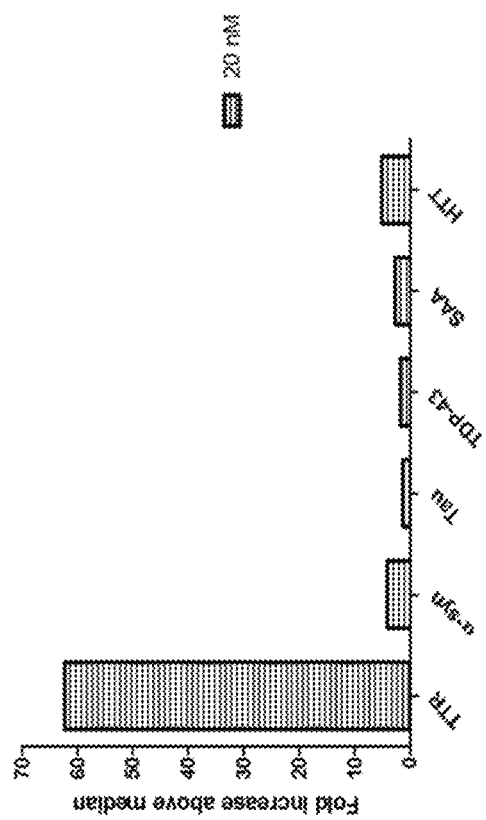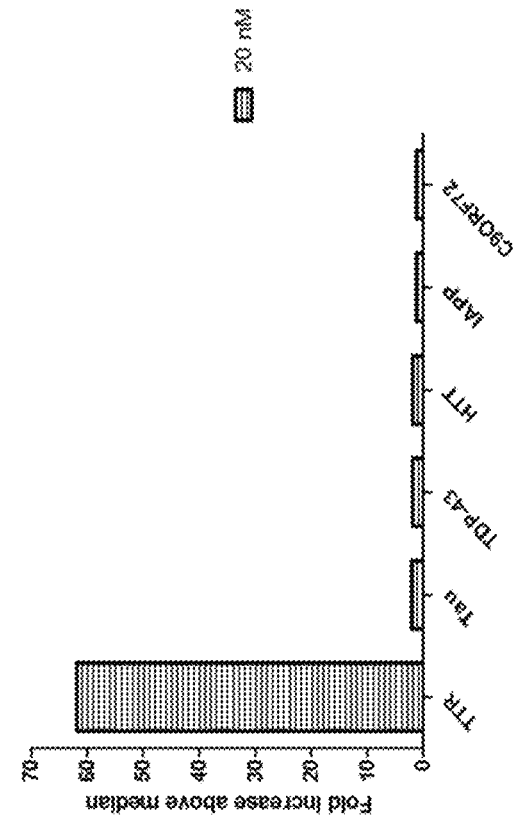

SEQUENCE LISTING

<160> NUMBER OF SEQ ID NOS: 210

<210> SEQ ID NO 1
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-301.59F1 variable heavy chain (VH) sequence
<220> FEATURE:
<221> NAME/KEY: V_region
<222> LOCATION: (91)..(105)
<223> OTHER INFORMATION: complementarity determining region (CDR) VH-CDR1
<220> FEATURE:
<221> NAME/KEY: V_region
<222> LOCATION: (148)..(195)
<223> OTHER INFORMATION: complementarity determining region (CDR) VH-CDR2
<220> FEATURE:
<221> NAME/KEY: V_region
<222> LOCATION: (292)..(345)
<223> OTHER INFORMATION: complementarity determining region (CDR) VH-CDR3

<400> SEQUENCE: 1

```
gag gtg cag ctg gtg gag tct ggg gga ggg ttg gtc cag cct ggg ggg      48
Glu Val Gln Leu Val Glu Ser Gly Gly Gly Leu Val Gln Pro Gly Gly
 1               5                   10                  15 tcc ctg aga ctc tcc tgt gta gcc tct gga ttc act ttt agt aat tat      96
Ser Leu Arg Leu Ser Cys Val Ala Ser Gly Phe Thr Phe Ser Asn Tyr
             20                  25                  30 tgg atg agt tgg gtc cgc cag gct cca ggg aag ggg ctg gag tgg gtg     144
Trp Met Ser Trp Val Arg Gln Ala Pro Gly Lys Gly Leu Glu Trp Val
         35                  40                  45 gcc aat ata aat caa gat agt gag aaa tac tat gtg gac tct gtg aag     192
Ala Asn Ile Asn Gln Asp Ser Glu Lys Tyr Tyr Val Asp Ser Val Lys
     50                  55                  60 ggc cga ttc gcc atc tcc aga gac aac tcc aag aac tca ctg tat ctg     240
Gly Arg Phe Ala Ile Ser Arg Asp Asn Ser Lys Asn Ser Leu Tyr Leu
 65                  70                  75                  80
```

```
caa atg aac agc ctg aga gtc gag gac acg ggc gtg tat tac tgt gcg       288
Gln Met Asn Ser Leu Arg Val Glu Asp Thr Gly Val Tyr Tyr Cys Ala
            85                  90                  95 aga gat cgc tat tgc agt ggt ggg aga tgc tcc cgg ggt aac aac tgg       336
Arg Asp Arg Tyr Cys Ser Gly Gly Arg Cys Ser Arg Gly Asn Asn Trp
                100                 105                 110 ttc gac ccc tgg ggc cag gga acc ctg gtc acc gtc tcc tcg               378
Phe Asp Pro Trp Gly Gln Gly Thr Leu Val Thr Val Ser Ser
        115                 120                 125
```

<210> SEQ ID NO 2
<211> LENGTH: 126
<212> TYPE: PRT
<213> ORGANISM: Homo sapiens

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Asn Gln Asp Ser Glu Lys Tyr Tyr Val Asp Ser Val Lys
    50                  55                  60

Gly Arg Phe Ala Ile Ser Arg Asp Asn Ser Lys Asn Ser Leu Tyr Leu
65                  70                  75                  80

Gln Met Asn Ser Leu Arg Val Glu Asp Thr Gly Val Tyr Tyr Cys Ala
                85                  90                  95

Arg Asp Arg Tyr Cys Ser Gly Gly Arg Cys Ser Arg Gly Asn Asn Trp
                100                 105                 110

Phe Asp Pro Trp Gly Gln Gly Thr Leu Val Thr Val Ser Ser
        115                 120                 125
```

<210> SEQ ID NO 3
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-301.59F1 variable K-light chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(294)
<223> OTHER INFORMATION: complementarity determining region (CDR)
      VK-CDR3

<400> SEQUENCE: 3

```
gaa att gtg ttg acg cag tct cca gcc act ctg tct ctg tct cca ggg        48
Glu Ile Val Leu Thr Gln Ser Pro Ala Thr Leu Ser Leu Ser Pro Gly
1               5                   10                  15 gag aga gcc acc ctc tcc tgc agg gcc agt cag agt gtt aga agc aac        96
Glu Arg Ala Thr Leu Ser Cys Arg Ala Ser Gln Ser Val Arg Ser Asn
            20                  25                  30
```

```
tta gcc tgg tac cag cag aaa cct ggc cag gct ccc agg ctc ctc atc      144
Leu Ala Trp Tyr Gln Gln Lys Pro Gly Gln Ala Pro Arg Leu Leu Ile
            35                  40                  45 tat ggt gca tcc acc agg gcc act gat atc cca gcc agg ttc agt ggc      192
Tyr Gly Ala Ser Thr Arg Ala Thr Asp Ile Pro Ala Arg Phe Ser Gly
    50                  55                  60 agt ggg tct ggg aca gaa ttc act ctc acc atc agc agc ctg cag tct      240
Ser Gly Ser Gly Thr Glu Phe Thr Leu Thr Ile Ser Ser Leu Gln Ser
65                  70                  75                  80 gag gat ttt gca gtt tat tac tgt cag caa tat aat aac tgg cct ccg      288
Glu Asp Phe Ala Val Tyr Tyr Cys Gln Gln Tyr Asn Asn Trp Pro Pro
                85                  90                  95 tac act ttt ggc cag ggg acc aaa gtg gat atc aaa                      324
Tyr Thr Phe Gly Gln Gly Thr Lys Val Asp Ile Lys
            100                 105
```

<210> SEQ ID NO 4
<211> LENGTH: 108
<212> TYPE: PRT
<213> ORGANISM: Homo sapiens

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Asp Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Tyr Thr Phe Gly Gln Gly Thr Lys Val Asp Ile Lys
            100                 105
```

<210> SEQ ID NO 5
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-301.35G11 variable heavy chain (VH) sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(327)
<223> OTHER INFORMATION: complementarity determining region (CDR)
      VH-CDR3

<400> SEQUENCE: 5

```
gag gtg cag ctg gtg gag tct ggg gga ggc ttg gtg cag cct ggg ggg       48
Glu Val Gln Leu Val Glu Ser Gly Gly Gly Leu Val Gln Pro Gly Gly
```

```
                1               5                      10                      15
     tcc ctg aga ctc tcc tgt gta gcc tct gga ttc act ttt agc agc tat          96
     Ser Leu Arg Leu Ser Cys Val Ala Ser Gly Phe Thr Phe Ser Ser Tyr
                     20                      25                      30 gcc atg agc tgg gtc cgc cag gtt cca ggg aag ggg ctg gag tgg gtc         144
     Ala Met Ser Trp Val Arg Gln Val Pro Gly Lys Gly Leu Glu Trp Val
                     35                      40                      45 tca tct att agt ggt agt ggt gat aca aca aaa tac aca gac tcc gtg         192
     Ser Ser Ile Ser Gly Ser Gly Asp Thr Thr Lys Tyr Thr Asp Ser Val
                 50                      55                      60 aag ggc cgg ttc acc atc tcc aga gac aat tcc aag aac acg gtg ttt         240
     Lys Gly Arg Phe Thr Ile Ser Arg Asp Asn Ser Lys Asn Thr Val Phe
     65                      70                      75                      80 ctg caa atg agc agc ctg aga gcc gag gac acg gcc cta tat tac tgt         288
     Leu Gln Met Ser Ser Leu Arg Ala Glu Asp Thr Ala Leu Tyr Tyr Cys
                         85                      90                      95 gtg aaa gat ggt agt gga cgg atc gat cct ttt gct tta tgg ggc caa         336
     Val Lys Asp Gly Ser Gly Arg Ile Asp Pro Phe Ala Leu Trp Gly Gln
                     100                     105                     110 ggg aca atg gtc acc gtc tct tcg                                         360
     Gly Thr Met Val Thr Val Ser Ser
                     115                 120

<210> SEQ ID NO 6
<211> LENGTH: 120
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Ala Met Ser Trp Val Arg Gln Val Pro Gly Lys Gly Leu Glu Trp Val
        35                  40                  45

Ser Ser Ile Ser Gly Ser Gly Asp Thr Thr Lys Tyr Thr Asp Ser Val
    50                  55                  60

Lys Gly Arg Phe Thr Ile Ser Arg Asp Asn Ser Lys Asn Thr Val Phe
65                  70                  75                  80

Leu Gln Met Ser Ser Leu Arg Ala Glu Asp Thr Ala Leu Tyr Tyr Cys
                85                  90                  95

Val Lys Asp Gly Ser Gly Arg Ile Asp Pro Phe Ala Leu Trp Gly Gln
            100                 105                 110

Gly Thr Met Val Thr Val Ser Ser
        115                 120

<210> SEQ ID NO 7
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-301.35G11 variable K-light chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
```

```
<222> LOCATION: (163)..(183)
<223> OTHER INFORMATION: complementarity determining region (CDR)
       VK-CDR2
<220> FEATURE:
<221> NAME/KEY: V_region
<222> LOCATION: (280)..(306)
<223> OTHER INFORMATION: complementarity determining region (CDR)
       VK-CDR3

<400> SEQUENCE: 7 gaa att gtg atg aca cag tct cca ctc tcc ctg ccc gtc acc ctt gga      48
Glu Ile Val Met Thr Gln Ser Pro Leu Ser Leu Pro Val Thr Leu Gly
1               5                  10                  15 cag ccg gcc tcc atc tcc tgc agg tct agt cgt agt ctc gta tac agt      96
Gln Pro Ala Ser Ile Ser Cys Arg Ser Ser Arg Ser Leu Val Tyr Ser
            20                  25                  30 gat gga aac att tac ttg aat tgg ttt cag cag agg cca ggc caa tct     144
Asp Gly Asn Ile Tyr Leu Asn Trp Phe Gln Gln Arg Pro Gly Gln Ser
        35                  40                  45 cca agg cgc cta att tat aag gtt tct aac cgg gac tct ggg gtc cca     192
Pro Arg Arg Leu Ile Tyr Lys Val Ser Asn Arg Asp Ser Gly Val Pro
    50                  55                  60 gac aga ttc agt ggc agt ggg tca gac act gac ttc aca ctg aga atc     240
Asp Arg Phe Ser Gly Ser Gly Ser Asp Thr Asp Phe Thr Leu Arg Ile
65                  70                  75                  80 agc agg gtg gag gct gag gat gtt ggg gtc tat tac tgc atg cag ggt     288
Ser Arg Val Glu Ala Glu Asp Val Gly Val Tyr Tyr Cys Met Gln Gly
                85                  90                  95 aca cac tgg cct agg acg ttc ggc caa ggg acc aag gtg gag atc aaa     336
Thr His Trp Pro Arg Thr Phe Gly Gln Gly Thr Lys Val Glu Ile Lys
            100                 105                 110

<210> SEQ ID NO 8
<211> LENGTH: 112
<212> TYPE: PRT
<213> ORGANISM: Homo sapiens

<400> SEQUENCE: 8

Glu Ile Val Met Thr Gln Ser Pro Leu Ser Leu Pro Val Thr Leu Gly
1               5                  10                  15

Gln Pro Ala Ser Ile Ser Cys Arg Ser Ser Arg Ser Leu Val Tyr Ser
            20                  25                  30

Asp Gly Asn Ile Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Asp Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys Val Glu Ile Lys
            100                 105                 110

<210> SEQ ID NO 9
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-301.37F1 variable heavy chain (VH) sequence
<220> FEATURE:
<221> NAME/KEY: V_region
```

<222> LOCATION: (91)..(105)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(327)
<223> OTHER INFORMATION: complementarity determining region (CDR)
      VH-CDR3

<400> SEQUENCE: 9

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc agt gtc tct ggt ggc tcc atc atc agt agg      96
Thr Leu Ser Leu Thr Cys Ser Val Ser Gly Gly Ser Ile Ile Ser Arg
            20                  25                  30 agt tcc tac tgg ggc tgg atc cgc cag ccc cca ggg aag ggg ctg gag     144
Ser Ser Tyr Trp Gly Trp Ile Arg Gln Pro Pro Gly Lys Gly Leu Glu
        35                  40                  45 tgg att ggg ggt atc tat cat agt ggg aac act tac gac aac ccg tcc     192
Trp Ile Gly Gly Ile Tyr His Ser Gly Asn Thr Tyr Asp Asn Pro Ser
50                  55                  60 ctc aag agt cga ctc acc atg tcc gta gac acg tcg aag aac cag ttc     240
Leu Lys Ser Arg Leu Thr Met Ser Val Asp Thr Ser Lys Asn Gln Phe
65                  70                  75                  80 tcc ctg aat ctg agg tct gtg acc gcc gca gac acg gct gtg tat tac     288
Ser Leu Asn Leu Arg Ser Val Thr Ala Ala Asp Thr Ala Val Tyr Tyr
                85                  90                  95 tgt gcg agg ata gtg ccg ggg ggt gat gct ttt gat atc tgg ggc caa     336
Cys Ala Arg Ile Val Pro Gly Gly Asp Ala Phe Asp Ile Trp Gly Gln
            100                 105                 110 ggg aca atg gtc acc gtc tct tcg                                     360
Gly Thr Met Val Thr Val Ser Ser
        115                 120
```

<210> SEQ ID NO 10
<211> LENGTH: 120
<212> TYPE: PRT
<213> ORGANISM: Homo sapiens

<400> SEQUENCE: 10

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ile Ser Arg
            20                  25                  30

Ser Ser Tyr Trp Gly Trp Ile Arg Gln Pro Pro Gly Lys Gly Leu Glu
        35                  40                  45

Trp Ile Gly Gly Ile Tyr His Ser Gly Asn Thr Tyr Asp Asn Pro Ser
50                  55                  60

Leu Lys Ser Arg Leu Thr Met Ser Val Asp Thr Ser Lys Asn Gln Phe
65                  70                  75                  80

Ser Leu Asn Leu Arg Ser Val Thr Ala Ala Asp Thr Ala Val Tyr Tyr
                85                  90                  95

Cys Ala Arg Ile Val Pro Gly Gly Asp Ala Phe Asp Ile Trp Gly Gln
            100                 105                 110

Gly Thr Met Val Thr Val Ser Ser
        115                 120
```

```
<210> SEQ ID NO 11
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-301.37F1 variable K-light chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 11 gac atc cag atg acc cag tct cca tcc tcc ctg tct gca tct gta gga        48
Asp Ile Gln Met Thr Gln Ser Pro Ser Ser Leu Ser Ala Ser Val Gly
1               5                   10                  15 gac aga gtc aca atc gct tgc cgg gcc agt cag agc gtt ggc acc tat        96
Asp Arg Val Thr Ile Ala Cys Arg Ala Ser Gln Ser Val Gly Thr Tyr
                20                  25                  30 tta aat tgg tat cag cag aaa aga ggg aaa gcc cct aaa ctc ctc atc       144
Leu Asn Trp Tyr Gln Gln Lys Arg Gly Lys Ala Pro Lys Leu Leu Ile
            35                  40                  45 ttt gct gca tcc agt ttg caa agt ggg gtc cca tca agg ttc agt ggc       192
Phe Ala Ala Ser Ser Leu Gln Ser Gly Val Pro Ser Arg Phe Ser Gly
        50                  55                  60 agt gga tct ggg aca gat ttc act ctc acc atc agc agt ctg caa cct       240
Ser Gly Ser Gly Thr Asp Phe Thr Leu Thr Ile Ser Ser Leu Gln Pro
65                  70                  75                  80 gaa gac ttt gca act tac tac tgt caa cag agt tac agt tct cct cca       288
Glu Asp Phe Ala Thr Tyr Tyr Cys Gln Gln Ser Tyr Ser Ser Pro Pro
                85                  90                  95 acg ttc ggc caa ggg acc aag gtg gag atc aaa                           321
Thr Phe Gly Gln Gly Thr Lys Val Glu Ile Lys
            100                 105

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Ser Val Gly Thr Tyr
                20                  25                  30

Leu Asn Trp Tyr Gln Gln Lys Arg Gly Lys Ala Pro Lys Leu Leu Ile
            35                  40                  45

Phe Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Ser Pro Pro
                85                  90                  95

Thr Phe Gly Gln Gly Thr Lys Val Glu Ile Lys
            100                 105

<210> SEQ ID NO 13
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-301.2F5 variable heavy chain (VH) sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(330)
<223> OTHER INFORMATION: complementarity determining region (CDR)
      VH-CDR3

<400> SEQUENCE: 13 gag gtg cag ctg gtg gag tct ggg gga ggc gtg gtc cgg tct agg agg      48
Glu Val Gln Leu Val Glu Ser Gly Gly Gly Val Val Arg Ser Arg Arg
1               5                   10                  15 tcc ctg aga ctc tcc tgt gca acc tct gga ttc acc ttc agt aac tat      96
Ser Leu Arg Leu Ser Cys Ala Thr Ser Gly Phe Thr Phe Ser Asn Tyr
                20                  25                  30 gcg atg cac tgg gtc cgc cag gct cca ggc aag ggg ctg gag tgg gtg     144
Ala Met His Trp Val Arg Gln Ala Pro Gly Lys Gly Leu Glu Trp Val
            35                  40                  45 gcc att att tca tat gat gga aac aat aaa tac tac gca gac tcc gtg     192
Ala Ile Ile Ser Tyr Asp Gly Asn Asn Lys Tyr Tyr Ala Asp Ser Val
        50                  55                  60 agg ggc cga ttc acc gtc tcc aga gac aat tcc aag aac aca ttc tat     240
Arg Gly Arg Phe Thr Val Ser Arg Asp Asn Ser Lys Asn Thr Phe Tyr
65                  70                  75                  80 ctg caa atg aac agc ctg aga att gag gac acg gct gta tat ttt tgt     288
Leu Gln Met Asn Ser Leu Arg Ile Glu Asp Thr Ala Val Tyr Phe Cys
                85                  90                  95 gcg aga ggg agc ggt aga gca gct cgt cac tgg ttc gac ccc tgg ggc     336
Ala Arg Gly Ser Gly Arg Ala Ala Arg His Trp Phe Asp Pro Trp Gly
            100                 105                 110 cag ggc acc ctg gtc acc gtc tcc tcg                                 363
Gln Gly Thr Leu Val Thr Val Ser Ser
        115                 120

<210> SEQ ID NO 14
<211> LENGTH: 121
<212> TYPE: PRT
<213> ORGANISM: Homo sapiens

<400> SEQUENCE: 14

Glu Val Gln Leu Val Glu Ser Gly Gly Gly Val Val Arg Ser Arg Arg
1               5                   10                  15

Ser Leu Arg Leu Ser Cys Ala Thr Ser Gly Phe Thr Phe Ser Asn Tyr
                20                  25                  30
```

```
Ala Met His Trp Val Arg Gln Ala Pro Gly Lys Gly Leu Glu Trp Val
        35                  40                  45

Ala Ile Ile Ser Tyr Asp Gly Asn Asn Lys Tyr Tyr Ala Asp Ser Val
    50                  55                  60

Arg Gly Arg Phe Thr Val Ser Arg Asp Asn Ser Lys Asn Thr Phe Tyr
65                  70                  75                  80

Leu Gln Met Asn Ser Leu Arg Ile Glu Asp Thr Ala Val Tyr Phe Cys
                85                  90                  95

Ala Arg Gly Ser Gly Arg Ala Ala Arg His Trp Phe Asp Pro Trp Gly
            100                 105                 110

Gln Gly Thr Leu Val Thr Val Ser Ser
            115                 120

<210> SEQ ID NO 15
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-301.2F5 variable light chain (VL) sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(306)
<223> OTHER INFORMATION: complementarity determining region (CDR)
      VL-CDR3

<400> SEQUENCE: 15 cag tct gcc ctg act cag cct gcc tcc gtg tct ggg tct cct gga cag        48
Gln Ser Ala Leu Thr Gln Pro Ala Ser Val Ser Gly Ser Pro Gly Gln
1               5                   10                  15 tcg atc acc atc tcc tgc act gga acc agc agt gac gtt ggt ggt tat        96
Ser Ile Thr Ile Ser Cys Thr Gly Thr Ser Ser Asp Val Gly Gly Tyr
            20                  25                  30 aac tat gtc tcc tgg tac caa caa tac cca ggc aaa gcc ccc aaa gtc       144
Asn Tyr Val Ser Trp Tyr Gln Gln Tyr Pro Gly Lys Ala Pro Lys Val
        35                  40                  45 atg att ttt gat gtt ttt aat cgg cct tca ggg gtt tct aat cgc ttc       192
Met Ile Phe Asp Val Phe Asn Arg Pro Ser Gly Val Ser Asn Arg Phe
    50                  55                  60 tct ggc tcc aag tct ggc aac acg gcc tcc ctg acc atc tct gga ctc       240
Ser Gly Ser Lys Ser Gly Asn Thr Ala Ser Leu Thr Ile Ser Gly Leu
65                  70                  75                  80 cag gca gag gac gag gct gat tat tac tgc agt tca tat aca agc agc       288
Gln Ala Glu Asp Glu Ala Asp Tyr Tyr Cys Ser Ser Tyr Thr Ser Ser
                85                  90                  95 gtc act cct cac tgg gtg ttc ggc gga ggg acc aag ctg acc gtc cta       336
Val Thr Pro His Trp Val Phe Gly Gly Gly Thr Lys Leu Thr Val Leu
            100                 105                 110

<210> SEQ ID NO 16
<211> LENGTH: 112
<212> TYPE: PRT
<213> ORGANISM: Homo sapiens
```

<400> SEQUENCE: 16

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln Tyr Pro Gly Lys Ala Pro Lys Val
            35                  40                  45

Met Ile Phe Asp Val Phe Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Val Thr Pro His Trp Val Phe Gly Gly Gly Thr Lys Leu Thr Val Leu
            100                 105                 110
```

<210> SEQ ID NO 17
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-301.28B3 variable heavy chain (VH) sequence
<220> FEATURE:
<221> NAME/KEY: V_region
<222> LOCATION: (91)..(111)
<223> OTHER INFORMATION: complementarity determining region (CDR) VH-CDR1
<220> FEATURE:
<221> NAME/KEY: V_region
<222> LOCATION: (154)..(201)
<223> OTHER INFORMATION: complementarity determining region (CDR) VH-CDR2
<220> FEATURE:
<221> NAME/KEY: V_region
<222> LOCATION: (298)..(348)
<223> OTHER INFORMATION: complementarity determining region (CDR) VH-CDR3

<400> SEQUENCE: 17

```
cag ctg cag ctg cag gag tcg ggc cca gga ctg gtg aag cct tcg gag     48
Gln Leu Gln Leu Gln Glu Ser Gly Pro Gly Leu Val Lys Pro Ser Glu
1               5                   10                  15 acc ctg tcc ctc acc tgc act gtc tcc ggt ggc tcc atc act agt agt     96
Thr Leu Ser Leu Thr Cys Thr Val Ser Gly Gly Ser Ile Thr Ser Ser
                20                  25                  30 aat ttc tac tgg ggc tgg atc cgc cag ccc cca ggg aag ggg ctg gag    144
Asn Phe Tyr Trp Gly Trp Ile Arg Gln Pro Pro Gly Lys Gly Leu Glu
            35                  40                  45 tgg att ggg gct att tat tct agt gga aac acc tac tac aac ccg tcc    192
Trp Ile Gly Ala Ile Tyr Ser Ser Gly Asn Thr Tyr Tyr Asn Pro Ser
    50                  55                  60 ctc aag agt cga gtc acc ata tcc gta gac acg tcc aag aaa aag ttc    240
Leu Lys Ser Arg Val Thr Ile Ser Val Asp Thr Ser Lys Lys Lys Phe
65              70                  75                  80 tcc ctg aag ctg agc tct gtg acc gcc gct gac acg gct gtc tat tac    288
Ser Leu Lys Leu Ser Ser Val Thr Ala Ala Asp Thr Ala Val Tyr Tyr
                85                  90                  95 tgt gcg aga cac tct tgt agt agt gcc agc tgc tat cct ccc ggt ttc    336
Cys Ala Arg His Ser Cys Ser Ser Ala Ser Cys Tyr Pro Pro Gly Phe
            100                 105                 110
```

```
tgg ttc gac ccc tgg ggc cag gga acc ctg gtc acc gtc tcc tcg    381
Trp Phe Asp Pro Trp Gly Gln Gly Thr Leu Val Thr Val Ser Ser
            115                 120                 125

<210> SEQ ID NO 18
<211> LENGTH: 127
<212> TYPE: PRT
<213> ORGANISM: Homo sapiens

<400> SEQUENCE: 18

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Ser
            20                  25                  30

Asn Phe Tyr Trp Gly Trp Ile Arg Gln Pro Pro Gly Lys Gly Leu Glu
        35                  40                  45

Trp Ile Gly Ala Ile Tyr Ser Ser Gly Asn Thr Tyr Tyr Asn Pro Ser
    50                  55                  60

Leu Lys Ser Arg Val Thr Ile Ser Val Asp Thr Ser Lys Lys Phe
65                  70                  75                  80

Ser Leu Lys Leu Ser Ser Val Thr Ala Ala Asp Thr Ala Val Tyr Tyr
            85                  90                  95

Cys Ala Arg His Ser Cys Ser Ser Ala Ser Cys Tyr Pro Pro Gly Phe
        100                 105                 110

Trp Phe Asp Pro Trp Gly Gln Gly Thr Leu Val Thr Val Ser Ser
            115                 120                 125

<210> SEQ ID NO 19
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-301.28B3 variable K-light chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(294)
<223> OTHER INFORMATION: complementarity determining region (CDR)
      VK-CDR3

<400> SEQUENCE: 19 gaa att gtg atg aca cag tct cca gcc acc ctg tct gcg tct cca ggg    48
Glu Ile Val Met Thr Gln Ser Pro Ala Thr Leu Ser Ala Ser Pro Gly
1               5                   10                  15 gaa aga gcc acc ctc tcc tgc agg gcc agt cag act gtt agt tac aac    96
Glu Arg Ala Thr Leu Ser Cys Arg Ala Ser Gln Thr Val Ser Tyr Asn
            20                  25                  30 tta gcc tgg tac cag cag aaa cct ggc cag gct ccc cgg ctc ctc atc   144
Leu Ala Trp Tyr Gln Gln Lys Pro Gly Gln Ala Pro Arg Leu Leu Ile
        35                  40                  45 tat ggc gcg tcc acc agg gcc act ggt atc cca ggc agg ttc agt ggc   192
Tyr Gly Ala Ser Thr Arg Ala Thr Gly Ile Pro Gly Arg Phe Ser Gly
    50                  55                  60
```

```
agt ggg tct ggg aca gag ttc act ctc acc atc agc agc ctg cag tct     240
Ser Gly Ser Gly Thr Glu Phe Thr Leu Thr Ile Ser Ser Leu Gln Ser
65                  70                  75                  80 gaa gat ttt gca gtt tat tac tgt cag caa tat aat aac tgg cct ccg     288
Glu Asp Phe Ala Val Tyr Tyr Cys Gln Gln Tyr Asn Asn Trp Pro Pro
                85                  90                  95 tgg acg ttc ggc caa ggg acc aag gtg gaa atc aaa                     324
Trp Thr Phe Gly Gln Gly Thr Lys Val Glu Ile Lys
            100                 105

<210> SEQ ID NO 20
<211> LENGTH: 108
<212> TYPE: PRT
<213> ORGANISM: Homo sapiens

<400> SEQUENCE: 20

Glu Ile Val Met Thr Gln Ser Pro Ala Thr Leu Ser Ala Ser Pro Gly
1               5                   10                  15

Glu Arg Ala Thr Leu Ser Cys Arg Ala Ser Gln Thr Val Ser Tyr Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Gly Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys
            100                 105

<210> SEQ ID NO 21
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION: NI-301.119C12 variable heavy chain (VH)
      sequence
<220> FEATURE:
<221> NAME/KEY: V_region
<222> LOCATION: (91)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(351)
<223> OTHER INFORMATION: complementarity determining region (CDR)
      VH-CDR3

<400> SEQUENCE: 21 cag gtg cag ctg cag gag tcg ggc cca aga ctg gtg aag cct tca cag    48
Gln Val Gln Leu Gln Glu Ser Gly Pro Arg Leu Val Lys Pro Ser Gln
1               5                   10                  15 acc ctg tcc ctc acc tgc act gtc tct ggt ggc tcc atc agc agt ggt    96
Thr Leu Ser Leu Thr Cys Thr Val Ser Gly Gly Ser Ile Ser Ser Gly
            20                  25                  30 gtt tac tac tgg agc tgg atc cgc cag cac cca ggg aag ggc ctg gag   144
```

```
                Val Tyr Tyr Trp Ser Trp Ile Arg Gln His Pro Gly Lys Gly Leu Glu
                             35                  40                  45 tgg att gga tat att tct aat act ggg aac acc tac tac aac ccg tcc        192
Trp Ile Gly Tyr Ile Ser Asn Thr Gly Asn Thr Tyr Tyr Asn Pro Ser
         50                  55                  60 ctc aag agt cga gtt acc ata tcg ata gac acc tcc aag aac cag ttc        240
Leu Lys Ser Arg Val Thr Ile Ser Ile Asp Thr Ser Lys Asn Gln Phe
 65                  70                  75                  80 tcc ctc aac ctg cgc tct gtg act gcc gcg gac acg gcc gac tat ttc        288
Ser Leu Asn Leu Arg Ser Val Thr Ala Ala Asp Thr Ala Asp Tyr Phe
                 85                  90                  95 tgt gcg aga gag tat tgt agt ggt ggt aat tgc tac tct cgc ttc tac        336
Cys Ala Arg Glu Tyr Cys Ser Gly Gly Asn Cys Tyr Ser Arg Phe Tyr
            100                 105                 110 tac tac atg gac gtc tgg ggc aaa ggg acc acg gtc acc gtc tcc tcg        384
Tyr Tyr Met Asp Val Trp Gly Lys Gly Thr Thr Val Thr Val Ser Ser
        115                 120                 125

<210> SEQ ID NO 22
<211> LENGTH: 128
<212> TYPE: PRT
<213> ORGANISM: Homo sapiens

<400> SEQUENCE: 22

Gln Val Gln Leu Gln Glu Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Val Tyr Tyr Trp Ser Trp Ile Arg Gln His Pro Gly Lys Gly Leu Glu
        35                  40                  45

Trp Ile Gly Tyr Ile Ser Asn Thr Gly Asn Thr Tyr Tyr Asn Pro Ser
    50                  55                  60

Leu Lys Ser Arg Val Thr Ile Ser Ile Asp Thr Ser Lys Asn Gln Phe
65                  70                  75                  80

Ser Leu Asn Leu Arg Ser Val Thr Ala Ala Asp Thr Ala Asp Tyr Phe
                85                  90                  95

Cys Ala Arg Glu Tyr Cys Ser Gly Gly Asn Cys Tyr Ser Arg Phe Tyr
            100                 105                 110

Tyr Tyr Met Asp Val Trp Gly Lys Gly Thr Thr Val Thr Val Ser Ser
        115                 120                 125

<210> SEQ ID NO 23
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-301.119C12 variable light chain (VL)
      sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(306)
<223> OTHER INFORMATION: complementarity determining region (CDR)
```

-continued

VL-CDR3

<400> SEQUENCE: 23

```
cag tct gtg ctg acg cag ccg ccc tca gtg tct ggg gcc cca ggg cag       48
Gln Ser Val Leu Thr Gln Pro Pro Ser Val Ser Gly Ala Pro Gly Gln
1               5                   10                  15 agg gtc acc atc tcc tgc act ggg agc agc tcc aac atc ggg gca ggt       96
Arg Val Thr Ile Ser Cys Thr Gly Ser Ser Ser Asn Ile Gly Ala Gly
            20                  25                  30 tat ggt gta cac tgg tac cag caa ctt tca gga aca ccc ccc aaa ctc      144
Tyr Gly Val His Trp Tyr Gln Gln Leu Ser Gly Thr Pro Pro Lys Leu
        35                  40                  45 ctc atc tat gga gac aac aat cgg ccc tca ggg gtc cct gac cga ttc      192
Leu Ile Tyr Gly Asp Asn Asn Arg Pro Ser Gly Val Pro Asp Arg Phe
    50                  55                  60 tct ggc tcc aag tct ggc acc tca gcc tcc ctg gcc atc act ggg ctc      240
Ser Gly Ser Lys Ser Gly Thr Ser Ala Ser Leu Ala Ile Thr Gly Leu
65                  70                  75                  80 cag gct gag gat gag gct cat tat tac tgc cag tcc tat gac acc acc      288
Gln Ala Glu Asp Glu Ala His Tyr Tyr Cys Gln Ser Tyr Asp Thr Thr
                85                  90                  95 ttg agt ggt tcg agg gtg ttc ggc gga ggg acc aag ctg acc gtc cta      336
Leu Ser Gly Ser Arg Val Phe Gly Gly Gly Thr Lys Leu Thr Val Leu
            100                 105                 110
```

<210> SEQ ID NO 24
<211> LENGTH: 112
<212> TYPE: PRT
<213> ORGANISM: Homo sapiens

<400> SEQUENCE: 24

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Ser Gly Thr Pro Pro Lys Leu
        35                  40                  45

Leu Ile Tyr Gly Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala His Tyr Tyr Cys Gln Ser Tyr Asp Thr Thr
                85                  90                  95

Leu Ser Gly Ser Arg Val Phe Gly Gly Gly Thr Lys Leu Thr Val Leu
            100                 105                 110
```

<210> SEQ ID NO 25
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-301.5D8 variable heavy chain (VH) sequence
<220> FEATURE:
<221> NAME/KEY: V_region
<222> LOCATION: (91)..(105)
<223> OTHER INFORMATION: complementarity determining region (CDR)
       VH-CDR1
<220> FEATURE:
<221> NAME/KEY: V_region
<222> LOCATION: (148)..(195)
<223> OTHER INFORMATION: complementarity determining region (CDR)

```
        VH-CDR2
<220> FEATURE:
<221> NAME/KEY: V_region
<222> LOCATION: (292)..(330)
<223> OTHER INFORMATION: complementarity determining region (CDR)
      VH-CDR3

<400> SEQUENCE: 25 cag gtg cag cta cag cag tgg ggc gca gga cgg ttg aag cct tcg gag      48
Gln Val Gln Leu Gln Gln Trp Gly Ala Gly Arg Leu Lys Pro Ser Glu
1               5                   10                  15 acc ctg tcc ctc acg tgc gct gtc tat ggt ggg tct ttc agt gct tac      96
Thr Leu Ser Leu Thr Cys Ala Val Tyr Gly Gly Ser Phe Ser Ala Tyr
                20                  25                  30 tac tgg aat tgg atc cgc cag gcc cca ggg aag ggg ctg gag tgg att     144
Tyr Trp Asn Trp Ile Arg Gln Ala Pro Gly Lys Gly Leu Glu Trp Ile
            35                  40                  45 ggt gaa gtc agt cat ggt ggc agc agc aac tac agc ccg tcc ctc agg     192
Gly Glu Val Ser His Gly Gly Ser Ser Asn Tyr Ser Pro Ser Leu Arg
        50                  55                  60 ggt cga gtc gcc att tct tta gac acg tcc aag agc cag ttc tcc ctg     240
Gly Arg Val Ala Ile Ser Leu Asp Thr Ser Lys Ser Gln Phe Ser Leu
65                  70                  75                  80 agg ctg aat tct gtg acc gcc gcg gac acg gct gtt tat tac tgt gcg     288
Arg Leu Asn Ser Val Thr Ala Ala Asp Thr Ala Val Tyr Tyr Cys Ala
                85                  90                  95 aga ggc agc cct gta gta cta cca ggt gcc aga ttc gac ccc tgg ggc     336
Arg Gly Ser Pro Val Val Leu Pro Gly Ala Arg Phe Asp Pro Trp Gly
            100                 105                 110 cag gga acc ctg gtc acc gtc tcc tcg                                 363
Gln Gly Thr Leu Val Thr Val Ser Ser
        115                 120

<210> SEQ ID NO 26
<211> LENGTH: 121
<212> TYPE: PRT
<213> ORGANISM: Homo sapiens

<400> SEQUENCE: 26

Gln Val Gln Leu Gln Gln Trp Gly Ala Gly Arg Leu Lys Pro Ser Glu
1               5                   10                  15

Thr Leu Ser Leu Thr Cys Ala Val Tyr Gly Gly Ser Phe Ser Ala Tyr
                20                  25                  30

Tyr Trp Asn Trp Ile Arg Gln Ala Pro Gly Lys Gly Leu Glu Trp Ile
            35                  40                  45

Gly Glu Val Ser His Gly Gly Ser Ser Asn Tyr Ser Pro Ser Leu Arg
        50                  55                  60

Gly Arg Val Ala Ile Ser Leu Asp Thr Ser Lys Ser Gln Phe Ser Leu
65                  70                  75                  80

Arg Leu Asn Ser Val Thr Ala Ala Asp Thr Ala Val Tyr Tyr Cys Ala
                85                  90                  95

Arg Gly Ser Pro Val Val Leu Pro Gly Ala Arg Phe Asp Pro Trp Gly
            100                 105                 110

Gln Gly Thr Leu Val Thr Val Ser Ser
        115                 120

<210> SEQ ID NO 27
<211> LENGTH: 327
<212> TYPE: DNA
<213> ORGANISM: Homo sapiens
<220> FEATURE:
```

```
<221> NAME/KEY: CDS
<222> LOCATION: (1)..(327)
<223> OTHER INFORMATION: NI-301.5D8 variable light chain (VL) sequence
<220> FEATURE:
<221> NAME/KEY: V_region
<222> LOCATION: (91)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(297)
<223> OTHER INFORMATION: complementarity determining region (CDR)
      VL-CDR3

<400> SEQUENCE: 27 cag tct gcc ctg act cag cct gcc tcc gtg tct ggg ttt cct gga cag       48
Gln Ser Ala Leu Thr Gln Pro Ala Ser Val Ser Gly Phe Pro Gly Gln
1               5                   10                  15 tcg atc acc atc tcc tgc act gga acc agc agt gat gtt ggg agt tat       96
Ser Ile Thr Ile Ser Cys Thr Gly Thr Ser Ser Asp Val Gly Ser Tyr
            20                  25                  30 aac ctt gtc tcc tgg tac caa caa cac cca ggc aaa gcc ccc aaa ctc      144
Asn Leu Val Ser Trp Tyr Gln Gln His Pro Gly Lys Ala Pro Lys Leu
        35                  40                  45 ttg att tat gag gtc aat aag cgg ccc tca gga gtt tct act cgc ttc      192
Leu Ile Tyr Glu Val Asn Lys Arg Pro Ser Gly Val Ser Thr Arg Phe
    50                  55                  60 tct ggc tcc aag tct ggc aac acg gcc tcc ctg acg atc tct ggg ctc      240
Ser Gly Ser Lys Ser Gly Asn Thr Ala Ser Leu Thr Ile Ser Gly Leu
65                  70                  75                  80 cag act gag gac gag gct gat tat tac tgc tgc tca tat gca ggt agt      288
Gln Thr Glu Asp Glu Ala Asp Tyr Tyr Cys Cys Ser Tyr Ala Gly Ser
                85                  90                  95 act aag gtc ttc gga att ggg acc aag gtc acc gtc cta                  327
Thr Lys Val Phe Gly Ile Gly Thr Lys Val Thr Val Leu
                100                 105

<210> SEQ ID NO 28
<211> LENGTH: 109
<212> TYPE: PRT
<213> ORGANISM: Homo sapiens

<400> SEQUENCE: 28

Gln Ser Ala Leu Thr Gln Pro Ala Ser Val Ser Gly Phe Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Leu Ile Tyr Glu Val Asn Lys Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95

Thr Lys Val Phe Gly Ile Gly Thr Lys Val Thr Val Leu
                100                 105
```

```
<210> SEQ ID NO 29
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-301.9D5 variable heavy chain (VH) sequence
<220> FEATURE:
<221> NAME/KEY: V_region
<222> LOCATION: (91)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(339)
<223> OTHER INFORMATION: complementarity determining region (CDR)
      VH-CDR3

<400> SEQUENCE: 29 cag gtg cag ctg cag gag tcg ggc cca ggc ctg gtg aag cct tca gag        48
Gln Val Gln Leu Gln Glu Ser Gly Pro Gly Leu Val Lys Pro Ser Glu
1               5                   10                  15 acc ctg tcc ctc acc tgc att gtc tct ggt gtc tcc atc aga agt ggt        96
Thr Leu Ser Leu Thr Cys Ile Val Ser Gly Val Ser Ile Arg Ser Gly
            20                  25                  30 ggt tac tac tgg agc tgg atc cgg cag cac cca ggg aag ggc ctg gag       144
Gly Tyr Tyr Trp Ser Trp Ile Arg Gln His Pro Gly Lys Gly Leu Glu
        35                  40                  45 tgg gtt ggg ttc atc tat tac act ggg aac acc tac tac aac ccg tcc       192
Trp Val Gly Phe Ile Tyr Tyr Thr Gly Asn Thr Tyr Tyr Asn Pro Ser
    50                  55                  60 ctc aag agt cga gct acc ata tca gta gac acc tct aag aac cag ttc       240
Leu Lys Ser Arg Ala Thr Ile Ser Val Asp Thr Ser Lys Asn Gln Phe
65                  70                  75                  80 tcc ctg agg ctg acc gct gtg act gcc gcg gac acg gcc gtg tat tac       288
Ser Leu Arg Leu Thr Ala Val Thr Ala Ala Asp Thr Ala Val Tyr Tyr
                85                  90                  95 tgt gcg aga gat tgt agt ggt ggc agc tgc ccc gag tcc tac ttt gac       336
Cys Ala Arg Asp Cys Ser Gly Gly Ser Cys Pro Glu Ser Tyr Phe Asp
            100                 105                 110 tcc tgg ggt cgg ggc acc ctg gtc acc gtc tcc tcg                       372
Ser Trp Gly Arg Gly Thr Leu Val Thr Val Ser Ser
        115                 120

<210> SEQ ID NO 30
<211> LENGTH: 124
<212> TYPE: PRT
<213> ORGANISM: Homo sapiens

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Ile Val Ser Gly Val Ser Ile Arg Ser Gly
            20                  25                  30

Gly Tyr Tyr Trp Ser Trp Ile Arg Gln His Pro Gly Lys Gly Leu Glu
        35                  40                  45

Trp Val Gly Phe Ile Tyr Tyr Thr Gly Asn Thr Tyr Tyr Asn Pro Ser
    50                  55                  60

Leu Lys Ser Arg Ala Thr Ile Ser Val Asp Thr Ser Lys Asn Gln Phe
```

```
                65                  70                  75                  80
Ser Leu Arg Leu Thr Ala Val Thr Ala Ala Asp Thr Ala Val Tyr Tyr
                        85                  90                  95

Cys Ala Arg Asp Cys Ser Gly Gly Ser Cys Pro Glu Ser Tyr Phe Asp
                100                 105                 110

Ser Trp Gly Arg Gly Thr Leu Val Thr Val Ser Ser
            115                 120
```

<210> SEQ ID NO 31
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-301.9D5 variable K-light chain (VK) sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (268)..(297)
<223> OTHER INFORMATION: complementarity determining region (CDR)
      VK-CDR3

<400> SEQUENCE: 31

```
gaa att gtg atg aca cag tct cca gcc acc ctg tct ttg tct cca ggg     48
Glu Ile Val Met Thr Gln Ser Pro Ala Thr Leu Ser Leu Ser Pro Gly
1               5                   10                  15 gaa aga gcc acc ctc tcc tgt agg gcc agt cag agt gtt cgc agt ttc     96
Glu Arg Ala Thr Leu Ser Cys Arg Ala Ser Gln Ser Val Arg Ser Phe
                20                  25                  30 tta gcc tgg tac caa cag aaa tct ggc cag gct ccc cga ctc ctc atc    144
Leu Ala Trp Tyr Gln Gln Lys Ser Gly Gln Ala Pro Arg Leu Leu Ile
            35                  40                  45 tat gat gca tcc aag agg gcc act ggc atc cca gcc agg ttc agt gac    192
Tyr Asp Ala Ser Lys Arg Ala Thr Gly Ile Pro Ala Arg Phe Ser Asp
        50                  55                  60 agt ggg tct gga aca gac ttc act ctc acc atc agc aga cta gag act    240
Ser Gly Ser Gly Thr Asp Phe Thr Leu Thr Ile Ser Arg Leu Glu Thr
65                  70                  75                  80 gaa gac tct gcg gtt tat tac tgt cag cag cgt acc aac tgg cct cca    288
Glu Asp Ser Ala Val Tyr Tyr Cys Gln Gln Arg Thr Asn Trp Pro Pro
                85                  90                  95 cac ctc act ttc ggc gga ggg acc aag gtg gaa atc aaa                327
His Leu Thr Phe Gly Gly Gly Thr Lys Val Glu Ile Lys
                100                 105
```

<210> SEQ ID NO 32
<211> LENGTH: 109
<212> TYPE: PRT
<213> ORGANISM: Homo sapiens

<400> SEQUENCE: 32

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Phe
                20                  25                  30
```

```
Leu Ala Trp Tyr Gln Gln Lys Ser Gly Gln Ala Pro Arg Leu Leu Ile
        35                  40                  45

Tyr Asp Ala Ser Lys Arg Ala Thr Gly Ile Pro Ala Arg Phe Ser Asp
 50                  55                  60

Ser Gly Ser Gly Thr Asp Phe Thr Leu Thr Ile Ser Arg Leu Glu Thr
 65                  70                  75                  80

Glu Asp Ser Ala Val Tyr Tyr Cys Gln Gln Arg Thr Asn Trp Pro Pro
                 85                  90                  95

His Leu Thr Phe Gly Gly Gly Thr Lys Val Glu Ile Lys
            100                 105
```

```
<210> SEQ ID NO 33
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-301.104F5 variable heavy chain (VH) sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3

<400> SEQUENCE: 33 cag gtg cag ctg gtg gag tct ggg gga ggc gtg gtc cag cct gag agg     48
Gln Val Gln Leu Val Glu Ser Gly Gly Gly Val Val Gln Pro Glu Arg
 1               5                  10                  15 tcc ctg aga ctc tcc tgt gca gcg tct gga ttc acc ttc agg agc tat     96
Ser Leu Arg Leu Ser Cys Ala Ala Ser Gly Phe Thr Phe Arg Ser Tyr
             20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
         35                  40                  45 gca gtt ata tgg ttt gat gga agt aat aaa tac tat gca gac tcc gtg    192
Ala Val Ile Trp Phe Asp Gly Ser Asn Lys Tyr Tyr Ala Asp Ser Val
 50                  55                  60 aag ggc cga ttc acc gtc tcc aga gac aat tcc aag aac acg ctg tat    240
Lys Gly Arg Phe Thr Val Ser Arg Asp Asn Ser Lys Asn Thr Leu Tyr
 65                  70                  75                  80 ctg caa atg aac agc ctg aga gcc gag gac acg gct gtc tac tac tgt    288
Leu Gln Met Asn Ser Leu Arg Ala Glu Asp Thr Ala Val Tyr Tyr Cys
                 85                  90                  95 gca aga gat ggt ata gca gcc act tat gcg gac tac tgg ggc cag gga    336
Ala Arg Asp Gly Ile Ala Ala Thr Tyr Ala Asp Tyr Trp Gly Gln Gly
            100                 105                 110 acc ctg gtc acc gtc tcc tcg                                        357
Thr Leu Val Thr Val Ser Ser
        115

<210> SEQ ID NO 34
<211> LENGTH: 119
<212> TYPE: PRT
```

<213> ORGANISM: Homo sapiens

<400> SEQUENCE: 34

```
Gln Val Gln Leu Val Glu Ser Gly Gly Val Val Gln Pro Glu Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Ala Ala Thr Tyr Ala Asp Tyr Trp Gly Gln Gly
            100                 105                 110

Thr Leu Val Thr Val Ser Ser
        115
```

<210> SEQ ID NO 35
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-301.104F5 variable K-light chain (VK) sequence
<220> FEATURE:
<221> NAME/KEY: V_region
<222> LOCATION: (70)..(102)
<223> OTHER INFORMATION: complementarity determining region (CDR) VK-CDR1
<220> FEATURE:
<221> NAME/KEY: V_region
<222> LOCATION: (148)..(168)
<223> OTHER INFORMATION: complementarity determining region (CDR) VK-CDR2
<220> FEATURE:
<221> NAME/KEY: V_region
<222> LOCATION: (265)..(291)
<223> OTHER INFORMATION: complementarity determining region (CDR) VK-CDR3

<400> SEQUENCE: 35

```
gaa att gtg ttg aca cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt cgc agc tac      96
Glu Arg Ala Thr Leu Ser Cys Arg Ala Ser Gln Ser Val Arg Ser Tyr
            20                  25                  30 tta gcc tgg tac caa caa aaa cct ggc cag gct ccc agg ctc ctc atc     144
Leu Ala Trp Tyr Gln Gln Lys Pro Gly Gln Ala Pro Arg Leu Leu Ile
        35                  40                  45 tat ggt gca tcc aac agg gcc act ggc atc cca gcc agg ttc agt ggc     192
Tyr Gly Ala Ser Asn Arg Ala Thr Gly Ile Pro Ala Arg Phe Ser Gly
    50                  55                  60 agt ggg tct ggg aca gac ttc act ctc acc atc agc agc ctg gag cct     240
Ser Gly Ser Gly Thr Asp Phe Thr Leu Thr Ile Ser Ser Leu Glu Pro
65                  70                  75                  80 gaa gat ttt gca gtt tat tac tgt cag caa cgt agc aac tgg ccg atc     288
Glu Asp Phe Ala Val Tyr Tyr Cys Gln Gln Arg Ser Asn Trp Pro Ile
                85                  90                  95
```

-continued

```
acc ttc ggc caa ggg aca cga ctg gag att aaa                    321
Thr Phe Gly Gln Gly Thr Arg Leu Glu Ile Lys
            100                 105
```

<210> SEQ ID NO 36
<211> LENGTH: 107
<212> TYPE: PRT
<213> ORGANISM: Homo sapiens

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 37
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION: NI-301.21F10 variable heavy chain (VH) sequence
<220> FEATURE:
<221> NAME/KEY: V_region
<222> LOCATION: (91)..(114)
<223> OTHER INFORMATION: complementarity determining region (CDR)
      VH-CDR1
<220> FEATURE:
<221> NAME/KEY: V_region
<222> LOCATION: (157)..(207)
<223> OTHER INFORMATION: complementarity determining region (CDR)
      VH-CDR2
<220> FEATURE:
<221> NAME/KEY: V_region
<222> LOCATION: (304)..(342)
<223> OTHER INFORMATION: complementarity determining region (CDR)
      VH-CDR3

<400> SEQUENCE: 37

```
cag gtg cag ctg gtg gag tcg ggg gga ggt ttg gtc cag cct ggg ggg      48
Gln Val Gln Leu Val Glu Ser Gly Gly Gly Leu Val Gln Pro Gly Gly
1               5                   10                  15 tcc ttg aga ctg tcc tgt gcg gtc tct gga ttc acc ctt agt agt ctt      96
Ser Leu Arg Leu Ser Cys Ala Val Ser Gly Phe Thr Leu Ser Ser Leu
            20                  25                  30 agt tct tat tac atg agt tgg gtc cgc cag gct cca ggg aag ggg ctg     144
Ser Ser Tyr Tyr Met Ser Trp Val Arg Gln Ala Pro Gly Lys Gly Leu
        35                  40                  45 gag tgg gtg gcc act ata aac cca ggt gga agt gag aag tcc tat gtg     192
Glu Trp Val Ala Thr Ile Asn Pro Gly Gly Ser Glu Lys Ser Tyr Val
50                  55                  60 gac tct gtg aag ggc cga ttc acc gtc tcc aga gac aac gcc agg agc     240
Asp Ser Val Lys Gly Arg Phe Thr Val Ser Arg Asp Asn Ala Arg Ser
```

```
                  65                  70                  75                  80
tca gta tat ttg caa atg gac agc ctg aca gtc gag gac acg gct att        288
Ser Val Tyr Leu Gln Met Asp Ser Leu Thr Val Glu Asp Thr Ala Ile
                      85                  90                  95 tat tac tgt gcg aga cca aga tat tgc act agt ggt ggt tgc tat ttt        336
Tyr Tyr Cys Ala Arg Pro Arg Tyr Cys Thr Ser Gly Gly Cys Tyr Phe
               100                 105                 110 gac aac tgg ggc cag gga acc ctg gtc acc gtc tcc tcg                    375
Asp Asn Trp Gly Gln Gly Thr Leu Val Thr Val Ser Ser
        115                 120                 125

<210> SEQ ID NO 38
<211> LENGTH: 125
<212> TYPE: PRT
<213> ORGANISM: Homo sapiens

<400> SEQUENCE: 38

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser Ser Leu
            20                  25                  30

Ser Ser Tyr Tyr Met Ser Trp Val Arg Gln Ala Pro Gly Lys Gly Leu
        35                  40                  45

Glu Trp Val Ala Thr Ile Asn Pro Gly Gly Ser Glu Lys Ser Tyr Val
    50                  55                  60

Asp Ser Val Lys Gly Arg Phe Thr Val Ser Arg Asp Asn Ala Arg Ser
65                  70                  75                  80

Ser Val Tyr Leu Gln Met Asp Ser Leu Thr Val Glu Asp Thr Ala Ile
                85                  90                  95

Tyr Tyr Cys Ala Arg Pro Arg Tyr Cys Thr Ser Gly Gly Cys Tyr Phe
            100                 105                 110

Asp Asn Trp Gly Gln Gly Thr Leu Val Thr Val Ser Ser
        115                 120                 125

<210> SEQ ID NO 39
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-301.21F10 variable light chain (VL) sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(297)
<223> OTHER INFORMATION: complementarity determining region (CDR)
      VL-CDR3

<400> SEQUENCE: 39 cag tct gcc ctg act cag cct cgc tca gtg tcc ggg tct cct gga cag        48
Gln Ser Ala Leu Thr Gln Pro Arg Ser Val Ser Gly Ser Pro Gly Gln
1               5                   10                  15 tca gtc acc atc tcc tgc act gca acc aat agt gat gtt ggc gat tat        96
Ser Val Thr Ile Ser Cys Thr Ala Thr Asn Ser Asp Val Gly Asp Tyr
```

```
                    20                  25                  30
aag tct gtc tcc tgg tac caa caa cac cca ggc aaa gcc ccc aaa ctc        144
Lys Ser Val Ser Trp Tyr Gln Gln His Pro Gly Lys Ala Pro Lys Leu
            35                  40                  45 atg att tat gat gtc ggt agg cgg ccc tca ggg gtc cct gat cgc ttc        192
Met Ile Tyr Asp Val Gly Arg Arg Pro Ser Gly Val Pro Asp Arg Phe
    50                  55                  60 tct ggc tcc aaa tct gac aac acg gcc ttc ctg acc atc tct ggg ctc        240
Ser Gly Ser Lys Ser Asp Asn Thr Ala Phe Leu Thr Ile Ser Gly Leu
65                  70                  75                  80 cag act gag gat gaa gct gat tac ttt tgc tgt ata tat gta ggc agg        288
Gln Thr Glu Asp Glu Ala Asp Tyr Phe Cys Cys Ile Tyr Val Gly Arg
                85                  90                  95 tct tcg gtg ttc ggc gga ggg acc aag ttg acc gtc ctg                    327
Ser Ser Val Phe Gly Gly Gly Thr Lys Leu Thr Val Leu
            100                 105
```

<210> SEQ ID NO 40
<211> LENGTH: 109
<212> TYPE: PRT
<213> ORGANISM: Homo sapiens

<400> SEQUENCE: 40

```
Gln Ser Ala Leu Thr Gln Pro Arg Ser Val Ser Gly Ser Pro Gly Gln
1               5                   10                  15

Ser Val Thr Ile Ser Cys Thr Ala Thr Asn Ser Asp Val Gly Asp Tyr
            20                  25                  30

Lys Ser Val Ser Trp Tyr Gln Gln His Pro Gly Lys Ala Pro Lys Leu
            35                  40                  45

Met Ile Tyr Asp Val Gly Arg Arg Pro Ser Gly Val Pro Asp Arg Phe
    50                  55                  60

Ser Gly Ser Lys Ser Asp Asn Thr Ala Phe Leu Thr Ile Ser Gly Leu
65                  70                  75                  80

Gln Thr Glu Asp Glu Ala Asp Tyr Phe Cys Cys Ile Tyr Val Gly Arg
                85                  90                  95

Ser Ser Val Phe Gly Gly Gly Thr Lys Leu Thr Val Leu
            100                 105
```

<210> SEQ ID NO 41
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-301.9G12 variable heavy chain (VH) sequence
<220> FEATURE:
<221> NAME/KEY: V_region
<222> LOCATION: (91)..(108)
<223> OTHER INFORMATION: complementarity determining region (CDR)
      VH-CDR1
<220> FEATURE:
<221> NAME/KEY: V_region
<222> LOCATION: (151)..(198)
<223> OTHER INFORMATION: complementarity determining region (CDR)
      VH-CDR2
<220> FEATURE:
<221> NAME/KEY: V_region
<222> LOCATION: (295)..(339)
<223> OTHER INFORMATION: complementarity determining region (CDR)
      VH-CDR3

<400> SEQUENCE: 41

```
cag gtg cag ctg cag gag tcg ggc cca gga ctg gtg aag cct tcg gag         48
```

```
Gln Val Gln Leu Gln Glu Ser Gly Pro Gly Leu Val Lys Pro Ser Glu
1               5                   10                  15 acc ctg tcc ctc acc tgc gct gtc tct ggt ttc tcc atc agc agt ggt        96
Thr Leu Ser Leu Thr Cys Ala Val Ser Gly Phe Ser Ile Ser Ser Gly
            20                  25                  30 tac tac tgg ggc tgg atc cgg cag ccc cca ggg acg ggg ctg gag tgg       144
Tyr Tyr Trp Gly Trp Ile Arg Gln Pro Pro Gly Thr Gly Leu Glu Trp
        35                  40                  45 att ggg agt atg tat cat agt ggg agg acc tac tac aac ccg tcc ctc       192
Ile Gly Ser Met Tyr His Ser Gly Arg Thr Tyr Tyr Asn Pro Ser Leu
    50                  55                  60 aag agt cga gtc acc ata tca gta gac acg tcc aag aac cag ttg tcc       240
Lys Ser Arg Val Thr Ile Ser Val Asp Thr Ser Lys Asn Gln Leu Ser
65                  70                  75                  80 ctg aag ctg agc tct gtg acc gcc gca gac acg gcc gtg tat tac tgt       288
Leu Lys Leu Ser Ser Val Thr Ala Ala Asp Thr Ala Val Tyr Tyr Cys
                85                  90                  95 gcg agg ggc ttc gat act agt ggt tcc cat cgg ccc ctc tcg act gac       336
Ala Arg Gly Phe Asp Thr Ser Gly Ser His Arg Pro Leu Ser Thr Asp
            100                 105                 110 tac tgg ggc cag ggc acc ctg gtc acc gtc tcc tcg                       372
Tyr Trp Gly Gln Gly Thr Leu Val Thr Val Ser Ser
        115                 120
```

<210> SEQ ID NO 42
<211> LENGTH: 124
<212> TYPE: PRT
<213> ORGANISM: Homo sapiens

<400> SEQUENCE: 42

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Phe Ser Ile Ser Ser Gly
            20                  25                  30

Tyr Tyr Trp Gly Trp Ile Arg Gln Pro Pro Gly Thr Gly Leu Glu Trp
        35                  40                  45

Ile Gly Ser Met Tyr His Ser Gly Arg Thr Tyr Tyr Asn Pro Ser Leu
    50                  55                  60

Lys Ser Arg Val Thr Ile Ser Val Asp Thr Ser Lys Asn Gln Leu Ser
65                  70                  75                  80

Leu Lys Leu Ser Ser Val Thr Ala Ala Asp Thr Ala Val Tyr Tyr Cys
                85                  90                  95

Ala Arg Gly Phe Asp Thr Ser Gly Ser His Arg Pro Leu Ser Thr Asp
            100                 105                 110

Tyr Trp Gly Gln Gly Thr Leu Val Thr Val Ser Ser
        115                 120
```

<210> SEQ ID NO 43
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-301.9G12 variable light chain (VL) sequence
<220> FEATURE:
<221> NAME/KEY: V_region
<222> LOCATION: (67)..(105)
<223> OTHER INFORMATION: complementarity determining region (CDR) VL-CDR1
<220> FEATURE:
<221> NAME/KEY: V_region -continued

```
<222> LOCATION: (151)..(171)
<223> OTHER INFORMATION: complementarity determining region (CDR)
      VL-CDR2
<220> FEATURE:
<221> NAME/KEY: V_region
<222> LOCATION: (268)..(300)
<223> OTHER INFORMATION: complementarity determining region (CDR)
      VL-CDR3

<400> SEQUENCE: 43 cag tct gtg ttg acg cag ccg ccc tca gtg tct gcg gcc cca gga cag    48
Gln Ser Val Leu Thr Gln Pro Pro Ser Val Ser Ala Ala Pro Gly Gln
1               5                   10                  15 aag gtc acc atc tcc tgc tct gga agc agc tcc aac att ggg aat aat    96
Lys Val Thr Ile Ser Cys Ser Gly Ser Ser Ser Asn Ile Gly Asn Asn
            20                  25                  30 tat gta tcc tgg tac cag cag ctc cca gga aca gcc ccc aaa ctc ctc   144
Tyr Val Ser Trp Tyr Gln Gln Leu Pro Gly Thr Ala Pro Lys Leu Leu
        35                  40                  45 att tat gac aat aat aag cga ccc tca ggg att cct gac cga atc tct   192
Ile Tyr Asp Asn Asn Lys Arg Pro Ser Gly Ile Pro Asp Arg Ile Ser
    50                  55                  60 ggc tcc aag tct ggc acg tca gcc acc ctg ggc atc acc gga ctc cag   240
Gly Ser Lys Ser Gly Thr Ser Ala Thr Leu Gly Ile Thr Gly Leu Gln
65                  70                  75                  80 act ggg gac gag gcc gat tat tac tgc gga acc tgg gat agc agc ctg   288
Thr Gly Asp Glu Ala Asp Tyr Tyr Cys Gly Thr Trp Asp Ser Ser Leu
                85                  90                  95 agt gct tat gtc ttc gga act ggg acc aag gtc acc gtc cta            330
Ser Ala Tyr Val Phe Gly Thr Gly Thr Lys Val Thr Val Leu
            100                 105                 110

<210> SEQ ID NO 44
<211> LENGTH: 110
<212> TYPE: PRT
<213> ORGANISM: Homo sapiens

<400> SEQUENCE: 44

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Ile Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
            100                 105                 110

<210> SEQ ID NO 45
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-301.12D3 variable heavy chain (VH) sequence
<220> FEATURE:
<221> NAME/KEY: V_region
```

```
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3

<400> SEQUENCE: 45 gag gtg cag ctg gtg gag act ggg gga ggc gtg gtc cag cct ggg agg        48
Glu Val Gln Leu Val Glu Thr Gly Gly Gly Val Val Gln Pro Gly Arg
1               5                   10                  15 tcc ctg aga ctc tcc tgt gta gcg tct gga ttc acc ttc agg aac tat        96
Ser Leu Arg Leu Ser Cys Val Ala Ser Gly Phe Thr Phe Arg Asn Tyr
            20                  25                  30 ggc atg cac tgg gtc cgc cgg gcc cca ggc agg ggg ctg gag tgg gta       144
Gly Met His Trp Val Arg Arg Ala Pro Gly Arg Gly Leu Glu Trp Val
        35                  40                  45 gca gtt ata tgg tct gat gga agt gat aaa tac tat gca gac tcc gtg       192
Ala Val Ile Trp Ser Asp Gly Ser Asp Lys Tyr Tyr Ala Asp Ser Val
 50                  55                  60 gag ggc cga ttc acc atc tcc aga gac aat tcc aag aac acg gtg ttt       240
Glu Gly Arg Phe Thr Ile Ser Arg Asp Asn Ser Lys Asn Thr Val Phe
65                  70                  75                  80 ctc caa atg aac agc ctg aga gcc gac gac acg gct gta tac ttc tgt       288
Leu Gln Met Asn Ser Leu Arg Ala Asp Asp Thr Ala Val Tyr Phe Cys
                85                  90                  95 gcg aga gag ccg agc agc acc tgg gct ttt gac tac tgg ggc cag gga       336
Ala Arg Glu Pro Ser Ser Thr Trp Ala Phe Asp Tyr Trp Gly Gln Gly
            100                 105                 110 acc ctg gtc acc gtc tcc tcg                                           357
Thr Leu Val Thr Val Ser Ser
        115

<210> SEQ ID NO 46
<211> LENGTH: 119
<212> TYPE: PRT
<213> ORGANISM: Homo sapiens

<400> SEQUENCE: 46

Glu Val Gln Leu Val Glu Thr Gly Gly Gly Val Val Gln Pro Gly Arg
1               5                   10                  15

Ser Leu Arg Leu Ser Cys Val Ala Ser Gly Phe Thr Phe Arg Asn Tyr
            20                  25                  30

Gly Met His Trp Val Arg Arg Ala Pro Gly Arg Gly Leu Glu Trp Val
        35                  40                  45

Ala Val Ile Trp Ser Asp Gly Ser Asp Lys Tyr Tyr Ala Asp Ser Val
 50                  55                  60

Glu Gly Arg Phe Thr Ile Ser Arg Asp Asn Ser Lys Asn Thr Val Phe
65                  70                  75                  80

Leu Gln Met Asn Ser Leu Arg Ala Asp Asp Thr Ala Val Tyr Phe Cys
                85                  90                  95

Ala Arg Glu Pro Ser Ser Thr Trp Ala Phe Asp Tyr Trp Gly Gln Gly
            100                 105                 110

Thr Leu Val Thr Val Ser Ser
        115
```

```
<210> SEQ ID NO 47
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-301.12D3 variable light chain (VL) sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(300)
<223> OTHER INFORMATION: complementarity determining region (CDR)
      VL-CDR3

<400> SEQUENCE: 47 cag tct gcc ctg act cag cct gcc tcc gtg tct ggg tct cct gga cag      48
Gln Ser Ala Leu Thr Gln Pro Ala Ser Val Ser Gly Ser Pro Gly Gln
 1               5                  10                  15 tcg atc acc atc tcc tgc act gga acc agc agt gat gtt ggg ggt tat      96
Ser Ile Thr Ile Ser Cys Thr Gly Thr Ser Ser Asp Val Gly Gly Tyr
                20                  25                  30 aac ctt gtc tcc tgg tac caa cag cac cca ggc aaa gcc ccc aaa ctc     144
Asn Leu Val Ser Trp Tyr Gln Gln His Pro Gly Lys Ala Pro Lys Leu
            35                  40                  45 atg att tat gag gac att aag ggg ccc tca ggg gtt tct aat cgc ttc     192
Met Ile Tyr Glu Asp Ile Lys Gly Pro Ser Gly Val Ser Asn Arg Phe
        50                  55                  60 tct ggc tcc aag tct ggc aac acg gcc tcc ctg aca atc tct ggg ctc     240
Ser Gly Ser Lys Ser Gly Asn Thr Ala Ser Leu Thr Ile Ser Gly Leu
65                  70                  75                  80 cag gct gag gac gag gct gat tat ttc tgc tgc tca tat gca ggt act     288
Gln Ala Glu Asp Glu Ala Asp Tyr Phe Cys Cys Ser Tyr Ala Gly Thr
                85                  90                  95 ggc act ctg gta ttc ggc gga ggg acc aag ctg acc gtc cta             330
Gly Thr Leu Val Phe Gly Gly Gly Thr Lys Leu Thr Val Leu
                100                 105                 110

<210> SEQ ID NO 48
<211> LENGTH: 110
<212> TYPE: PRT
<213> ORGANISM: Homo sapiens

<400> SEQUENCE: 48

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Leu Val Ser Trp Tyr Gln Gln His Pro Gly Lys Ala Pro Lys Leu
            35                  40                  45

Met Ile Tyr Glu Asp Ile Lys Gly Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Phe Cys Cys Ser Tyr Ala Gly Thr
            85                  90                  95

Gly Thr Leu Val Phe Gly Gly Gly Thr Lys Leu Thr Val Leu
            100                 105                 110

<210> SEQ ID NO 49
<211> LENGTH: 9
<212> TYPE: PRT
<213> ORGANISM: Artificial Sequence
<220> FEATURE:
<223> OTHER INFORMATION: Epitope recognized by NI-301.59F1 antibody
<220> FEATURE:
<221> NAME/KEY: PEPTIDE
<222> LOCATION: (1)..(9)
<223> OTHER INFORMATION: Epitope of NI-301.59F1 antibody, aa 61to aa 69
<220> FEATURE:
<221> NAME/KEY: PEPTIDE
<222> LOCATION: (1)..(9)
<223> OTHER INFORMATION: Epitope of NI-301.59F1 antibody, aa 61 to aa 69

<400> SEQUENCE: 49

Glu Glu Glu Phe Val Glu Gly Ile Tyr
1               5

<210> SEQ ID NO 50
<211> LENGTH: 11
<212> TYPE: PRT
<213> ORGANISM: Artificial Sequence
<220> FEATURE:
<223> OTHER INFORMATION: Epitope recognized by NI-301.35G11 antibody
<220> FEATURE:
<221> NAME/KEY: PEPTIDE
<222> LOCATION: (1)..(11)
<223> OTHER INFORMATION: Epitope of NI-301.35G11 antibody, aa 53 to aa
      63

<400> SEQUENCE: 50

Gly Glu Leu His Gly Leu Thr Thr Glu Glu Glu
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Epitope recognized by NI-301.37F1 antibody
<220> FEATURE:
<221> NAME/KEY: PEPTIDE
<222> LOCATION: (1)..(5)
<223> OTHER INFORMATION: Epitope of NI-301.37F1 antibody, aa 41 to aa 45

<400> SEQUENCE: 51

Trp Glu Pro Phe Ala
1               5

<210> SEQ ID NO 52
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-301.37F1-PIMC variable heavy chain (VH)
      sequence after correction of primer induced mutations
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
```

```
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(327)
<223> OTHER INFORMATION: complementarity determining region (CDR)
      VH-CDR3

<400> SEQUENCE: 52 cag ctg cag ctg cag gag tcg ggc cca gga ctg gtg aag cct tcg gag       48
Gln Leu Gln Leu Gln Glu Ser Gly Pro Gly Leu Val Lys Pro Ser Glu
1               5                   10                  15 acc ctg tcc ctc acc tgc agt gtc tct ggt ggc tcc atc atc agt agg       96
Thr Leu Ser Leu Thr Cys Ser Val Ser Gly Gly Ser Ile Ile Ser Arg
            20                  25                  30 agt tcc tac tgg ggc tgg atc cgc cag ccc cca ggg aag ggg ctg gag      144
Ser Ser Tyr Trp Gly Trp Ile Arg Gln Pro Pro Gly Lys Gly Leu Glu
        35                  40                  45 tgg att ggg ggt atc tat cat agt ggg aac act tac gac aac ccg tcc      192
Trp Ile Gly Gly Ile Tyr His Ser Gly Asn Thr Tyr Asp Asn Pro Ser
    50                  55                  60 ctc aag agt cga ctc acc atg tcc gta gac acg tcg aag aac cag ttc      240
Leu Lys Ser Arg Leu Thr Met Ser Val Asp Thr Ser Lys Asn Gln Phe
65                  70                  75                  80 tcc ctg aat ctg agg tct gtg acc gcc gca gac acg gct gtg tat tac      288
Ser Leu Asn Leu Arg Ser Val Thr Ala Ala Asp Thr Ala Val Tyr Tyr
                85                  90                  95 tgt gcg agg ata gtg ccg ggg ggt gat gct ttt gat atc tgg ggc caa      336
Cys Ala Arg Ile Val Pro Gly Gly Asp Ala Phe Asp Ile Trp Gly Gln
            100                 105                 110 ggg aca atg gtc acc gtc tct tcg                                      360
Gly Thr Met Val Thr Val Ser Ser
        115                 120

<210> SEQ ID NO 53
<211> LENGTH: 120
<212> TYPE: PRT
<213> ORGANISM: Homo sapiens

<400> SEQUENCE: 53

Gln Leu Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ile Ser Arg
            20                  25                  30

Ser Ser Tyr Trp Gly Trp Ile Arg Gln Pro Pro Gly Lys Gly Leu Glu
        35                  40                  45

Trp Ile Gly Gly Ile Tyr His Ser Gly Asn Thr Tyr Asp Asn Pro Ser
    50                  55                  60

Leu Lys Ser Arg Leu Thr Met Ser Val Asp Thr Ser Lys Asn Gln Phe
65                  70                  75                  80

Ser Leu Asn Leu Arg Ser Val Thr Ala Ala Asp Thr Ala Val Tyr Tyr
                85                  90                  95

Cys Ala Arg Ile Val Pro Gly Gly Asp Ala Phe Asp Ile Trp Gly Gln
            100                 105                 110

Gly Thr Met Val Thr Val Ser Ser
        115                 120

<210> SEQ ID NO 54
<211> LENGTH: 360
<212> TYPE: DNA
```

```
<213> ORGANISM: Homo sapiens
<220> FEATURE:
<221> NAME/KEY: CDS
<222> LOCATION: (1)..(360)
<223> OTHER INFORMATION: NI-301.44E4 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(327)
<223> OTHER INFORMATION: complementarity determining region (CDR)
      VH-CDR3

<400> SEQUENCE: 54 gag gtg cag ctg gtg gag tct ggg gga ggc ttg gta cag ccg ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg atc tgg gtc cgc cag gct cca ggg aag ggg ctg gag tgg gtc     144
Ala Met Ile Trp Val Arg Gln Ala Pro Gly Lys Gly Leu Glu Trp Val
        35                  40                  45 tca ggt att agt ggc agt ggc agt acg aca tac tac gca gac tcc gtg     192
Ser Gly Ile Ser Gly Ser Gly Ser Thr Thr Tyr Tyr Ala Asp Ser Val
    50                  55                  60 aag ggc cgg ttc gcc atc tcc aga gac aaa tcc aag aac acg ctg tcc     240
Lys Gly Arg Phe Ala Ile Ser Arg Asp Lys Ser Lys Asn Thr Leu Ser
65                  70                  75                  80 cta caa atg aac agc ctg aga gcc gag gac acg gcc gta tat tac tgt     288
Leu Gln Met Asn Ser Leu Arg Ala Glu Asp Thr Ala Val Tyr Tyr Cys
                85                  90                  95 gca aaa ggg gca tgg gag ata ccc acc tac ttt gac aac tgg ggc cag     336
Ala Lys Gly Ala Trp Glu Ile Pro Thr Tyr Phe Asp Asn Trp Gly Gln
            100                 105                 110 gga acc ctg gtc acc gtc tcc tcg                                     360
Gly Thr Leu Val Thr Val Ser Ser
        115                 120

<210> SEQ ID NO 55
<211> LENGTH: 120
<212> TYPE: PRT
<213> ORGANISM: Homo sapiens

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Lys Gly Leu Glu Trp Val
        35                  40                  45

Ser Gly Ile Ser Gly Ser Gly Ser Thr Thr Tyr Tyr Ala Asp Ser Val
    50                  55                  60

Lys Gly Arg Phe Ala Ile Ser Arg Asp Lys Ser Lys Asn Thr Leu Ser
65                  70                  75                  80
```

```
Leu Gln Met Asn Ser Leu Arg Ala Glu Asp Thr Ala Val Tyr Tyr Cys
                 85                  90                  95

Ala Lys Gly Ala Trp Glu Ile Pro Thr Tyr Phe Asp Asn Trp Gly Gln
            100                 105                 110

Gly Thr Leu Val Thr Val Ser Ser
        115                 120

<210> SEQ ID NO 56
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-301.44E4 VK variable light-kappa chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(297)
<223> OTHER INFORMATION: complementarity determining region (CDR)
      VK-CDR3

<400> SEQUENCE: 56 gaa att gtg ctg act cag tct cca gcc acc ctg tct gtg tct cca ggg      48
Glu Ile Val Leu Thr Gln Ser Pro Ala Thr Leu Ser Val Ser Pro Gly
1               5                   10                  15 gaa aga gcc acc ctc tcc tgc agg gcc agt cag agt att agg aac aac      96
Glu Arg Ala Thr Leu Ser Cys Arg Ala Ser Gln Ser Ile Arg Asn Asn
            20                  25                  30 tta gcc tgg tac cag cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat ggt gca tcc acc agg gcc act ggt atc cca gcc agg ttc agt ggc     192
Tyr Gly Ala Ser Thr Arg Ala Thr Gly Ile Pro Ala Arg Phe Ser Gly
    50                  55                  60 act ggg tct ggg aca gag ttc act ctc atc gtc agc agc ctg cag tct     240
Thr Gly Ser Gly Thr Glu Phe Thr Leu Ile Val Ser Ser Leu Gln Ser
65                  70                  75                  80 gaa gat ttt gca gtt tat tac tgt cag cag tat aat aac tgg cct ccc     288
Glu Asp Phe Ala Val Tyr Tyr Cys Gln Gln Tyr Asn Asn Trp Pro Pro
                85                  90                  95 acg tgg acg ttc ggc caa ggg acc aag gtg gaa atc aaa                 327
Thr Trp Thr Phe Gly Gln Gly Thr Lys Val Glu Ile Lys
            100                 105

<210> SEQ ID NO 57
<211> LENGTH: 109
<212> TYPE: PRT
<213> ORGANISM: Homo sapiens

<400> SEQUENCE: 57

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Arg Asn Asn
            20                  25                  30
```

```
Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
 50                  55                  60

Thr Gly Ser Gly Thr Glu Phe Thr Leu Ile Val Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Thr Trp Thr Phe Gly Gln Gly Thr Lys Val Glu Ile Lys
            100                 105
```

<210> SEQ ID NO 58
<211> LENGTH: 8
<212> TYPE: PRT
<213> ORGANISM: Artificial Sequence
<220> FEATURE:
<223> OTHER INFORMATION: Epitope of NI-301.59F1 antibody, aa 62 to aa 69
      after alanine scan
<220> FEATURE:
<221> NAME/KEY: misc_feature
<222> LOCATION: (4)..(4)
<223> OTHER INFORMATION: Xaa can be any naturally occurring amino acid

<400> SEQUENCE: 58

```
Glu Glu Phe Xaa Glu Gly Ile Tyr
1               5
```

<210> SEQ ID NO 59
<211> LENGTH: 8
<212> TYPE: PRT
<213> ORGANISM: Artificial Sequence
<220> FEATURE:
<223> OTHER INFORMATION: Epitope of NI-301.35G11 antibody, aa 54 to aa
      61 after alanine scan
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 59

```
Glu Leu Xaa Gly Leu Thr Xaa Glu
1               5
```

<210> SEQ ID NO 60
<211> LENGTH: 5
<212> TYPE: PRT
<213> ORGANISM: Artificial Sequence
<220> FEATURE:
<223> OTHER INFORMATION: Epitope of NI-301.37F1 antibody, aa 41 to aa 45
      after alanine scan

<400> SEQUENCE: 60

```
Trp Glu Pro Phe Ala
1               5
```

<210> SEQ ID NO 61
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION: NI-301.18C4 VH variable heavy chain (VH)
      sequence

```
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(342)
<223> OTHER INFORMATION: complementarity determining region (CDR)
      VH-CDR3

<400> SEQUENCE: 61 gag gtg cag ctg gtg gag tct ggg gga acc ttg gtc cag ccg ggg ggg     48
Glu Val Gln Leu Val Glu Ser Gly Gly Thr Leu Val Gln Pro Gly Gly
1               5                   10                  15 tcc ctg agg ctc tcc tgc gca gcg tcg gga ttc aca ttc aac att tat     96
Ser Leu Arg Leu Ser Cys Ala Ala Ser Gly Phe Thr Phe Asn Ile Tyr
            20                  25                  30 gcc atg acc tgg gtc cgc ctg tct cca gtg agg gga ctg gag tgg gtc    144
Ala Met Thr Trp Val Arg Leu Ser Pro Val Arg Gly Leu Glu Trp Val
        35                  40                  45 tct act att act agt ggt ggc gtc agc ata tat tac gca gac tcc ata    192
Ser Thr Ile Thr Ser Gly Gly Val Ser Ile Tyr Tyr Ala Asp Ser Ile
    50                  55                  60 aag ggc cgc ttc acc gtc tcc aga gac aat gcc aag aac atg gtg ttt    240
Lys Gly Arg Phe Thr Val Ser Arg Asp Asn Ala Lys Asn Met Val Phe
65                  70                  75                  80 cta caa ctg gac aac ctg aca gtc gat gac acg gcc ata tat tac tgt    288
Leu Gln Leu Asp Asn Leu Thr Val Asp Asp Thr Ala Ile Tyr Tyr Cys
                85                  90                  95 ggg aag gac gga aac tgc gat gag aca agt tgt tac tta agg ggg atg    336
Gly Lys Asp Gly Asn Cys Asp Glu Thr Ser Cys Tyr Leu Arg Gly Met
            100                 105                 110 gac gtc tgg ggc caa ggg acc acg gtc acc gtc tcc tcg                375
Asp Val Trp Gly Gln Gly Thr Thr Val Thr Val Ser Ser
        115                 120                 125

<210> SEQ ID NO 62
<211> LENGTH: 125
<212> TYPE: PRT
<213> ORGANISM: Homo sapiens

<400> SEQUENCE: 62

Glu Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Asn Ile Tyr
            20                  25                  30

Ala Met Thr Trp Val Arg Leu Ser Pro Val Arg Gly Leu Glu Trp Val
        35                  40                  45

Ser Thr Ile Thr Ser Gly Gly Val Ser Ile Tyr Tyr Ala Asp Ser Ile
    50                  55                  60

Lys Gly Arg Phe Thr Val Ser Arg Asp Asn Ala Lys Asn Met Val Phe
65                  70                  75                  80

Leu Gln Leu Asp Asn Leu Thr Val Asp Asp Thr Ala Ile Tyr Tyr Cys
                85                  90                  95

Gly Lys Asp Gly Asn Cys Asp Glu Thr Ser Cys Tyr Leu Arg Gly Met
            100                 105                 110
```

```
Asp Val Trp Gly Gln Gly Thr Thr Val Thr Val Ser Ser
        115                 120                 125
```

<210> SEQ ID NO 63
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-301.18C4 VL variable light chain (VL)
      sequence
<220> FEATURE:
<221> NAME/KEY: V_region
<222> LOCATION: (67)..(105)
<223> OTHER INFORMATION: complementarity determining region (CDR)
      VL-CDR1
<220> FEATURE:
<221> NAME/KEY: V_region
<222> LOCATION: (151)..(171)
<223> OTHER INFORMATION: complementarity determining region (CDR)
      VL-CDR2
<220> FEATURE:
<221> NAME/KEY: V_region
<222> LOCATION: (268)..(303)
<223> OTHER INFORMATION: complementarity determining region (CDR)
      VL-CDR3

<400> SEQUENCE: 63

```
cag tct gtg ttg acg cag ccg ccc tca gtg tca gcg gcc cca gga cag      48
Gln Ser Val Leu Thr Gln Pro Pro Ser Val Ser Ala Ala Pro Gly Gln
1               5                   10                  15 aag gtc acc atc tcc tgc tct ggt agc agg tcc gac att ggg tct aaa      96
Lys Val Thr Ile Ser Cys Ser Gly Ser Arg Ser Asp Ile Gly Ser Lys
            20                  25                  30 ctt gtt tcc tgg tac cag gta atc cca gga aga gcc ccc cgg ctc gtc     144
Leu Val Ser Trp Tyr Gln Val Ile Pro Gly Arg Ala Pro Arg Leu Val
        35                  40                  45 att ttt gac act tat aag cgg ccc tca ggg gta cct gcc cgc ttc tct     192
Ile Phe Asp Thr Tyr Lys Arg Pro Ser Gly Val Pro Ala Arg Phe Ser
    50                  55                  60 gcc tcc aag tct ggc acg tca gcc acc ctg gac atc gcc ggg ctc cag     240
Ala Ser Lys Ser Gly Thr Ser Ala Thr Leu Asp Ile Ala Gly Leu Gln
65                  70                  75                  80 cct ggg gac gag gcc gaa tat ttc tgc gga tca tgg ggt aac agt gag     288
Pro Gly Asp Glu Ala Glu Tyr Phe Cys Gly Ser Trp Gly Asn Ser Glu
                85                  90                  95 aat ttt tat tat gtc ttc gga tct ggg acc cgg gtc acc gtc ctg         333
Asn Phe Tyr Tyr Val Phe Gly Ser Gly Thr Arg Val Thr Val Leu
            100                 105                 110
```

<210> SEQ ID NO 64
<211> LENGTH: 111
<212> TYPE: PRT
<213> ORGANISM: Homo sapiens

<400> SEQUENCE: 64

```
Gln Ser Val Leu Thr Gln Pro Pro Ser Val Ser Ala Ala Pro Gly Gln
1               5                   10                  15

Lys Val Thr Ile Ser Cys Ser Gly Ser Arg Ser Asp Ile Gly Ser Lys
            20                  25                  30

Leu Val Ser Trp Tyr Gln Val Ile Pro Gly Arg Ala Pro Arg Leu Val
        35                  40                  45

Ile Phe Asp Thr Tyr Lys Arg Pro Ser Gly Val Pro Ala Arg Phe Ser
    50                  55                  60
```

```
Ala Ser Lys Ser Gly Thr Ser Ala Thr Leu Asp Ile Ala Gly Leu Gln
 65                  70                  75                  80

Pro Gly Asp Glu Ala Glu Tyr Phe Cys Gly Ser Trp Gly Asn Ser Glu
                 85                  90                  95

Asn Phe Tyr Tyr Val Phe Gly Ser Gly Thr Arg Val Thr Val Leu
            100                 105                 110

<210> SEQ ID NO 65
<211> LENGTH: 354
<212> TYPE: DNA
<213> ORGANISM: Homo sapiens
<220> FEATURE:
<221> NAME/KEY: CDS
<222> LOCATION: (1)..(354)
<223> OTHER INFORMATION: NI-301.11A10 variable heavy chain (VH) sequence
      (PIMC by default)
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(321)
<223> OTHER INFORMATION: complementarity determining region (CDR)
      VH-CDR3

<400> SEQUENCE: 65 cag ctg cag ctg cag gag tcg ggc cca gga ctg gtg aag cct tcg gag        48
Gln Leu Gln Leu Gln Glu Ser Gly Pro Gly Leu Val Lys Pro Ser Glu
  1               5                  10                  15 acc ctg tcc ctc acc tgc act gtg tct ggt ggc tcc atc agc agt aga        96
Thr Leu Ser Leu Thr Cys Thr Val Ser Gly Gly Ser Ile Ser Ser Arg
             20                  25                  30 agt tac tac tgg ggc tgg atg cgc cag ccc cca ggg aag ggg ctg gag       144
Ser Tyr Tyr Trp Gly Trp Met Arg Gln Pro Pro Gly Lys Gly Leu Glu
         35                  40                  45 tgg att ggg agt att tat tat agt ggg agc acc ctc tac aat ccg tcc       192
Trp Ile Gly Ser Ile Tyr Tyr Ser Gly Ser Thr Leu Tyr Asn Pro Ser
 50                  55                  60 ctc aag agt cga gtc acc atg tca ata gtc acg tcg agg aac cag ttc       240
Leu Lys Ser Arg Val Thr Met Ser Ile Val Thr Ser Arg Asn Gln Phe
 65                  70                  75                  80 tcc ctg aag ctg agt tct gtg acc gcc gcg gac acg gcc gtg tat tat       288
Ser Leu Lys Leu Ser Ser Val Thr Ala Ala Asp Thr Ala Val Tyr Tyr
                 85                  90                  95 tgt acc cga atg ggg gag ggg ggg cgg gac tac tgg ggc cag gga acc       336
Cys Thr Arg Met Gly Glu Gly Gly Arg Asp Tyr Trp Gly Gln Gly Thr
            100                 105                 110 ctg gtc acc gtc tcc tcg                                               354
Leu Val Thr Val Ser Ser
            115

<210> SEQ ID NO 66
<211> LENGTH: 118
<212> TYPE: PRT
<213> ORGANISM: Homo sapiens

<400> SEQUENCE: 66

Gln Leu Gln Leu Gln Glu Ser Gly Pro Gly Leu Val Lys Pro Ser Glu
  1               5                  10                  15
```

```
Thr Leu Ser Leu Thr Cys Thr Val Ser Gly Gly Ser Ile Ser Ser Arg
            20                  25                  30

Ser Tyr Tyr Trp Gly Trp Met Arg Gln Pro Pro Gly Lys Gly Leu Glu
            35                  40                  45

Trp Ile Gly Ser Ile Tyr Tyr Ser Gly Ser Thr Leu Tyr Asn Pro Ser
 50                  55                  60

Leu Lys Ser Arg Val Thr Met Ser Ile Val Thr Ser Arg Asn Gln Phe
 65                  70                  75                  80

Ser Leu Lys Leu Ser Ser Val Thr Ala Ala Asp Thr Ala Val Tyr Tyr
                85                  90                  95

Cys Thr Arg Met Gly Glu Gly Gly Arg Asp Tyr Trp Gly Gln Gly Thr
            100                 105                 110

Leu Val Thr Val Ser Ser
            115

<210> SEQ ID NO 67
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-301.11A10 variable K-light chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 67 gac atc cag atg acc cag tct cct tcc acc ctg tct gca tct gta gga      48
Asp Ile Gln Met Thr Gln Ser Pro Ser Thr Leu Ser Ala Ser Val Gly
 1               5                  10                  15 gac aga gtc acc atc act tgc cgg gcc agt cag agt att agt agt tgg      96
Asp Arg Val Thr Ile Thr Cys Arg Ala Ser Gln Ser Ile Ser Ser Trp
            20                  25                  30 ttg gcc tgg tat cag cag aaa cca ggg aaa gcc cct aag gtc ctg atc     144
Leu Ala Trp Tyr Gln Gln Lys Pro Gly Lys Ala Pro Lys Val Leu Ile
            35                  40                  45 tat gat gcc tcc agt ttg gaa aga ggg gtc cca tca agg ttc agc ggc     192
Tyr Asp Ala Ser Ser Leu Glu Arg Gly Val Pro Ser Arg Phe Ser Gly
 50                  55                  60 agt ggg tct ggg aca gaa ttc act ctc acc atc agc agc ctg cag cct     240
Ser Gly Ser Gly Thr Glu Phe Thr Leu Thr Ile Ser Ser Leu Gln Pro
 65                  70                  75                  80 gat gat tct gca act tat tac tgc caa cac tat aat ggt tat tca agg     288
Asp Asp Ser Ala Thr Tyr Tyr Cys Gln His Tyr Asn Gly Tyr Ser Arg
                85                  90                  95 acg ttc ggc cgc ggg acc aag gtg gaa atc aaa                         321
Thr Phe Gly Arg Gly Thr Lys Val Glu Ile Lys
            100                 105
```

```
<210> SEQ ID NO 68
<211> LENGTH: 107
<212> TYPE: PRT
<213> ORGANISM: Homo sapiens

<400> SEQUENCE: 68

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Asp Ala Ser Ser Leu Glu Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln His Tyr Asn Gly Tyr Ser Arg
                85                  90                  95

Thr Phe Gly Arg Gly Thr Lys Val Glu Ile Lys
            100                 105

<210> SEQ ID NO 69
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-301.3C9 variable heavy chain (VH) sequence
      (PIMC by default)
<220> FEATURE:
<221> NAME/KEY: V_region
<222> LOCATION: (91)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(339)
<223> OTHER INFORMATION: complementarity determining region (CDR)
      VH-CDR3

<400> SEQUENCE: 69 cag gtg cag ctg cag gag tcg ggc cca gga ctg gtg aag tct tcg cag     48
Gln Val Gln Leu Gln Glu Ser Gly Pro Gly Leu Val Lys Ser Ser Gln
1               5                   10                  15 acc ctg tcc ctc acc tgc act gtc tct ggt gcc tcc ttc acc agg ggt     96
Thr Leu Ser Leu Thr Cys Thr Val Ser Gly Ala Ser Phe Thr Arg Gly
            20                  25                  30 gat ttc tac tgg agt tgg atc cgc cag gtc cca ggg aag ggc ctg gaa    144
Asp Phe Tyr Trp Ser Trp Ile Arg Gln Val Pro Gly Lys Gly Leu Glu
        35                  40                  45 tgg att ggt tac ata tat tcc act ggg gac gtc tac tac aat ccg tct    192
Trp Ile Gly Tyr Ile Tyr Ser Thr Gly Asp Val Tyr Tyr Asn Pro Ser
    50                  55                  60 ctc aag agt cga gca aac atc tcg gtc gac acg ccc aag aag cag ttc    240
Leu Lys Ser Arg Ala Asn Ile Ser Val Asp Thr Pro Lys Lys Gln Phe
65                  70                  75                  80 ttc ctg aaa ttg acc tct ttg act gcc gca gac acg gcc gtc tat ttt    288
Phe Leu Lys Leu Thr Ser Leu Thr Ala Ala Asp Thr Ala Val Tyr Phe
                85                  90                  95
```

```
tgt gcc agg gaa gga caa tat tgt agc ggt ggt agt tgc tac cct gaa    336
Cys Ala Arg Glu Gly Gln Tyr Cys Ser Gly Gly Ser Cys Tyr Pro Glu
            100                 105                 110 tac tgg ggc cag gga acc ctg gtc acc gtc tcc tcg                    372
Tyr Trp Gly Gln Gly Thr Leu Val Thr Val Ser Ser
        115                 120

<210> SEQ ID NO 70
<211> LENGTH: 124
<212> TYPE: PRT
<213> ORGANISM: Homo sapiens

<400> SEQUENCE: 70

Gln Val Gln Leu Gln Glu Ser Gly Pro Gly Leu Val Lys Ser Ser Gln
1               5                   10                  15

Thr Leu Ser Leu Thr Cys Thr Val Ser Gly Ala Ser Phe Thr Arg Gly
            20                  25                  30

Asp Phe Tyr Trp Ser Trp Ile Arg Gln Val Pro Gly Lys Gly Leu Glu
        35                  40                  45

Trp Ile Gly Tyr Ile Tyr Ser Thr Gly Asp Val Tyr Tyr Asn Pro Ser
    50                  55                  60

Leu Lys Ser Arg Ala Asn Ile Ser Val Asp Thr Pro Lys Lys Gln Phe
65                  70                  75                  80

Phe Leu Lys Leu Thr Ser Leu Thr Ala Ala Asp Thr Ala Val Tyr Phe
                85                  90                  95

Cys Ala Arg Glu Gly Gln Tyr Cys Ser Gly Gly Ser Cys Tyr Pro Glu
            100                 105                 110

Tyr Trp Gly Gln Gly Thr Leu Val Thr Val Ser Ser
        115                 120

<210> SEQ ID NO 71
<211> LENGTH: 318
<212> TYPE: DNA
<213> ORGANISM: Homo sapiens
<220> FEATURE:
<221> NAME/KEY: CDS
<222> LOCATION: (1)..(318)
<223> OTHER INFORMATION: NI-301.3C9 variable light chain (VL) sequence
      (PIMC by default)
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(288)
<223> OTHER INFORMATION: complementarity determining region (CDR)
      VL-CDR3

<400> SEQUENCE: 71 tcc tat gag ctg act cag cca ccc tca gtg tcc gtg tcc cca gga cag    48
Ser Tyr Glu Leu Thr Gln Pro Pro Ser Val Ser Val Ser Pro Gly Gln
1               5                   10                  15 aca gcc acc atc acc tgc tct gga gat aat ttg gga cat aaa ttt act    96
Thr Ala Thr Ile Thr Cys Ser Gly Asp Asn Leu Gly His Lys Phe Thr
            20                  25                  30 tgc tgg tat cag cag aag cca ggc cag tcc cct gtc ctg gtc atc tat    144
Cys Trp Tyr Gln Gln Lys Pro Gly Gln Ser Pro Val Leu Val Ile Tyr
```

```
                35                  40                  45
caa gat cac aag cgg ccc tca ggg atc cct gag cga ttc tcc ggc tcc      192
Gln Asp His Lys Arg Pro Ser Gly Ile Pro Glu Arg Phe Ser Gly Ser
     50                  55                  60 aac tct ggg gac aca gcc act ctg acc atc agc ggg acc cag gct atg      240
Asn Ser Gly Asp Thr Ala Thr Leu Thr Ile Ser Gly Thr Gln Ala Met
 65                  70                  75                  80 gat gag gct gag tat tac tgt cag gcg tgg gcc ttc ccc tat gtg gtc      288
Asp Glu Ala Glu Tyr Tyr Cys Gln Ala Trp Ala Phe Pro Tyr Val Val
                 85                  90                  95 ttc ggc gga ggg acc aag ctg acc gtc cta                              318
Phe Gly Gly Gly Thr Lys Leu Thr Val Leu
                100                 105

<210> SEQ ID NO 72
<211> LENGTH: 106
<212> TYPE: PRT
<213> ORGANISM: Homo sapiens

<400> SEQUENCE: 72

Ser Tyr Glu Leu Thr Gln Pro Pro Ser Val Ser Val Ser Pro Gly Gln
 1               5                   10                  15

Thr Ala Thr Ile Thr Cys Ser Gly Asp Asn Leu Gly His Lys Phe Thr
                 20                  25                  30

Cys Trp Tyr Gln Gln Lys Pro Gly Gln Ser Pro Val Leu Val Ile Tyr
                 35                  40                  45

Gln Asp His Lys Arg Pro Ser Gly Ile Pro Glu Arg Phe Ser Gly Ser
     50                  55                  60

Asn Ser Gly Asp Thr Ala Thr Leu Thr Ile Ser Gly Thr Gln Ala Met
 65                  70                  75                  80

Asp Glu Ala Glu Tyr Tyr Cys Gln Ala Trp Ala Phe Pro Tyr Val Val
                 85                  90                  95

Phe Gly Gly Gly Thr Lys Leu Thr Val Leu
                100                 105

<210> SEQ ID NO 73
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-301.14D8 variable heavy chain (VH) sequence
      (not PIMC)
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(339)
<223> OTHER INFORMATION: complementarity determining region (CDR)
      VH-CDR3

<400> SEQUENCE: 73 gag gtg cag ctg gtg gag act ggg gga cgc ttg gtc cag ccg ggg ggg      48
Glu Val Gln Leu Val Glu Thr Gly Gly Arg Leu Val Gln Pro Gly Gly
 1               5                   10                  15
```

| | | |
|---|---|---|
| tcc gtg aga ctc tcc tgt ata gcc tct gga ttt ccc ttt agg aat tat<br>Ser Val Arg Leu Ser Cys Ile Ala Ser Gly Phe Pro Phe Arg Asn Tyr<br>          20                       25                       30 | | 96 |
| tgg atg agt tgg gtc cgc cag cct cca ggg aag ggg ctg gag tgg gtg<br>Trp Met Ser Trp Val Arg Gln Pro Pro Gly Lys Gly Leu Glu Trp Val<br>          35                       40                       45 | | 144 |
| gcc aac ata aag gaa gat ggc agt gac aga tac tat gtg gac tct gtg<br>Ala Asn Ile Lys Glu Asp Gly Ser Asp Arg Tyr Tyr Val Asp Ser Val<br>50                         55                       60 | | 192 |
| aag ggc cgc ttc acc atc ttt aga gac aac gcc aag aat ttt ctg agt<br>Lys Gly Arg Phe Thr Ile Phe Arg Asp Asn Ala Lys Asn Phe Leu Ser<br>65                       70                         75                       80 | | 240 |
| cta caa atg aat cgc ctg aga gcc gag gac acg gcg gta tac ttc tgt<br>Leu Gln Met Asn Arg Leu Arg Ala Glu Asp Thr Ala Val Tyr Phe Cys<br>          85                       90                       95 | | 288 |
| gcg aga att gta ggg gta atc ccg tcc gct gac cca tac tac ctt gac<br>Ala Arg Ile Val Gly Val Ile Pro Ser Ala Asp Pro Tyr Tyr Leu Asp<br>             100                     105                     110 | | 336 |
| tcc tgg ggc cag gga acc ctg gtc acc gtc tcc tcg<br>Ser Trp Gly Gln Gly Thr Leu Val Thr Val Ser Ser<br>         115                       120 | | 372 |

<210> SEQ ID NO 74
<211> LENGTH: 124
<212> TYPE: PRT
<213> ORGANISM: Homo sapiens

<400> SEQUENCE: 74

Glu Val Gln Leu Val Glu Thr Gly Gly Arg Leu Val Gln Pro Gly Gly
1               5                   10                  15

Ser Val Arg Leu Ser Cys Ile Ala Ser Gly Phe Pro Phe Arg Asn Tyr
            20                  25                  30

Trp Met Ser Trp Val Arg Gln Pro Pro Gly Lys Gly Leu Glu Trp Val
        35                  40                  45

Ala Asn Ile Lys Glu Asp Gly Ser Asp Arg Tyr Tyr Val Asp Ser Val
    50                  55                  60

Lys Gly Arg Phe Thr Ile Phe Arg Asp Asn Ala Lys Asn Phe Leu Ser
65                  70                  75                  80

Leu Gln Met Asn Arg Leu Arg Ala Glu Asp Thr Ala Val Tyr Phe Cys
                85                  90                  95

Ala Arg Ile Val Gly Val Ile Pro Ser Ala Asp Pro Tyr Tyr Leu Asp
            100                 105                 110

Ser Trp Gly Gln Gly Thr Leu Val Thr Val Ser Ser
        115                 120

<210> SEQ ID NO 75
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-301.14D8 variable light chain (VL) sequence
      (PIMC by default)
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)

```
        VL-CDR2
<220> FEATURE:
<221> NAME/KEY: V_region
<222> LOCATION: (271)..(300)
<223> OTHER INFORMATION: complementarity determining region (CDR)
      VL-CDR3

<400> SEQUENCE: 75 cag tct gcc ctg act cag cct gcc tcc gtg tct ggg ttt gct gga cag      48
Gln Ser Ala Leu Thr Gln Pro Ala Ser Val Ser Gly Phe Ala Gly Gln
1               5                   10                  15 tcg gtc acc atc tcc tgc act gga acc agc ctt aac att ggg act tac      96
Ser Val Thr Ile Ser Cys Thr Gly Thr Ser Leu Asn Ile Gly Thr Tyr
                20                  25                  30 aac ctt atc tcc tgg tac caa caa cac cca ggc aga gcc ccc aga ctc     144
Asn Leu Ile Ser Trp Tyr Gln Gln His Pro Gly Arg Ala Pro Arg Leu
            35                  40                  45 atc att ttt gag ggc aat agg cgg ccc ccc ggg att tct aat cgc ttc     192
Ile Ile Phe Glu Gly Asn Arg Arg Pro Pro Gly Ile Ser Asn Arg Phe
        50                  55                  60 tct gcc tcc aag tct ggc aac acg gcc tcc ttg aca gtc tct ggg ctg     240
Ser Ala Ser Lys Ser Gly Asn Thr Ala Ser Leu Thr Val Ser Gly Leu
65                  70                  75                  80 ctg gct ggc gac gag gct gat tat tac tgt tgc tca ttt gca gga aga     288
Leu Ala Gly Asp Glu Ala Asp Tyr Tyr Cys Cys Ser Phe Ala Gly Arg
                85                  90                  95 gtc tct ttg gtg ttt ggc gga ggg acc aag ttg acc gtc cta             330
Val Ser Leu Val Phe Gly Gly Gly Thr Lys Leu Thr Val Leu
                100                 105                 110

<210> SEQ ID NO 76
<211> LENGTH: 110
<212> TYPE: PRT
<213> ORGANISM: Homo sapiens

<400> SEQUENCE: 76

Gln Ser Ala Leu Thr Gln Pro Ala Ser Val Ser Gly Phe Ala Gly Gln
1               5                   10                  15

Ser Val Thr Ile Ser Cys Thr Gly Thr Ser Leu Asn Ile Gly Thr Tyr
                20                  25                  30

Asn Leu Ile Ser Trp Tyr Gln Gln His Pro Gly Arg Ala Pro Arg Leu
            35                  40                  45

Ile Ile Phe Glu Gly Asn Arg Arg Pro Pro Gly Ile Ser Asn Arg Phe
        50                  55                  60

Ser Ala Ser Lys Ser Gly Asn Thr Ala Ser Leu Thr Val Ser Gly Leu
65                  70                  75                  80

Leu Ala Gly Asp Glu Ala Asp Tyr Tyr Cys Cys Ser Phe Ala Gly Arg
                85                  90                  95

Val Ser Leu Val Phe Gly Gly Gly Thr Lys Leu Thr Val Leu
                100                 105                 110

<210> SEQ ID NO 77
<211> LENGTH: 348
<212> TYPE: DNA
<213> ORGANISM: Homo sapiens
<220> FEATURE:
<221> NAME/KEY: CDS
<222> LOCATION: (1)..(348)
<223> OTHER INFORMATION: NI-301.9X4 variable heavy chain (VH) sequence
      (PIMC by default)
<220> FEATURE:
<221> NAME/KEY: V_region
<222> LOCATION: (91)..(105)
```

```
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(315)
<223> OTHER INFORMATION: complementarity determining region (CDR)
      VH-CDR3

<400> SEQUENCE: 77
```

| | | | | | | | | | | | | | | | | |
|---|---|---|---|---|---|---|---|---|---|---|---|---|---|---|---|---|
| cag | gtg | cag | ctg | cag | gag | tcg | ggc | cca | gga | ctg | gtg | aaa | cct | tcg | gag | 48 |
| Gln | Val | Gln | Leu | Gln | Glu | Ser | Gly | Pro | Gly | Leu | Val | Lys | Pro | Ser | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acc | ctg | tcc | ctc | acc | tgc | agt | gtc | tct | gct | ggc | tcc | atc | agt | agt | cac | 96 |
| Thr | Leu | Ser | Leu | Thr | Cys | Ser | Val | Ser | Ala | Gly | Ser | Ile | Ser | Ser | His | |
| | | | 20 | | | | | 25 | | | | | 30 | | | |

| | | | | | | | | | | | | | | | | |
|---|---|---|---|---|---|---|---|---|---|---|---|---|---|---|---|---|
| tac | tgg | aac | tgg | atc | cgg | cag | ccc | cca | ggg | aag | gga | ctg | gaa | tgg | att | 144 |
| Tyr | Trp | Asn | Trp | Ile | Arg | Gln | Pro | Pro | Gly | Lys | Gly | Leu | Glu | Trp | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| ggg | tct | atc | tat | cac | agt | ggg | agc | acc | aac | tac | aac | ccc | tcc | ctc | aag | 192 |
| Gly | Ser | Ile | Tyr | His | Ser | Gly | Ser | Thr | Asn | Tyr | Asn | Pro | Ser | Leu | Lys | |
| 50 | | | | | 55 | | | | | 60 | | | | | | |

| | | | | | | | | | | | | | | | | |
|---|---|---|---|---|---|---|---|---|---|---|---|---|---|---|---|---|
| agt | cga | gtc | acc | ata | tca | gta | gac | acg | tcc | aag | aac | cac | gtc | tcc | ctg | 240 |
| Ser | Arg | Val | Thr | Ile | Ser | Val | Asp | Thr | Ser | Lys | Asn | His | Val | Ser | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agg | ttg | acg | tct | gtg | acc | gcc | gca | gac | acg | gcc | gtg | tat | tac | tgt | gcg | 288 |
| Arg | Leu | Thr | Ser | Val | Thr | Ala | Ala | Asp | Thr | Ala | Val | Tyr | Tyr | Cys | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| aga | gac | tac | tac | tac | tac | atg | gac | gtc | tgg | ggc | aaa | ggg | acc | acg | gtc | 336 |
| Arg | Asp | Tyr | Tyr | Tyr | Tyr | Met | Asp | Val | Trp | Gly | Lys | Gly | Thr | Thr | Val | |
| | | | 100 | | | | | 105 | | | | | 110 | | | |

| | | | | |
|---|---|---|---|---|
| acc | gtc | tcc | tcg | 348 |
| Thr | Val | Ser | Ser | |
| | | 115 | | |

```
<210> SEQ ID NO 78
<211> LENGTH: 116
<212> TYPE: PRT
<213> ORGANISM: Homo sapiens

<400> SEQUENCE: 78
```

Gln Val Gln Leu Gln Glu Ser Gly Pro Gly Leu Val Lys Pro Ser Glu
1               5                   10                  15

Thr Leu Ser Leu Thr Cys Ser Val Ser Ala Gly Ser Ile Ser Ser His
            20                  25                  30

Tyr Trp Asn Trp Ile Arg Gln Pro Pro Gly Lys Gly Leu Glu Trp Ile
        35                  40                  45

Gly Ser Ile Tyr His Ser Gly Ser Thr Asn Tyr Asn Pro Ser Leu Lys
50                  55                  60

Ser Arg Val Thr Ile Ser Val Asp Thr Ser Lys Asn His Val Ser Leu
65                  70                  75                  80

Arg Leu Thr Ser Val Thr Ala Ala Asp Thr Ala Val Tyr Tyr Cys Ala
                85                  90                  95

Arg Asp Tyr Tyr Tyr Tyr Met Asp Val Trp Gly Lys Gly Thr Thr Val
            100                 105                 110

Thr Val Ser Ser
            115

```
<210> SEQ ID NO 79
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-301.9X4 variable light chain (VL) sequence
      (PIMC by default)
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(294)
<223> OTHER INFORMATION: complementarity determining region (CDR)
      VL-CDR3

<400> SEQUENCE: 79 tcc tat gag ctg act cag cca ccc tcg gtg tca gtg tcc cca gga cag        48
Ser Tyr Glu Leu Thr Gln Pro Pro Ser Val Ser Val Ser Pro Gly Gln
1               5                   10                  15 acg gcc agg atc acc tgc tct gga gat gcg ttg cca gac aag tat gct        96
Thr Ala Arg Ile Thr Cys Ser Gly Asp Ala Leu Pro Asp Lys Tyr Ala
            20                  25                  30 tat tgg tac cag cag aag cca ggc cag gcc cct atg ttg gtt ata tat       144
Tyr Trp Tyr Gln Gln Lys Pro Gly Gln Ala Pro Met Leu Val Ile Tyr
        35                  40                  45 aag gac agt gag agg ccc tca ggg atc cct gag cga ttc tct ggc tcc       192
Lys Asp Ser Glu Arg Pro Ser Gly Ile Pro Glu Arg Phe Ser Gly Ser
50                  55                  60 agt ttg ggg aca aca gtc atg ctg acc atc agt gga gtc cag gca gag       240
Ser Leu Gly Thr Thr Val Met Leu Thr Ile Ser Gly Val Gln Ala Glu
65                  70                  75                  80 gac gag gct gac tat tac tgt aaa tca gca gac agc agt ggt act tat       288
Asp Glu Ala Asp Tyr Tyr Cys Lys Ser Ala Asp Ser Ser Gly Thr Tyr
                85                  90                  95 tgg gtg ttc ggc ggg ggg acc aag ctg acc gtc cta                       324
Trp Val Phe Gly Gly Gly Thr Lys Leu Thr Val Leu
            100                 105

<210> SEQ ID NO 80
<211> LENGTH: 108
<212> TYPE: PRT
<213> ORGANISM: Homo sapiens

<400> SEQUENCE: 80

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Asp Lys Tyr Ala
            20                  25                  30

Tyr Trp Tyr Gln Gln Lys Pro Gly Gln Ala Pro Met Leu Val Ile Tyr
        35                  40                  45

Lys Asp Ser Glu Arg Pro Ser Gly Ile Pro Glu Arg Phe Ser Gly Ser
    50                  55                  60

Ser Leu Gly Thr Thr Val Met Leu Thr Ile Ser Gly Val Gln Ala Glu
65                  70                  75                  80
```

```
Asp Glu Ala Asp Tyr Tyr Cys Lys Ser Ala Asp Ser Ser Gly Thr Tyr
            85                  90                  95

Trp Val Phe Gly Gly Gly Thr Lys Leu Thr Val Leu
        100                 105

<210> SEQ ID NO 81
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-301.14C3 variable heavy chain (VH) sequence
      (PIMC by default)
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(330)
<223> OTHER INFORMATION: complementarity determining region (CDR)
      VH-CDR3

<400> SEQUENCE: 81 gag gtg cag ctg gtg gag act gga gga ggc ttg atc cag cct ggg ggg        48
Glu Val Gln Leu Val Glu Thr Gly Gly Gly Leu Ile Gln Pro Gly Gly
1               5                   10                  15 tcc ctg aga ctc tcc tgt gca gcc tct ggg ttc acc gtc agt agc cac        96
Ser Leu Arg Leu Ser Cys Ala Ala Ser Gly Phe Thr Val Ser Ser His
            20                  25                  30 tac atg agc tgg gtc cgc cag gct cca ggg aag ggg ctg gag tgg gtc       144
Tyr Met Ser Trp Val Arg Gln Ala Pro Gly Lys Gly Leu Glu Trp Val
        35                  40                  45 tca att att tat agc ggt ggt ggc aca tac tac gca gac tcc gtg aag       192
Ser Ile Ile Tyr Ser Gly Gly Gly Thr Tyr Tyr Ala Asp Ser Val Lys
    50                  55                  60 ggc cga ttc acc atc tcc aga gac aat tcc aag aac acg ctg tat ctt       240
Gly Arg Phe Thr Ile Ser Arg Asp Asn Ser Lys Asn Thr Leu Tyr Leu
65                  70                  75                  80 caa atg aac agc ctg aga gcc gag gac acg gcc gtg tat tac tgt gcg       288
Gln Met Asn Ser Leu Arg Ala Glu Asp Thr Ala Val Tyr Tyr Cys Ala
                85                  90                  95 aag atc tac agg tcg ggt aat act ggt tat tct tac gac tac tgg ggc       336
Lys Ile Tyr Arg Ser Gly Asn Thr Gly Tyr Ser Tyr Asp Tyr Trp Gly
            100                 105                 110 cag gga acc ctg gtc acc gtc tcc tcg                                   363
Gln Gly Thr Leu Val Thr Val Ser Ser
        115                 120

<210> SEQ ID NO 82
<211> LENGTH: 121
<212> TYPE: PRT
<213> ORGANISM: Homo sapiens

<400> SEQUENCE: 82

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser His
            20                  25                  30
```

```
Tyr Met Ser Trp Val Arg Gln Ala Pro Gly Lys Gly Leu Glu Trp Val
        35                  40                  45

Ser Ile Ile Tyr Ser Gly Gly Gly Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Ile Tyr Arg Ser Gly Asn Thr Gly Tyr Ser Tyr Asp Tyr Trp Gly
                100                 105                 110

Gln Gly Thr Leu Val Thr Val Ser Ser
        115                 120
```

<210> SEQ ID NO 83  
<211> LENGTH: 324  
<212> TYPE: DNA  
<213> ORGANISM: Homo sapiens  
<220> FEATURE:  
<221> NAME/KEY: CDS  
<222> LOCATION: (1)..(324)  
<223> OTHER INFORMATION: NI-301.14C3 variable light chain (VL) sequence  
<220> FEATURE:  
<221> NAME/KEY: V_region  
<222> LOCATION: (67)..(99)  
<223> OTHER INFORMATION: complementarity determining region (CDR) VL-CDR1  
<220> FEATURE:  
<221> NAME/KEY: V_region  
<222> LOCATION: (145)..(165)  
<223> OTHER INFORMATION: complementarity determining region (CDR) VL-CDR2  
<220> FEATURE:  
<221> NAME/KEY: V_region  
<222> LOCATION: (262)..(294)  
<223> OTHER INFORMATION: complementarity determining region (CDR) VL-CDR3

<400> SEQUENCE: 83

```
tcc tat gag ctg act cag cca ccc tca gtg tcc gtg tcc cca ggg cag      48
Ser Tyr Glu Leu Thr Gln Pro Pro Ser Val Ser Val Ser Pro Gly Gln
 1               5                  10                  15 aca gcc agc atc acc tgc tct gga gat aaa ttg ggg agt aaa tat gct      96
Thr Ala Ser Ile Thr Cys Ser Gly Asp Lys Leu Gly Ser Lys Tyr Ala
             20                  25                  30 tgc tgg tat cag cag aag cca ggc cag tcc cct gta ctg gtc atc tat     144
Cys Trp Tyr Gln Gln Lys Pro Gly Gln Ser Pro Val Leu Val Ile Tyr
         35                  40                  45 gaa gat aag aag cgg ccc tca ggg atc cct gag cga ttc tct ggc tcc     192
Glu Asp Lys Lys Arg Pro Ser Gly Ile Pro Glu Arg Phe Ser Gly Ser
 50                  55                  60 aac tct ggg aac aca gcc act ctg acc atc agc ggg acc cag gct atg     240
Asn Ser Gly Asn Thr Ala Thr Leu Thr Ile Ser Gly Thr Gln Ala Met
 65                  70                  75                  80 gat gag gct gac tat ttc tgt cag gcg tgg gac agc agc act tct cat     288
Asp Glu Ala Asp Tyr Phe Cys Gln Ala Trp Asp Ser Ser Thr Ser His
                 85                  90                  95 gtg gta ttc ggc gga ggg acc agg ctg acc gtc cta                     324
Val Val Phe Gly Gly Gly Thr Arg Leu Thr Val Leu
                100                 105
```

<210> SEQ ID NO 84  
<211> LENGTH: 108  
<212> TYPE: PRT  
<213> ORGANISM: Homo sapiens

<400> SEQUENCE: 84

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Ser Lys Tyr Ala
            20                  25                  30

Cys Trp Tyr Gln Gln Lys Pro Gly Gln Ser Pro Val Leu Val Ile Tyr
        35                  40                  45

Glu Asp Lys Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Asp Ser Ser Thr Ser His
                85                  90                  95

Val Val Phe Gly Gly Gly Thr Arg Leu Thr Val Leu
            100                 105

<210> SEQ ID NO 85
<211> LENGTH: 15
<212> TYPE: PRT
<213> ORGANISM: Artificial Sequence
<220> FEATURE:
<223> OTHER INFORMATION: Peptide sequence recognized by NI-301.59F1 in
      the epitope mapping - Spot 15

<400> SEQUENCE: 85

Gly Leu Thr Thr Glu Glu Glu Phe Val Glu Gly Ile Tyr Lys Val
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Peptide sequence recognized by NI-301.59F1 in
      the epitope mapping - Spot 16

<400> SEQUENCE: 86

Glu Glu Glu Phe Val Glu Gly Ile Tyr Lys Val Glu Ile Asp Thr
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Peptide sequence recognized by NI-301.35G11 in
      the epitope mapping - Spot 13

<400> SEQUENCE: 87

Thr Ser Glu Ser Gly Glu Leu His Gly Leu Thr Thr Glu Glu Glu
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Peptide sequence recognized by NI-301.35G11 in
      the epitope mapping - Spot 14

<400> SEQUENCE: 88

Gly Glu Leu His Gly Leu Thr Thr Glu Glu Glu Phe Val Glu Gly
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Peptide sequence recognized by NI-301.37F1 in
      the epitope mapping - Spot 9

<400> SEQUENCE: 89

Phe Arg Lys Ala Ala Asp Asp Thr Trp Glu Pro Phe Ala Ser Gly
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Peptide sequence recognized by NI-301.37F1 in
      the epitope mapping - Spot 10

<400> SEQUENCE: 90

Ala Asp Asp Thr Trp Glu Pro Phe Ala Ser Gly Lys Thr Ser Glu
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Peptide sequence recognized by NI-301.37F1 in
      the epitope mapping - Spot 11

<400> SEQUENCE: 91

Trp Glu Pro Phe Ala Ser Gly Lys Thr Ser Glu Ser Gly Glu Leu
1               5                   10                  15

<210> SEQ ID NO 92
<211> LENGTH: 5
<212> TYPE: PRT
<213> ORGANISM: Homo sapiens

<400> SEQUENCE: 92

Asn Tyr Trp Met Ser
1               5

<210> SEQ ID NO 93
<211> LENGTH: 16
<212> TYPE: PRT
<213> ORGANISM: Homo sapiens

<400> SEQUENCE: 93

Asn Ile Asn Gln Asp Ser Glu Lys Tyr Tyr Val Asp Ser Val Lys Gly
1               5                   10                  15

<210> SEQ ID NO 94
<211> LENGTH: 18
<212> TYPE: PRT
<213> ORGANISM: Homo sapiens

<400> SEQUENCE: 94

Asp Arg Tyr Cys Ser Gly Gly Arg Cys Ser Arg Gly Asn Asn Trp Phe
1               5                   10                  15
Asp Pro

<210> SEQ ID NO 95
<211> LENGTH: 11
<212> TYPE: PRT
<213> ORGANISM: Homo sapiens

<400> SEQUENCE: 95

Arg Ala Ser Gln Ser Val Arg Ser Asn Leu Ala
1               5                   10

<210> SEQ ID NO 96
<211> LENGTH: 7
<212> TYPE: PRT
<213> ORGANISM: Homo sapiens

<400> SEQUENCE: 96

Gly Ala Ser Thr Arg Ala Thr
1               5

<210> SEQ ID NO 97
<211> LENGTH: 10
<212> TYPE: PRT
<213> ORGANISM: Homo sapiens

<400> SEQUENCE: 97

Gln Gln Tyr Asn Asn Trp Pro Pro Tyr Thr
1               5                   10

<210> SEQ ID NO 98
<211> LENGTH: 5
<212> TYPE: PRT
<213> ORGANISM: Homo sapiens

<400> SEQUENCE: 98

Ser Tyr Ala Met Ser
1               5

<210> SEQ ID NO 99
<211> LENGTH: 17
<212> TYPE: PRT
<213> ORGANISM: Homo sapiens

<400> SEQUENCE: 99

Ser Ile Ser Gly Ser Gly Asp Thr Thr Lys Tyr Thr Asp Ser Val Lys
1               5                   10                  15

Gly

<210> SEQ ID NO 100
<211> LENGTH: 11
<212> TYPE: PRT
<213> ORGANISM: Homo sapiens

<400> SEQUENCE: 100

Asp Gly Ser Gly Arg Ile Asp Pro Phe Ala Leu
1               5                   10

<210> SEQ ID NO 101
<211> LENGTH: 16
<212> TYPE: PRT
<213> ORGANISM: Homo sapiens

<400> SEQUENCE: 101

Arg Ser Ser Arg Ser Leu Val Tyr Ser Asp Gly Asn Ile Tyr Leu Asn
1               5                   10                  15

```
<210> SEQ ID NO 102
<211> LENGTH: 7
<212> TYPE: PRT
<213> ORGANISM: Homo sapiens

<400> SEQUENCE: 102

Lys Val Ser Asn Arg Asp Ser
1               5

<210> SEQ ID NO 103
<211> LENGTH: 9
<212> TYPE: PRT
<213> ORGANISM: Homo sapiens

<400> SEQUENCE: 103

Met Gln Gly Thr His Trp Pro Arg Thr
1               5

<210> SEQ ID NO 104
<211> LENGTH: 5
<212> TYPE: PRT
<213> ORGANISM: Homo sapiens

<400> SEQUENCE: 104

Ser Arg Ser Ser Tyr
1               5

<210> SEQ ID NO 105
<211> LENGTH: 16
<212> TYPE: PRT
<213> ORGANISM: Homo sapiens

<400> SEQUENCE: 105

Gly Ile Tyr His Ser Gly Asn Thr Tyr Asp Asn Pro Ser Leu Lys Ser
1               5                   10                  15

<210> SEQ ID NO 106
<211> LENGTH: 10
<212> TYPE: PRT
<213> ORGANISM: Homo sapiens

<400> SEQUENCE: 106

Ile Val Pro Gly Gly Asp Ala Phe Asp Ile
1               5                   10

<210> SEQ ID NO 107
<211> LENGTH: 11
<212> TYPE: PRT
<213> ORGANISM: Homo sapiens

<400> SEQUENCE: 107

Arg Ala Ser Gln Ser Val Gly Thr Tyr Leu Asn
1               5                   10

<210> SEQ ID NO 108
<211> LENGTH: 7
<212> TYPE: PRT
<213> ORGANISM: Homo sapiens

<400> SEQUENCE: 108

Ala Ala Ser Ser Leu Gln Ser
1               5

<210> SEQ ID NO 109
<211> LENGTH: 9
```

```
<212> TYPE: PRT
<213> ORGANISM: Homo sapiens

<400> SEQUENCE: 109

Gln Gln Ser Tyr Ser Ser Pro Pro Thr
1               5

<210> SEQ ID NO 110
<211> LENGTH: 5
<212> TYPE: PRT
<213> ORGANISM: Homo sapiens

<400> SEQUENCE: 110

Asn Tyr Ala Met His
1               5

<210> SEQ ID NO 111
<211> LENGTH: 17
<212> TYPE: PRT
<213> ORGANISM: Homo sapiens

<400> SEQUENCE: 111

Ile Ile Ser Tyr Asp Gly Asn Asn Lys Tyr Tyr Ala Asp Ser Val Arg
1               5                   10                  15

Gly

<210> SEQ ID NO 112
<211> LENGTH: 12
<212> TYPE: PRT
<213> ORGANISM: Homo sapiens

<400> SEQUENCE: 112

Gly Ser Gly Arg Ala Ala Arg His Trp Phe Asp Pro
1               5                   10

<210> SEQ ID NO 113
<211> LENGTH: 14
<212> TYPE: PRT
<213> ORGANISM: Homo sapiens

<400> SEQUENCE: 113

Thr Gly Thr Ser Ser Asp Val Gly Gly Tyr Asn Tyr Val Ser
1               5                   10

<210> SEQ ID NO 114
<211> LENGTH: 7
<212> TYPE: PRT
<213> ORGANISM: Homo sapiens

<400> SEQUENCE: 114

Asp Val Phe Asn Arg Pro Ser
1               5

<210> SEQ ID NO 115
<211> LENGTH: 12
<212> TYPE: PRT
<213> ORGANISM: Homo sapiens

<400> SEQUENCE: 115

Ser Ser Tyr Thr Ser Ser Val Thr Pro His Trp Val
1               5                   10

<210> SEQ ID NO 116
<211> LENGTH: 7
```

```
<212> TYPE: PRT
<213> ORGANISM: Homo sapiens

<400> SEQUENCE: 116

Ser Ser Asn Phe Tyr Trp Gly
1               5

<210> SEQ ID NO 117
<211> LENGTH: 16
<212> TYPE: PRT
<213> ORGANISM: Homo sapiens

<400> SEQUENCE: 117

Ala Ile Tyr Ser Ser Gly Asn Thr Tyr Tyr Asn Pro Ser Leu Lys Ser
1               5                   10                  15

<210> SEQ ID NO 118
<211> LENGTH: 17
<212> TYPE: PRT
<213> ORGANISM: Homo sapiens

<400> SEQUENCE: 118

His Ser Cys Ser Ser Ala Ser Cys Tyr Pro Pro Gly Phe Trp Phe Asp
1               5                   10                  15

Pro

<210> SEQ ID NO 119
<211> LENGTH: 11
<212> TYPE: PRT
<213> ORGANISM: Homo sapiens

<400> SEQUENCE: 119

Arg Ala Ser Gln Thr Val Ser Tyr Asn Leu Ala
1               5                   10

<210> SEQ ID NO 120
<211> LENGTH: 7
<212> TYPE: PRT
<213> ORGANISM: Homo sapiens

<400> SEQUENCE: 120

Gly Ala Ser Thr Arg Ala Thr
1               5

<210> SEQ ID NO 121
<211> LENGTH: 10
<212> TYPE: PRT
<213> ORGANISM: Homo sapiens

<400> SEQUENCE: 121

Gln Gln Tyr Asn Asn Trp Pro Pro Trp Thr
1               5                   10

<210> SEQ ID NO 122
<211> LENGTH: 7
<212> TYPE: PRT
<213> ORGANISM: Homo sapiens

<400> SEQUENCE: 122

Ser Gly Val Tyr Tyr Trp Ser
1               5

<210> SEQ ID NO 123
<211> LENGTH: 16
```

<212> TYPE: PRT
<213> ORGANISM: Homo sapiens

<400> SEQUENCE: 123

Tyr Ile Ser Asn Thr Gly Asn Thr Tyr Tyr Asn Pro Ser Leu Lys Ser
1               5                   10                  15

<210> SEQ ID NO 124
<211> LENGTH: 18
<212> TYPE: PRT
<213> ORGANISM: Homo sapiens

<400> SEQUENCE: 124

Glu Tyr Cys Ser Gly Gly Asn Cys Tyr Ser Arg Phe Tyr Tyr Tyr Met
1               5                   10                  15

Asp Val

<210> SEQ ID NO 125
<211> LENGTH: 14
<212> TYPE: PRT
<213> ORGANISM: Homo sapiens

<400> SEQUENCE: 125

Thr Gly Ser Ser Ser Asn Ile Gly Ala Gly Tyr Gly Val His
1               5                   10

<210> SEQ ID NO 126
<211> LENGTH: 7
<212> TYPE: PRT
<213> ORGANISM: Homo sapiens

<400> SEQUENCE: 126

Gly Asp Asn Asn Arg Pro Ser
1               5

<210> SEQ ID NO 127
<211> LENGTH: 12
<212> TYPE: PRT
<213> ORGANISM: Homo sapiens

<400> SEQUENCE: 127

Gln Ser Tyr Asp Thr Thr Leu Ser Gly Ser Arg Val
1               5                   10

<210> SEQ ID NO 128
<211> LENGTH: 5
<212> TYPE: PRT
<213> ORGANISM: Homo sapiens

<400> SEQUENCE: 128

Ala Tyr Tyr Trp Asn
1               5

<210> SEQ ID NO 129
<211> LENGTH: 16
<212> TYPE: PRT
<213> ORGANISM: Homo sapiens

<400> SEQUENCE: 129

Glu Val Ser His Gly Gly Ser Ser Asn Tyr Ser Pro Ser Leu Arg Gly
1               5                   10                  15

<210> SEQ ID NO 130
<211> LENGTH: 13

```
<212> TYPE: PRT
<213> ORGANISM: Homo sapiens

<400> SEQUENCE: 130

Gly Ser Pro Val Val Leu Pro Gly Ala Arg Phe Asp Pro
1               5                   10

<210> SEQ ID NO 131
<211> LENGTH: 6
<212> TYPE: PRT
<213> ORGANISM: Homo sapiens

<400> SEQUENCE: 131

Ser Tyr Asn Leu Val Ser
1               5

<210> SEQ ID NO 132
<211> LENGTH: 7
<212> TYPE: PRT
<213> ORGANISM: Homo sapiens

<400> SEQUENCE: 132

Glu Val Asn Lys Arg Pro Ser
1               5

<210> SEQ ID NO 133
<211> LENGTH: 9
<212> TYPE: PRT
<213> ORGANISM: Homo sapiens

<400> SEQUENCE: 133

Cys Ser Tyr Ala Gly Ser Thr Lys Val
1               5

<210> SEQ ID NO 134
<211> LENGTH: 7
<212> TYPE: PRT
<213> ORGANISM: Homo sapiens

<400> SEQUENCE: 134

Ser Gly Gly Tyr Tyr Trp Ser
1               5

<210> SEQ ID NO 135
<211> LENGTH: 16
<212> TYPE: PRT
<213> ORGANISM: Homo sapiens

<400> SEQUENCE: 135

Phe Ile Tyr Tyr Thr Gly Asn Thr Tyr Tyr Asn Pro Ser Leu Lys Ser
1               5                   10                  15

<210> SEQ ID NO 136
<211> LENGTH: 14
<212> TYPE: PRT
<213> ORGANISM: Homo sapiens

<400> SEQUENCE: 136

Asp Cys Ser Gly Gly Ser Cys Pro Glu Ser Tyr Phe Asp Ser
1               5                   10

<210> SEQ ID NO 137
<211> LENGTH: 11
<212> TYPE: PRT
<213> ORGANISM: Homo sapiens
```

<400> SEQUENCE: 137

Arg Ala Ser Gln Ser Val Arg Ser Phe Leu Ala
1               5                   10

<210> SEQ ID NO 138
<211> LENGTH: 7
<212> TYPE: PRT
<213> ORGANISM: Homo sapiens

<400> SEQUENCE: 138

Asp Ala Ser Lys Arg Ala Thr
1               5

<210> SEQ ID NO 139
<211> LENGTH: 10
<212> TYPE: PRT
<213> ORGANISM: Homo sapiens

<400> SEQUENCE: 139

Gln Arg Thr Asn Trp Pro Pro His Leu Thr
1               5                   10

<210> SEQ ID NO 140
<211> LENGTH: 5
<212> TYPE: PRT
<213> ORGANISM: Homo sapiens

<400> SEQUENCE: 140

Ser Tyr Gly Met His
1               5

<210> SEQ ID NO 141
<211> LENGTH: 17
<212> TYPE: PRT
<213> ORGANISM: Homo sapiens

<400> SEQUENCE: 141

Val Ile Trp Phe Asp Gly Ser Asn Lys Tyr Tyr Ala Asp Ser Val Lys
1               5                   10                  15

Gly

<210> SEQ ID NO 142
<211> LENGTH: 10
<212> TYPE: PRT
<213> ORGANISM: Homo sapiens

<400> SEQUENCE: 142

Asp Gly Ile Ala Ala Thr Tyr Ala Asp Tyr
1               5                   10

<210> SEQ ID NO 143
<211> LENGTH: 11
<212> TYPE: PRT
<213> ORGANISM: Homo sapiens

<400> SEQUENCE: 143

Arg Ala Ser Gln Ser Val Arg Ser Tyr Leu Ala
1               5                   10

<210> SEQ ID NO 144
<211> LENGTH: 7
<212> TYPE: PRT
<213> ORGANISM: Homo sapiens

```
<400> SEQUENCE: 144

Gly Ala Ser Asn Arg Ala Thr
1               5

<210> SEQ ID NO 145
<211> LENGTH: 9
<212> TYPE: PRT
<213> ORGANISM: Homo sapiens

<400> SEQUENCE: 145

Gln Gln Arg Ser Asn Trp Pro Ile Thr
1               5

<210> SEQ ID NO 146
<211> LENGTH: 8
<212> TYPE: PRT
<213> ORGANISM: Homo sapiens

<400> SEQUENCE: 146

Ser Leu Ser Ser Tyr Tyr Met Ser
1               5

<210> SEQ ID NO 147
<211> LENGTH: 17
<212> TYPE: PRT
<213> ORGANISM: Homo sapiens

<400> SEQUENCE: 147

Thr Ile Asn Pro Gly Gly Ser Glu Lys Ser Tyr Val Asp Ser Val Lys
1               5                   10                  15

Gly

<210> SEQ ID NO 148
<211> LENGTH: 13
<212> TYPE: PRT
<213> ORGANISM: Homo sapiens

<400> SEQUENCE: 148

Pro Arg Tyr Cys Thr Ser Gly Gly Cys Tyr Phe Asp Asn
1               5                   10

<210> SEQ ID NO 149
<211> LENGTH: 14
<212> TYPE: PRT
<213> ORGANISM: Homo sapiens

<400> SEQUENCE: 149

Thr Ala Thr Asn Ser Asp Val Gly Asp Tyr Lys Ser Val Ser
1               5                   10

<210> SEQ ID NO 150
<211> LENGTH: 7
<212> TYPE: PRT
<213> ORGANISM: Homo sapiens

<400> SEQUENCE: 150

Asp Val Gly Arg Arg Pro Ser
1               5

<210> SEQ ID NO 151
<211> LENGTH: 9
<212> TYPE: PRT
<213> ORGANISM: Homo sapiens
```

<400> SEQUENCE: 151

Cys Ile Tyr Val Gly Arg Ser Ser Val
1               5

<210> SEQ ID NO 152
<211> LENGTH: 6
<212> TYPE: PRT
<213> ORGANISM: Homo sapiens

<400> SEQUENCE: 152

Ser Gly Tyr Tyr Trp Gly
1               5

<210> SEQ ID NO 153
<211> LENGTH: 16
<212> TYPE: PRT
<213> ORGANISM: Homo sapiens

<400> SEQUENCE: 153

Ser Met Tyr His Ser Gly Arg Thr Tyr Tyr Asn Pro Ser Leu Lys Ser
1               5                   10                  15

<210> SEQ ID NO 154
<211> LENGTH: 15
<212> TYPE: PRT
<213> ORGANISM: Homo sapiens

<400> SEQUENCE: 154

Gly Phe Asp Thr Ser Gly Ser His Arg Pro Leu Ser Thr Asp Tyr
1               5                   10                  15

<210> SEQ ID NO 155
<211> LENGTH: 13
<212> TYPE: PRT
<213> ORGANISM: Homo sapiens

<400> SEQUENCE: 155

Ser Gly Ser Ser Ser Asn Ile Gly Asn Asn Tyr Val Ser
1               5                   10

<210> SEQ ID NO 156
<211> LENGTH: 7
<212> TYPE: PRT
<213> ORGANISM: Homo sapiens

<400> SEQUENCE: 156

Asp Asn Asn Lys Arg Pro Ser
1               5

<210> SEQ ID NO 157
<211> LENGTH: 11
<212> TYPE: PRT
<213> ORGANISM: Homo sapiens

<400> SEQUENCE: 157

Gly Thr Trp Asp Ser Ser Leu Ser Ala Tyr Val
1               5                   10

<210> SEQ ID NO 158
<211> LENGTH: 5
<212> TYPE: PRT
<213> ORGANISM: Homo sapiens

<400> SEQUENCE: 158

Asn Tyr Gly Met His
1               5

<210> SEQ ID NO 159
<211> LENGTH: 17
<212> TYPE: PRT
<213> ORGANISM: Homo sapiens

<400> SEQUENCE: 159

Val Ile Trp Ser Asp Gly Ser Asp Lys Tyr Tyr Ala Asp Ser Val Glu
1               5                   10                  15

Gly

<210> SEQ ID NO 160
<211> LENGTH: 10
<212> TYPE: PRT
<213> ORGANISM: Homo sapiens

<400> SEQUENCE: 160

Glu Pro Ser Ser Thr Trp Ala Phe Asp Tyr
1               5                   10

<210> SEQ ID NO 161
<211> LENGTH: 14
<212> TYPE: PRT
<213> ORGANISM: Homo sapiens

<400> SEQUENCE: 161

Thr Gly Thr Ser Ser Asp Val Gly Gly Tyr Asn Leu Val Ser
1               5                   10

<210> SEQ ID NO 162
<211> LENGTH: 7
<212> TYPE: PRT
<213> ORGANISM: Homo sapiens

<400> SEQUENCE: 162

Glu Asp Ile Lys Gly Pro Ser
1               5

<210> SEQ ID NO 163
<211> LENGTH: 10
<212> TYPE: PRT
<213> ORGANISM: Homo sapiens

<400> SEQUENCE: 163

Cys Ser Tyr Ala Gly Thr Gly Thr Leu Val
1               5                   10

<210> SEQ ID NO 164
<211> LENGTH: 5
<212> TYPE: PRT
<213> ORGANISM: Homo sapiens

<400> SEQUENCE: 164

Ser Arg Ser Ser Tyr
1               5

<210> SEQ ID NO 165
<211> LENGTH: 16
<212> TYPE: PRT
<213> ORGANISM: Homo sapiens

<400> SEQUENCE: 165

Gly Ile Tyr His Ser Gly Asn Thr Tyr Asp Asn Pro Ser Leu Lys Ser
1               5                   10                  15

<210> SEQ ID NO 166
<211> LENGTH: 10
<212> TYPE: PRT
<213> ORGANISM: Homo sapiens

<400> SEQUENCE: 166

Ile Val Pro Gly Gly Asp Ala Phe Asp Ile
1               5                   10

<210> SEQ ID NO 167
<211> LENGTH: 5
<212> TYPE: PRT
<213> ORGANISM: Homo sapiens

<400> SEQUENCE: 167

Ser Tyr Ala Met Ile
1               5

<210> SEQ ID NO 168
<211> LENGTH: 17
<212> TYPE: PRT
<213> ORGANISM: Homo sapiens

<400> SEQUENCE: 168

Gly Ile Ser Gly Ser Gly Ser Thr Thr Tyr Tyr Ala Asp Ser Val Lys
1               5                   10                  15

Gly

<210> SEQ ID NO 169
<211> LENGTH: 11
<212> TYPE: PRT
<213> ORGANISM: Homo sapiens

<400> SEQUENCE: 169

Gly Ala Trp Glu Ile Pro Thr Tyr Phe Asp Asn
1               5                   10

<210> SEQ ID NO 170
<211> LENGTH: 11
<212> TYPE: PRT
<213> ORGANISM: Homo sapiens

<400> SEQUENCE: 170

Arg Ala Ser Gln Ser Ile Arg Asn Asn Leu Ala
1               5                   10

<210> SEQ ID NO 171
<211> LENGTH: 7
<212> TYPE: PRT
<213> ORGANISM: Homo sapiens

<400> SEQUENCE: 171

Gly Ala Ser Thr Arg Ala Thr
1               5

<210> SEQ ID NO 172
<211> LENGTH: 11
<212> TYPE: PRT
<213> ORGANISM: Homo sapiens

<400> SEQUENCE: 172

Gln Gln Tyr Asn Asn Trp Pro Pro Thr Trp Thr
1               5                   10

<210> SEQ ID NO 173
<211> LENGTH: 5
<212> TYPE: PRT
<213> ORGANISM: Homo sapiens

<400> SEQUENCE: 173

Ile Tyr Ala Met Thr
1               5

<210> SEQ ID NO 174
<211> LENGTH: 17
<212> TYPE: PRT
<213> ORGANISM: Homo sapiens

<400> SEQUENCE: 174

Thr Ile Thr Ser Gly Gly Val Ser Ile Tyr Tyr Ala Asp Ser Ile Lys
1               5                   10                  15

Gly

<210> SEQ ID NO 175
<211> LENGTH: 16
<212> TYPE: PRT
<213> ORGANISM: Homo sapiens

<400> SEQUENCE: 175

Asp Gly Asn Cys Asp Glu Thr Ser Cys Tyr Leu Arg Gly Met Asp Val
1               5                   10                  15

<210> SEQ ID NO 176
<211> LENGTH: 13
<212> TYPE: PRT
<213> ORGANISM: Homo sapiens

<400> SEQUENCE: 176

Ser Gly Ser Arg Ser Asp Ile Gly Ser Lys Leu Val Ser
1               5                   10

<210> SEQ ID NO 177
<211> LENGTH: 7
<212> TYPE: PRT
<213> ORGANISM: Homo sapiens

<400> SEQUENCE: 177

Asp Thr Tyr Lys Arg Pro Ser
1               5

<210> SEQ ID NO 178
<211> LENGTH: 12
<212> TYPE: PRT
<213> ORGANISM: Homo sapiens

<400> SEQUENCE: 178

Gly Ser Trp Gly Asn Ser Glu Asn Phe Tyr Tyr Val
1               5                   10

<210> SEQ ID NO 179
<211> LENGTH: 5
<212> TYPE: PRT
<213> ORGANISM: Homo sapiens

<400> SEQUENCE: 179

```
Ser Arg Ser Tyr Tyr
1               5

<210> SEQ ID NO 180
<211> LENGTH: 16
<212> TYPE: PRT
<213> ORGANISM: Homo sapiens

<400> SEQUENCE: 180

Ser Ile Tyr Tyr Ser Gly Ser Thr Leu Tyr Asn Pro Ser Leu Lys Ser
1               5                   10                  15

<210> SEQ ID NO 181
<211> LENGTH: 8
<212> TYPE: PRT
<213> ORGANISM: Homo sapiens

<400> SEQUENCE: 181

Met Gly Glu Gly Gly Arg Asp Tyr
1               5

<210> SEQ ID NO 182
<211> LENGTH: 11
<212> TYPE: PRT
<213> ORGANISM: Homo sapiens

<400> SEQUENCE: 182

Arg Ala Ser Gln Ser Ile Ser Ser Trp Leu Ala
1               5                   10

<210> SEQ ID NO 183
<211> LENGTH: 7
<212> TYPE: PRT
<213> ORGANISM: Homo sapiens

<400> SEQUENCE: 183

Asp Ala Ser Ser Leu Glu Arg
1               5

<210> SEQ ID NO 184
<211> LENGTH: 9
<212> TYPE: PRT
<213> ORGANISM: Homo sapiens

<400> SEQUENCE: 184

Gln His Tyr Asn Gly Tyr Ser Arg Thr
1               5

<210> SEQ ID NO 185
<211> LENGTH: 7
<212> TYPE: PRT
<213> ORGANISM: Homo sapiens

<400> SEQUENCE: 185

Arg Gly Asp Phe Tyr Trp Ser
1               5

<210> SEQ ID NO 186
<211> LENGTH: 16
<212> TYPE: PRT
<213> ORGANISM: Homo sapiens

<400> SEQUENCE: 186

Tyr Ile Tyr Ser Thr Gly Asp Val Tyr Tyr Asn Pro Ser Leu Lys Ser
```

<210> SEQ ID NO 187
<211> LENGTH: 14
<212> TYPE: PRT
<213> ORGANISM: Homo sapiens

<400> SEQUENCE: 187

Glu Gly Gln Tyr Cys Ser Gly Gly Ser Cys Tyr Pro Glu Tyr
1               5                   10

<210> SEQ ID NO 188
<211> LENGTH: 11
<212> TYPE: PRT
<213> ORGANISM: Homo sapiens

<400> SEQUENCE: 188

Ser Gly Asp Asn Leu Gly His Lys Phe Thr Cys
1               5                   10

<210> SEQ ID NO 189
<211> LENGTH: 7
<212> TYPE: PRT
<213> ORGANISM: Homo sapiens

<400> SEQUENCE: 189

Gln Asp His Lys Arg Pro Ser
1               5

<210> SEQ ID NO 190
<211> LENGTH: 9
<212> TYPE: PRT
<213> ORGANISM: Homo sapiens

<400> SEQUENCE: 190

Gln Ala Trp Ala Phe Pro Tyr Val Val
1               5

<210> SEQ ID NO 191
<211> LENGTH: 5
<212> TYPE: PRT
<213> ORGANISM: Homo sapiens

<400> SEQUENCE: 191

Asn Tyr Trp Met Ser
1               5

<210> SEQ ID NO 192
<211> LENGTH: 17
<212> TYPE: PRT
<213> ORGANISM: Homo sapiens

<400> SEQUENCE: 192

Asn Ile Lys Glu Asp Gly Ser Asp Arg Tyr Tyr Val Asp Ser Val Lys
1               5                   10                  15

Gly

<210> SEQ ID NO 193
<211> LENGTH: 15
<212> TYPE: PRT
<213> ORGANISM: Homo sapiens

<400> SEQUENCE: 193

Ile Val Gly Val Ile Pro Ser Ala Asp Pro Tyr Tyr Leu Asp Ser

<210> SEQ ID NO 194
<211> LENGTH: 14
<212> TYPE: PRT
<213> ORGANISM: Homo sapiens

<400> SEQUENCE: 194

Thr Gly Thr Ser Leu Asn Ile Gly Thr Tyr Asn Leu Ile Ser
1               5                   10

<210> SEQ ID NO 195
<211> LENGTH: 7
<212> TYPE: PRT
<213> ORGANISM: Homo sapiens

<400> SEQUENCE: 195

Glu Gly Asn Arg Arg Pro Pro
1               5

<210> SEQ ID NO 196
<211> LENGTH: 10
<212> TYPE: PRT
<213> ORGANISM: Homo sapiens

<400> SEQUENCE: 196

Cys Ser Phe Ala Gly Arg Val Ser Leu Val
1               5                   10

<210> SEQ ID NO 197
<211> LENGTH: 5
<212> TYPE: PRT
<213> ORGANISM: Homo sapiens

<400> SEQUENCE: 197

Ser His Tyr Trp Asn
1               5

<210> SEQ ID NO 198
<211> LENGTH: 16
<212> TYPE: PRT
<213> ORGANISM: Homo sapiens

<400> SEQUENCE: 198

Ser Ile Tyr His Ser Gly Ser Thr Asn Tyr Asn Pro Ser Leu Lys Ser
1               5                   10                  15

<210> SEQ ID NO 199
<211> LENGTH: 8
<212> TYPE: PRT
<213> ORGANISM: Homo sapiens

<400> SEQUENCE: 199

Asp Tyr Tyr Tyr Tyr Met Asp Val
1               5

<210> SEQ ID NO 200
<211> LENGTH: 11
<212> TYPE: PRT
<213> ORGANISM: Homo sapiens

<400> SEQUENCE: 200

Ser Gly Asp Ala Leu Pro Asp Lys Tyr Ala Tyr
1               5                   10

```
<210> SEQ ID NO 201
<211> LENGTH: 7
<212> TYPE: PRT
<213> ORGANISM: Homo sapiens

<400> SEQUENCE: 201

Lys Asp Ser Glu Arg Pro Ser
1               5

<210> SEQ ID NO 202
<211> LENGTH: 11
<212> TYPE: PRT
<213> ORGANISM: Homo sapiens

<400> SEQUENCE: 202

Lys Ser Ala Asp Ser Ser Gly Thr Tyr Trp Val
1               5                   10

<210> SEQ ID NO 203
<211> LENGTH: 5
<212> TYPE: PRT
<213> ORGANISM: Homo sapiens

<400> SEQUENCE: 203

Ser His Tyr Met Ser
1               5

<210> SEQ ID NO 204
<211> LENGTH: 16
<212> TYPE: PRT
<213> ORGANISM: Homo sapiens

<400> SEQUENCE: 204

Ile Ile Tyr Ser Gly Gly Gly Thr Tyr Tyr Ala Asp Ser Val Lys Gly
1               5                   10                  15

<210> SEQ ID NO 205
<211> LENGTH: 13
<212> TYPE: PRT
<213> ORGANISM: Homo sapiens

<400> SEQUENCE: 205

Ile Tyr Arg Ser Gly Asn Thr Gly Tyr Ser Tyr Asp Tyr
1               5                   10

<210> SEQ ID NO 206
<211> LENGTH: 11
<212> TYPE: PRT
<213> ORGANISM: Homo sapiens

<400> SEQUENCE: 206

Ser Gly Asp Lys Leu Gly Ser Lys Tyr Ala Cys
1               5                   10

<210> SEQ ID NO 207
<211> LENGTH: 7
<212> TYPE: PRT
<213> ORGANISM: Homo sapiens

<400> SEQUENCE: 207

Glu Asp Lys Lys Arg Pro Ser
1               5

<210> SEQ ID NO 208
```

```
<211> LENGTH: 11
<212> TYPE: PRT
<213> ORGANISM: Homo sapiens

<400> SEQUENCE: 208

Gln Ala Trp Asp Ser Ser Thr Ser His Val Val
1               5                   10

<210> SEQ ID NO 209
<211> LENGTH: 11
<212> TYPE: PRT
<213> ORGANISM: Homo sapiens

<400> SEQUENCE: 209

Gly Glu Leu His Gly Pro Thr Thr Glu Glu Glu
1               5                   10

<210> SEQ ID NO 210
<211> LENGTH: 5
<212> TYPE: PRT
<213> ORGANISM: Homo sapiens

<400> SEQUENCE: 210

Trp Gly Pro Phe Ala
1               5
```

ANTIBODY-BASED THERAPY OF TRANSTHYRETIN (TTR) AMYLOIDOSIS AND HUMAN-DERIVED ANTIBODIES THEREFOR

SEQUENCE LISTING

The instant application contains a Sequence Listing which has been submitted electronically in ASCII format and is hereby incorporated by reference in its entirety. Said ASCII copy, created on Jun. 26, 2024, is named "51705-008004_Sequence_Listing_6_26_24_ST25.txt" and is 151,844 bytes in size.

FIELD OF THE INVENTION

The present invention generally relates to antibody-based therapy of transthyretin (TTR) amyloidosis. In particular, the present invention relates to novel molecules specifically binding to human transthyretin (TTR) and antigens thereof, particularly human-derived recombinant antibodies as well as fragments, derivatives and variants thereof that recognize the misfolded, misassembled or aggregated forms of TTR or a fragments thereof, and which are useful in the treatment of diseases and conditions induced by such pathogenic TTR isoforms.

In addition, the present invention relates to pharmaceutical and diagnostic compositions comprising such binding molecules, antibodies and mimics thereof valuable both as a diagnostic tool to identify diseases associated with TTR amyloidosis and also a passive vaccination strategy for treating disorders related to diseases associated with TTR amyloidosis such as Familial Amyloid Polyneuropathy (FAP), Familial Amyloid Cardiomyopathy (FAC), Senile Systemic Amyloidosis (SSA), systemic familial amyloidosis, leptomeningeal/Central Nervous System (CNS) amyloidosis including Alzheimer disease, TTR-related ocular amyloidosis, TTR-related renal amyloidosis, TTR-related hyperthyroxinemia, TTR-related ligament amyloidosis including carpal tunnel syndrome, rotator cuff tears and lumbar spinal stenosis, and preeclampsia.

Furthermore, the present invention relates to a method of diagnosing a disease or condition induced by pathogenic TTR isoforms, such as misfolded and/or aggregated TTR present in amyloid deposits, wherein levels of pathological TTR isoforms are assayed in a sample of a body fluid from a subject after administration of an anti-TTR antibody, wherein when compared to a control sample taken before administration the presence or alteration in the level of the pathogenic TTR isoforms, for example as determined by the presence of an immuno-complex of TTR and the anti-TTR antibody indicate the disease and/or condition.

BACKGROUND OF THE INVENTION

Transthyretin (TTR), previously named prealbumin, is a soluble protein of 127 amino-acids (NCBI reference sequence: NP_000362.1) which is involved in thyroxin and retinol transport in the body. TTR is secreted in the blood by the liver and in the cerebrospinal fluid by the choroid plexus, and is also expressed in specific tissues like the pancreatic alpha cells or retinal epithelium. TTR synthesis starts at embryonic ages and continues during the whole life. It is present at high concentration in the plasma (3.6-7.2 µM) and CSF (0.04-0.4 µM) and typically forms under physiological conditions a soluble homotetramer of ~55 kDa.

Under specific conditions which have been poorly elucidated and may include acidic pH, oxidative stress and local factors, the TTR protein adopts an alternative tridimensional conformation and becomes toxic.

The toxicity of misfolded TTR protein has been discovered by investigating a rare, autosomal dominant, neurodegenerative disorder named Familial Amyloid Polyneuropathy (FAP), which affects adult people in their midlife (Planté-Bordeneuve et al., Lancet Neurol. 10 (2011), 1086-1097). FAP is characterized by progressive sensory, motor and autonomic impairments leading to death a decade after diagnosis. Nerve lesions are associated with the deposition of amorphous aggregates and amyloid fibrils made of TTR protein. The Val30Met substitution is the most frequent mutation causing FAP, especially in areas where the disease is endemic such as northern Portugal, but more than 100 different mutations have been already identified in the TTR gene; see Table IV below. The pathophysiological mechanism at play is identical for all the pathogenic mutations, in that the mutations alter the structural stability of TTR tetramer, promoting TTR misfolding and leading to the formation of toxic TTR species (Saraiva et al., Curr. Med. Chem. 19 (2012), 2304-2311).

TTR toxicity is also observed as a consequence of the Val122Ile mutation, which is found with high frequency (3-5%) in the African-American and West African populations. This mutation is associated with Familial Amyloid Cardiomyopathy (FAC), a condition where massive TTR accumulation in the myocardium leads to cardiac weaknesses and ultimately cardiac failure (Ruberg et al., Circulation. 126 (2012), 1286-1300).

Mutations in the TTR protein sequence are not a strict requirement for TTR toxicity, and the wild-type TTR protein is also prone to misfolding and formation of toxic aggregates. For example, Senile Systemic Amyloidosis (SSA) is characterized by cardiac weakness and the accumulation of wild-type TTR aggregates in the myocardium (Ikeda, Amyloid. 18 Suppl 1(2011), 155-156; Dungu et al., Heart. 98 (2012), 1546-1554). Wild-type TTR deposits are also observed in multiple cases of ligament and tendon inflammations including carpal tunnel syndrome, rotator cuff tears and lumbar spinal stenosis (Sueyoshi et al., Hum. Pathol. 42 (2011), 1259-1264; Gioeva et al., Amyloid. 20 (2013), 1-6). Furthermore, TTR amyloidosis has been recently reported in the placenta of mothers suffering from preeclampsia (Kalkunte et al., Am. J. Pathol. 183 (2013) 1425-1436).

Treatments for diseases with TTR amyloidosis are limited and mainly invasive, wherein primarily the treatment is due to the symptoms. In the case of FAP, treatments rely on analgesics for the management of neuropathic pain, on liver transplantation to remove the main source for mutated TTR protein, and on treatment with Tafamidis. Tafamidis is a small molecule which binds to TTR tetramer and stabilizes its conformation. It acts against the dissociation of the TTR tetramer, the rate limiting step in the misfolding pathway leading to the formation of toxic TTR species. Tafamidis has been approved for the treatment of FAP in Europe but has not been approved in the USA, and its therapeutic efficacy is limited, in the best of cases, to slowing down disease progression. There is currently no treatment available targeting misfolded TTR protein.

In view of the above, novel therapeutic strategies are needed for an efficacious and safe therapy of diseases associated with TTR amyloidosis.

This technical problem is solved by the embodiments characterized in the claims and described further below and illustrated in the Examples and Figures.

SUMMARY OF THE INVENTION

The present invention provides anti-transthyretin (TTR) antibodies and equivalent TTR-binding molecules for use in the prophylactic or therapeutic treatment of diseases and conditions associated with TTR amyloidosis. More specifically, therapeutically useful human-derived recombinant antibodies as well as fragments and derivatives thereof that recognize misfolded, misassembled or aggregated forms of TTR are provided.

Misfolded TTR aggregates are associated with markers of cellular stress, oxidative stress, inflammatory response and apoptosis many years before symptom onset (Macedo et al., Mol. Med. 13 (2007), 584-91). The natural capacity of the body to recognize abnormally folded proteins and degrade them is a protective factor, and differences between patients in their capacity to eliminate toxic TTR proteins certainly contribute to differences in age of disease onset and speed of disease progression. In support of this hypothesis, it has been shown that patients receiving a liver transplantation from a FAP donor quickly develop antibodies against the pathogenic TTR protein (Ando et al., Transplantation. 73 (2002), 751-755), and that FAP patients with high antibody titers against the mutated TTR protein have a later disease onset than patients without such antibodies (Obayashi et al., Clin. Chim. Acta. 419 (2013), 127-131). In addition, active immunization against the pathogenic TTR conformation has been shown to almost completely remove TTR depositions in FAP transgenic mice (Terazaki et al., Lab. Invest. 86 (2006), 23-31).

However, though it might have seem tempting to investigate an immune-based strategy for therapeutic intervention hitherto the use of anti-TTR antibodies for the treatment of TTR related diseases has not been pursued. For example, in international application WO2010/030203 a particular isolated mouse monoclonal antibody for TTR has been described and proposed for use in screening for FAP and in research and treatment of associated diseases. However, since mouse monoclonal antibodies induce human antimouse antibody (HAMA) response they are not suitable for therapy in human. Hence, since the international application lapsed and no subsequent development published yet, apparently a therapeutic antibody-based approach has not been followed. Rather, so far for anti-TTR antibodies only their diagnostic utility for patients with TTR amyloidosis has been further investigated; see, e.g., Phay M. et al., Rejuvenation Res. 2013 Oct. 28. [Epub ahead of print].

In contrast, experiments performed in accordance with the present invention were successful in the isolation of human-derived monoclonal TTR-specific antibodies which maturated in the human body and are specific for misfolded, misassembled, mutated, and/or aggregated TTR species and/or fragments thereof. The human subjects and patients, respectively, being the source of the B cells from which the human-derived monoclonal anti-TTR antibodies and the cDNA encoding their variable domain, respectively, have been isolated, did not show a substantial amount of misfolded TTR and were symptom-free of conditions associated with pathogenic isoforms. However, in another embodiment of the present invention, the source of the B cells from which the human-derived monoclonal anti-TTR antibodies and the cDNA encoding their variable domain, respectively, might be isolated are patients showing symptoms of a disease and/or disorder associated with TTR amyloidosis. Therefore, it is prudent to expect that the human monoclonal anti-TTR antibodies of the present invention and derivatives thereof besides being non-immunogenic in human exhibit a therapeutically beneficial effect.

The present invention is thus directed to human-derived recombinant antibodies, antigen-binding fragments and similar antigen-binding molecules which are capable of specifically recognizing TTR. If not indicated otherwise, by "specifically recognizing TTR", "antibody specific to/for TTR" and "anti-TTR antibody" antibodies are meant which specifically, generally, and collectively binds to the native monomeric form of TTR; antibodies binding specifically to either forms of TTR, e.g. mutated TTR, oligomeric, fibrillar and/or non-fibrillar TTR. Provided herein are human-derived antibodies selective for full-length and/or fragments and/or misfolded, misassembled and/or aggregated forms of TTR.

As mentioned before, preferably the anti-TTR antibody of the present invention is a recombinant antibody, wherein at least one, preferably two or more preferably all three complementarity determining regions (CDRs) of the variable heavy and/or light chain, and/or substantially the entire variable region are encoded by a cDNA derived from an mRNA obtained from a human memory B cell which produced an anti-TTR antibody. In a preferred embodiment, the anti-TTR antibody of the present invention displays, in any combination one more of the binding and biological properties as demonstrated for the subject antibodies illustrated in the appended Examples and Figures, preferably one more of the binding and biological properties as demonstrated for exemplary antibodies NI-301.59.F1, NI-301.35G11, and NI-301.37F1.

In a particularly preferred embodiment of the present invention, the anti-TTR antibody or TTR-binding fragment thereof demonstrates the immunological binding characteristics of an antibody characterized by the variable regions $V_H$ and/or $V_L$ as set forth in FIGS. 1A-1T.

The antigen-binding fragment of the antibody can be a single chain Fv fragment, an F(ab') fragment, an F(ab) fragment, and an F(ab')$_2$ fragment, or any other antigen-binding fragment. In a specific embodiment, infra, the antibody or fragment thereof is a human IgG isotype antibody. Alternatively, the antibody is a chimeric human-rodent or rodentized antibody such as murine or murinized, rat or ratinized antibody, the rodent versions being particularly useful for diagnostic methods and studies in animals.

Furthermore, the present invention relates to compositions comprising the antibody of the present invention or active fragments thereof and to immunotherapeutic and immunodiagnostic methods using such compositions in the prevention, diagnosis or treatment of disorders associated with TTR amyloidosis, wherein an effective amount of the composition is administered to a patient in need thereof.

The present invention also relates to polynucleotides encoding at least a variable region of an immunoglobulin chain of the antibody of the invention. Preferably, said variable region comprises at least one complementarity determining region (CDR) of the $V_H$ and/or $V_L$ of the variable region as set forth in FIGS. 1A-1T. In a preferred embodiment of the present invention, the polynucleotide is a cDNA, preferably derived from mRNA obtained from human memory B cells which produce antibodies reactive with mutant, misfolded, misassembled and/or aggregated TTR species.

Accordingly, the present invention also encompasses vectors comprising said polynucleotides and host cells transformed therewith as well as their use for the production of an antibody and equivalent binding molecules which are specific for TTR. In a further embodiment of the present invention, the antibodies or binding molecules are capable of binding misfolded, misassembled or aggregated TTR species or fragments thereof. Means and methods for the recombinant production of antibodies and mimics thereof as well as methods of screening for competing binding molecules, which may or may not be antibodies, are known in the art. However, as described herein, in particular with respect to therapeutic applications in human the antibody of the present invention is a human antibody in the sense that application of said antibody is substantially free of an immune response directed against such antibody otherwise observed for chimeric and even humanized antibodies.

Furthermore, disclosed herein are compositions and methods that can be used to identify TTR, in particular mutated, misfolded, misassembled, or aggregated TTR species or fragments in samples and/or in vivo. The disclosed anti-TTR antibodies and binding fragments thereof can be used to screen human blood, plasma, serum, saliva, peritoneal fluid, cerebrospinal fluid ("CSF"), and urine for the presence of TTR and/or mutated, misfolded, misassembled, or aggregated TTR species or fragments thereof in samples, for example, by using ELISA-based or surface adapted assay. In one embodiment the present invention relates to a method of diagnosing or monitoring the progression of a disorder related to mutated, misfolded, misassembled, or aggregated TTR species or fragments thereof in a subject, the method comprising determining the presence of mutated, misfolded, misassembled, or aggregated TTR species or fragments in a sample from the subject to be diagnosed with at least one antibody of the present invention or an TTR binding molecule and/or binding molecules for misfolded, misassembled, or aggregated TTR species or fragments having substantially the same binding specificities of any one thereof, wherein the presence of misfolded, misassembled, or aggregated TTR species or fragments is indicative of the disorder.

Furthermore, in one embodiment of the present invention the anti-TTR antibodies and TTR-binding molecules comprising at least one CDR of an antibody of the present invention are provided for the preparation of a composition for in vivo detection (also called in vivo imaging) of or targeting a therapeutic and/or diagnostic agent to TTR, in particular mutated, misfolded, misassembled, or aggregated TTR species or fragments in the human or animal body. The methods and compositions disclosed herein can aid in disorders associated with TTR amyloidosis and characterized, e.g., by the occurrence of forms of TTR and can be used to monitor disease progression and therapeutic efficacy of the therapy provided to the subject, for example in in vivo imaging related diagnostic methods. Therefore, in one embodiment the anti-TTR antibody and/or TTR binding molecule of the present invention is provided, wherein said in vivo detection (imaging) comprises scintigraphy, positron emission tomography (PET), single photon emission tomography (SPECT), near infrared (NIR) optical imaging or magnetic resonance imaging (MRI).

Hence, it is a particular object of the present invention to provide methods for treating, diagnosing or preventing a disease associated with TTR amyloidosis. The methods comprise administering an effective concentration of a preferably human antibody or antibody derivative to the subject where the antibody targets TTR or fragments thereof, preferably misfolded, misassembled, or aggregated TTR species or fragments thereof.

In a further aspect the present invention provides a peptide having an epitope of TTR, preferably of misfolded, misassembled, or aggregated TTR species or fragments thereof specifically recognized by an antibody of the present invention. Said peptide comprises or consists of an amino acid sequence as indicated below in the detailed description and in the examples or a modified sequence thereof in which one or more amino acids are substituted, deleted and/or added, with the proviso that the peptide is still recognized by the cognate antibody. As mentioned, such peptide can be used as an antigen, i.e. being an immunogen and thus useful for eliciting an immune response in a subject and stimulating the production of an antibody of the present invention in vivo. Accordingly, the peptide of the present invention is particularly useful as a vaccine.

Additionally, the present invention provides a method for diagnosing diseases associated with TTR amyloidosis in a subject, comprising a step of determining the presence of an antibody that binds to said peptide in a biological sample of said subject.

In a further aspect, the present invention relates to a method of diagnosing a disease associated with TTR amyloidosis, monitoring the treatment of the disease with an anti-TTR antibody or determining the diagnostic or therapeutic utility of an anti-TTR antibody comprising assaying the level of misfolded and/or aggregated TTR in a sample, for example blood obtained from a subject following administration of an anti-TTR antibody to the subject, wherein the presence or elevated the level of misfolded and/or aggregated TTR in the sample of the subject compared to the control such as a sample obtained from the subject prior to administration of the anti-TTR antibody indicates a disease associated with TTR amyloidosis.

In one preferred embodiment of the present invention, in particular when using non-human animals for testing recombinant human-derived antibodies as illustrated in Example 13 and other anti-TTR antibodies intended for use in humans in general the level of misfolded and/or aggregated TTR in the sample is assayed by determining a complex formed between the anti-TTR antibody and the misfolded and/or aggregated TTR, for example by immuno-precipitation with an anti-human IgG or anti-idiotypic antibody.

With respect to the diagnostic aspect in particular for a human subject and patient, the presence and elevated level of misfolded and/or aggregated TTR and complex thereof with the anti-TTR antibody, respectively, indicates the presence of TTR amyloid deposits in the human body, for example in the heart, peripheral nervous system (PNS), eyes, muscles, gastro-intestinal tract, kidneys, vascular system and the central nervous system (CNS) of a patient or subject. Thus, the method of the present invention allows the identification and determination of a disease associated with TTR amyloidosis in the subject body on the one hand and removal of TTR deposits from patient's body on the other, thereby also indicating the therapeutic progress of a given treatment and efficacy of a drug for the treatment of TTR amyloidosis such as an anti-TTR antibody.

Hence, as demonstrated in Example 13 the anti-TTR antibody of the present invention is capable of binding misfolded and/or aggregated TTR with sufficient affinity to alter the stability of pathological TTR deposits such as to capture and remove misfolded and/or aggregated TTR from the deposits into a body fluid, in particular blood. The specified time interval following administration, i.e. the time frame after which the level of pathological TTR and complex with the anti-TTR antibody, respectively, is measured is determined by a practicing physician. Normally, a time interval less than a week is used. In a preferred embodiment, the level of pathological TTR in a sample from a patient or subject after administration of an anti-TTR antibody or antigen-binding fragment thereof to the patient or subject is determined after less than or equal to 48 hours; see also Example 13.

The present invention also relates to the use of any anti-TTR antibody and TTR-binding molecule in the method described above. However, due to the advantageous properties and in particular because being human-derived the use of an anti-TTR antibody of the present disclosed herein is preferred. In a preferred embodiment, the antibody shows substantially the same binding and biological activities as any antibody selected from NI-301.59F1, NI-301.35G11, NI-301.37F1, NI-301.2F5, NI-301.28B3, NI-301.119C12, NI-301.5D8, NI-301.9D5, NI-301.104F5, NI-301.21F10, NI-301.9G12, NI-301.12D3, NI-301.37F1-PIMC, NI-301.44E4, NI-301.18C4, NI-301.11A10, NI-301.3C9, NI-301.14D8, NI-301.9X4, and NI-301.14C3. The anti-TTR antibody can also be altered to facilitate the handling of the method of diagnosing including the labeling of the antibody as described in detail below.

Further embodiments of the present invention will be apparent from the description and Examples that follow.

BRIEF DESCRIPTION OF THE DRAWINGS

FIGS. 1A-1T: FIG. 1A: Amino acid sequences of the variable heavy chain (VH) region (SEQ ID NO: 2) and the variable kappa light chain (VL) region (SEQ ID NO: 4) of human antibody NI-301.59F1. FIG. 1B: Amino acid sequences of the VH region (SEQ ID NO: 6) and the VL region (SEQ ID NO: 8) of human antibody NI-301.35G11. FIG. 1C: Amino acid sequences of the VH region (SEQ ID NO: 10) and the VL region (SEQ ID NO: 12) of human antibody NI-301.37F1. FIG. 1D: Amino acid sequences of the VH region (SEQ ID NO: 14) and the VL region (SEQ ID NO: 16) of human antibody NI-301.2F5. FIG. 1E: Amino acid sequences of the VH region (SEQ ID NO: 18) and the VL region (SEQ ID NO: 20) of human antibody NI-301.28B3. FIG. 1F: Amino acid sequences of the VH region (SEQ ID NO: 22) and the VL region (SEQ ID NO: 24) of human antibody NI-301.119C12. FIG. 1G: Amino acid sequences of the VH region (SEQ ID NO: 26) and the VL region (SEQ ID NO: 28) of human antibody NI-301.5D8. FIG. 1H: Amino acid sequences of the VH region (SEQ ID NO: 30) and the VL region (SEQ ID NO: 32) of human antibody NI-301.9D5. FIG. 1I: Amino acid sequences of the VH region (SEQ ID NO: 34) and the VL region (SEQ ID NO: 36) of human antibody NI-301.104F5. FIG. 1J: Amino acid sequences of the VH region (SEQ ID NO: 38) and the VL region (SEQ ID NO: 40) of human antibody NI-301.21F10. FIG. 1K: Amino acid sequences of the VH region (SEQ ID NO: 42) and the VL region (SEQ ID NO: 44) of human antibody NI-301.9G12. FIG. 1L: Amino acid sequences of the VH region (SEQ ID NO: 46) and the VL region (SEQ ID NO: 48) of human antibody NI-301.12D3. FIG. 1M: Amino acid sequences of the VH region of human antibody NI-301.37F1-PIMC (SEQ ID NO: 53). FIG. 1N: Amino acid sequences of the VH region (SEQ ID NO: 55) and the VL region (SEQ ID NO: 57) of human antibody NI-301.44E4. FIG. 1O: Amino acid sequences of the VH region (SEQ ID NO: 62) and the VL region (SEQ ID NO: 64) of human antibody NI-301.18C4. FIG. 1P: Amino acid sequences of the VH region (SEQ ID NO: 66) and the VL region (SEQ ID NO: 68) of human antibody NI-301.11A10. FIG. 1Q: Amino acid sequences of the VH region (SEQ ID NO: 70) and the VL region (SEQ ID NO: 72) of human antibody NI-301.3C9. FIG. 1R: Amino acid sequences of the VH region (SEQ ID NO: 74) and the VL region (SEQ ID NO: 76) of human antibody NI-301.14D8. FIG. 1S: Amino acid sequences of the VH region (SEQ ID NO: 78) and the VL region (SEQ ID NO: 80) of human antibody NI-301.9X4. FIG. 1T: Amino acid sequences of the VH region (SEQ ID NO: 82) and the VL region (SEQ ID NO: 84) of human antibody NI-301.14C3). Framework (FR) and complementarity determining regions (CDRs) are indicated with the CDRs being underlined. The Kabat numbering scheme was used (bioinf.org.uk/abs/).

FIGS. 2A-2C: Binding to aggregated, wild-type and mutant TTR by direct ELISA.

FIGS. 2A, 2B, and 2C: ELISA plates were coated with aggregated human wild-type TTR (●), aggregated recombinant V30M-TTR (▼) and bovine serum albumin (BSA) (■) at 10 μg/ml, and incubated with the following human monoclonal antibodies at a concentration range from 4 pM to 400 nM: FIG. 2A) NI-301.59F1, FIG. 2B) NI-301.35G11 and FIG. 2C) NI-301.37F1.

$EC_{50}$ values were estimated by fitting data points with the least square method.

NI-301.59F1: aggregated wt-TTR $EC_{50}$=3.0 nM, aggregated V30M-TTR $EC_{50}$=15.5 nM NI-301.35G11: aggregated wt-TTR $EC_{50}$=3.9 nM, aggregated V30M-TTR $EC_{50}$=5.0 nM NI-301.37F1: aggregated wt-TTR $EC_{50}$=0.35 nM, aggregated V30M-TTR $EC_{50}$=0.15 nM FIGS. 3A-3D: Specificity for aggregated TTR on dot blot.

Figure 3A:
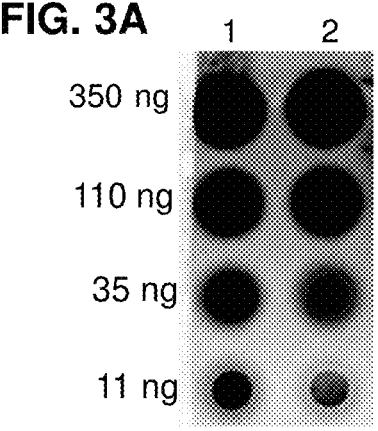
Figure 3B:
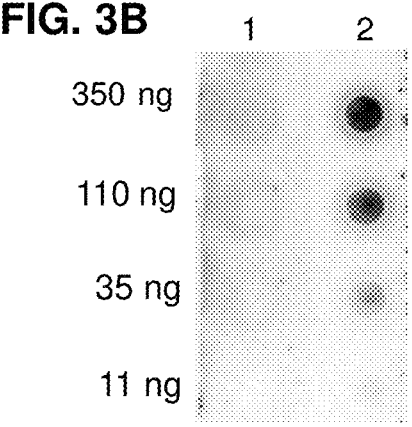
Figure 3C:
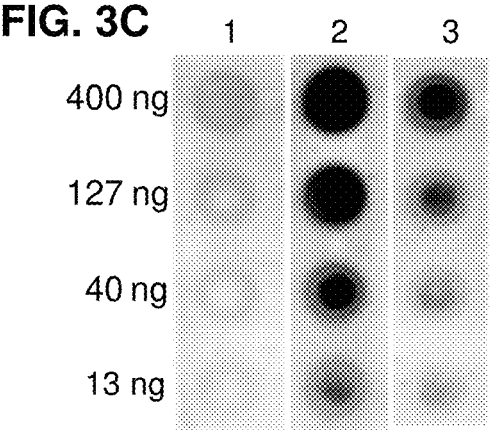
Figure 3D:
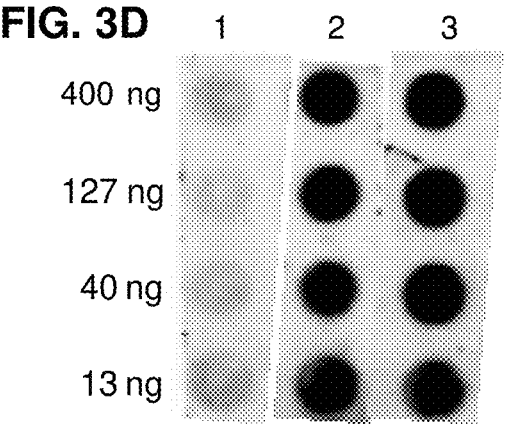
Figure 4A:
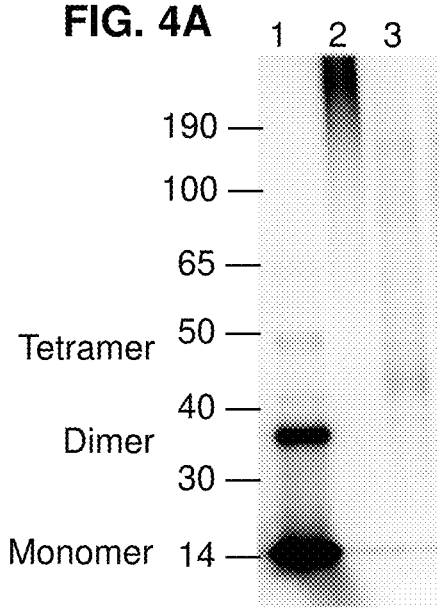
Figure 4B:
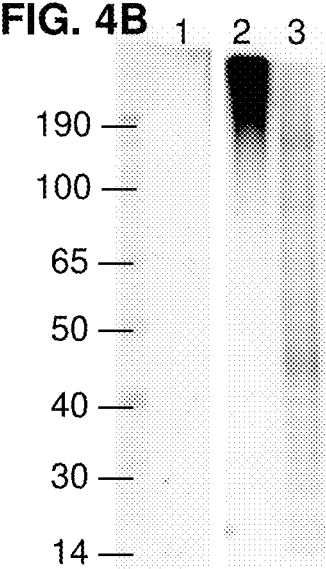
Figure 4C:
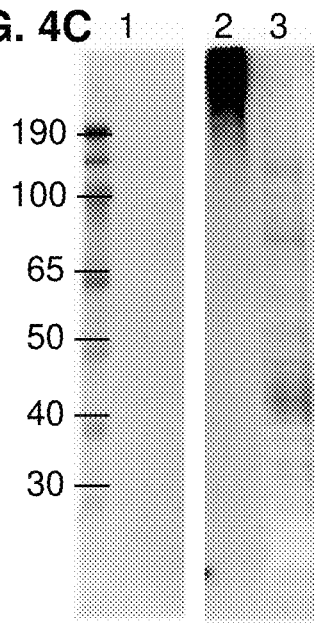
Figure 4D:
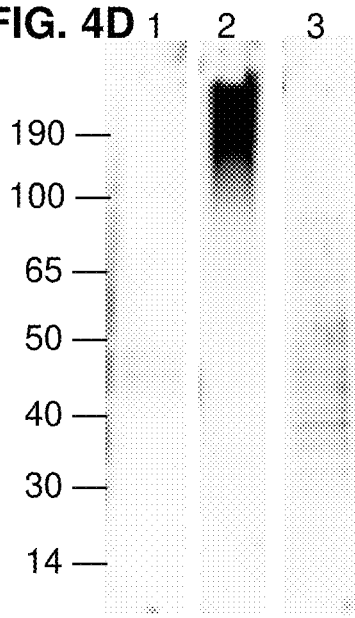

Human wild-type TTR protein in native (1) or aggregated (2) conformations, and aggregated recombinant V30M-TTR protein (3) were deposited on a nitrocellulose membrane and incubated with the following antibodies: commercial rabbit polyclonal antibody against TTR (Dako-A0002; 150 ng/ml) (FIG. 3A), NI-301.59F1 (FIG. 3B), NI-301.35G11 (FIG. 3C), and NI-301.37F1 (FIG. 3D). (FIGS. 3B, 3C, and 3D: human monoclonal antibodies at 50 nM).

FIGS. 4A-4D: Specificity for aggregated TTR on western blot.

Human wild-type TTR protein (300 ng) in native (1) or aggregated (2) conformations, and wild-type mouse liver extract (10 μg total protein) (3) were loaded on a SDS-PAGE gel and processed for western-blot with the following antibodies: commercial rabbit polyclonal antibody against TTR (Dako-A0002; 150 ng/ml) (FIG. 4A), NI-301.59F1 (FIG. 4B), NI-301.35G11 (FIG. 4C), and NI-301.37F1 (FIG. 4D) (FIGS. 4B, 4C, and 4D): human monoclonal antibodies at 50 nM). To prevent dissociation of the high molecular weight aggregates, the aggregated TTR sample was crosslinked with glutaraldehyde (1%, 5 min) prior to loading on the gel.

FIGS. 5A-5D: Absence of binding to human plasma TTR on western blot.

Plasma samples (0.5 μl) from controls (n=5), asymptomatic mutation carriers (n=5) and FAP patients (n=4) were loaded on a SDS-PAGE gel and processed for western blot with the following antibodies: commercial rabbit polyclonal antibody against TTR (Dako-A0002; 150 ng/ml) (FIG. 5A), secondary antibody only (anti-human IgG-HRP, 1/10 000 dilution) (FIG. 5B), NI-301.35G11 (FIG. 5C), and NI-301.37F1 (FIG. 5D) (FIGS. 5C and 5D: human monoclonal antibodies at 50 nM).

FIGS. 6A-6C: Absence of binding to human plasma TTR on dot blot.

Pure wild-type and mutant TTR protein in native and aggregated conformations, and plasma samples from controls, asymptomatic mutation carriers and FAP patients were deposited on a nitrocellulose membrane and incubated with the following antibodies: commercial rabbit polyclonal antibody against TTR (Dako-A0002; 150 ng/ml) (FIG. 6A), secondary antibody only (anti-mouse IgG2a-HRP, 1/10 000 dilution) (FIG. 6B), and mouse chimeric antibody NI-301.mur35G11 (10 nM) (FIG. 6C).

Samples 1-6: 150 ng of 1) aggregated wt-TTR, 2) native wt-TTR, 3) BSA, 4) native V30M-TTR, 5) native L55P-TTR and 6) native Y78F-TTR.

Samples 7-18: 2 μl of plasma collected from 7-10) controls (n=4), 11-14) asymptomatic mutation carriers (n=4) and 15-18) FAP patients (n=4).

FIGS. 7A-7C: Specific binding to aggregated TTR in solution.

Human wild-type and recombinant TTR protein in native and aggregated conformations, and a human plasma sample at 3 different dilutions were used for TTR immunoprecipitation (IP) using the following antibodies: commercial rabbit polyclonal antibody against TTR (Dako-A0002) (FIG. 7A), NI-301.35G11 (FIG. 7B), and NI-301.37F1 (FIG. 7C). The immunoprecipitated proteins were submitted to SDS-PAGE and detected by western blot (WB) with the Dako-A0002 antibody (150 ng/ml).

Lanes 1-2: WB loading controls: 300 ng of 1) human wt-TTR, 2) recombinant wt-TTR Lanes 3-6: IP on pure TTR protein: 3) human native wt-TTR, 4) human aggregated wt-TTR, 5) recombinant native wt-TTR and 6) recombinant aggregated wt-TTR Lanes 7-10: IP on human plasma diluted 7) 10 times, 8) 100 times, 9) 1000 times with PBS, and 10) PBS only FIGS. 8A-8F: Specific binding to TTR on FAP mouse tissue.

Transgenic mice expressing the human V30M-TTR allele on a TTR knock-out (KO) background reproduce the histopathological hallmarks of FAP, including amorphous and amyloid TTR deposits in various tissues. Liver and intestine tissue sections collected from FAP mice (FIG. 8A, FIG. 8C, and FIG. 8E) and TTR-KO mice (FIGS. 8B, 8D, and 8F) were processed for immunohistochemistry using the following antibodies: commercial rabbit polyclonal antibody against TTR (Dako-A0002; 1/1000 dilution) (FIG. 8A and FIG. 8B), NI-301.35G11 (FIGS. 8C and 8D), and NI-301.37F1 (FIGS. 8E and 8F). (FIGS. 8C, 8D, 8E, and 8F: human monoclonal antibodies at 50 nM).

FIGS. 9A-9F: Specific binding to misfolded TTR deposits but not native TTR in human tissue.

Antibodies were characterized for their capacity to bind TTR on sections from FAP patient skin biopsy and healthy control pancreas: the misfolded TTR accumulations that are characteristic for FAP are present in the patient skin biopsy, whereas pancreatic alpha cells show endogenous expression of TTR. Sections were processed for immunohistochemistry using the following antibodies: commercial rabbit polyclonal antibody against TTR (Dako-A0002; 1/1000 dilution) (FIG. 9A), HRP-coupled anti-rabbit IgG antibody (1/125 dilution) (FIG. 9B), mouse chimeric antibody NI-301.mur35G11 (50 nM) (FIG. 9C), HRP-coupled anti-mouse IgG2a antibody (1/125 dilution) (FIG. 9D), NI-301.37F1 (50 nM) (FIG. 9E), and HRP-coupled anti-human IgG (1/125 dilution) (FIG. 9F).

FIGS. 10A-10H: TTR binding epitopes assessed by pep-scan analysis.

The antibody binding epitopes on TTR were determined using the peptide scan method. In addition to the peptides covering the full human wild-type TTR sequence (spots 1 to 29), selected TTR mutations were also represented on the membrane (spots 30 to 44). The peptide scan membrane was incubated with the following antibodies at 50 nM: NI-301.59F1 (FIG. 10A), NI-301.35G11 (FIG. 10B), and NI-301.37F1 (FIG. 10C). As summarized in the table in FIG. 10D:

NI-301.59F1 binds EEEFVEGIY (TTR 61-69) (SEQ ID NO: 49); NI-301.35G11 binds GELHGLTTEEE (TTR 53-63) (SEQ ID NO: 50); the L55P mutation prevents antibody binding; and NI-301.37F1 binds WEPFA (TTR 41-45) (SEQ ID NO: 51); the E42G mutation prevents antibody binding. In order to determine the sequence requirements of the mentioned epitopes, the antibody binding epitopes on TTR were further identified using the alanine scan method. The whole sequence of human wild-type TTR protein was represented on the membrane as a set of 151 successive peptides of 15 amino-acids in length, starting at every amino-acid of the TTR protein. For each peptide, the amino-acid in position 10 was replaced by an alanine, or by glycine or proline when the initial amino-acid was an alanine. The peptide scan membrane was incubated with the following antibodies at 20 nM: NI-301.59F1 (FIG. 10E), NI-301.35G11 (FIG. 10F), and NI-301.37F1 (FIG. 10G). As summarized in the table in FIG. 10H:

NI-301.59F1 binds EEFXEGIY (TTR 62-69) (SEQ ID NO: 58).

NI-301.35G11 binds ELXGLTXE (TTR 54-61) (SEQ ID NO: 59).

NI-301.37F1 binds WEPFA (TTR 41-45) (SEQ ID NO: 51), wherein X denotes amino acid; Replacement of E42 by alanine did not disrupt binding but replacement by guanine prevented antibody binding as reported in C.

Figure 11A:
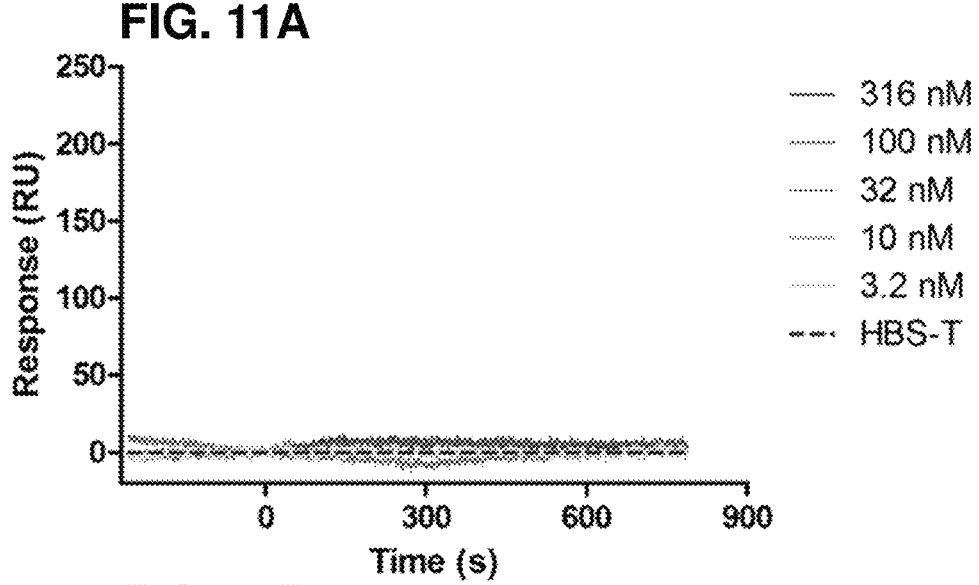
Figure 11B:
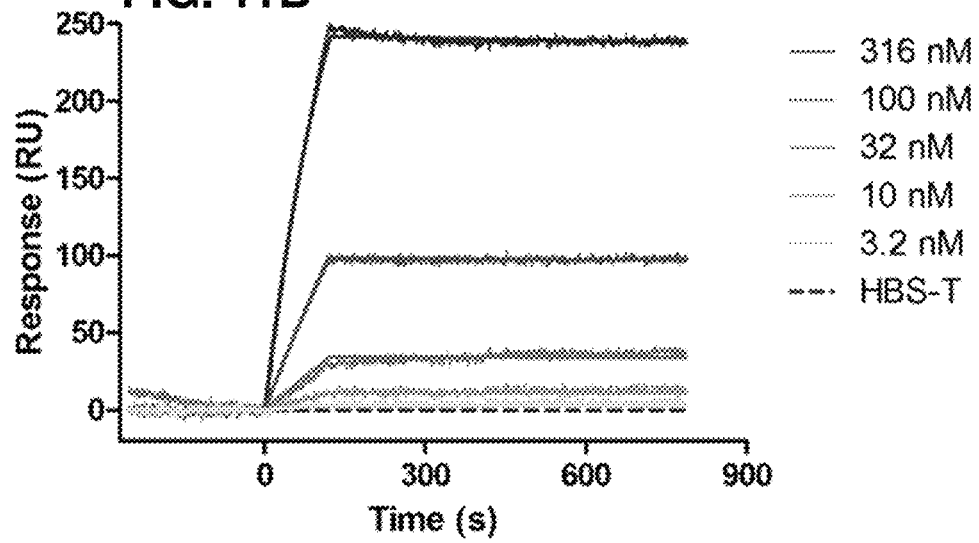
Figure 11C:
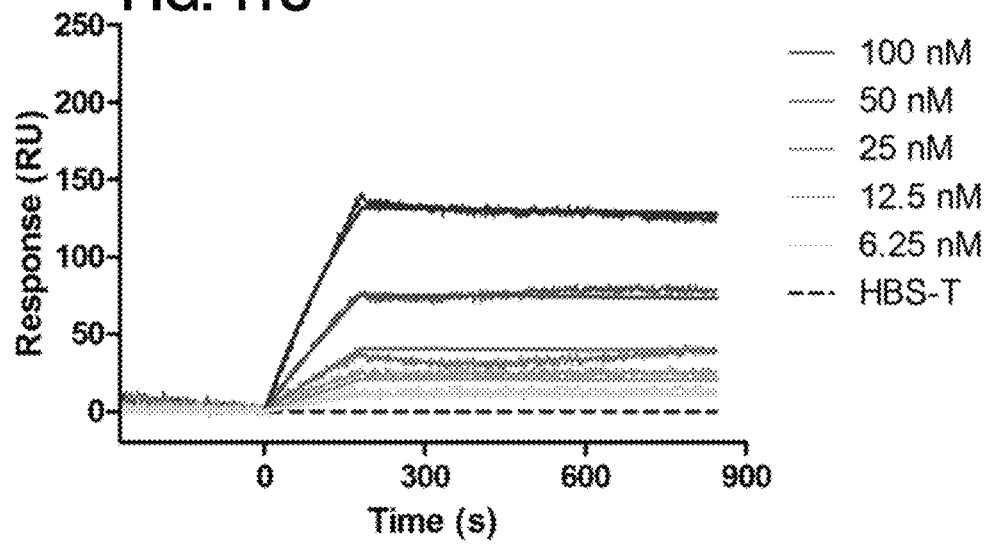

FIGS. 11A-11C: Antibody binding kinetics to TTR protein in solution assessed by surface plasmon resonance.

The binding kinetics of antibody NI-301.37F1 to TTR protein was measured by surface plasmon resonance (SPR). Antibody NI-301.37F1 was captured on the sensor by means of an anti-human IgG antibody, and TTR protein solution was flown over the sensor surface, at concentrations ranging from 3.2 to 316 nM. A simple 1:1 binding model was used to fit the data and derive the respective association (ka) and dissociation (kd) constants and the affinity (KD). Binding properties were determined for human wild-type TTR protein in native conformation (FIG. 11A), denaturated, human wild-type TTR protein (misfolded conformation) (FIG. 11B), and recombinant mutant TTR-L55P protein (FIG. 11C).

Native wild-type TTR: ka=not determined, kd=not determined, KD>316 nM

Denaturated wild-type TTR: ka=2.1 10$^4$ M-1s-1, kd=2.6 10-5 s-1, KD=1.2 nM

Recombinant TTR-L55P: ka=3.3 10$^4$ M-1s-1, kd=4.6 10-5 s-1, KD=1.4 nM

Figure 12A:
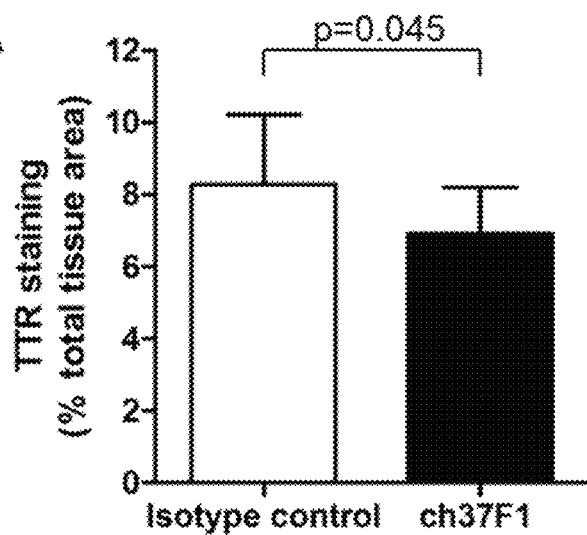
Figure 12B:
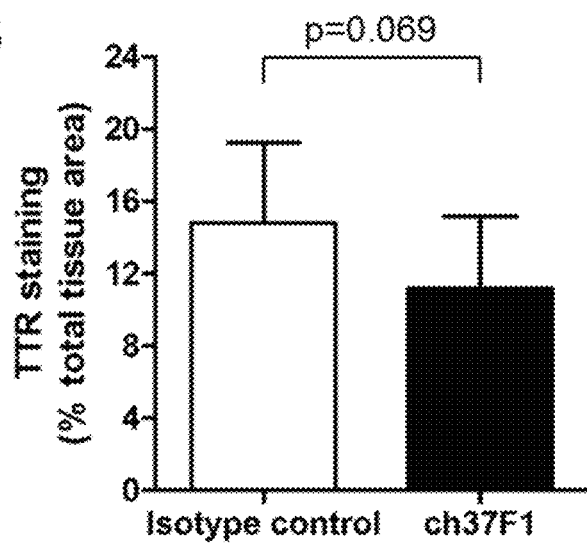

FIGS. 12A-12B: Chronic treatment with anti-TTR antibody reduces pathological TTR deposition in FAP mouse model.

FAP mice (Tg(6.0hMet30)×muTTR-KO) received weekly administration of mouse chimeric NI-301.37F1 or isotype control antibody at 3 mg/kg i.p. for 12 weeks. At the end of the treatment period, tissues were collected and the extent of TTR deposition was quantified by immunofluorescence. FIG. 12A: Effect of treatment in 7-month old mice (n=14-15 mice per group); FIG. 12B: Effect of treatment in 17-month old mice (n=10 mice per group). Group comparisons with two tailed, unpaired t-test.

FIGS. 13A-13F: Antibody binding to pathological TTR deposits in vivo.

Target engagement was characterized in adult FAP mice (7 months) 48 hours after administration of a single dose of antibody NI-301.37F1 at 30 mg/kg i.p, or PBS. Pathological TTR deposits and localization of the injected antibody were detected simultaneously by immunofluorescence.

Figure 13A:
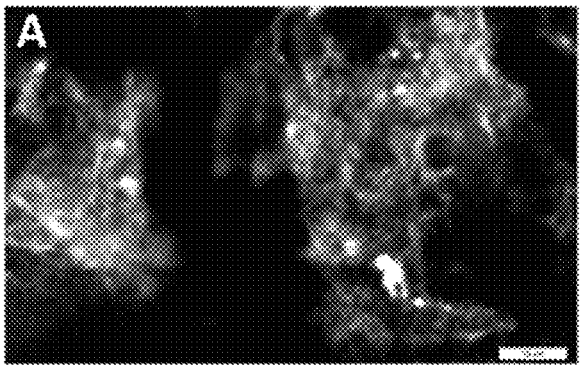
Figure 13B:
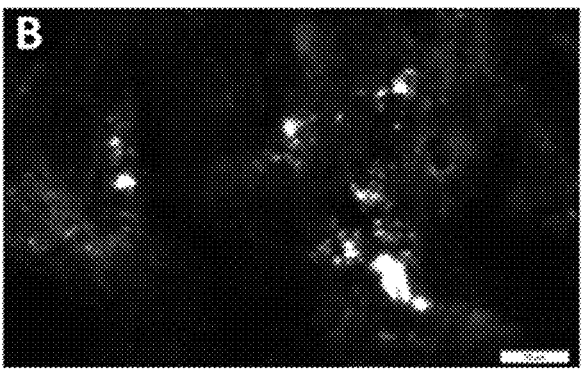
Figure 13C:
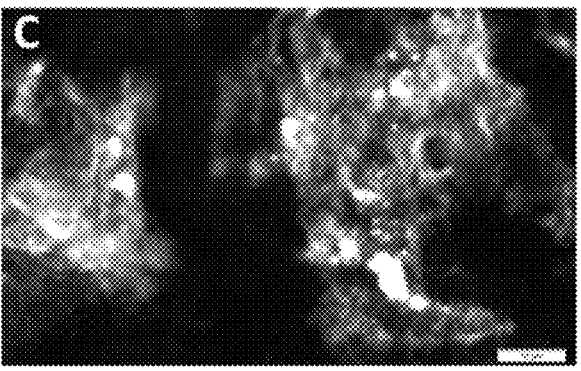
Figure 13D:
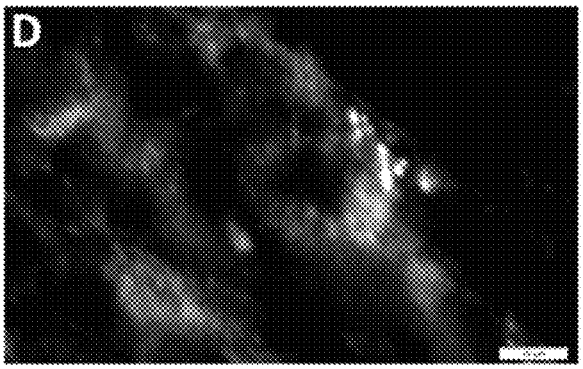
Figure 13E:
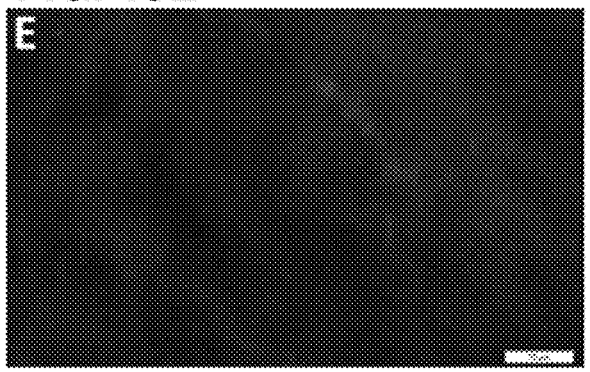
Figure 13F:
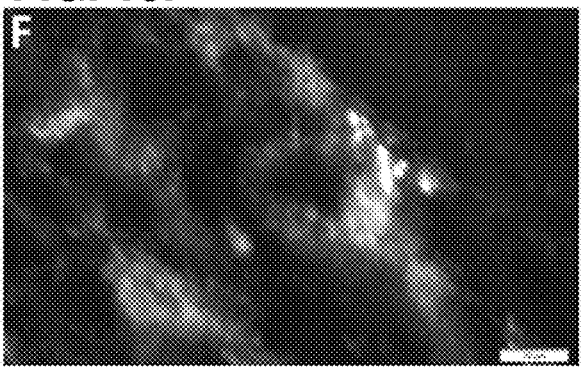

FIGS. 13A and 13D: Pathological TTR deposits in the kidneys of NI-301.37F1- (FIG. 13A) or PBS-injected mice (FIG. 13D). FIGS. 13B and 13E: Detection of human antibody in NI-301.37F1- (FIG. 13B) or PBS-injected mice (FIG. 13E). FIGS. 13C and 13F: Overlayed images showing TTR and NI-301.37F1 colocalization (FIG. 13C) and absence of unspecific staining (FIG. 13F).

Figure 14A:
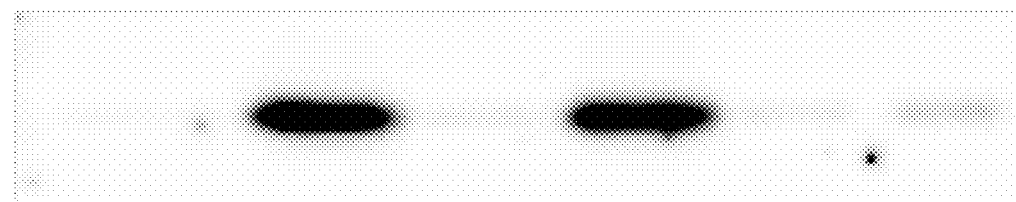
Figure 14B:
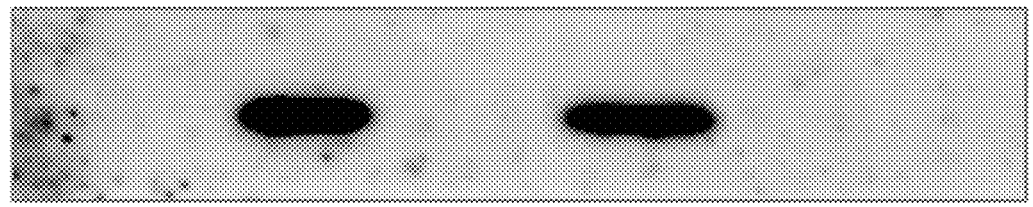

FIGS. 14A-14B: Tissue-free detection of misfolded TTR in vivo.

Adult FAP mice received a single administration of NI-301.37F1 or isotype control antibody at 3 mg/kg i.p. Blood samples were collected prior antibody injection (t=0) and 48 hours after antibody injection (t=48 h). Plasma samples were processed by immunoprecipitation with an anti-human IgG antibody, and analyzed by western blot using for detection: a conformation-independent, anti-TTR polyclonal antibody (Dako A0002, 150 ng/ml) (FIG. 14A), and NI-301.37F1 (20 nM) (FIG. 14B). In parallel, a plasma sample obtained from an uninjected FAP mouse was incubated with antibody NI-301.37F1 in vitro, before processing.

FIGS. 15A-15D: Antibody specificity evaluated against aggregating proteins by ELISA Antibody specificity for TTR protein was evaluated by measuring binding to selected aggregating proteins by direct ELISA. Antibody binding was evaluated at 4 and 20 nM and signal intensity was expressed in fold change relative to background levels, measured for each assay in absence of anti-TTR antibody.

FIGS. 15A and 15B: NI-301.37F1 binding assayed at 20 (FIG. 15A) and 4 nM (FIG. 15B)

FIGS. 15C and 15D: NI-301.44E4 binding assayed at 20 (FIG. 15C) and 4 nM (FIG. 15D).

DETAILED DESCRIPTION OF THE INVENTION

The present invention generally relates to immunotherapy and non-invasive methods for the detection of diseases and conditions associated with the presence of pathologic, often mutant and/or misfolded isoforms of transthyretin (TTR). More specifically, the present invention relates to recombinant human-derived monoclonal antibodies and antigen binding fragments thereof, which have been generated based on sequence information obtained from selected human donor populations and are capable of binding to such TTR isoforms and antigens thereof. The recombinant human-derived monoclonal antibody of the present invention is advantageously characterized by specifically binding to misfolded, misassembled, mutated, and/or aggregated TTR species and/or fragments thereof allowing a targeting for treatment and/or diagnosis of pathological altered TTR species. Due to their human derivation, the resulting recombinant antibodies of the present invention can be reasonably expected to be efficacious and safe as therapeutic agent, and highly specific as a diagnostic reagent for the detection of pathological TTR without giving false positives.

In addition, the antibody of the present invention as well as the derivatives thereof can be used for combination therapy of patients after organ transplantations who nevertheless bear the risk of developing a TTR amyloidosis due to e.g. their deposition, e.g. inheritable mutations in the TTR or a defect in the production of TTR in the liver. Thus, as a particular advantageous embodiment, the present invention relates to the human monoclonal antibody and any derivatives thereof described herein for use in the treatment of patients either alone or in the treatment of patients receiving e.g. immunosuppressive drugs after organ transplantation or other agents utilized for symptoms associated with TTR amyloidosis, wherein the antibody of the present invention and any of its derivatives is designed to be administered concomitantly with the immunosuppressive drug and/or the agent suppressing further side effects or sequentially before or after administration of the same. In this context, the anti-TTR antibody and TTR-binding fragment of the present invention are preferably substantially non-immunogenic in human. In one embodiment of the present invention, pharmaceutical compositions are provided comprising both a human monoclonal antibody of the present invention or any derivatives thereof and one or more immunosuppressive drugs and/or utilized for symptoms associated with TTR amyloidosis.

I. Definitions

Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

If not specifically indicated otherwise, the term "TTR", is used interchangeably to specifically refer to the different forms of transthyretin (TTR). The term "TTR" is also used to generally identify other conformers of TTR, for example, oligomers and/or misfolded, misassembled and/or aggregated forms of TTR. The term "TTR" is also used to refer collectively to all types and forms of TTR, such as mutated TTR. Added letters in front of the terms TTR are used to indicate the organism the particular ortholog is originating from, e.g. hTTR for human TTR or mTTR for murine origin. In addition, unless indicated otherwise the numbering system for TTR amino acid sequence used herein refers to the mature TTR protein, i.e. the TTR protein as secreted by the cells after cleavage of the signal peptide. This numbering is the one used to define TTR mutations found in patients, such as TTR-V30M or TTR-L55P, but differs from the one used for transthyretin precursor protein sequence (NCBI reference sequence: NP_000362.1). In this context, the position and substituted amino acid in a mutant TTR may be indicated in different but equivalent ways; see, e.g., "TTR-V30M" and "V30M-TTR".

The anti-TTR antibodies disclosed herein specifically bind TTR and epitopes thereof and to various conformations of TTR and epitopes thereof. For example, disclosed herein are antibodies that specifically bind pathologically altered TTR species or fragments thereof, such as oligomers/fibrils and/or mutated, misfolded, misassembled and/or aggregated forms of TTR or fragments thereof. The term (pathologically) mutated, misfolded, misassembled aggregated/aggregates of TTR is used interchangeable to specifically refer to the aforementioned forms. The term (pathological) "aggregated forms" or "aggregates" as used herein describes the products of an accumulation or cluster formation due to TTR erroneous/pathological interaction with one another. These aggregates, accumulations or cluster forms may be, substantially consist or consist of both TTR and/or TTR fragments and of non-fibrillar oligomers and/or fibrillar oligomers and fibrils thereof. As used herein, reference to an antibody that "specifically binds", "selectively binds", or "preferentially binds" TTR refers to an antibody that does not bind other unrelated proteins. In one example, a TTR antibody disclosed herein can bind TTR or an epitope thereof and show no binding above about 2 times background for other proteins. In a preferred embodiment, the antibody of the present invention does not substantially recognize unrelated amyloid-forming proteins selected from the group consisting of alpha-synuclein (α-syn), Tau, transactive response DNA binding protein 43 (TDP-43), serum amyloid A (SAA), huntingtin protein (HTT); see, e.g. FIGS. 15A-15D. An antibody that "specifically binds" or "selectively binds" a TTR conformer refers to an antibody that does not bind all conformations of TTR, i.e., does not bind at least one other TTR conformer.

For example, disclosed herein are antibodies that can preferentially bind to misfolded, misassembled and/or aggregated forms of TTR both in vitro and in tissues obtained from patients with diseases associated with TTR amyloidosis or with a risk to develop diseases associated with TTR amyloidosis. Since the sequences of the TTR antibodies of the present invention have been obtained from human subjects, the TTR antibodies of the present invention may also be called "human auto-antibodies" or "human-derived antibodies" in order to emphasize that those antibodies were indeed expressed initially by the subjects and are not synthetic constructs generated, for example, by means of human immunoglobulin expressing phage libraries, which hitherto represented one common method for trying to provide human-like antibodies.

The term "peptide" is understood to include the terms "polypeptide" and "protein" (which, at times, may be used interchangeably herein) within its meaning. Similarly, fragments of proteins and polypeptides are also contemplated and may be referred to herein as "peptides". Nevertheless, the term "peptide" preferably denotes an amino acid polymer including at least 5 contiguous amino acids, preferably at least 10 contiguous amino acids, more preferably at least 15 contiguous amino acids, still more preferably at least 20 contiguous amino acids, and particularly preferred at least 25 contiguous amino acids. In addition, the peptide in accordance with present invention typically has no more than 100 contiguous amino acids, preferably less than 80 contiguous amino acids, more preferably less than 50 contiguous amino acids and still more preferred no more than 15 contiguous amino acids of the TTR polypeptide.

Polypeptides:

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation and derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan. Proteins or polypeptides expressed in yeast may have a glycosylation pattern different from that expressed in mammalian cells.

Included as polypeptides of the present invention are fragments, derivatives, analogs or variants of the foregoing polypeptides and any combinations thereof as well. The terms "fragment," "variant," "derivative", and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the preferred peptides of the present invention, in particular to TTR, variants, derivatives or analogs of either of them. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

Furthermore, the terms "fragment," "variant," "derivative", and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of TTR specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Determination of Similarity and/or Identity of Molecules:

"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

"Similarity" between two polynucleotides is determined by comparing the nucleic acid sequence of one polynucleotide to the sequence of a polynucleotide. A nucleic acid of one polynucleotide is similar to the corresponding nucleic acid of a second polynucleotide if it is identical or, if the nucleic acid is part of a coding sequence, the respective triplet comprising the nucleic acid encodes for the same amino acid or for a conservative amino acid substitution.

The determination of percent identity or similarity between two sequences is preferably accomplished using the mathematical algorithm of Karlin and Altschul (1993) Proc. Natl. Acad. Sci USA 90: 5873-5877. Such an algorithm is incorporated into the BLASTn and BLASTp programs of Altschul et al. (1990) J. Mol. Biol. 215: 403-410 available at NCBI (ncbi.nlm.nih.gov/blast/Blast.cge).

The determination of percent identity or similarity is performed with the standard parameters of the BLASTn programs for BLAST polynucleotide searches and BLASTp programs for BLAST protein search, as recommended on the NCBI webpage and in the "BLAST Program Selection Guide" in respect of sequences of a specific length and composition.

BLAST polynucleotide searches are performed with the BLASTn program.

For the general parameters, the "Max Target Sequences" box may be set to 100, the "Short queries" box may be ticked, the "Expect threshold" box may be set to 1000 and the "Word Size" box may be set to 7 as recommended for short sequences (less than 20 bases) on the NCBI webpage. For longer sequences the "Expect threshold" box may be set to 10 and the "Word Size" box may be set to 11. For the scoring parameters the "Match/mismatch Scores" may be set to 1,-2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "DUST Filter Settings" may be ticked and the "Mask lower case letters" box may not be ticked. In general the "Search for short nearly exact matches" may be used in this respect, which provides most of the above indicated settings. Further information in this respect may be found in the "BLAST Program Selection Guide" published on the NCBI webpage.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Modifications of both programs, e.g., in respect of the length of the searched sequences, are performed according to the recommendations in the "BLAST Program Selection Guide" published in a HTML and a PDF version on the NCBI webpage.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operable associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operable associated" or "operable linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operable associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operable associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operable associated with it. Alternatively, a heterologous mammalian signal peptide, or a functional derivative thereof, may be used. For example, the wild-type leader sequence may be substituted with the leader sequence of human tissue plasminogen activator (TPA) or mouse ß-glucuronidase.

A "binding molecule" as used in the context of the present invention relates primarily to antibodies, and fragments thereof, but may also refer to other non-antibody molecules that bind to TTR including but not limited to hormones, receptors, ligands, major histocompatibility complex (MHC) molecules, chaperones such as heat shock proteins (HSPs) as well as cell-cell adhesion molecules such as members of the cadherin, integrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

Antibodies:

The terms "antibody" and "immunoglobulin" are used interchangeably herein. An antibody or immunoglobulin is a binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to TTR is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE I

| CDR Definitions[1] | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table I is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particularly preferred embodiment, the antibody of the present invention is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are TTR binding fragments which comprise any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (vbase.mrc-cpe.cam.ac.uk) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural TTR in its relevant conformation in the human body, (ii) having protected the individual or is at least significant for the presence of TTR, and (iii) since the antibody is of human origin the risks of cross-reactivity against self-antigens is minimized. Thus, in accordance with the present invention the terms "human monoclonal antibody", "human monoclonal autoantibody", "human antibody" and the like are used to denote a TTR binding molecule which is of human origin, i.e. which has been isolated from a human cell such as a B cell or hybridoma thereof or the cDNA of which has been directly cloned from mRNA of a human cell, for example a human memory B cell. A human antibody is still "human", i.e. human-derived even if amino acid substitutions are made in the antibody, e.g., to improve binding characteristics.

In one embodiment the human-derived antibodies of the present invention comprises heterologous regions compared to the natural occurring antibodies, e.g. amino acid substitutions in the framework region, constant region exogenously fused to the variable region, different amino acids at the C- or N-terminal ends and the like.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility and their tolerance in man.

As used herein, the term "rodentized antibody" or "rodentized immunoglobulin" refers to an antibody comprising one or more CDRs from a human antibody of the present invention; and a human framework region that contains amino acid substitutions and/or deletions and/or insertions that are based on a rodent antibody sequence. When referred to rodents, preferably sequences originating in mice and rats are used, wherein the antibodies comprising such sequences are referred to as "murinized" or "ratinized" respectively. The human immunoglobulin providing the CDRs is called the "parent" or "acceptor" and the rodent antibody providing the framework changes is called the "donor". Constant regions need not be present, but if they are, they are usually substantially identical to the rodent antibody constant regions, i.e. at least about 85% to 90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody. The above explanations in respect of "murinized" antibodies apply analogously for oder "rodentized" antibodies, such as "ratinized antibodies", wherein rat sequences are used instead of the murine.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or CL domain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of TTR.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind TTR or a fragment, variant or specific conformation thereof with an off rate (k(off)) of less than or equal to $5\times10^{-2}$ $sec^{-1}$, $10^{-2}$ $sec^{-1}$, $5\times10^{-3}$ $sec^{-1}$ or $10^{-3}$ $sec^{-1}$. More preferably, an antibody of the invention may be said to bind TTR or a fragment, variant or specific conformation thereof with an off rate (k(off)) less than or equal to $5\times10^{-4}$ $sec^{-1}$, $10^{-4}$ $sec^{-1}$, $5\times10^{-5}$ $sec^{-1}$, or $10^{-5}$ $sec^{-1}$ $5\times10^{-6}$ $sec^{-1}$, $10^{-6}$ $sec^{-1}$, $5\times10^{-7}$ $sec^{-1}$ or $10^{-7}$ $sec^{-1}$.

A binding molecule, e.g., an antibody or antigen-binding fragment, variant, or derivative disclosed herein may be said to bind TTR or a fragment, variant or specific conformation thereof with an on rate (k(on)) of greater than or equal to $10^3$ $M^{-1}$ $sec^{-1}$, $5 \times 10^3$ $M^{-1}$ $sec^{-1}$, $10^4$ $M^{-1}$ $sec^{-1}$ or $5 \times 10^4$ $M^{-1}$ $sec^{-1}$. More preferably, an antibody of the invention may be said to bind TTR or a fragment, variant or specific conformation thereof with an on rate (k(on)) greater than or equal to $10^5$ $M^{-1}$ $sec^{-1}$, $5 \times 10^5$ $M^{-1}$ $sec^{-1}$, $10^6$ $M^{-1}$ $sec^{-1}$, or $5 \times 10^6$ $M^{-1}$ $sec^{-1}$ or $10^7$ $M^{-1}$ $sec^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to TTR and/or mutated, misfolded, misassembled and/or aggregated TTR species and/or fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In one embodiment, the antibody of the present invention has a Kd for different TTR isoforms as illustrated for the exemplary antibodies in Table V below, i.e a Kd of >300 nM for wild-type native TTR, and/or a Kd of ≤15 nM, preferably ≤5 nM, and most preferably ≤2 nM for denatured TTR, and/or a Kd of ≤35 nM, preferably of ≤20 nM for native TTR-V30M, and/or a Kd of ≤150 nM, preferably of ≤5 nM, and most preferably ≤2 nM for native TTR-L55P.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083-4090.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 µl buffer (20 mM Tris, pH. 7.5, 0.5% Nonidet, 1 mM EDTA, 1 mM PMSF, 0.1 M NaCl, IX Sigma Protease Inhibitor, and IX Sigma Phosphatase Inhibitors 1 and 2). The suspension can be kept on ice for 20 min. with intermittent vortexing. After spinning at 15,000×g for 5 min at about 4° C., aliquots of supernatant can be stored at about −70° C.

Diseases:

Unless stated otherwise, the terms "disorder" and "disease" are used interchangeably herein and comprise any undesired physiological change in a subject, an animal, an isolated organ, tissue or cell/cell culture.

Transthyretin (TTR) amyloidosis is a pathophysiological mechanism at play in many different diseases which are characterized by abnormal deposition of the TTR protein in various tissues as a result of a structural (i.e. conformational) change of the TTR protein. The misfolded and misassembled TTR protein is toxic and occurs often as a consequence of mutations in the TTR gene. Misfolded TTR toxicity leads to local tissue damages, which upon accumulation over time can lead to organ dysfunction and even organ failure. There are many types of tissues and organs that are susceptible to TTR amyloidosis, such as the peripheral and autonomic nervous system, the heart, leptomeninges, eyes, tendons, ligaments or kidneys. The broad range of tissues that can be affected by TTR amyloidosis is a reason for the diversity of symptoms the patients with TTR amyloidosis exhibit. In fact, patients with TTR amyloidosis are clinically categorized as suffering from different diseases, depending on the tissue or organ that is the most affected by TTR amyloidosis and the corresponding symptoms.

On this basis, TTR amyloidosis has been classified in a neuropathic form, wherein the peripheral and autonomic nervous system are primarily affected and patients exhibit mostly pain, paresthesia, muscular weakness and autonomic dysfunction. There is also a cardiac form of TTR amyloidosis, wherein the heart is primarily affected and patients exhibit mostly orthostatic hypo- or hyper-tension, arrhythmia and cardiomegaly. These two forms are not mutually exclusive, and many patients present with a combination of the two. When TTR amyloidosis affect other tissues, this can lead to vitreous opacity, dry eyes or glaucoma, proteinurea, hyperthyroxinemia, carpal tunnel syndrome or preeclampsia.

Therefore, in one embodiment of the present invention, the antibodies of the present invention, binding molecules having substantially the same binding specificities of any one thereof, the polynucleotides, the vectors, the cells and/or peptides of the present invention are used for preparation of a pharmaceutical or diagnostic composition for prophylactic and/or therapeutic treatment of TTR amyloidosis diseases, for monitoring disease progression and/or treatment response, and for the diagnosis of diseases associated with TTR amyloidosis comprising Familial Amyloid Polyneuropathy (FAP), Familial Amyloid Cardiomyopathy (FAC), Senile Systemic Amyloidosis (SSA), leptomeningeal/Central Nervous System (CNS) amyloidosis including Alzheimer disease, ocular amyloidosis, renal amyloidosis, hyperthyroxinemia, carpal tunnel syndrome, rotator cuff tears and lumbar spinal stenosis, and preeclampsia.

Treatment:

As used herein, the terms "treat" or "treatment" refer to both therapeutic treatment and prophylactic or preventative measures, wherein the object is to prevent or slow down (lessen) an undesired physiological change or disorder, such as the development of cardiac deficiency. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug," "medicine," or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents," "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug," "medicine," or "medicament" at an intended target location within the body of man or other animals, e.g., at the skin, in the stomach or the intestine. The terms "agent," "compound", or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

By "subject" or "individual" or "animal" or "patient" or "mammal," is meant any subject, particularly a mammalian subject, e.g., a human patient, for whom diagnosis, prognosis, prevention, or therapy is desired.

Pharmaceutical Carriers:

Pharmaceutically acceptable carriers and administration routes can be taken from corresponding literature known to the person skilled in the art. The pharmaceutical compositions of the present invention can be formulated according to methods well known in the art; see for example Remington: The Science and Practice of Pharmacy (2000) by the University of Sciences in Philadelphia, ISBN 0-683-306472, Vaccine Protocols 2nd Edition by Robinson et al., Humana Press, Totowa, New Jersey, USA, 2003; Banga, Therapeutic Peptides and Proteins: Formulation, Processing, and Delivery Systems. 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are preferably adjusted to a pH and isotonic state compatible with the nasal mucous membranes. Pharmaceutical compositions for oral administration, such as single domain antibody molecules (e.g., "Nanobodies™") etc. are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., Nature Reviews, Drug Discovery 2(9) (2003), 727-735. Further guidance regarding formulations that are suitable for various types of administration can be found in Remington's Pharmaceutical Sciences, Mace Publishing Company, Philadelphia, PA, 17th ed. (1985) and corresponding updates. For a brief review of methods for drug delivery see Langer, Science 249 (1990), 1527-1533.

II. Antibodies of the Present Invention

The present invention generally relates to human-derived anti-TTR antibodies and antigen-binding fragments thereof, which preferably demonstrate the immunological binding characteristics and/or biological properties as outlined for the antibodies illustrated in the Examples. In accordance with the present invention human monoclonal antibodies specific for TTR were cloned from a pool of healthy human subjects. However, in another embodiment of the present invention, the human monoclonal anti-TTR antibodies might also be cloned from patients showing symptoms of a disease and/or disorder associated with TTR amyloidosis In the course of the experiments performed in accordance with the present invention, antibodies present in the conditioned media of cultured human memory B cell were evaluated for their capacity to bind to TTR and to more than 10 other proteins including bovine serum albumin (BSA). Only the B-cell supernatants able to bind to the TTR protein but not to any of the other proteins in the screen were selected for further analysis, including determination of the antibody class and light chain subclass. The selected B-cells were then processed for antibody cloning.

In brief, this consisted in the extraction of messenger RNAs from the selected B-cells, retro-transcription by RT-PCR, amplification of the antibody-coding regions by PCR, cloning into plasmid vectors and sequencing. Selected human antibodies were then produced by recombinant expression in HEK293 or CHO cells and purification, and subsequently characterized for their capacity to bind human TTR protein. The combination of various tests, e.g. recombinant expression of the antibodies in HEK293 or CHO cells and the subsequent characterization of their binding specificities towards human TTR protein, and their distinctive binding to pathologically misfolded, misassembled and/or aggregated forms thereof confirmed that for the first time human antibodies have been cloned that are highly specific for TTR and distinctively recognize and selectively bind the pathologically aggregated forms of TTR protein, such as TTR fibrils. In some cases, mouse chimeric antibodies were also generated on the basis of the variable domains of the human antibodies of the present invention. These mouse chimeric antibodies have shown equal binding affinity, specificity and selectivity to human TTR as the human antibodies as shown in FIGS. 6A-6C and 9A-9F and in Examples 4 and 8.

Thus, the present invention generally relates to recombinant human-derived monoclonal anti-TTR antibody and binding fragments, derivatives and variants thereof. In one embodiment of the invention, the antibody is capable of binding human TTR.

In one embodiment, the present invention is directed to an anti-TTR antibody, or antigen-binding fragment, variant or derivatives thereof, where the antibody specifically binds to the same epitope of TTR as a reference antibody selected from the group consisting of NI-301.59F1, NI-301.35G11, NI-301.37F1 and NI-301.12D3. Epitope mapping identified a sequence within the human TTR including amino acids 61-EEEFVEGIY-69 (SEQ ID NO: 49) as the unique linear epitope recognized by antibody NI-301.59F1 of this invention, a sequence within the human TTR including amino acids 53-GELHGLTTEEE-63 (SEQ ID NO: 50) as the unique linear epitope recognized by antibody NI-301.35G11 of this invention, a sequence within the human TTR including amino acids 41-WEPFA-45 (SEQ ID NO: 51) as the unique linear epitope recognized by antibody NI-301.37F1 (see FIGS. 10A-10H and Example 9). Therefore, in one embodiment the antibody of the present invention is provided, wherein the antibody specifically binds a TTR epitope which comprises the amino acid sequence EEEFVEGIY (SEQ ID NO: 49), GELHGLTTEEE (SEQ ID NO: 50), or WEPFA (SEQ ID NO: 51).

In this context, as explained in Example 9 the binding epitopes of the exemplary antibodies NI-301.59F1, NI301.35G11, and NI-301.37F1 have been analyzed by using a panel of 29 sequential peptides 15 amino acid long and 11 amino acid overlap (i.e. first peptide TTRaa$_{1-15}$; second peptide TTRaa$_{5-19}$; etc.), wherein antibody NI-301.59F1 and 301.35G11 recognize two overlapping peptides, (15 and 16) and (13 and 14), respectively, and antibody NI 301.37F1 recognizes three overlapping peptides (9, 10 and 11); see Example 9 and FIG. 10A-10H.

Thus, with respect to the amino acid sequence of the mature TTR polypeptide and corresponding peptide mapping this means that antibody NI-301.59F1 binding to the epitope EEEFVEGIY (SEQ ID NO: 49) is capable of recognizing peptides having the amino acid sequence GLT-TEEEFVEGIYKV (SEQ ID NO: 85) and EEEFVEG-IYKVEIDT (SEQ ID NO: 86).

Likewise, anti-TTR antibody NI-301.35G11 binding to epitope GELHGLTTEEE (SEQ ID NO: 50) is capable of recognizing peptides having the amino acid sequence TSESGELHGLTTEEE (SEQ ID NO: 87) and GELHGLT-TEEEFVEG (SEQ ID NO: 88).

Similarly, anti-TTR antibody NI-301.37F1 which binds to the epitope WEPFA (SEQ ID NO: 51) is capable of recognizing peptides with the amino acid sequences FRKAADDTWEPFASG (SEQ ID NO: 89), ADDTWEP-FASGKTSE (SEQ ID NO: 90), and WEPFASGKTSESGEL (SEQ ID NO: 91).

Thus, the subject antibodies of the present invention illustrated in the Examples are different from antibodies which recognize any of the mentioned epitopes in context additional N- and/or C-terminal amino acids only. Therefore, in a preferred embodiment of the present invention, specific binding of an anti-TTR antibody to a TTR epitope which comprises the amino acid sequence EEEFVEGIY (SEQ ID NO: 49), GELHGLTTEEE (SEQ ID NO: 50), or WEPFA (SEQ ID NO: 51) is determined with sequential peptides 15 amino acid long and 11 amino acid overlap in accordance with Example 9 and FIGS. 10A to 10D.

In this context, extended epitope mapping performed in accordance with the present invention and described in Example 9 using a panel of 151 sequential peptides 15 amino acid long and 14 amino acid overlap, wherein for each peptide the amino-acid in position 10 was replaced by an alanine for non-alanine amino-acids, whereas alanines were replaced by glycine or proline revealed that antibody NI-301.59F1 binds epitope EEFXEGIY (TTRaa$_{62-69}$) (SEQ ID NO: 58) and antibody NI-301.35G11 binds ELXGLTXE (TTRaa$_{54-61}$) (SEQ ID NO: 59) while no further sequence requirements have been determined for the epitope of antibody NI-301.37F1. Accordingly, in another embodiment determination whether a given antibody binds to the same epitope as antibodies NI-301.59F1, NI301.35G11, and NI-301.37F1 is performed according Example 9 and FIGS. 10E to 10H.

It goes without saying that epitope mapping and determination whether a given antibody binds the same epitope as a subject antibody used in Example 9 and shown in FIGS. 10A-H can also be applied to any other anti-TTR antibody of the present invention described in the Examples with the variable region depicted in FIG. 1A-1T.

Accordingly, the present invention generally relates to any anti-TTR antibody and antibody-like molecule which binds to the same epitope as an antibody illustrated in the Examples and having at least the CDRs and/or variable heavy and light region as depicted in any one of FIGS. 1A-1T.

In a further embodiment, the antibody specifically binds the amino acid sequence GELHGLTTEEE (SEQ ID NO: 50) but not GELHGPTTEEE (SEQ ID NO: 209), corresponding to the TTR-L55P mutant epitope, or the antibody specifically binds the amino acid sequence WEPFA (SEQ ID NO: 51) but not WGPFA (SEQ ID NO: 210), corresponding to the TTR-E42G mutant epitope.

Furthermore, without intending to be bound by initial experimental observations as demonstrated in the Examples 3 to 8 and shown in FIGS. 2A-2C, 3A-3D, 4A-4D, 7A-7C, and 9A-9F, the human monoclonal NI-301.59F1, NI-301.35G11, and NI-301.37F1 anti-TTR antibodies of the present invention are preferably characterized in specifically binding to pathological misfolded, misassembled or aggregated TTR and not substantially recognizing TTR in the physiological form. Hence, the present invention provides a set of human anti-TTR antibodies with binding properties particularly useful for diagnostic and therapeutic purposes. Thus, in one embodiment the present invention provides antibodies which are capable of specifically binding pathologically aggregated forms of TTR.

In one embodiment, the antibody of the present invention exhibits the binding properties of the exemplary NI-301.59F1, NI-301.35G11, and NI-301.37F1 antibodies as described in the Examples. The anti-TTR antibody of the present invention preferentially recognizes pathologically altered TTR, such as mutated, misfolded, misassembled or aggregated TTR species and fragments thereof rather than physiological TTR. Thus, in one embodiment, the antibody of the present invention does not substantially recognize physiological TTR species.

The term "does not substantially recognize" when used in the present application to describe the binding affinity of a molecule of a group comprising an antibody, a fragment thereof or a binding molecule for a specific target molecule, antigen and/or conformation of the target molecule and/or antigen means that the molecule of the aforementioned group binds said molecule, antigen and/or conformation with a binding affinity which is at least 2-fold, 3-fold, 4-fold, 5-fold, 6-fold, 7-fold, 8-fold or 9-fold less than the binding affinity of the molecule of the aforementioned group for binding another molecule, antigen and/or conformation. Very often the dissociation constant (KD) is used as a measure of the binding affinity. Sometimes, it is the EC50 on a specific assay as for example an ELISA assay that is used as a measure of the binding affinity. Preferably the term "does not substantially recognize" when used in the present application means that the molecule of the aforementioned group binds said molecule, antigen and/or conformation with a binding affinity which is at least or 10-fold, 20-fold, 50-fold, 100-fold, 1000-fold or 10000-fold less than the binding affinity of said molecule of the aforementioned group for binding to another molecule, antigen and/or conformation.

In addition, or alternatively, the anti-TTR antibody of the present invention binds to disease causing misfolded, misassembled or aggregated forms of human TTR. In this context, the binding affinities may be in the range as shown for the exemplary NI-301.59F1, NI-301.35G11, and NI-301.37F1 antibodies in FIG. 2A-2C, respective FIG. 10A-10H, i.e. having half maximal effective concentrations (EC50) of about 1 pM to 500 nM, preferably an EC50 of about 50 pM to 100 nM, most preferably an EC50 of about 1 nM to 20 nM for human aggregated TTR and aggregated recombinant TTR as shown for NI-301.59F1 and NI-301.35G11, or an EC50 of about 100 pM to 1 nM for human aggregated TTR and aggregated recombinant TTR as shown for NI-301.37F1.

In particular, the anti-TTR antibody, binding fragment or derivative thereof has a binding affinity corresponding to an EC50 value of ≤5 nM for binding aggregated wild-type and/or an EC50 of ≤20 nM, preferably ≤10 nM and most preferably ≤1 nM for binding aggregated V30M-TTR; see Example 3 and FIG. 2A-2C.

Some antibodies are able to bind to a wide array of biomolecules, e.g., proteins. As the skilled artisan will appreciate, the term specific is used herein to indicate that other biomolecules than TTR proteins or fragments thereof do not significantly bind to the antigen-binding molecule, e.g., one of the antibodies of the present invention. Preferably, the level of binding to a biomolecule other than TTR results in a binding affinity which is at most only 20% or less, 10% or less, only 5% or less, only 2% or less or only 1% or less (i.e. at least 5, 10, 20, 50 or 100 fold lower, or anything beyond that) of the affinity to TTR, respectively; see e.g., FIG. 2A-2C.

In one embodiment the anti-TTR antibody of the present invention binds preferentially to aggregated forms of TTR, misfolded TTR, misassembled TTR, and/or fragments, derivatives, fibrils and/or oligomers thereof. In another embodiment the anti-TTR antibody of the present invention preferentially binds to both native TTR and pathologically misfolded, misassembled, or aggregated forms of TTR.

As mentioned before, amorphous and amyloid TTR deposits can lead to different diseases depending on where in the body the misfolded, misassembled, and/or aggregated TTR species or fragments thereof occur. For example patients with Familial Amyloid Polyneuropathy (FAP) exhibit TTR deposits primarily in the small diameter nerve fibers, and therefore present primarily symptoms such as altered sensory perceptions and autonomic dysfunctions, including gastro-intestinal dysfunctions or impotence; Patients with Familial Amyloid Cardiomyopathy (FAC) or Senile Systemic Amyloidosis (SSA) exhibit TTR deposits primarily in the heart, and therefore present symptoms such as cardiac insufficiency or cardiac arrhythmia; Patients with TTR deposits in kidneys may present renal dysfunctions and proteinurea.

Therefore, in one embodiment the antibody of the present invention is useful for the treatment of Familial Amyloid Polyneuropathy (FAP), Familial Amyloid Cardiomyopathy (FAC), Senile Systemic Amyloidosis (SSA), systemic familial amyloidosis, leptomeningeal/Central Nervous System (CNS) amyloidosis including Alzheimer disease, ocular amyloidosis, renal amyloidosis, hyperthyroxinemia, ligament amyloidosis including carpal tunnel syndrome, rotator cuff tears and lumbar spinal stenosis, and preeclampsia, and symptoms thereof.

The present invention is also drawn to an antibody, or antigen-binding fragment, variant or derivatives thereof, where the antibody comprises an antigen-binding domain identical to that of an antibody selected from the group consisting of NI-301.59F1, NI-301.35G11, NI-301.37F1, NI-301.2F5, NI-301.28B3, NI-301.119C12, NI-301.5D8, NI-301.9D5, NI-301.104F5, NI-301.21F10, NI-301.9G12, NI-301.12D3, NI-301.44E4, NI-301.18C4, NI-301.11A10, NI-301.3C9, NI-301.14D8, NI-301.9X4, and NI-301.14C3.

The present invention further exemplifies several binding molecules, e.g., antibodies and binding fragments thereof, which may be characterized by comprising in their variable region, e.g., binding domain at least one complementarity determining region (CDR) of the $V_H$ and/or $V_L$ variable region comprising any one of the amino acid sequences depicted in FIG. 1A-1T. The corresponding nucleotide sequences encoding the above-identified variable regions are set forth in Table II below. Exemplary sets of CDRs of the above amino acid sequences of the $V_H$ and/or $V_L$ region are depicted in FIG. 1A-1T. However, as discussed in the following the person skilled in the art is well aware of the fact that in addition or alternatively CDRs may be used, which differ in their amino acid sequence from those set forth in FIG. 1A-1T by one, two, three or even more amino acids in case of CDR2 and CDR3. Therefore, in one embodiment the antibody of the present invention or a TTR-binding fragment thereof is provided comprising in its variable region at least one complementarity determining region (CDR) as depicted in FIG. 1A-1T and/or one or more CDRs thereof comprising one or more amino acid substitutions.

In one embodiment, the antibody of the present invention is any one of the antibodies comprising an amino acid sequence of the $V_H$ and/or $V_L$ region as depicted in FIG. 1A-1T or a $V_H$ and/or $V_L$ region thereof comprising one or more amino acid substitutions. Preferably, the antibody of the present invention is characterized by the preservation of the cognate pairing of the heavy and light chain as was present in the human B-cell.

In a further embodiment of the present invention the anti-TTR antibody, TTR-binding fragment, synthetic or biotechnological variant thereof can be optimized to have appropriate binding affinity to the target and pharmacokinetic properties. Therefore, at least one amino acid in the CDR or variable region, which is prone to modifications selected from the group consisting of glycosylation, oxidation, deamination, peptide bond cleavage, iso-aspartate formation and/or unpaired cysteine is substituted by a mutated amino acid that lack such alteration or wherein at least one carbohydrate moiety is deleted or added chemically or enzymatically to the antibody. Examples for amino acid optimization can be found in e.g. international applications WO 2010/121140 and WO 2012/049570. Additional modification optimizing the antibody properties are described in Gavel et al., Protein Engineering 3 (1990), 433-442 and Helenius et al., Annu. Rev. Biochem. 73 (2004), 1019-1049.

Alternatively, the antibody of the present invention is an antibody or antigen-binding fragment, derivative or variant thereof, which competes for binding to TTR with at least one of the antibodies having the $V_H$ and/or $V_L$ region as depicted in any one of FIG. 1A to 1T.

Experimental results provided in FIG. 2A-2C and Example 3 suggest that some of the anti-TTR antibodies of the present invention preferentially bind to disease causing misfolded, misassembled or aggregated forms of human anti-TTR over the physiological forms of the proteins. In one embodiment thus, the antibody of the present invention preferentially recognizes misfolded, misassembled and/or aggregated TTR and/or fragment and/or derivatives thereof over physiological TTR.

The antibody of the present invention may be human, in particular for therapeutic applications. Alternatively, the antibody of the present invention is a rodent, rodentized or chimeric rodent-human antibody, preferably a murine, murinized or chimeric murine-human antibody or a rat, ratinized or chimeric rat-human antibody which are particularly useful for diagnostic methods and studies in animals. In one embodiment the antibody of the present invention is a chimeric rodent-human or a rodentized antibody.

Furthermore, in one embodiment, the chimeric antibody of the present invention, i.e. comprising the variable domains of a human antibody, e.g. NI-301.35G11 and generic murine light and heavy constant domains, exhibits the binding properties of the exemplary NI-301.mur35G11 murine chimeric antibodies as described in the Examples. Further, the mouse chimeric antibodies of the present invention bind with a high affinity to human TTR as described in Example 4 and 8. Preferably, the binding affinity of chimeric antibodies is similar to their human counterparts.

In one embodiment the antibody of the present invention is provided by cultures of single or oligoclonal B-cells that are cultured and the supernatant of the culture, which contains antibodies produced by said B-cells, is screened for presence and affinity of anti-TTR antibodies therein. The screening process comprises screening for binding to native monomeric, fibrillar or non-fibrillar aggregates like oligomers of hTTR derived from a synthetic full-length hTTR peptide or e.g. purified from human plasma or recombinant expression.

In addition or alternatively the screening process for presence and affinity of anti-TTR antibodies may comprise the steps of a sensitive tissue amyloid plaque immunoreactivity (TAPIR) assay such as described in international application WO 2004/095031, the disclosure content of which is incorporated herein by reference. Furthermore or alternatively, screens on renal, heart sections for binding to anti-TTR such as described in analogy in international application WO 2008/081008 for brain and spinal cord sections may be performed.

As mentioned above, due to its generation upon a human immune response the human monoclonal antibody of the present invention will recognize epitopes which are of particular pathological relevance and which might not be accessible or less immunogenic in case of immunization processes for the generation of, for example, mouse monoclonal antibodies and in vitro screening of phage display libraries, respectively. Accordingly, it is prudent to stipulate that the epitope of the human anti-TTR antibody of the present invention is unique and no other antibody which is capable of binding to the epitope recognized by the human monoclonal antibody of the present invention exists; see also FIG. 10A-10H. A further indication for the uniqueness of the antibodies of the present invention is the fact that, as indicated in Example 8, antibodies NI-301.59F1, NI-301.35G11, and NI-301.37F1 of the present invention bind epitopes that are specific for the misfolded, misassembled, and/or aggregated TTR conformation, which as indicated above, are of particular pathological relevance and may not be obtainable by the usual processes for antibody generation, such as immunization or in vitro library screenings.

Therefore, in one embodiment the present invention also extends generally to anti-TTR antibodies and TTR-binding molecules which compete with the human monoclonal antibody of the present invention for specific binding to TTR. The present invention is more specifically directed to an antibody, or antigen-binding fragment, variant or derivatives thereof, where the antibody specifically binds to the same epitope of TTR as a reference antibody selected from the group consisting of NI-301.59F1, NI-301.35G11, NI-301.37F1 and/or NI-301.12D3.

Furthermore, in one embodiment the present invention also extends generally to anti-TTR antibodies and TTR-binding molecules which compete with the human monoclonal antibody of the present invention for specific binding to misfolded, misassembled and/or aggregated TTR species or fragments thereof. The present invention is therefore, more specifically also directed to an antibody, or antigen-binding fragment, variant or derivatives thereof, where the antibody specifically binds to the same epitope of misfolded, misassembled or aggregated TTR species or fragments thereof as a reference antibody selected from the group consisting of NI-301.59F1, NI-301.35G11, NI-301.37F1 and/or NI-301.12D3.

Competition between antibodies is determined by an assay in which the immunoglobulin under test inhibits specific binding of a reference antibody to a common antigen, such as TTR. Numerous types of competitive binding assays are known, for example: solid phase direct or indirect radioimmunoassay (RIA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $I^{125}$ label; see Morel et al., Molec. Immunol. 25 (1988), 7-15 and Moldenhauer et al., Scand. J. Immunol. 32 (1990), 77-82. Typically, such an assay involves the use of purified TTR or misfolded, misassembled or aggregated TTR, such as oligomers and/or fibrils thereof bound to a solid surface or cells bearing either of these, an unlabeled test immunoglobulin and a labeled reference immunoglobulin, i.e. the human monoclonal antibody of the present invention. Competitive inhibition is measured by determining the amount of label bound to the solid surface or cells in the presence of the test immunoglobulin. Usually the test immunoglobulin is present in excess. Preferably, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody selected from the group consisting of NI-301.59F1, NI-301.35G11, NI-301.37F1, NI-305.2F5, NI-301.28B3, NI-301.119C12, NI-301.5D8, NI-301.9D5, NI-301.104F5, NI-301.21F10, NI-301.9G12, NI-301.12D3, NI.301.44E4, NI-301.18C4 NI-301.11A10, NI-301.3C9, NI-301.14D8, NI-301.9X4, and/or NI-301.14C3 from binding to TTR.

In addition, the present invention is further drawn to an antibody, or antigen-binding fragment, variant or derivatives thereof, where the antibody competitively inhibits a reference antibody selected from the group consisting of NI-301.59F1, NI-301.35G11, NI-301.37F1, NI-305.2F5, NI-301.28B3, NI-301.119C12, NI-301.5D8, NI-301.9D5, NI-301.104F5, NI-301.21F10, NI-301.9G12, NI-301.12D3, NI-301.44E4 NI-301.18C4, NI-301.11A10, NI-301.3C9, NI-301.14D8, NI-301.9X4, and/or NI-301.14C3 from binding to misfolded, misassembled or aggregated TTR species or fragments thereof.

In another embodiment, the present invention provides an isolated polypeptide comprising, consisting essentially of, or consisting of an immunoglobulin heavy chain variable region ($V_H$), where at least one of $V_H$-CDRs of the heavy chain variable region or at least two of the $V_H$-CDRs of the heavy chain variable region are at least 80%, 85%, 90% or 95% identical to reference heavy chain $V_H$-CDR1, $V_H$-CDR2 or $V_H$-CDR3 amino acid sequences from the antibodies disclosed herein. Alternatively, the $V_H$-CDR1, $V_H$-CDR2 and $V_H$-CDR3 regions of the $V_H$ are at least 80%, 85%, 90% or 95% identical to reference heavy chain $V_H$-CDR1, $V_H$-CDR2 and $V_H$-CDR3 amino acid sequences from the antibodies disclosed herein. Thus, according to this embodiment a heavy chain variable region of the invention has $V_H$-CDR1, $V_H$-CDR2 and $V_H$-CDR3 polypeptide sequences related to the groups shown in FIG. 1A-1T respectively. While FIG. 1A-1T shows $V_H$-CDRs defined by the Kabat system, other CDR definitions, e.g., $V_H$-CDRs defined by the Chothia system, are also included in the present invention, and can be easily identified by a person of ordinary skill in the art using the data presented in FIG. 1A-1T.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 1A-1T respectively.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 1A-1T respectively, except for one, two, three, four, five, or six amino acid substitutions in any one $V_H$-CDR. In certain embodiments the amino acid substitutions are conservative.

In another embodiment, the present invention provides an isolated polypeptide comprising, consisting essentially of, or consisting of an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2 or $V_L$-CDR3 amino acid sequences from antibodies disclosed herein. Alternatively, the $V_L$-CDR1, $V_L$-CDR2 and $V_L$-CDR3 regions of the $V_L$ are at least 80%, 85%, 90% or 95% identical to reference light chain $V_L$-CDR1, $V_L$-CDR2 and $V_L$-CDR3 amino acid sequences from antibodies disclosed herein. Thus, according to this embodiment a light chain variable region of the invention has $V_L$-CDR1, $V_L$-CDR2 and $V_L$-CDR3 polypeptide sequences related to the polypeptides shown in FIG. 1A-1T respectively. While FIG. 1A-1T shows $V_L$-CDRs defined by the Kabat system, other CDR definitions, e.g., $V_L$-CDRs defined by the Chothia system, are also included in the present invention.

In another embodiment, the present invention provides an isolated polypeptide comprising, consisting essentially of, or consisting of an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 1A-T respectively.

In another embodiment, the present invention provides an isolated polypeptide comprising, consisting essentially of, or consisting of an immunoglobulin heavy chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 1A-T respectively, except for one, two, three, four, five, or six amino acid substitutions in any one $V_L$-CDR. In certain embodiments the amino acid substitutions are conservative.

An immunoglobulin or its encoding cDNA may be further modified. Thus, in a further embodiment the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO 89/09622. Methods for the production of humanized antibodies are described in, e.g., European application EP-A1 0 239 400 and international application WO 90/07861. Further sources of antibodies to be utilized in accordance with the present invention are so-called xenogeneic antibodies. The general principle for the production of xenogeneic antibodies such as human-like antibodies in mice is described in, e.g., international applications WO 91/10741, WO 94/02602, WO 96/34096 and WO 96/33735. As discussed above, the antibody of the invention may exist in a variety of forms besides complete antibodies; including, for example, Fv, Fab and F(ab)$_2$, as well as in single chains; see e.g. international application WO 88/09344. In one embodiment therefore, the antibody of the present invention is provided, which is selected from the group consisting of a single chain Fv fragment (scFv), a F(ab') fragment, a F(ab) fragment, and a F(ab')$_2$ fragment.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO 00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the anti-TTR antibodies and/or antibodies capable of binding mutated, misfolded, misassembled or aggregated TTR species and/or fragments thereof of the present invention and displays the mentioned properties, i.e. which specifically recognizes TTR and/or mutated, misfolded, misassembled or aggregated TTR species and/or fragments thereof. Such antibodies and binding molecules can be tested for their binding specificity and affinity by ELISA and immunohistochemistry as described herein, see, e.g., the Examples. These characteristics of the antibodies and binding molecules can be tested by Western Blot as well.

The exemplary human antibody NI-301.37F1 showed prominent staining of misfolded TTR on sections from FAP patient skin biopsy but showed no staining on healthy control pancreas, wherein pancreatic alpha cells show endogenous expression of TTR, i.e. native TTR (see Example 8 and FIG. 9A-9F). The exemplary antibodies NI-301.35G11 and NI-301.37F1 of the present invention also gave positive results on FAP mouse tissue showing abnormal TTR deposits in various tissues including the intestine; see FIG. 8A-8F. This binding specificity towards pathological forms of TTR in human and animal tissue emphasizes besides the biochemical experiments showed herein (see FIG. 10A-10H) the usability of the antibodies of the present invention in treatment and diagnosis of diseases associated with TTR amyloidosis, which occurs preferably due to the occurrence of misfolded, misassembled, and/or aggregated TTR species and/or fragments, derivatives thereof.

As an alternative to obtaining immunoglobulins directly from the culture of B cells or memory B cells, the cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells are preferred. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

In accordance with the above, the present invention also relates to a polynucleotide encoding the antibody or equivalent binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody. In one embodiment of the present invention, the polynucleotide is a cDNA.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in FIG. 1A-1T.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of TTR aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO 2005/018572, which is incorporated by reference in its entirety.

In certain antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing TTR localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as TTR localization, biodistribution and serum half-life, may easily be measured and quantified using well know immunological techniques without undue experimentation.

In certain antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences binding to TTR as well as a cell surface receptor may be engineered using techniques known in the art.

In certain antibodies, or antigen-binding fragments, variants, or derivatives thereof described herein, the Fc portion may be mutated or exchanged for alternative protein sequences or the antibody may be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced", i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular preferred embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO 98/52976 and WO 00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., TTR-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus, as described herein.

In the well-known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press (1986), 59-103. It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and F(ab')$_2$ fragments may be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

In one embodiment, an antibody of the invention comprises at least one CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules.

Exemplary antibody molecules comprising at least one CDR that can be included in the subject antibodies are described herein.

Antibodies of the present invention can be produced by any method known in the art for the synthesis of antibodies, in particular, by chemical synthesis or preferably by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an $IgG_1$ human constant domain, see, e.g., international applications WO 02/060955 and WO 02/096948A2. This vector is engineered to delete the CH2 domain and provide a synthetic vector expressing a domain deleted $IgG_1$ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase TTR localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as an effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to TTR. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$-CDR1, $V_H$-CDR2, $V_H$-CDR3, $V_L$ region, $V_L$-CDR1, $V_L$-CDR2, or $V_L$-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind TTR and/or misfolded, misassembled or aggregated TTR species and/or fragments thereof).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies of the present invention are disclosed elsewhere herein. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of TTR and/or mutated, misfolded, misassembled or aggregated TTR species and/or fragments thereof) can be determined using techniques described herein or by routinely modifying techniques known in the art.

III. Polynucleotides Encoding Antibodies

A polynucleotide encoding an antibody, or antigen-binding fragment, variant, or derivative thereof can be composed of any polyribonucleotide or polydeoxyribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single-stranded and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

As is well known, RNA may be isolated from the original B cells, hybridoma cells or from other transformed cells by standard techniques, such as a guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In this context, the present invention also relates to a polynucleotide encoding at least the binding domain or variable region of an immunoglobulin chain of the antibody of the present invention. In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90%, or 95% identical to reference heavy chain $V_H$-CDR1, $V_H$-CDR2, or $V_H$-CDR3 amino acid sequences from the antibodies disclosed herein. Alternatively, the $V_H$-CDR1, $V_H$-CDR2, or $V_H$-CDR3 regions of the $V_H$ are at least 80%, 85%, 90%, or 95% identical to reference heavy chain $V_H$-CDR1, $V_H$-CDR2, and $V_H$-CDR3 amino acid sequences from the antibodies disclosed herein. Thus, according to this embodiment a heavy chain variable region of the invention has $V_H$-CDR1, $V_H$-CDR2, or $V_H$-CDR3 polypeptide sequences related to the polypeptide sequences shown in FIG. 1A-1T.

In another embodiment, the present invention provides an isolated polynucleotide comprising, consisting essentially of, or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90%, or 95% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90%, or 95% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$-CDR3 polypeptide sequences related to the polypeptide sequences shown in FIG. 1A-1T.

In another embodiment, the present invention provides an isolated polynucleotide comprising, consisting essentially of, or consisting of a nucleic acid encoding an immunoglobulin heavy chain variable region ($V_H$) in which the $V_H$-CDR1, $V_H$-CDR2, and $V_H$-CDR3 regions have polypeptide sequences which are identical to the $V_H$-CDR1, $V_H$-CDR2, and $V_H$-CDR3 groups shown in FIG. 1A-1T.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90%, or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, WI 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In a preferred embodiment of the present invention, the polynucleotide comprises, consists essentially of, or consists of a nucleic acid having a polynucleotide sequence of the $V_H$ or $V_L$ region of an anti-TTR antibody and/or antibody recognizing misfolded, misassembled or aggregated TTR species and/or fragments thereof as depicted in and Table II. In this respect, the person skilled in the art will readily appreciate that the polynucleotides encoding at least the variable domain of the light and/or heavy chain may encode the variable domain of both immunoglobulin chains or only one. In one embodiment therefore, the polynucleotide comprises, consists essentially of, or consists of a nucleic acid having a polynucleotide sequence of the $V_H$ and the $V_L$ region of an anti-TTR antibody recognizing misfolded, misassembled or aggregated TTR species and/or fragments thereof as depicted in Table II.

Table II

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| NI-301.59F1-VH | GAGGTGCAGC TGGTGGAGTC TGGGGGAGGG TTGGTCCAGC CTGGGGGGTC CCTGAGACTC TCCTGTGTAG CCTCTGGATT CACTTTTAGT AATTATTGGA TGAGTTGGGT CCGCCAGGCT CCAGGGAAGG GGCTGGAGTG GGTGGCCAAT ATAAATCAAG ATAGTGAGAA ATACTATGTG GACTCTGTGA AGGGCCGATT CGCCATCTCC AGAGACAACT CCAAGAACTC ACTGTATCTG CAAATGAACA GCCTGAGAGT CGAGGACACG GGCGTGTATT ACTGTGCGAG AGATCGCTAT TGCAGTGGTG GGAGATGCTC CCGGGGTAAC AACTGGTTCG ACCCCTGGGG CCAGGGAACC CTGGTCACCG TCTCCTCG SEQ ID NO.: 1 |
| NI-301.59F1-VL | GAAATTGTGT TGACGCAGTC TCCAGCCACT CTGTCTCTGT CTCCAGGGGA GAGAGCCACC CTCTCCTGCA GGGCCAGTCA GAGTGTTAGA AGCAACTTAG CCTGGTACCA GCAGAAACCT GGCCAGGCTC CCAGGCTCCT CATCTATGGT GCATCCACCA GGGCCACTGA TATCCCAGCC AGGTTCAGTG |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| | GCAGTGGGTC TGGGACAGAA TTCACTCTCA CCATCAGCAG CCTGCAGTCT GAGGATTTTG CAGTTTATTA CTGTCAGCAA TATAATAACT GGCCTCCGTA CACTTTTGGC CAGGGGACCA AAGTGGATAT CAAA SEQ ID NO.: 3 |
| NI-301.35G11-VH | GAGGTGCAGC TGGTGGAGTC TGGGGGAGGC TTGGTGCAGC CTGGGGGGTC CCTGAGACTC TCCTGTGTAG CCTCTGGATT CACTTTTAGC AGCTATGCCA TGAGCTGGGT CCGCCAGGTT CCAGGGAAGG GGCTGGAGTG GGTCTCATCT ATTAGTGGTA GTGGTGATAC AACAAAATAC ACAGACTCCG TGAAGGGCCG GTTCACCATC TCCAGAGACA ATTCCAAGAA CACGGTGTTT CTGCAAATGA GCAGCCTGAG AGCCGAGGAC ACGGCCCTAT ATTACTGTGT GAAAGATGGT AGTGGACGGA TCGATCCTTT TGCTTTATGG GGCCAAGGGA CAATGGTCAC CGTCTCTTCG SEQ ID NO.: 5 |
| NI-301.35G11-VL | GAAATTGTGA TGACACAGTC TCCACTCTCC CTGCCCGTCA CCCTTGGACA GCCGGCCTCC ATCTCCTGCA GGTCTAGTCG TAGTCTCGTA TACAGTGATG GAAACATTTA CTTGAATTGG TTTCAGCAGA |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
|  | GGCCAGGCCA ATCTCCAAGG CGCCTAATTT ATAAGGTTTC TAACCGGGAC TCTGGGGTCC CAGACAGATT CAGTGGCAGT GGGTCAGACA CTGACTTCAC ACTGAGAATC AGCAGGGTGG AGGCTGAGGA TGTTGGGGTC TATTACTGCA TGCAGGGTAC ACACTGGCCT AGGACGTTCG GCCAAGGGAC CAAGGTGGAG ATCAAA SEQ ID NO.: 7 |
| NI-301.37F1-VH | CAGGTGCAGC TGCAGGAGTC GGGCCCAGGA CTGGTGAAGC CTTCGGAGAC CCTGTCCCTC ACCTGCAGTG TCTCTGGTGG CTCCATCATC AGTAGGAGTT CCTACTGGGG CTGGATCCGC CAGCCCCCAG GGAAGGGGCT GGAGTGGATT GGGGGTATCT ATCATAGTGG GAACACTTAC GACAACCCGT CCCTCAAGAG TCGACTCACC ATGTCCGTAG ACACGTCGAA GAACCAGTTC TCCCTGAATC TGAGGTCTGT GACCGCCGCA GACACGGCTG TGTATTACTG TGCGAGGATA GTGCCGGGGG GTGATGCTTT TGATATCTGG GGCCAAGGGA CAATGGTCAC CGTCTCTTCG SEQ ID NO.: 9 |
| NI-301.37F1-VL | GACATCCAGA TGACCCAGTC TCCATCCTCC CTGTCTGCAT CTGTAGGAGA CAGAGTCACA ATCGCTTGCC GGGCCAGTCA GAGCGTTGGC ACCTATTTAA ATTGGTATCA GCAGAAAAGA GGGAAAGCCC CTAAACTCCT CATCTTTGCT GCATCCAGTT TGCAAAGTGG GGTCCCATCA AGGTTCAGTG GCAGTGGATC TGGGACAGAT TTCACTCTCA CCATCAGCAG TCTGCAACCT GAAGACTTTG CAACTTACTA CTGTCAACAG AGTTACAGTT CTCCTCCAAC GTTCGGCCAA GGGACCAAGG TGGAGATCAA A SEQ ID NO.: 11 |
| NI-301.2F5-VH | GAGGTGCAGC TGGTGGAGTC TGGGGGAGGC GTGGTCCGGT CTAGGAGGTC CCTGAGACTC TCCTGTGCAA CCTCTGGATT CACCTTCAGT AACTATGCGA TGCACTGGGT CCGCCAGGCT CCAGGCAAGG GGCTGGAGTG GGTGGCCATT ATTTCATATG ATGGAAACAA TAAATACTAC GCAGACTCCG TGAGGGGCCG ATTCACCGTC TCCAGAGACA ATTCCAAGAA CACATTCTAT CTGCAAATGA ACAGCCTGAG AATTGAGGAC ACGGCTGTAT ATTTTTGTGC GAGAGGGAGC GGTAGAGCAG CTCGTCACTG GTTCGACCCC TGGGGCCAGG GCACCCTGGT CACCGTCTCC TCG SEQ ID NO.: 13 |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| NI-301.2F5-VL | CAGTCTGCCC TGACTCAGCC TGCCTCCGTG TCTGGGTCTC CTGGACAGTC GATCACCATC TCCTGCACTG GAACCAGCAG TGACGTTGGT GGTTATAACT ATGTCTCCTG GTACCAACAA TACCCAGGCA AAGCCCCCAA AGTCATGATT TTTGATGTTT TTAATCGGCC TTCAGGGGTT TCTAATCGCT TCTCTGGCTC CAAGTCTGGC AACACGGCCT CCCTGACCAT CTCTGGACTC CAGGCAGAGG ACGAGGCTGA TTATTACTGC AGTTCATATA CAAGCAGCGT CACTCCTCAC TGGGTGTTCG GCGGAGGGAC CAAGCTGACC GTCCTA SEQ ID NO.: 15 |
| NI-301.28B3-VH | CAGCTGCAGC TGCAGGAGTC GGGCCCAGGA CTGGTGAAGC CTTCGGAGAC CCTGTCCCTC ACCTGCACTG TCTCCGGTGG CTCCATCACT AGTAGTAATT TCTACTGGGG CTGGATCCGC CAGCCCCCAG GGAAGGGGCT GGAGTGGATT GGGGCTATTT ATTCTAGTGG AAACACCTAC TACAACCCGT CCCTCAAGAG TCGAGTCACC ATATCCGTAG ACACGTCCAA GAAAAAGTTC TCCCTGAAGC TGAGCTCTGT GACCGCCGCT GACACGGCTG TCTATTACTG TGCGAGACAC TCTTGTAGTA GTGCCAGCTG CTATCCTCCC GGTTTCTGGT TCGACCCCTG GGGCCAGGGA ACCCTGGTCA CCGTCTCCTC G SEQ ID NO.: 17 |
| NI-301.28B3-VL | GAAATTGTGA TGACACAGTC TCCAGCCACC CTGTCTGCGT CTCCAGGGGA AAGAGCCACC CTCTCCTGCA GGGCCAGTCA GACTGTTAGT TACAACTTAG CCTGGTACCA GCAGAAACCT GGCCAGGCTC CCCGGCTCCT CATCTATGGC GCGTCCACCA GGGCCACTGG TATCCCAGGC AGGTTCAGTG GCAGTGGGTC TGGGACAGAG TTCACTCTCA CCATCAGCAG CCTGCAGTCT GAAGATTTTG CAGTTTATTA CTGTCAGCAA TATAATAACT GGCCTCCGTG GACGTTCGGC CAAGGGACCA AGGTGGAAAT CAAA SEQ ID NO.: 19 |
| NI-301.119C12-VH | CAGGTGCAGC TGCAGGAGTC GGGCCCAAGA CTGGTGAAGC CTTCACAGAC CCTGTCCCTC ACCTGCACTG TCTCTGGTGG CTCCATCAGC AGTGGTGTTT ACTACTGGAG CTGGATCCGC CAGCACCCAG GGAAGGGCCT GGAGTGGATT GGATATATTT CTAATACTGG GAACACCTAC TACAACCCGT CCCTCAAGAG TCGAGTTACC ATATCGATAG |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
|  | ACACCTCCAA |
|  | GAACCAGTTC |
|  | TCCCTCAACC |
|  | TGCGCTCTGT |
|  | GACTGCCGCG |
|  | GACACGGCCG |
|  | ACTATTTCTG |
|  | TGCGAGAGAG |
|  | TATTGTAGTG |
|  | GTGGTAATTG |
|  | CTACTCTCGC |
|  | TTCTACTACT |
|  | ACATGGACGT |
|  | CTGGGGCAAA |
|  | GGGACCACGG |
|  | TCACCGTCTC |
|  | CTCG |
|  | SEQ ID NO.: 21 |
| NI-301.119C12-VL | CAGTCTGTGC |
|  | TGACGCAGCC |
|  | GCCCTCAGTG |
|  | TCTGGGGCCC |
|  | CAGGGCAGAG |
|  | GGTCACCATC |
|  | TCCTGCACTG |
|  | GGAGCAGCTC |
|  | CAACATCGGG |
|  | GCAGGTTATG |
|  | GTGTACACTG |
|  | GTACCAGCAA |
|  | CTTTCAGGAA |
|  | CACCCCCCAA |
|  | ACTCCTCATC |
|  | TATGGAGACA |
|  | ACAATCGGCC |
|  | CTCAGGGGTC |
|  | CCTGACCGAT |
|  | TCTCTGGCTC |
|  | CAAGTCTGGC |
|  | ACCTCAGCCT |
|  | CCCTGGCCAT |
|  | CACTGGGCTC |
|  | CAGGCTGAGG |
|  | ATGAGGCTCA |
|  | TTATTACTGC |
|  | CAGTCCTATG |
|  | ACACCACCTT |
|  | GAGTGGTTCG |
|  | AGGGTGTTCG |
|  | GCGGAGGGAC |
|  | CAAGCTGACC |
|  | GTCCTA |
|  | SEQ ID NO.: 23 |
| NI-301.5D8-VH | CAGGTGCAGC |
|  | TACAGCAGTG |
|  | GGGCGCAGGA |
|  | CGGTTGAAGC |
|  | CTTCGGAGAC |
|  | CCTGTCCCTC |
|  | ACGTGCGCTG |
|  | TCTATGGTGG |
|  | GTCTTTCAGT |
|  | GCTTACTACT |
|  | GGAATTGGAT |
|  | CCGCCAGGCC |

| Antibody | Nucleotide sequences of variable heavy (VH) and variable light (VL) chains or variable kappa-light chains (VK) |
|---|---|
|  | CCAGGGAAGG |
|  | GGCTGGAGTG |
|  | GATTGGTGAA |
|  | GTCAGTCATG |
|  | GTGGCAGCAG |
|  | CAACTACAGC |
|  | CCGTCCCTCA |
|  | GGGGTCGAGT |
|  | CGCCATTTCT |
|  | TTAGACACGT |
|  | CCAAGAGCCA |
|  | GTTCTCCCTG |
|  | AGGCTGAATT |
|  | CTGTGACCGC |
|  | CGCGGACACG |
|  | GCTGTTTATT |
|  | ACTGTGCGAG |
|  | AGGCAGCCCT |
|  | GTAGTACTAC |
|  | CAGGTGCCAG |
|  | ATTCGACCCC |
|  | TGGGGCCAGG |
|  | GAACCCTGGT |
|  | CACCGTCTCC |
|  | TCG |
|  | SEQ ID NO.: 25 |
| NI-301.5D8-VL | CAGTCTGCCC |
|  | TGACTCAGCC |
|  | TGCCTCCGTG |
|  | TCTGGGTTTC |
|  | CTGGACAGTC |
|  | GATCACCATC |
|  | TCCTGCACTG |
|  | GAACCAGCAG |
|  | TGATGTTGGG |
|  | AGTTATAACC |
|  | TTGTCTCCTG |
|  | GTACCAACAA |
|  | CACCCAGGCA |
|  | AAGCCCCCAA |
|  | ACTCTTGATT |
|  | TATGAGGTCA |
|  | ATAAGCGGCC |
|  | CTCAGGAGTT |
|  | TCTACTCGCT |
|  | TCTCTGGCTC |
|  | CAAGTCTGGC |
|  | AACACGGCCT |
|  | CCCTGACGAT |
|  | CTCTGGGCTC |
|  | CAGACTGAGG |
|  | ACGAGGCTGA |
|  | TTATTACTGC |
|  | TGCTCATATG |
|  | CAGGTAGTAC |
|  | TAAGGTCTTC |
|  | GGAATTGGGA |
|  | CCAAGGTCAC |
|  | CGTCCTA |
|  | SEQ ID NO.: 27 |
| NI-301.9D5-VH | CAGGTGCAGC |
|  | TGCAGGAGTC |
|  | GGGCCCAGGC |
|  | CTGGTGAAGC |
|  | CTTCAGAGAC |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
|  | CCTGTCCCTC ACCTGCATTG TCTCTGGTGT CTCCATCAGA AGTGGTGGTT ACTACTGGAG CTGGATCCGG CAGCACCCAG GGAAGGGCCT GGAGTGGGTT GGGTTCATCT ATTACACTGG GAACACCTAC TACAACCCGT CCCTCAAGAG TCGAGCTACC ATATCAGTAG ACACCTCTAA GAACCAGTTC TCCCTGAGGC TGACCGCTGT GACTGCCGCG GACACGGCCG TGTATTACTG TGCAGAGAT TGTAGTGGTG GCAGCTGCCC CGAGTCCTAC TTTGACTCCT GGGGTCGGGG CACCCTGGTC ACCGTCTCCT CG SEQ ID NO.: 29 |
| NI-301.9D5-VL | GAAATTGTGA TGACACAGTC TCCAGCCACC CTGTCTTTGT CTCCAGGGGA AAGAGCCACC CTCTCCTGTA GGGCCAGTCA GAGTGTTCGC AGTTTCTTAG CCTGGTACCA ACAGAAATCT GGCCAGGCTC CCCGACTCCT CATCTATGAT GCATCCAAGA GGGCCACTGG CATCCCAGCC AGGTTCAGTG ACAGTGGGTC TGGAACAGAC TTCACTCTCA CCATCAGCAG ACTAGAGACT GAAGACTCTG CGGTTTATTA CTGTCAGCAG CGTACCAACT GGCCTCCACA CCTCACTTTC |
| | GGCGGAGGGA CCAAGGTGGA AATCAAA SEQ ID NO.: 31 |
| NI-301.104F5-VH | CAGGTGCAGC TGGTGGAGTC TGGGGGAGGC GTGGTCCAGC CTGAGAGGTC CCTGAGACTC TCCTGTGCAG CGTCTGGATT CACCTTCAGG AGCTATGCA TGCACTGGGT CCGCCAGGCT CCAGGCAAGG GGCTGGAGTG GGTGGCAGTT ATATGGTTTG ATGGAAGTAA TAAATACTAT GCAGACTCCG TGAAGGGCCG ATTCACCGTC TCCAGAGACA ATTCCAAGAA CACGCTGTAT CTGCAAATGA ACAGCCTGAG AGCCGAGGAC ACGGCTGTCT ACTACTGTGC AAGAGATGGT ATAGCAGCCA CTTATGCGGA CTACTGGGGC CAGGGAACCC TGGTCACCGT CTCCTCGSEQ IDNO.:33 |
| NI-301.104F5-VL | GAAATTGTGT TGACACAGTC TCCAGCCACC CTGTCTTTGT CTCCAGGGGA AAGAGCCACC CTCTCCTGCA GGGCCAGTCA GAGTGTTCGC AGCTACTTAG CCTGGTACCA ACAAAAACCT GGCCAGGCTC CCAGGCTCCT CATCTATGGT GCATCCAACA GGGCCACTGG CATCCCAGCC AGGTTCAGTG GCAGTGGGTC TGGGACAGAC TTCACTCTCA CCATCAGCAG CCTGGAGCCT GAAGATTTTG |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| | CAGTTTATTA<br>CTGTCAGCAA<br>CGTAGCAACT<br>GGCCGATCAC<br>CTTCGGCCAA<br>GGGACACGAC<br>TGGAGATTAA<br>A<br>SEQ ID<br>NO.: 35 |
| NI-301.21F10-VH | CAGGTGCAGC<br>TGGTGGAGTC<br>GGGGGGAGGT<br>TTGGTCCAGC<br>CTGGGGGGTC<br>CTTGAGACTG<br>TCCTGTGCGG<br>TCTCTGGATT<br>CACCCTTAGT<br>AGTCTTAGTT<br>CTTATTACAT<br>GAGTTGGGTC<br>CGCCAGGCTC<br>CAGGGAAGGG<br>GCTGGAGTGG<br>GTGGCCACTA<br>TAAACCCAGG<br>TGGAAGTGAG<br>AAGTCCTATG<br>TGGACTCTGT<br>GAAGGGCCGA<br>TTCACCGTCT<br>CCAGAGACAA<br>CGCCAGGAGC<br>TCAGTATATT<br>TGCAAATGGA<br>CAGCCTGACA<br>GTCGAGGACA<br>CGGCTATTTA<br>TTACTGTGCG<br>AGACCAAGAT<br>ATTGCACTAG<br>TGGTGGTTGC<br>TATTTTGACA<br>ACTGGGGCCA<br>GGGAACCCTG<br>GTCACCGTCT<br>CCTCG<br>SEQ ID<br>NO.: 37 |
| NI-301.21F10-VL | CAGTCTGCCC<br>TGACTCAGCC<br>TCGCTCAGTG<br>TCCGGGTCTC<br>CTGGACAGTC<br>AGTCACCATC<br>TCCTGCACTG<br>CAACCAATAG<br>TGATGTTGGC<br>GATTATAAGT<br>CTGTCTCCTG<br>GTACCAACAA<br>CACCCAGGCA<br>AAGCCCCCAA<br>ACTCATGATT<br>TATGATGTCG<br>GTAGGCGGCC |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| | CTCAGGGGTC<br>CCTGATCGCT<br>TCTCTGGCTC<br>CAAATCTGAC<br>AACACGGCCT<br>TCCTGACCAT<br>CTCTGGGCTC<br>CAGACTGAGG<br>ATGAAGCTGA<br>TTACTTTTGC<br>TGTATATATG<br>TAGGCAGGTC<br>TTCGGTGTTC<br>GGCGGAGGGA<br>CCAAGTTGAC<br>CGTCCTG<br>SEQ ID<br>NO.: 39 |
| NI-301.9G12-VH | CAGGTGCAGC<br>TGCAGGAGTC<br>GGGCCCAGGA<br>CTGGTGAAGC<br>CTTCGGAGAC<br>CCTGTCCCTC<br>ACCTGCGCTG<br>TCTCTGGTTT<br>CTCCATCAGC<br>AGTGGTTACT<br>ACTGGGGCTG<br>GATCCGGCAG<br>CCCCCAGGGA<br>CGGGGCTGGA<br>GTGGATTGGG<br>AGTATGTATC<br>ATAGTGGGAG<br>GACCTACTAC<br>AACCCGTCCC<br>TCAAGAGTCG<br>AGTCACCATA<br>TCAGTAGACA<br>CGTCCAAGAA<br>CCAGTTGTCC<br>CTGAAGCTGA<br>GCTCTGTGAC<br>CGCCGCAGAC<br>ACGGCCGTGT<br>ATTACTGTGC<br>GAGGGGCTTC<br>GATACTAGTG<br>GTTCCCATCG<br>GCCCCTCTCG<br>ACTGACTACT<br>GGGGCCAGGG<br>CACCCTGGTC<br>ACCGTCTCCT<br>CG<br>SEQ ID<br>NO.: 41 |
| NI-301.9G12-VL | CAGTCTGTGT<br>TGACGCAGCC<br>GCCCTCAGTG<br>TCTGCGGCCC<br>CAGGACAGAA<br>GGTCACCATC<br>TCCTGCTCTG<br>GAAGCAGCTC<br>CAACATTGGG |

TABLE II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| | AATAATTATG TATCCTGGTA CCAGCAGCTC CCAGGAACAG CCCCCAAACT CCTCATTTAT GACAATAATA AGCGACCCTC AGGGATTCCT GACCGAATCT CTGGCTCCAA GTCTGGCACG TCAGCCACCC TGGGCATCAC CGGACTCCAG ACTGGGGACG AGGCCGATTA TTACTGCGGA ACCTGGGATA GCAGCCTGAG TGCTTATGTC TTCGGAACTG GGACCAAGGT CACCGTCCTA SEQ ID NO.: 43 |
| NI-301.12D3-VH | GAGGTGCAGC TGGTGGAGAC TGGGGGAGGC GTGGTCCAGC CTGGGAGGTC CCTGAGACTC TCCTGTGTAG CGTCTGGATT CACCTTCAGG AACTATGGCA TGCACTGGGT CCGCCGGGCC CCAGGCAGGG GGCTGGAGTG GGTAGCAGTT ATATGGTCTG ATGGAAGTGA TAAATACTAT GCAGACTCCG TGGAGGGCCG ATTCACCATC TCCAGAGACA ATTCCAAGAA CACGGTGTTT CTCCAAATGA ACAGCCTGAG AGCCGACGAC ACGGCTGTAT ACTTCTGTGC GAGAGAGCCG AGCAGCACCT GGGCTTTTGA CTACTGGGGC CAGGGAACCC TGGTCACCGT CTCCTCG SEQ ID NO.: 45 |
| NI-301.12D3-VL | CAGTCTGCCC TGACTCAGCC TGCCTCCGTG TCTGGGTCTC CTGGACAGTC GATCACCATC TCCTGCACTG GAACCAGCAG TGATGTTGGG GGTTATAACC TTGTCTCCTG GTACCAACAG CACCCAGGCA AAGCCCCCAA ACTCATGATT TATGAGGACA TTAAGGGGCC CTCAGGGGTT TCTAATCGCT TCTCTGGCTC CAAGTCTGGC AACACGGCCT CCCTGACAAT CTCTGGGCTC CAGGCTGAGG ACGAGGCTGA TTATTTCTGC TGCTCATATG CAGGTACTGG CACTCTGGTA TTCGGCGGAG GGACCAAGCT GACCGTCCTA SEQ ID NO.: 47 |
| NI-301.44E4-VH | GAGGTGCAGC TGGTGGAGTC TGGGGGAGGC TTGGTACAGC CGGGGGGGTC CCTGAGACTC TCCTGTGCAG CCTCTGGATT CACCTTTAGC AGCTATGCCA TGATCTGGGT CCGCCAGGCT CCAGGGAAGG GGCTGGAGTG GGTCTCAGGT ATTAGTGGCA GTGGCAGTAC GACATACTAC GCAGACTCCG TGAAGGGCCG GTTCGCCATC TCCAGAGACA AATCCAAGAA CACGCTGTCC CTACAAATGA ACAGCCTGAG AGCCGAGGAC ACGGCCGTAT ATTACTGTGC AAAAGGGGCA TGGGAGATAC CCACCTACTT TGACAACTGG |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
|  | GGCCAGGGAA CCCTGGTCAC CGTCTCCTCG SEQ ID NO.: 54 |
| NI-301.44E4-VK | GAAATTGTGC TGACTCAGTC TCCAGCCACC CTGTCTGTGT CTCCAGGGGA AAGAGCCACC CTCTCCTGCA GGGCCAGTCA GAGTATTAGG AACAACTTAG CCTGGTACCA GCAGAAACCT GGCCAGGCTC CCAGGCTCCT CATCTATGGT GCATCCACCA GGGCCACTGG TATCCCAGCC AGGTTCAGTG GCACTGGGTC TGGGACAGAG TTCACTCTCA TCGTCAGCAG CCTGCAGTCT GAAGATTTTG CAGTTTATTA CTGTCAGCAG TATAATAACT GGCCTCCCAC GTGGACGTTC GGCCAAGGGA CCAAGGTGGA AATCAAA SEQ ID NO.: 56 |
| NI-301.18C4-VH | GAGGTGCAGC TGGTGGAGTC TGGGGGAACC TTGGTCCAGC CGGGGGGGTC CCTGAGGCTC TCCTGCGCAG CGTCGGGATT CACATTCAAC ATTTATGCCA TGACCTGGGT CCGCCTGTCT CCAGTGAGGG GACTGGAGTG GGTCTCTACT ATTACTAGTG GTGGCGTCAG CATATATTAC GCAGACTCCA TAAAGGGCCG CTTCACCGTC TCCAGAGACA ATGCCAAGAA CATGGTGTTT CTACAACTGG ACAACCTGAC AGTCGATGAC |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
|  | ACGGCCATAT ATTACTGTGG GAAGGACGGA AACTGCGATG AGACAAGTTG TTACTTAAGG GGGATGGACG TCTGGGGCCA AGGGACCACG GTCACCGTCT CCTCG SEQ ID NO.: 61 |
| NI-301.18C4-VL | CAGTCTGTGT TGACGCAGCC GCCCTCAGTG TCAGCGGCCC CAGGACAGAA GGTCACCATC TCCTGCTCTG GTAGCAGGTC CGACATTGGG TCTAAACTTG TTTCCTGGTA CCAGGTAATC CCAGGAAGAG CCCCCCGGCT CGTCATTTTT GACACTTATA AGCGGCCCTC AGGGGTACCT GCCCGCTTCT CTGCCTCCAA GTCTGGCACG TCAGCCACCC TGGACATCGC CGGGCTCCAG CCTGGGGACG AGGCCGAATA TTTCTGCGGA TCATGGGTA ACAGTGAGAA TTTTTATTAT GTCTTCGGAT CTGGGACCCG GGTCACCGTC CTG SEQ ID NO.: 63 |
| NI-301.11A10-VH | CAGCTGCAGC TGCAGGAGTC GGGCCCAGGA CTGGTGAAGC CTTCGGAGAC CCTGTCCCTC ACCTGCACTG TGTCTGGTGG CTCCATCAGC AGTAGAAGTT ACTACTGGGG CTGGATGCGC CAGCCCCCAG GGAAGGGGCT GGAGTGGATT GGGAGTATTT ATTATAGTGG GAGCACCCTC |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| | TACAATCCGT CCCTCAAGAG TCGAGTCACC ATGTCAATAG TCACGTCGAG GAACCAGTTC TCCCTGAAGC TGAGTTCTGT GACCGCCGCG GACACGGCCG TGTATTATTG TACCCGAATG GGGGAGGGGG GGCGGGACTA CTGGGGCCAG GGAACCCTGG TCACCGTCTC CTCG SEQ ID NO.: 65 |
| NI-301.11A10-VK | GACATCCAGA TGACCCAGTC TCCTTCCACC CTGTCTGCAT CTGTAGGAGA CAGAGTCACC ATCACTTGCC GGGCCAGTCA GAGTATTAGT AGTTGGTTGG CCTGGTATCA GCAGAAACCA GGGAAAGCCC CTAAGGTCCT GATCTATGAT GCCTCCAGTT TGGAAAGAGG GGTCCCATCA AGGTTCAGCG GCAGTGGGTC TGGGACAGAA TTCACTCTCA CCATCAGCAG CCTGCAGCCT GATGATTCTG CAACTTATTA CTGCCAACAC TATAATGGTT ATTCAAGGAC GTTCGGCCGC GGGACCAAGG TGGAAATCAA A SEQ ID NO.: 67 |
| NI-301.3C9 VH | CAGGTGCAGC TGCAGGAGTC GGGCCCAGGA CTGGTGAAGT CTTCGCAGAC CCTGTCCCTC ACCTGCACTG TCTCTGGTGC CTCCTTCACC AGGGGTGATT TCTACTGGAG TTGGATCCGC |

| Antibody | Nucleotide sequences of variable heavy (VH) and variable light (VL) chains or variable kappa-light chains (VK) |
|---|---|
| | CAGGTCCCAG GGAAGGGCCT GGAATGGATT GGTTACATAT ATTCCACTGG GGACGTCTAC TACAATCCGT CTCTCAAGAG TCGAGCAAAC ATCTCGGTCG ACACGCCCAA GAAGCAGTTC TTCCTGAAAT TGACCTCTTT GACTGCCGCA GACACGGCCG TCTATTTTTG TGCCAGGGAA GGACAATATT GTAGCGGTGG TAGTTGCTAC CCTGAATACT GGGGCCAGGG AACCCTGGTC ACCGTCTCCT CG SEQ ID NO.: 69 |
| NI-301.3C9 VL | TCCTATGAGC TGACTCAGCC ACCCTCAGTG TCCGTGTCCC CAGGACAGAC AGCCACCATC ACCTGCTCTG GAGATAATTT GGGACATAAA TTTACTTGCT GGTATCAGCA GAAGCCAGGC CAGTCCCCTG TCCTGGTCAT CTATCAAGAT CACAAGCGGC CCTCAGGGAT CCCTGAGCGA TTCTCCGGCT CCAACTCTGG GACACAGCC ACTCTGACCA TCAGCGGGAC CCAGGCTATG GATGAGGCTG AGTATTACTG TCAGGCGTGG GCCTTCCCCT ATGTGGTCTT CGGCGGAGGG ACCAAGCTGA CCGTCCTA SEQ ID NO.: 71 |
| NI-301.14D8 VH | GAGGTGCAGC TGGTGGAGAC TGGGGGACGC TTGGTCCAGC CGGGGGGGTC |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
|  | CGTGAGACTC TCCTGTATAG CCTCTGGATT TCCCTTTAGG AATTATTGGA TGAGTTGGGT CCGCCAGCCT CCAGGGAAGG GGCTGGAGTG GGTGGCCAAC ATAAAGGAAG ATGGCAGTGA CAGATACTAT GTGGACTCTG TGAAGGGCCG CTTCACCATC TTTAGAGACA ACGCCAAGAA TTTTCTGAGT CTACAAATGA ATCGCCTGAG AGCCGAGGAC ACGGCGGTAT ACTTCTGTGC GAGAATTGTA GGGGTAATCC CGTCCGCTGA CCCATACTAC CTTGACTCCT GGGGCCAGGG AACCCTGGTC ACCGTCTCCT CG SEQ ID NO.: 73 |
| NI-301.14D8 VL | CAGTCTGCCC TGACTCAGCC TGCCTCCGTG TCTGGGTTTG CTGGACAGTC GGTCACCATC TCCTGCACTG GAACCAGCCT TAACATTGGG ACTTACAACC TTATCTCCTG GTACCAACAA CACCCAGGCA GAGCCCCCAG ACTCATCATT TTTGAGGGCA ATAGGCGGCC CCCCGGGATT TCTAATCGCT TCTCTGCCTC CAAGTCTGGC AACACGGCCT CCTTGACAGT CTCTGGGCTG CTGGCTGGCG ACGAGGCTGA TTATTACTGT TGCTCATTTG CAGGAAGAGT CTCTTTGGTG |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
|  | TTTGGCGGAG GGACCAAGTT GACCGTCCTA SEQ ID NO.: 75 |
| NI-301.9X4 VH | CAGGTGCAGC TGCAGGAGTC GGGCCCAGGA CTGGTGAAAC CTTCGGAGAC CCTGTCCCTC ACCTGCAGTG TCTCTGCTGG CTCCATCAGT AGTCACTACT GGAACTGGAT CCGGCAGCCC CCAGGGAAGG GACTGGAATG GATTGGGTCT ATCTATCACA GTGGGAGCAC CAACTACAAC CCCTCCCTCA AGAGTCGAGT CACCATATCA GTAGACACGT CCAAGAACCA CGTCTCCCTG AGGTTGACGT CTGTGACCGC CGCAGACACG GCCGTGTATT ACTGTGCGAG AGACTACTAC TACTACATGG ACGTCTGGGG CAAAGGGACC ACGGTCACCG TCTCCTCG SEQ ID NO.: 77 |
| NI-301.9X4 VL | TCCTATGAGC TGACTCAGCC ACCCTCGGTG TCAGTGTCCC CAGGACAGAC GGCCAGGATC ACCTGCTCTG GAGATGCGTT GCCAGACAAG TATGCTTATT GGTACCAGCA GAAGCCAGGC CAGGCCCCTA TGTTGGTTAT ATATAAGGAC AGTGAGAGGC CCTCAGGGAT CCCTGAGCGA TTCTCTGGCT CCAGTTTGGG GACAACAGTC ATGCTGACCA TCAGTGGAGT CCAGGCAGAG GACGAGGCTG |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| | ACTATTACTG TAAATCAGCA GACAGCAGTG GTACTTATTG GGTGTTCGGC GGGGGGACCA AGCTGACCGT CCTA SEQ ID NO.: 79 |
| NI-301.14C3 VH | GAGGTGCAGC TGGTGGAGAC TGGAGGAGGC TTGATCCAGC CTGGGGGGTC CCTGAGACTC TCCTGTGCAG CCTCTGGGTT CACCGTCAGT AGCCACTACA TGAGCTGGGT CCGCCAGGCT CCAGGGAAGG GGCTGGAGTG GGTCTCAATT ATTTATAGCG GTGGTGGCAC ATACTACGCA GACTCCGTGA AGGGCCGATT CACCATCTCC AGAGACAATT CCAAGAACAC GCTGTATCTT CAAATGAACA GCCTGAGAGC CGAGGACACG GCCGTGTATT ACTGTGCGAA GATCTACAGG TCGGGTAATA CTGGTTATTC TTACGACTAC TGGGGCCAGG GAACCCTGGT CACCGTCTCC TCG SEQ ID NO.: 81 |
| NI-301.14C3 VL | TCCTATGAGC TGACTCAGCC ACCCTCAGTG TCCGTGTCCC CAGGGCAGAC AGCCAGCATC ACCTGCTCTG GAGATAAATT GGGGAGTAAA TATGCTTGCT GGTATCAGCA GAAGCCAGGC CAGTCCCCTG TACTGGTCAT CTATGAAGAT AAGAAGCGGC CCTCAGGGAT CCCTGAGCGA |

Table II-continued

Nucleotide sequences of the VH and VL region of antibodies recognizing mutated, misfolded, misassembled or aggregated TTR species and/or fragments thereof.

| Antibody | Nucleotide sequences of variable heavy (VH) and variable light (VL) chains or variable kappa-light chains (VK) |
|---|---|
| | TTCTCTGGCT CCAACTCTGG GAACACAGCC ACTCTGACCA TCAGCGGGAC CCAGGCTATG GATGAGGCTG ACTATTTCTG TCAGGCGTGG GACAGCAGCA CTTCTCATGT GGTATTCGGC GGAGGGACCA GGCTGACCGT CCTA SEQ ID NO.: 83 |

Due to the cloning strategy the amino acid sequence at the N- and C-terminus of the heavy chain and light chains may potentially contain primer-induced alterations in FR1 and FR4, which however do not substantially affect the biological activity of the antibody. In order to provide a consensus human antibody, the nucleotide and amino acid sequences of the original clone can be aligned with and tuned in accordance with the pertinent human germ line variable region sequences in the database; see, e.g., Vbase2, as described above. The amino acid sequence of human antibodies are indicated in bold when N- and C-terminus amino acids are considered to potentially deviate from the consensus germ line sequence due to the PCR primer and thus have been replaced by primer-induced mutation correction (PIMC), see Table III. Accordingly, in one embodiment of the present invention, the polynucleotide comprises, consists essentially of, or consists of a nucleic acid having a polynucleotide sequence of the VH as depicted in Table III and the corresponding VL region of an anti-TTR antibody as shown in Table II.

TABLE III

Nucleotide sequences of the VH and VL region of antibodies recognizing mutated, misfolded, misassembled or aggregated TTR species and/or fragments thereof showing replacement by PIMC (bold).

| Alternative with PIMC | Nucleotide sequences of variable heavy (V$_H$) chains Antibody-regions |
|---|---|
| NI-301.37F1-PIMC-VH | CAGCTGCAGCTGCAG GAGTCGGGCCCAGGA CTGGTGAAGCCTTCG GAGACCCTGTCCCTC ACCTGCAGTGTCTCT GGTGGCTCCATCATC AGTAGGAGTTCCTAC TGGGGCTGGATCCGC CAGCCCCAGGGAAG GGGCTGGAGTGGATT |

TABLE III-continued

Nucleotide sequences of the VH and VL region of antibodies recognizing mutated, misfolded, misassembled or aggregated TTR species and/or fragments thereof showing replacement by PIMC (bold).

| Alternative with PIMC | Nucleotide sequences of variable heavy (V$_H$) chains Antibody-regions |
|---|---|
| | GGGGGTATCTATCAT |
| | AGTGGGAACACTTAC |
| | GACAACCCGTCCCTC |
| | AAGAGTCGACTCACC |
| | ATGTCCGTAGACACG |
| | TCGAAGAACCAGTTC |
| | TCCCTGAATCTGAGG |
| | TCTGTGACCGCCGCA |
| | GACACGGCTGTGTAT |
| | TACTGTGCGAGGATA |
| | GTGCCGGGGGTGAT |
| | GCTTTTGATATCTGG |
| | GGCCAAGGGACAATG |
| | GTCACCGTCTCTTCG |
| | SEQ ID NO.: 52 |

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA$^+$ RNA, isolated from, any tissue or cells expressing the TTR-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art. Accordingly, in one embodiment of the present invention the cDNA encoding an antibody, immunoglobulin chain, or fragment thereof is used for the production of an anti-TTR antibody.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that may be used to produce the desired quantity of antibody. Recombinant expression of an antibody, or fragment, derivative, or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operable linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses, and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics), or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) as discussed above. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene, and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, CA), and plasmid pCI (available from Promega, Madison, WI). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the antibodies, or antigen-binding fragments, variants, or derivatives thereof of the invention may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application. Therefore, in one embodiment the present invention provides a vector comprising the polynucleotide encoding at least the binding domain or variable region of an immunoglobulin chain of the antibody, optionally in combination with a polynucleotide that encodes the variable region of the other immunoglobulin chain of said binding molecule.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells comprising a polynucleotide encoding an antibody of the invention, or a heavy or light chain thereof, or at least the binding domain or variable region of an immunoglobulin thereof, which preferably are operable linked to a heterologous promoter. In addition or alternatively the invention also includes host cells comprising a vector, as defined hereinabove, comprising a polynucleotide encoding at least the binding domain or variable region of an immunoglobulin chain of the antibody, optionally in combination with a polynucleotide that encodes the variable region of the other immunoglobulin chain of said binding molecule. In preferred embodiments for the expression of double-chained antibodies, a single vector or vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *Escherichia coli, Bacillus subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as E. coli, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO and 293 cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska and Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan and Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification, for a review; see Bebbington and Hentschel, The use of vectors based on gene amplification for the expression of cloned genes in mammalian cells in DNA cloning, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein.

Genes encoding antibodies, or antigen-binding fragments, variants or derivatives thereof of the invention can also be expressed in non-mammalian cells such as bacteria or insect or yeast or plant cells. Bacteria which readily take up nucleic acids include members of the enterobacteriaceae, such as strains of *E. coli* or *Salmonella*; Bacillaceae, such as *B. subtilis*; Pneumococcus; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO 02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye and Inouye, Nucleic Acids Res. 13 (1985), 3101-3109; Van Heeke and Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g.,
Scopes, "Protein Purification", Springer Verlag, N.Y. (1982). Alternatively, a preferred method for increasing the affinity of antibodies of the invention is disclosed in US patent publication 2002-0123057 A1. In one embodiment therefore, the present invention also provides a method for preparing an anti-TTR antibody or an antibody recognizing mutated, misfolded, misassembled or aggregated TTR species and/or fragments thereof or immunoglobulin chain(s) thereof, said method comprising:

(a) culturing the host cell as defined hereinabove, which cell comprised a polynucleotide or a vector as defined hereinbefore; and (b) isolating said antibody or immunoglobulin chain(s) thereof from the culture.

Furthermore, in one embodiment the present invention also relates to an antibody or immunoglobulin chain(s) thereof encoded by a polynucleotide as defined hereinabove or obtainable by the method for preparing an anti-TTR antibody.

V. Fusion Proteins and Conjugates

In certain embodiments, the antibody polypeptide comprises an amino acid sequence or one or more moieties not normally associated with an antibody. Exemplary modifications are described in more detail below. For example, a single-chain Fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like).

An antibody polypeptide of the invention may comprise, consist essentially of, or consist of a fusion protein. Fusion proteins are chimeric molecules which comprise, for example, an immunoglobulin TTR-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species. As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO 92/08495; WO 91/14438; WO 89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids.

Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., Proteins—Structure And Molecular Properties, T. E. Creighton, W. H. Freeman and Company, New York 2nd Ed., (1993); Posttranslational Covalent Modification Of Proteins, B. C. Johnson, Ed., Academic Press, New York, (1983) 1-12; Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to TTR. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds TTR. In yet another embodiment, a fusion protein for use in the diagnostic and treatment methods disclosed herein comprises a polypeptide having the amino acid sequence of any one, two, three, or more of the $V_H$ CDRs of an antibody and the amino acid sequence of any one, two, three, or more of the $V_L$ CDRs of an antibody, or fragments or variants thereof, and a heterologous polypeptide sequence. Preferably, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767), GST, c-mycand the "flag" tag; see, e.g., Bill Brizzard, BioTechniques 44 (2008) 693-695 for a review of epitope tagging techniques, and Table 1 on page 694 therein listing the most common epitope tags usable in the present invention, the subject matter of which is hereby expressly incorporated by reference.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression, which is performed as described hereinbefore.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared, e.g., by reacting a TTR-binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antibodies, or antigen-binding fragments, variants or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a TTR amyloidosis to indicate the risk of getting a disease or disorder associated with misfolded, misassembled or aggregated TTR, to monitor the development or progression of such a disease, i.e. a disease showing the occurrence of, or related to aggregated TTR misfolded, misassembled, or as part of a clinical testing procedure to, e.g., determine the efficacy of a given treatment and/or prevention regimen. In one embodiment thus, the present invention relates to an antibody, which is detectably labeled. Furthermore, in one embodiment, the present invention relates to an antibody, which is attached to a drug. Detection can be facilitated by coupling the antibody, or antigen-binding fragment, variant, or derivative thereof to a detectable substance. The detectable substances or label may be in general an enzyme; a heavy metal, preferably gold; a dye, preferably a fluorescent or luminescent dye; or a radioactive label. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc. Therefore, in one embodiment the present invention provides a detectably labeled antibody, wherein the detectable label is selected from the group consisting of an enzyme, a radioisotope, a fluorophore and a heavy metal.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, (ed.), Enzyme Immunoassay, CRC Press, Boca Raton, Fla., (1980); Ishikawa, et al., (eds.), Enzyme Immunoassay, Kgaku Shoin, Tokyo (1981). The enzyme, which is bound to the antibody, will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., (1987) 623-53; Thorpe, "Antibody Carriers Of Cytotoxic Agents In Cancer Therapy: A Review", in Monoclonal Antibodies '84: Biological And Clinical Applications, Pinchera et al. (eds.), (1985) 475-506; "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press (1985) 303-16, and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned TTR-binding molecule, e.g., antibody or antigen-binding fragment thereof of the present invention or derivative or variant thereof, or the polynucleotide, vector, cell or peptide of the invention as defined hereinbefore. In one embodiment, the composition of the present invention is a pharmaceutical composition and further comprises a pharmaceutically acceptable carrier. Furthermore, the pharmaceutical composition of the present invention may comprise further agents such as interleukins or interferons depending on the intended use of the pharmaceutical composition. For use in the treatment of a disease or disorder showing the occurrence of, or related to mutated, misfolded, misassembled, or aggregated TTR, such as TTR amyloidosis, the additional agent may be selected from the group consisting of small organic molecules, anti-TTR antibodies, and combinations thereof. Hence, in a particular preferred embodiment the present invention relates to the use of the TTR-binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of a disease or disorder associated with TTR amyloidosis, monitoring the progression of a disease or disorder associated with TTR amyloidosis or a response to a TTR amyloidosis treatment in a subject or for determining a subject's risk for developing a disease or disorder associated with TTR amyloidosis.

Hence, in one embodiment the present invention relates to a method of treating a disease or disorder characterized by abnormal accumulation and/or deposition of TTR and/or misfolded, misassembled, aggregated, mutated TTR in affected systems and organs such as peripheral nervous system, autonomic nervous system, central nervous system, gastrointestinal system, vascular system especially leptomeninges, lymphoid system especially the lymphoid nodes, musculoskeletal system especially tendons and ligaments, the heart, eyes, kidneys, lungs, skin, tongue, thyroid gland and bladder which method comprises administering to a subject in need thereof a therapeutically effective amount of any one of the afore-described TTR-binding molecules, antibodies, polynucleotides, vectors, cells or peptides of the instant invention.

A particular advantage of the therapeutic approach of the present invention lies in the fact that the recombinant antibodies of the present invention are derived from B cells or memory B cells from healthy human subjects with no signs or symptoms of a disease, e.g. carrying an asymptomatic mutation and/or mutations, showing the occurrence of, or related to aggregated TTR and thus are, with a certain probability, capable of preventing a clinically manifest disease related to misfolded, misassembled, mutated, and/or aggregated TTR, or of diminishing the risk of the occurrence of the clinically manifest disease or disorder, or of delaying the onset or progression of the clinically manifest disease or disorder. Typically, the antibodies of the present invention also have already successfully gone through somatic maturation, i.e. the optimization with respect to selectivity and effectiveness in the high affinity binding to the target TTR molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-TTR antibodies of the present invention, both its target structure-specific efficiency as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-TTR antibody, binding fragment, derivative or variant thereof, polynucleotide, vector, cell and/or peptide of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disease or disorder which is accompanied with the presence of mutated, misfolded, misassembled, and/or aggregated TTR, and in particular applicable for the treatment of disorders generally characterized by TTR amyloidosis comprising diseases and/or disorders such as Familial Amyloid Polyneuropathy (FAP), Familial Amyloid Cardiomyopathy (FAC), Senile Systemic Amyloidosis (SSA), systemic familial amyloidosis, leptomeningeal/Central Nervous System (CNS) amyloidosis including Alzheimer disease, TTR-related ocular amyloidosis, TTR-related renal amyloidosis, TTR-related hyperthyroxinemia, TTR-related ligament amyloidosis including carpal tunnel syndrome, rotator cuff tears and lumbar spinal stenosis, and preeclampsia.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline, and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like. Furthermore, the pharmaceutical composition of the invention may comprise further agents such as dopamine or psychopharmacologic drugs, depending on the intended use of the pharmaceutical composition.

Furthermore, in a preferred embodiment of the present invention the pharmaceutical composition may be formulated as a vaccine, for example, if the pharmaceutical composition of the invention comprises a TTR antibody or binding fragment, derivative or variant thereof for passive immunization. As mentioned in the background section misfolded, misassembled, mutated and/or aggregated TTR species and/or fragments or derivatives thereof are a major trigger for TTR amyloidosis. Accordingly, it is prudent to expect that passive immunization with human anti-TTR antibodies and equivalent TTR-binding molecules of the present invention will help to circumvent several adverse effects of active immunization therapy concepts and lead to a reduced aggregation of TTR. Therefore, the present anti-TTR antibodies and their equivalents of the present invention will be particularly useful as a vaccine for the prevention or amelioration of diseases or disorders showing the presence of, or caused by aggregated TTR such as Familial Amyloid Polyneuropathy (FAP), Familial Amyloid Cardiomyopathy (FAC), Senile Systemic Amyloidosis (SSA), systemic familial amyloidosis, leptomeningeal/Central Nervous System (CNS) amyloidosis including Alzheimer disease, TTR-related ocular amyloidosis, TTR-related renal amyloidosis, TTR-related hyperthyroxinemia, TTR-related ligament amyloidosis including carpal tunnel syndrome, rotator cuff tears and lumbar spinal stenosis, and preeclampsia for example.

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008); S1741-0134, published online ahead, describe the use of chimeric recombinant Fab (rFab) and single chain fragments (scFvs) of monoclonal antibody WO-2 which recognizes an epitope in the N-terminal region of Abeta. The engineered fragments were able to (i) prevent amyloid fibrillization, (ii) disaggregate preformed Abeta1-42 fibrils and (iii) inhibit Abeta1-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other antibodies useful for treating a disease or disorder related to the occurrence of mutated, misfolded, misassembled, and/or aggregated TTR may be desirable. In one embodiment, the additional antibody is comprised in the pharmaceutical composition of the present invention. Examples of antibodies which can be used to treat a subject include, but are not limited to, antibodies targeting CD33, SGLT2, IL-6, and IL-1.

In a further embodiment, co-administration or sequential administration of other agents useful for treating a disease or disorder related to misfolded, misassembled, mutated, and/or aggregated TTR, may be desirable. In one embodiment, the additional agent is comprised in the pharmaceutical composition of the present invention. Examples of agents which can be used to treat a subject include, but are not limited to: Agents which stabilize the TTR-tetramer, such as Tafamidis Meglumin, diflusinal, doxycyclin with ursodeoxycholic acid; anti-inflammatory agents such as diflusinal, corticosteroids, 2-(2,6-dichloranilino) phenylacetic acid (diclofenac), iso-butyl-propanoic-phenolic acid (ibuprofen); diuretics, Epigallocatechin gallate, Melphalan hydrochloride, dexamethasone, Bortezomib, Bortezomib-Melphalan, Bortezomib-dexamethasone, Melphalan-dexamethasone, Bortezomib-Melphalan-dexamethasone; antidepressants, antipsychotic drugs, neuroleptics, antidementiva (e.g. the NMDA-rezeptor antagonist memantine), acetylcholinesterase inhibitors (e.g. Donepezil, HCI, Rivastigmine, Galantamine), glutamat-antagonists and other nootropics blood pressure medication (e.g. Dihydralazin, Methyldopa), cytostatics, glucocorticoides, angiotensin-converting-enzyme (ACE) inhibitors; anti-inflammatory agents or any combination thereof. Examples of agents which may be used for treating or preventing organ rejection following clinical organ transplantation include but are not limited to the agents of the group which lead to a weakening of the immune system, i.e. immunosuppressive comprising such as calcineurin inhibitors such as cyclosporine and Tacrolimus, inhibitors of proliferation such as mTOR inhibitors comprising Everolimus and Sirolimus (rapamycin) as well as antimetabolites such as Azathioprin, Mycophenolat Mofetil/MMF and mycophenolic acid, and corticosteroids such as cortisone and cortisol as well as synthetical substances such as Prednison or Prednisolon can be used. Additionally antibodies can be used such as anti-IL2-receptor monoclonal antibodies (e.g. Basiliximab, Daclizumab) as well as anti-CD3 monoclonal antibodies (e.g. Muromonab-CD3), and polyclonal compositions such as anti-thymocyte globulin (ATG); and glucagon-like peptide-1 (GLP-1) receptor agonists (see, e.g., Noguchi et al., Acta Med. Okayama, 60 (2006), and the international application WO 2012/088157). Furthermore, additional agents might comprise agents for the prophylaxis and or treatment of infections and other side effects after an organ transplantation comprising valganciclovir, cytomegalie-immunoglobulin, gancyclovir, amphotericin B, pyrimethamin, ranitidine, ramipril, furosemide, benzbromaron. Therefore, in one embodiment a composition is provided further comprising an additional agent useful for treating TTR amyloidosis and/or in treating or preventing organ rejection following, e.g. clinical liver transplantation. Examples of other agents that may be used concomitant with a pharmaceutical composition of the present invention are described in the art; see, e.g. international applications WO 2009005672, WO 2010128092, WO 2012088157 or European application EP 11 158 212.8.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

From the foregoing, it is evident that the present invention encompasses any use of an TTR-binding molecule and/or fragments thereof comprising at least one CDR of the above described antibody, in particular for diagnosing and/or treatment of a disease or disorder related to mutated, misfolded, misassembled, or aggregated TTR species and/or fragments thereof as mentioned above, such as TTR amyloidosis. Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-TTR antibodies in a sample obtained from a subject. In one embodiment thus, the present invention provides an antibody as defined hereinabove and below or a TTR-binding molecule having substantially the same binding specificities of any one thereof, the polynucleotide, the vector or the cell as defined herein or a pharmaceutical or diagnostic composition comprising any one thereof for use in prophylactic treatment, therapeutic treatment and/or monitoring the progression or a response to treatment of a disease or disorder related to TTR, preferably wherein the disorder is selected from the group comprising Familial Amyloid Polyneuropathy (FAP), Familial Amyloid Cardiomyopathy (FAC), Senile Systemic Amyloidosis (SSA), systemic familial amyloidosis, leptomeningeal/Central Nervous System (CNS) amyloidosis including Alzheimer disease, TTR-related ocular amyloidosis, TTR-related renal amyloidosis, TTR-related hyperthyroxinemia, TTR-related ligament amyloidosis including carpal tunnel syndrome, rotator cuff tears and lumbar spinal stenosis, and preeclampsia. The above group of diseases or disorders will be referred to as the group of disorders associated with TTR amyloidosis.

In another embodiment the present invention relates to a diagnostic composition comprising any one of the above described TTR-binding molecules, antibodies, antigen-binding fragments, polynucleotides, vectors, cells and/or peptides of the invention and optionally suitable means for detection such as reagents conventionally used in immuno- or nucleic acid-based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry, and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the TTR-binding molecules, in particular antibodies of the present invention may also be used in a method for the diagnosis of a disease or disorder in an individual by obtaining a body fluid sample from the tested individual which may be a blood sample, a plasma sample, a serum sample, a lymph sample or any other body fluid sample, such as a saliva or a urine sample and contacting the body fluid sample with an antibody of the instant invention under conditions enabling the formation of antibody-antigen complexes. The level of such complexes is then determined by methods known in the art, a level significantly higher than that formed in a control sample indicating the disease or disorder in the tested individual. In the same manner, the specific antigen bound by the antibodies of the invention may also be used. Thus, the present invention relates to an in vitro immunoassay comprising the binding molecule, e.g., antibody or antigen-binding fragment thereof of the invention.

In a further embodiment of the present invention the TTR-binding molecules, in particular antibodies of the present invention may also be used in a method for the diagnosis of a disease or disorder in an individual by obtaining a biopsy from the tested individual which may be skin, salivary gland, hair roots, heart, colon, nerve, subcutaneous fat biopsies, or a biopsy from any affected organs.

In this context, the present invention also relates to means specifically designed for this purpose. For example, an antibody-based array may be used, which is for example loaded with antibodies or equivalent antigen-binding molecules of the present invention which specifically recognize TTR. Design of microarray immunoassays is summarized in Kusnezow et al., Mol. Cell Proteomics 5 (2006), 1681-1696. Accordingly, the present invention also relates to microarrays loaded with TTR-binding molecules identified in accordance with the present invention.

In one embodiment, the present invention relates to a method of diagnosing a disease or disorder related to mutated, misfolded, misassembled and/or aggregated TTR species and/or fragments thereof in a subject, the method comprising determining the presence of TTR and/or misfolded, misassembled or aggregated TTR in a sample from the subject to be diagnosed with at least one antibody of the present invention, a TTR-binding fragment thereof or an TTR-binding molecule having substantially the same binding specificities of any one thereof, wherein the presence of pathologically mutated, misfolded, misassembled or aggregated TTR is indicative for TTR amyloidosis and an increase of the level of the pathologically misfolded, misassembled or aggregated TTR in comparison to the level of the physiological TTR is indicative for progression of TTR amyloidosis in said subject.

The subject to be diagnosed may be asymptomatic or preclinical for the disease. Preferably, the control subject has a disease associated with misfolded, misassembled or aggregated TTR, e.g. Familial Amyloid Polyneuropathy (FAP), Familial Amyloid Cardiomyopathy (FAC) or Senile Systemic Amyloidosis (SSA), wherein a similarity between the level of pathologically misfolded, misassembled or aggregated TTR and the reference standard indicates that the subject to be diagnosed has a TTR amyloidosis or is at risk to develop a TTR amyloidosis. Alternatively, or in addition as a second control the control subject does not have a TTR amyloidosis, wherein a difference between the level of physiological TTR and/or of misfolded, misassembled or aggregated TTR and the reference standard indicates that the subject to be diagnosed has a TTR amyloidosis or is at risk to develop a TTR amyloidosis. Preferably, the subject to be diagnosed and the control subject(s) are age-matched. The sample to be analyzed may be any body fluid suspected to contain pathologically misfolded, misassembled or aggregated TTR, for example a blood, blood plasma, blood serum, urine, peritoneal fluid, saliva or cerebral spinal fluid (CSF).

The level of physiological TTR and/or of pathologically misfolded, misassembled or aggregated TTR may be assessed by any suitable method known in the art comprising, e.g., analyzing TTR by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. Preferably, said in vivo imaging of TTR comprises scintigraphy, positron emission tomography (PET), single photon emission tomography (SPECT), near infrared (NIR) optical imaging or magnetic resonance imaging (MRI).

In a further aspect, the present invention relates to the diagnosis of TTR amyloidosis, monitoring the treatment of this disease and determining the diagnostic or therapeutic utility of an anti-TTR drug in a tissue- and biopsy-free, i.e. non-invasive method.

Normally, the concentration of TTR aggregates and/or misfolded TTR which can be detected in a body fluid, for example blood plasma is very low and thus the diagnosis of TTR amyloidosis is burdensome and time-consuming. In particular, the diagnosis of TTR amyloidosis diseases is a difficult and lengthy process, since various diseases present very similar signs and symptoms, such that the formal diagnosis of Familial Amyloid Polyneuropathy (FAP), Familial Amyloid Cardiomyopathy (FAC) and Senile Systemic Amyloidosis (SSA) typically requires collection of tissue biopsies and identification of TTR amyloid deposits by means of complex histological staining techniques. As tissue biopsies are very small and TTR amyloid deposits dispersed, histological determination of TTR amyloidosis is typically associated with high frequency of false negative results and delays for the patients.

However, in accordance with the present invention it could surprisingly be shown that after a single administration of a subject anti-TTR antibody a measurement of aggregates and/or misfolded TTR bound to anti-TTR antibodies in blood was possible; see Example 13 and FIG. 14A-14B. Therefore, thanks to the probably unique property of the anti-TTR antibody of the present invention to remove TTR from amyloidogenic TTR deposits and transport into blood a novel method of diagnosing disorders associated with misfolded, mutated, and/or aggregated TTR in a patient or subject has been developed, which method has the potential to replace tissue biopsy and histological analysis in the diagnostic process of TTR amyloid diseases. The method relies on the use of an antibody specific for the pathological conformation of TTR protein, which is injected to the patient and used to probe for the presence of misfolded and/or aggregated TTR protein anywhere in patient's body. After a short delay, for example 2 days, following antibody injection in a patient, a blood sample is drawn and used to detect if the antibody has captured and detached misfolded and/or aggregated TTR particles from TTR deposits. The major advantage of this method compared to histology has to do with the injection of the anti-TTR antibody directly in patients, where blood circulation allows its circulation through every tissue and organ, and detection of misfolded and/or aggregated TTR protein deposits independently of their localization.

Thus, in a further aspect the present invention relates to a method of diagnosing a disease associated with TTR amyloidosis comprising assaying the level of misfolded and/or aggregated TTR in a sample from a subject following administration of an anti-TTR antibody to the subject, wherein the presence or elevated the level of misfolded and/or aggregated TTR in the sample of the subject compared to the control such as a sample obtained from the subject prior to administration of the anti-TTR antibody indicates a disease associated with TTR amyloidosis. Furthermore, since as shown in Example 13 the novel method is also useful for characterizing anti-TTR drugs and the course of treatment of TTR amyloidosis, respectively, the novel method of the present invention is also intended for monitoring the treatment of the disease with an anti-TTR antibody or determining the diagnostic or therapeutic utility of an anti-TTR antibody. In this context, the person skilled in the art will recognize that the method of the present invention is not limited to the investigation of the therapeutic utility and efficacy of anti-TTR antibodies but also applicable to other kinds of anti-TTR drugs which are capable of degrading TTR amyloid deposits. For example, an anti-TTR antibody of the present invention may be administered in conjunction with another anti-TTR drug and the level of misfolded and/or aggregated TTR in the sample of the subject having been treated is compared to a control obtained from the subject prior to administration of both the anti-TTR antibody and the anti-TTR drug but only after anti-TTR antibody treatment.

In one preferred embodiment of the present invention, in particular when using non-human animals for testing recombinant human-derived antibodies as illustrated in Example 13 and other anti-TTR antibodies intended for use in humans in general the level of misfolded and/or aggregated TTR in the sample is assayed by determining a complex formed between the anti-TTR antibody and the misfolded and/or aggregated TTR, for example by immuno-precipitation with an anti-human IgG or anti-idiotypic antibody. Alternatively, a second anti-TTR antibody may be used which recognizes TTR at an epitope different substantially different from the epitope of the drug candidate anti-TTR antibody so as to bind the complex formed by the drug candidate anti-TTR antibody and TTR and thus detected its presence, for example by way of ELISA or immune-precipitation.

With respect to the diagnostic aspect in particular for a human subject and patient, the presence and elevated level of misfolded and/or aggregated TTR and complex thereof with the anti-TTR antibody, respectively, indicates the presence of TTR amyloid deposits in the human body, for example in the heart, peripheral nervous system (PNS), eyes, muscles, gastro-intestinal tract, kidneys, vascular system and the central nervous system (CNS) of a patient or subject. Thus, the method of the present invention allows the identification and determination of a disease associated with TTR amyloidosis in the subject's body on the one hand and removal of TTR deposits from patient's body on the other, thereby also indicating the therapeutic progress of a given treatment and efficacy of a TTR amyloidosis specific drug such as an anti-TTR antibody.

Hence, as demonstrated in Example 13 the anti-TTR antibody of the present invention is capable of binding misfolded and/or aggregated TTR with sufficient affinity to alter the stability of pathological TTR deposits such as to capture and remove misfolded and/or aggregated TTR from the deposits into a body fluid, in particular blood.

The anti-TTR antibody to be used in accordance with the method of the present invention may be any TTR antibody which is specific for the pathological conformation of TTR, i.e. misfolded, mutated, and/or aggregated TTR. However, in a preferred embodiment the anti-TTR antibody utilized in the tissue-free method is an anti-TTR antibody or TTR-binding molecule of the present invention described herein and illustrated in the Examples.

In this context, the anti-TTR antibody may be modified and for example attached to a detectable label as described for any of the other embodiments hereinbefore. In addition, immunoassays such as western blot, dot blot, (sandwich) ELISA and the like known in the art and described for other diagnostic methods and uses based on the anti-TTR antibody and peptide of the present invention may be adapted to the novel TTR amyloid assay of the present invention.

As shown in Example 13 and FIG. 14A-14B using the TTR amyloid assay it could be shown that anti-TTR antibodies of the present invention are capable of capturing and detaching misfolded and/or aggregated TTR from TTR amyloid deposits and the corresponding immuno-complex can be measured in a sample of body fluid, in particular blood of the patient or subject; see Example 13 and FIG. 14A-14B. Accordingly, in one embodiment of the present invention the anti-TTR antibody can bind misfolded and/or aggregated TTR with sufficient affinity to alter the net efflux of the misfolded and/or aggregated TTR from e.g. heart, peripheral nervous system (PNS), eyes, muscles, gastro-intestinal tract, kidneys, vascular system and the central nervous system (CNS).

The body fluid sample, preferably blood or CSF from the subject, wherein captured and detached misfolded and/or aggregated TTR bound to the anti-TTR antibody is present, is obtained at a specified time interval following administration. This specified time interval following administration is typically less than one week. In a preferred embodiment this time interval after administration of the anti-TTR antibody is less than or equal to 48 hours.

As mentioned supra, the tissue-free method described supra, can also be utilized to determine the success of the treatment, i.e. by measurement of misfolded and/or aggregated TTR species captures by anti-TTR antibodies before and after treatment. Thus, in a further or additional embodiment, the tissue-free method of the present invention may further comprise the comparison between the level of the misfolded and/or aggregated TTR in the sample of a body fluid to a sample obtained from the subject prior to administration of an anti-TTR antibody. Accordingly, in one embodiment the method of the present invention is used to determine the effectiveness of a treatment of TTR amyloidosis or for monitoring the progression of a disease or condition associated with pathological TTR in a patient or subject.

As mentioned, samples of subjects utilized in the methods described above can be obtained before or after administration of an anti-TTR antibody. However, samples can also be obtained from medical facilities or practicing physicians as well as other institutions from which clinical samples from a subject can be obtained. The facilities, physicians, etc. can not only perform the administration of an anti-TTR antibody to the subject and the collection of appropriate samples for use in the above method, but monitor and/or the treatment of the patient, i.e. by varying the amount, time, frequency of administration of the antibody, interrupting a therapy, replace or combine the anti-TTR antibody by at least another anti-TTR antibody or therapeutic agent. The level of TTR can be assessed by any suitable method known in the art. Methods suitable are described below and in international application WO 2013/066818, the disclosure content of which is incorporated herein by reference.

In one aspect of the present invention, an antibody of the present invention or a TTR-binding molecule having substantially the same binding specificities of any one thereof, the polynucleotide, the vector or the cell as defined hereinabove or a pharmaceutical or diagnostic composition comprising any one thereof is provided for use in prophylactic treatment, therapeutic treatment, and/or monitoring the progression or a response to treatment of a disease or disorder related to TTR. In general thus, the present invention also relates to a method of diagnosing or monitoring the progression of a disease or disorder related to TTR (such as TTR amyloidosis) in a subject, the method comprising determining the presence of TTR in a sample from the subject to be diagnosed with at least one antibody of the present invention or a TTR-binding molecule having substantially the same binding specificities of any one thereof, wherein the presence of mutated, misfolded, misassembled or aggregated TTR species or fragments thereof is indicative for the disease or disorder. In one embodiment said method of diagnosing or monitoring the progression of TTR amyloidosis in a subject is provided, the method comprising determining the presence of mutated, misfolded, misassembled or aggregated TTR and/or fragments thereof in a sample from the subject to be diagnosed with at least one antibody of the present invention or a TTR-binding molecule having substantially the same binding specificities of any one thereof, wherein the presence of mutated, misfolded, misassembled or aggregated TTR and/or fragment thereof is indicative of presymptomatic, prodromal or clinical TTR amyloidosis an increase of the level of TTR oligomers, aggregates or fibrils in comparison to the level of the physiological TTR or in comparison to a reference sample derived from a healthy control subject or a control sample from the same subject is indicative for progression of presymptomatic, prodromal or established TTR amyloidosis. It would be appreciated by any person skilled in the art that in one embodiment said method is used as well for the diagnosing or monitoring the progression of any other disease or disorder from the group of disorders related to TTR as defined hereinabove.

As indicated above, the antibodies of the present invention, fragments thereof and molecules of the same binding specificity as the antibodies and fragments thereof may be used not only in vitro but in vivo as well, wherein besides diagnostic, therapeutic applications as well may be pursued.

In one embodiment thus, the present invention also relates to a TTR binding molecule comprising at least one CDR of an antibody of the present invention for the preparation of a composition for in vivo detection/imaging of or targeting a therapeutic and/or diagnostic agent to TTR in the human or animal body. Potential therapeutic and/or diagnostic agents may be chosen from the nonexhaustive enumerations of the therapeutic agents useful in treatment TTR amyloidosis and potential labels as indicated hereinbefore. In respect of the in vivo imaging, in one preferred embodiment the present invention provides said TTR binding molecule comprising at least one CDR of an antibody of the present invention, wherein said in vivo imaging comprises scintigraphy, positron emission tomography (PET), single photon emission tomography (SPECT), near infrared (NIR) optical imaging or magnetic resonance imaging (MRI). In a further embodiment the present invention also provides said TTR-binding molecule comprising at least one CDR of an antibody of the present invention, or said molecule for the preparation of a composition for the above specified in vivo imaging methods, for the use in the method of diagnosing or monitoring the progression of a disease or disorder related to TTR in a subject, as defined hereinabove.

VII. Peptides with Aggregation Specific TTR Epitopes

In a further aspect the present invention relates to peptides having an epitope of TTR specifically recognized by any antibody of the present invention. Preferably, such peptide comprises or consists of an amino acid sequence as indicated in SEQ ID NO: 49, SEQ ID NO: 50, or in SEQ ID NO: 51 as the unique linear epitope recognized by the antibody or a modified sequence thereof in which one or more amino acids are substituted, deleted and/or added, wherein the peptide is recognized by any antibody of the present invention, preferably by antibody NI-301.59F1, NI-301.35G11, NI-301.37F1, or NI-301.12D3.

In one embodiment of this invention such a peptide may be used for diagnosing or monitoring a disease or disorder related to misfolded, misassembled or aggregated TTR species and/or fragment thereof in a subject, such as TTR amyloidosis comprising a step of determining the presence of an antibody that binds to a peptide in a biological sample of said subject, and being used for diagnosis of such a disease in said subject by measuring the levels of antibodies which recognize the above described peptide of the present invention and comparing the measurements to the levels which are found in healthy subjects of comparable age and gender. Thus in one embodiment the present invention relates to a method for diagnosing TTR amyloidosis indicative of presymptomatic or clinical FAP and/or FAC in a subject, comprising a step of determining the presence of an antibody that binds to a peptide as defined above in a biological sample of said subject. According to this method, an elevated level of measured antibodies specific for said peptide of the present invention is indicative for diagnosing in said subject presymptomatic or clinical FAP and/or FAC or for diagnosing in said subject any other disease or disorder from the group of disorders related to TTR as defined hereinabove. Furthermore, since the peptide of the present invention contains an epitope of a therapeutically effective antibody derived from a human such peptide can of course be used as an antigen, i.e. an immunogen for eliciting an immune response in a subject and stimulating the production of an antibody of the present invention in vivo. The peptide of the present invention may be formulated in an array, a kit and composition such as a vaccine, respectively, as described hereinbefore. In this context, the present invention also relates to a kit useful in the diagnosis or monitoring the progression of TTR amyloidosis, said kit comprising at least one antibody of the present invention or a TTR-binding molecule having substantially the same binding specificities of any one thereof, the polynucleotide, the vector or the cell and/or the peptide as respectively defined hereinbefore, optionally with reagents and/or instructions for use.

These and other embodiments are disclosed and encompassed by the description and examples of the present invention. Further literature concerning any one of the materials, methods, uses, and compounds to be employed in accordance with the present invention may be retrieved from public libraries and databases, using for example electronic devices. For example the public database "Medline" may be utilized, which is hosted by the National Center for Biotechnology Information (NCBI) and/or the National Library of Medicine at the National Institutes of Health (NLM.NIH). Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention. A more complete understanding can be obtained by reference to the following specific examples which are provided herein for purposes of illustration only and are not intended to limit the scope of the invention.

EXAMPLES

Example 1: Isolation and Identification of Anti-TTR Antibodies

Human-derived antibodies targeting TTR and/or mutated, misfolded, misassembled, and/or aggregated TTR species and/or fragments thereof were identified utilizing the method described in the international application WO 2008/081008, the disclosure content of which is incorporated herein by reference, with modifications. In particular, human wild-type TTR protein obtained by purification from human plasma, and wild-type and mutant TTR proteins obtained by recombinant expression were used in both native and misfolded-aggregated conformations for the identification of TTR-targeting antibodies. The misfolded-aggregated conformations were produced in vitro under acidic conditions, using a procedure similar to the one described in Colon W. et al, Biochemistry, 31 (1992), 8654-8660, with minor modifications.

Example 2: Determination of Antibody Sequence

The amino acid sequences of the variable regions of the above identified anti-TTR antibodies were determined on the basis of their mRNA sequences, see FIG. 1A-1T. In brief, living B cells of selected non-immortalized memory B cell cultures were harvested. Subsequently, the mRNAs from cells producing selected anti-TTR antibodies were extracted and converted in cDNA, and the sequences encoding the antibody's variable regions were amplified by PCR, cloned into plasmid vectors and sequenced. In brief, a combination of primers representing all sequence families of the human immunoglobulin germline repertoire was used for the amplifications of leader peptides, V-segments and J-segments. The first round of amplification was performed using leader peptide-specific primers in 5'-end and constant region-specific primers in 3'-end (Smith et al., Nat Protoc. 4 (2009), 372-384). For heavy chains and kappa light chains, the second round of amplification was performed using V-segment-specific primers at the 5'-end and J-segment-specific primers at the 3'-end. For lambda light chains, the second round amplification was performed using V-segment-specific primers at the 5'-end and a C-region-specific primer at the 3'-end (Marks et al., Mol. Biol. 222 (1991), 581-597; de Haard et al., J. Biol. Chem. 26 (1999), 18218-18230).

Identification of the antibody clone with the desired specificity was performed by re-screening on ELISA upon recombinant expression of complete antibodies. Recombinant expression of complete human IgG1 antibodies was achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulins were expressed by inserting the immunoglobulin heavy chain RT-PCR product in frame into a heavy chain expression vector bearing a signal peptide and the constant domains of human or mouse immunoglobulin gamma 1. Kappa light chain immunoglobulins were expressed by inserting the kappa light chain RT-PCR-product in frame into a light chain expression vector providing a signal peptide and the constant domain of human kappa light chain immunoglobulin. Lambda light chain immunoglobulins were expressed by inserting the lambda light chain RT-PCR-product in frame into a lambda light chain expression vector providing a signal peptide and the constant domain of human or mouse lambda light chain immunoglobulin.

Functional recombinant monoclonal antibodies were obtained upon co-transfection into HEK 293 or CHO cells (or any other appropriate recipient cell line of human or mouse origin) of an Ig-heavy-chain expression vector and a kappa or lambda Ig-light-chain expression vector. Recombinant human monoclonal antibody was subsequently purified from the conditioned medium using a standard Protein A column purification. Recombinant human monoclonal antibody can produced in unlimited quantities using either transiently or stably transfected cells. Cell lines producing recombinant human monoclonal antibody can be established either by using the Ig-expression vectors directly or by re-cloning of Ig-variable regions into different expression vectors. Derivatives such as F(ab), F(ab)2 and scFv can also be generated from these Ig-variable regions.

The framework and complementarity determining regions were determined by comparison with reference antibody sequences available in databases such as Abysis (bioinf.org.uk/abysis/), and annotated using the Kabat numbering scheme (bioinf.org.uk/abs/). The amino acid sequences of the variable regions of the subject antibodies NI-301.59F1, NI-301.35G11, NI-301.37F1, NI-301.2F5, NI-301.28B3, NI-301.119C12, NI-301.5D8, NI-301.9D5, NI-301.104F5, NI-301.21F10, NI-301.9G12, NI-301.12D3, NI-301.37F1-PIMC, NI-301.44E4, NI-301.18C4, NI-301.11A10, NI-301.3C9, NI-301.14D8, NI-301.9X4, and NI-301.14C3 including indication of the framework (FR) and complementarity determining regions (CDRs) are shown in FIG. 1A-1T.

In the following, the high affinity of the subject antibodies to misfolded-aggregated TTR conformations and substantial lack of binding to native wild-type TTR conformations, thereby demonstrating a strong selectivity for mutant, misfolded, misassembled and/or aggregated TTR is exemplary illustrated for antibodies NI-301.59.F1, NI-301.35G11, and NI-301.37F1. However, preliminary experiments for other subject antibodies suggest substantially the same preferential binding to mutant, misfolded, misassembled and/or aggregated TTR over physiological TTR species like antibodies NI-301.59.F1, NI-301.35G11, and NI-301.37F1.

Example 3: Binding Affinity of Anti-TTR Antibodies Utilizing Direct ELISA and EC50 Determination The antibody capacity to bind TTR and/or misfolded, misassembled and/or aggregated forms of TTR was evaluated by means of direct ELISA assays at varying antibody concentrations. This allows to determinate for each antibody its half maximal effective concentration (EC50) in this assay, which is a commonly used proxy for the antibody binding affinity, see FIG. 2A-2C. In brief, ELISA plates (high-bind, clear polystyrene, half-area, flat bottom) were coated with misfolded-aggregated human wild-type TTR, misfolded-aggregated recombinant V30M-TTR (both prepared as described in the Example 1) and bovine serum albumin (BSA) at a concentration of 10 µg/ml in phosphate buffer saline (PBS) for 1 h at 37° C., and subsequently blocked with a solution of 2% BSA and 0.1% tween-20 in PBS (PBS-T) for 1 h at room temperature (RT). Antibodies against TTR were diluted in PBS at 11 different concentrations ranging from 4 to 400 nM, and incubated in the ELISA plates overnight at 4° C. After 3 washes with PBS-T, ELISA plates were incubated with a HRP-coupled, human IgG-specific secondary antibody for 1 h at RT (1/4000 dilution). After 3 washes with PBS-T, the ELISA reactions were developed with TMB for exactly 10 min at RT and quantified by measuring the optical density at 450 nm (OD450 nm).

The exemplary antibodies NI-301.59F1, NI-301.35G11, and NI-301.37F1 exhibited strong binding to misfolded-aggregated wild-type and mutant TTR, but not to the control BSA, see FIG. 2 A-C. Subsequently, the antibody's EC50s were determined by fitting the data with a non-linear regression using the least square method in order to estimate the antibody binding affinity under these conditions.

The exemplary antibodies NI-301.59F1, NI.35G11, and NI-301.37F1 exhibited high affinity for misfolded-aggregated human wild-type TTR corresponding to EC50s of 3.0 nM, 3.9 nM, and 0.35 nM respectively. The exemplary antibodies also exhibited high affinity for misfolded-aggregated recombinant mutant V30M-TTR corresponding to EC50s of 15.5 nM, 5.0 nM, and 0.15 nM respectively.

Example 4: Binding Selectivity of Anti-TTR Antibodies Utilizing Dot Blot

To evaluate the binding selectivity of the TTR-antibodies and/or fragments thereof for native or misfolded, misassembled and/or aggregated TTR conformations, human wild-type TTR protein in native or misfolded-aggregated conformations and recombinant V30M-TTR protein in misfolded-aggregated conformations were diluted in PBS at 4 different concentrations, and deposited by vacuum filtration on a nitrocellulose membrane. The membrane was briefly dried (10 min) and blocked with 3% milk in PBS-T for 1 h at RT, and subsequently incubated with anti-TTR antibodies overnight at 4° C. After 3 washes with PBS-T for 5 min at RT, the membrane was incubated with the appropriate secondary antibody (HRP-coupled; 1/10000 dilution) for 1 h at RT. After 3 washes with PBS-T, the membrane was developed with luminol and the signal intensity quantified by measuring luminescence.

The exemplary commercial anti-TTR antibody bound to native as well as misfolded-aggregated TTR conformations with similar affinity, thereby demonstrating its absence of binding selectivity for native or misfolded, misassembled and/or aggregated TTR conformations, see FIG. 3A. In contrast, the exemplary antibodies NI-301.59.F1, NI-301.35G11, and NI-301.37F1 bound with high affinity to misfolded-aggregated TTR conformations only, and showed no binding to native TTR conformations, thereby demonstrating a strong selectivity for misfolded, misassembled and/or aggregated TTR (FIGS. 3B2, 3C2, 3D2). Accordingly, the antibodies NI-301.35G11 and NI-301.37F1 also showed strong binding to the misfolded-aggregated recombinant V30M-TTR protein, as shown in FIGS. 3C3 and 3D3.

To further characterize the antibody binding selectivity, various TTR preparations including wild-type and mutant, native and misfolded-aggregated conformations, and a collection of 12 human plasma samples were processed similarly for analysis by dot blot, using murine chimeric anti-TTR antibodies and HRP-coupled, anti-mouse IgG2a secondary antibody for detection (FIG. 6A-6C).

The commercial antibody exhibited strong binding to all TTR preparation, including wild-type and mutant, native and misfolded-aggregated TTR preparations, and was able to detect TTR in all human plasma samples. This further demonstrates the absence of selectivity for native or aggregated conformations, see FIG. 6A. In contrast, the exemplary mouse chimeric antibody NI-301.mur35G11 exhibited very strong binding to the misfolded-aggregated wild-type TTR sample (FIG. 6C1), and also strong binding to the mutantV30M-TTR protein (FIG. 6C4), and to the mutant Y78F-TTR protein (FIG. 6C6). However, the NI-301.mur35G11 antibody did not bind to TTR in the human plasma samples. This further demonstrates the strong selectivity of NI-301.mur35G11 for mutated, misfolded, misassembled and/or aggregated TTR protein.

Example 5: Binding Specificity and Selectivity of Anti-TTR Antibodies Utilizing Western Blot The binding specificity and selectivity of anti-TTR antibodies was evaluated by means of western blot, see FIG. 4A-4D. In brief, human wild-type TTR protein (300 ng) in native or misfolded-aggregated conformations, and wild-type mouse liver extract (10 µg total protein) were loaded on a SDS-PAGE gel and transferred onto a nitrocellulose membrane using a semi-dry transfer system. The membrane was subsequently blocked with 2% BSA in PBS-T for 1 h at RT, and incubated overnight at 4° C. with anti-TTR antibodies diluted in blocking buffer. After 4 washes with PBS-T for 5 min at RT, the membrane was incubated with the appropriate secondary antibody (HRP-coupled; 1/10000 dilution in blocking buffer) for 1 h at RT. After 3 washes with PBS-T and a final one in PBS, the membrane was developed with luminol and the signal intensity quantified by measuring luminescence. Shortly before use, the misfolded-aggregated TTR sample was submitted to crosslinking with glutaraldehyde (1%, 5 min, 37° C.) to prevent the dissociation of TTR aggregates during the preparation process for SDS-PAGE. In contrast, the native TTR sample was not crosslinked before use, such that the TTR homotetramer (which is the native TTR conformation under physiological conditions) almost entirely dissociated into monomers and dimers.

The commercial anti-TTR antibody showed very strong binding to the TTR monomers and dimers of the human native TTR sample (FIG. 4A1), and a similarly strong binding to cross-linked misfolded-aggregated TTR sample (FIG. 4A2), thereby demonstrating the absence of selectivity for native or misfolded, misassembled and/or aggregated TTR conformations. In contrast, the exemplary anti-TTR antibodies NI-301.59F1, NI-301.35G11, and NI-301.37F1 showed very strong binding to the cross-linked misfolded-aggregated TTR sample (FIGS. 4B2, 4C2, 4D2) but no binding at all to the TTR monomers and dimers of the human native TTR sample (FIGS. 4B1, 4C1, 4D1), thereby demonstrating strong selectivity for misfolded, misassembled and/or aggregated TTR conformations over native TTR conformations.

In addition to that, the commercial and the exemplary anti-TTR antibodies had very low levels of binding to the proteins contained in the mouse liver extract (FIGS. 4A3, 4B3, 4C3, 4D3). In view of the high amount of liver proteins used for the experiment and the high antibody concentrations with respect to their binding affinity, this indicates that the exemplary antibodies have a remarkable specificity for TTR and do not bind significantly to other proteins. Furthermore, it appears that the exemplary antibodies do not bind to the mouse TTR protein contained at high levels in the mouse liver extract, indicating that the exemplary antibodies show specificity for the human misfolded TTR protein. However, the epitope of the antibody NI-301.37F1 is present on the TTR protein of rat and mouse. Accordingly, the primary amino acid sequence of the epitope may not be necessarily decisive for the detection of misfolded TTR, but the conformation.

To further characterize the antibody binding capacity, or its absence thereof, to native TTR protein, the exemplary antibodies were evaluated for their capacity to bind to the TTR protein contained in human plasma samples using the same western blot technique as described here above, (FIGS. 5A-5D). The only technical difference consisted in trimming the upper part of the gel at about 25-30 kDa, and using only the lower part of the gel for transfer of the proteins onto the nitrocellulose membrane. This is to eliminate the heavy and light chains of the human antibodies present at high concentration in the plasma samples, which could potentially interfere with the analysis.

In contrast with the commercial antibody used as reference, the exemplary antibodies NI-301.35G11 and NI-301.37F1 did not detect at all the human TTR protein contained in human plasma samples, thereby indicating binding selectivity for a TTR conformation which in not present in the analyzed samples under these conditions.

Example 6: Binding Selectivity of Anti-TTR Antibodies in Solution Utilizing Immunoprecipitation To further verify the binding selectivity of the anti-TTR antibodies of the present invention, human wild-type and recombinant TTR protein in native and misfolded-aggregated conformations, and a human plasma sample at 3 different dilutions in PBS were used for TTR immunoprecipitation (IP).

In brief, protein-A coated magnetic beads were incubated with anti-TTR antibodies diluted in manufacturer binding buffer for 30 min at RT. The antibody/protein A complex was retrieved and incubated overnight at 4° C. with TTR preparations and human plasma samples. After washes, the antibody/protein A complex was resuspended in SDS loading buffer, heated 5 min at 90° C. and processed for western blot analysis.

As shown in FIG. 7A-7C the exemplary TTR antibodies NI-301.35G11 and NI-301.37F1 showed in contrast to the commercial TTR antibody Dako A0002 no binding to the plasma samples (FIGS. 7A7-9, 7B7-9, 7C7-9), as well as no binding to the native wild-type and recombinant TTR samples (FIGS. 7B3, 7C3, 7B5, 7C5). However, a strong binding was assessed in the sample, wherein misfolded-aggregated forms of TTR were present (FIGS. 7B4, 7C4, 7B6, 7C6).

These results indicate that the exemplary antibodies NI-301.35G11 and NI-301.37F1 are able to bind misfolded, misassembled and/or aggregated TTR conformations in solution, and show remarkable selectivity for these conformations.

Example 7: Binding to Pathological TTR Aggregates in FAP Mouse Tissue

Exemplary anti-TTR antibodies were evaluated by immunohistochemistry (IHC) for their capacity to bind pathological and non-pathological TTR protein as present in the tissues of transgenic mice expressing exclusively the human V30M-TTR protein and not the mouse TTR protein (thereafter named FAP mice). These antibodies were also evaluated for non-specific binding on tissues from TTR knockout (TTR-KO) mice not expressing any TTR protein, and the corresponding transgenic and knockout mouse lines were initially generated and described by Prof. Suichiro Maeda (Kohno K. et al., American Journal of Pathology 140(4) (1997), 1497-1508). In brief, immunohistochemistry was performed on paraffin embedded mouse tissues cut in 3-5 µm thick sections. Sections were initially dewaxed and rehydrated, and treated with 3% H2O2 in methanol for 20 min at RT. Blocking buffer (PBS+5% serum (horse/goat)+4% BSA) was applied for 1 h at RT, and replaced with anti-TTR antibody diluted in PBS for overnight incubation at 4° C. After 3 washes in PBS, sections were successively incubated with the appropriate biotinylated secondary antibodies (anti human IgG, anti rabbit IgG dilution 1/125 in PBS, incubation 1 h at RT) and the avidin-HRP detection system (dilution 1/125 in PBS, incubation 1 h at RT). The reaction was developed with diaminobenzidine for exactly 15 min at RT. Tissue sections were counterstained with hemalun for 1 min at RT, dehydrated in ascending ethanol series and coverslipped.

As shown in FIG. 8A-8F, a commercial TTR antibody Dako A0002 generated a strong staining in liver and intestine sections of FAP mice and did not produce any stain in the corresponding TTR KO sections (FIGS. 8A, 8B). The exemplary TTR antibody NI-301.35G11 generated a staining of similar pattern and intensity in both liver and intestine sections of FAP mice (FIG. 8C). In contrast, the exemplary antibody NI-301.37F1 generated a strong staining only in the intestine section but not on the liver section of FAP mouse (FIG. 8E). This indicates that the NI-301.37F1 antibody binds only to the pathological (i.e. non-physiological) TTR aggregates that accumulate over time in the gastrointestinal tract of FAP mice, and not to TTR in native conformation as synthesized by the liver.

In addition to that, both exemplary antibodies NI-301.35G11 and NI-301.37F1 did not generate any staining in liver and intestine tissue sections from TTR-KO mice (FIGS. 8D, 8F). In view of the high antibody concentrations used in this experiment with respect to the antibody's binding affinity, this absence of staining on TTR-KO sections is indicating high binding specificity for the TTR protein.

Example 8: Binding Selectivity for Misfolded, Misassembled and/or Aggregated TTR Deposits in Human Tissue The antibodies of the present invention were also evaluated for their capacity to bind pathological TTR deposits in human tissue. Sections of a skin biopsy from an FAP patient and sections of pancreas tissue from a healthy individual were processed for immunohistochemistry using the same procedure as described under Example 7, supra. Skin biopsy was selected for this experiment as it contains an important amount of pathological TTR amyloid deposits. In contrast, pancreas tissue was used in this experiment because pancreatic alpha cells express TTR at high level.

As shown in FIGS. 9A-9F, the commercial antibody Dako A0002 revealed an equally strong staining of pathological TTR deposits in the skin and native TTR in pancreatic alpha cells (FIG. 9A). Similarly, the exemplary mouse chimeric antibody NI-301.mur35G11 produced an equally strong staining of both pathological TTR deposits in the skin and native TTR in pancreatic alpha cells (FIG. 9B). In contrast, the antibody NI-301.37F1 stained only the pathological TTR deposit in the skin and not the native TTR in pancreatic alpha cells (FIG. 9A). This result demonstrates that NI-301.37F1 is highly selective by IHC for pathological TTR deposits, which include mutated, misfolded, misassembled and/or aggregated TTR conformations.

The "secondary antibody only" control condition presented in panels FIGS. 9B, 9D, and 9F reveals the tissue staining that occurs in absence of primary antibody. The absence (FIG. 9D) or very low level (FIG. 9B, 9F) of staining indicates that the staining observed in FIGS. 9A, 9C, and 9E is indeed specific for the corresponding primary antibodies.

Example 9: Assessment of the Binding Epitope of the TTR Antibodies

To determine the binding epitope of the exemplary antibodies NI-301.59F1, NI301.35G11, and NI-301.37F1, the entire TTR amino acid sequence was analyzed using a panel of 29 sequential peptides 15 amino acid long and 11 amino acid overlap, covalently bound to a membrane. Additional peptides including selected mutations were also plotted on the membrane. The membrane was blocked in Roti blocking buffer overnight at 4° C., incubated first with the anti-TTR antibody diluted in blocking buffer for 2 h at RT, then with an HRP-coupled anti human IgG antibody for 45 min at RT (dilution 1/20000 in TBS). The reaction was developed with luminol and imaged by luminescence.

The antibody NI-301.59F1 recognizes the spots 15, 16 and 44 which correspond to the sequence 61-EEEFVEGIY-69 (SEQ ID NO: 49) on full human wild-type TTR, see FIG. 10A. The antibody NI-301.35G11 recognizes the spots 13, 14, 42, and 44 which correspond to the sequence 53-GELHGLTTEEE-63 (SEQ ID NO: 50) on full human wild-type TTR, see FIG. 10B. However, the antibody NI-301.35G11 does not recognize the spot 43, indicating this antibody cannot bind the sequence 53-GELHGPTTEEE-63 (SEQ ID NO: 209) corresponding to the L55P-TTR variant. The antibody NI-301.37F1 recognizes the spots 9, 10, 11, 38, and 40 which correspond to the sequence 41-WEPFA-45 (SEQ ID NO: 51) on full human wild-type TTR, see FIG. 10C. However, the antibody NI-301.37F1 does not recognize the spot 43, indicating this antibody cannot bind the sequence 41-WGPFA-45 (SEQ ID NO: 210) corresponding to the E42G-TTR variant.

To refine determination of the binding epitope of the exemplary antibodies NI-301.59F1, NI301.35G11, and NI-301.37F1, the entire TTR amino acid sequence was analyzed using a panel of 151 sequential peptides 15 amino acid long and 14 amino acid overlap, covalently bound to a membrane. For each peptide, the amino-acid in position 10 was replaced by an alanine for non-alanine amino-acids, whereas alanines were replaced by glycine or proline. The membrane was blocked in Roti blocking buffer overnight at 4° C., incubated first with the anti-TTR antibody diluted in blocking buffer for 2 h at RT, then with an HRP-coupled anti human IgG antibody for 45 min at RT (dilution 1/20000). The reaction was developed with luminol and imaged by luminescence.

The antibody NI-301.59F1 recognizes only the spots 77 and 83, indicating that E61 and V65 are not required for 59F1 binding whereas E62, E63, F64, E66, G67, I68 and Y69 are required for antibody binding. The exact contribution of K70 is a matter of interpretation: strong antibody binding to peptide 44 shown in FIG. 10A clearly indicates that absence of K70 in C-terminal position does not prevent antibody binding; in the subsequent experiment shown in FIG. 10E, however, K70A substitution in position 10 on the peptide prevented antibody binding. These seemingly opposite results suggest that NI-301.59F1 binds to a specific conformation of the amino-acid sequence 62-EEFXEGIY-69 (SEQ ID NO: 58), wherein X can be any amino acid.

The antibody NI-301.35G11 recognizes the spots 68, 71, 72, 73, 74 and 75, indicating that G53 is not required for 35G11 binding whereas E54, L55, G57 and L58 are required for antibody binding. 35G11 binding pattern also indicates that presence of E61 or E62 is required for antibody binding. The exact contribution of T59 and T60 could not be determined in this experiment, but it is hypothesized that the presence of one of the two tyrosines is required for antibody binding. Taken together, NI-301.35G11 binding profile on the alanine scan indicates that this antibody recognizes the sequence 54 ELXGLTXE 61 (SEQ ID NO: 59), wherein X can encompass all known amino acids, see FIG. 10F.

The antibody NI-301.37F1 binds to the spots 50, 52, 55, 56 and 58-62 on the alanine scan membrane, and not to the spots 51, 53, 54 and 57. This indicates that W41, P43, F44 and A45 are required for antibody binding. Combined with the earlier observation that mutation E42G disrupts antibody binding (FIG. 10C), these results indicate that NI-301.37F1 binds to the sequence 41-WEPFA-45 (SEQ ID NO: 60), see FIG. 10G.

Example 10: Determination of Antibody Binding Characteristics by Surface Plasmon Resonance The antibody binding characteristics to various soluble TTR preparations were determined by means of surface plasmon resonance (SPR), using a Biorad Proteon XPR36 machine, see Table V.

SPR analysis was performed on a BioRad ProteOn XPR36 fitted with a GLM sensor chip. An anti-human antibody directed against the Fc gamma domain was covalently coupled to the detection surface and saturated with the antibody under investigation. Wild-type and mutant TTR protein in native and misfolded conformations were diluted in HBS-T buffer at concentrations ranging from 3.2 to 316 nM. The antibody-antigen association was analyzed during 180 s and the dissociation during 600 s. A Langmuir binding model (simple 1:1 association) was used to fit the data and derive the association (ka) and dissociation (kd) constants, and the affinity (KD).

An anti-human IgG-Fcγ antibody was covalently coated on the detection surfaces, and used to capture the human TTR-specific antibodies. The antibodies were probed with 4 different TTR preparations, including native and misfolded-aggregated wild-type TTR, and native V30M and L55P TTR mutants, all prepared at concentrations from 3.2 to 316 nM in HBS-T buffer (10 mM Hepes, 150 mM NaCl, 3 mM EDTA, 0.05% Tween 20, pH7.4). Misfolded-aggregated wild-type TTR was prepared by acidic denaturation at 65° C. for 80 min in acetate buffer (50 mM acetate HCl, 100 mM KCl, 1 mM EDTA, pH 3.0), with subsequent buffer exchange with HBS-T. 59F1, 35G11 and 37F1 exhibited linear binding and dissociation characteristics which were best fitted with the Langmuir model.

The results show that these three antibodies bind with high affinity the V30M- and L55P-TTR variants in solution, as well as the misfolded-aggregated wild-type TTR preparation. In contrast, these exemplary antibodies do not bind native wild-type TTR in solution.

Accordingly, the results show that NI-301.37F1 binds with high affinity to misfolded human wild-type TTR protein in solution, with a KD of 1.2 nM, but not to the same protein in its native conformation. Similar binding affinity (KD=1.4 nM) was measured for the mutant TTR-L55P protein.

TABLE V

Determination of antibody binding characteristics by surface plasmon resonance.

| Antibody | | Langmuir fit (1:1 interaction model) | | |
|---|---|---|---|---|
| NI-301. | Antigen | ka ($M^{-1}s^{-1}$) | kd ($s^{-1}$) | KD |
| 59F1 | native TTR | n.a | n.a | >316 nM |
| | misfolded-aggregated TTR | $9.7\ 10^4$ | $3.4\ 10^{-4}$ | 3.5 nM |
| | native TTR-V30M | $1.3\ 10^4$ | $2.2\ 10^{-4}$ | 16 nM |
| | native TTR-L55P | $5.1\ 10^4$ | $1.5\ 10^{-4}$ | 3.1 nM |
| 35G11 | native TTR-WT | n.a | n.a | >316 nM |
| | misfolded-aggregated TTR | $2.3\ 10^4$ | $2.7\ 10^{-4}$ | 12 nM |
| | native TTR-V30M | $7.4\ 10^3$ | $2.4\ 10^{-4}$ | 33 nM |
| | native TTR-L55P | n.a. | n.a. | >100 nM |

TABLE V-continued

Determination of antibody binding characteristics by surface plasmon resonance.

| Antibody | | Langmuir fit (1:1 interaction model) | | |
|---|---|---|---|---|
| NI-301. | Antigen | ka ($M^{-1}s^{-1}$) | kd ($s^{-1}$) | KD |
| 37F1 | native TTR-WT | n.a | n.a | >316 nM |
| | misfolded-aggregated TTR | $2.1\ 10^4$ | $2.6\ 10^{-5}$ | 1.2 nM |
| | native TTR-V30M | $1.1\ 10^4$ | $1.9\ 10^{-4}$ | 17 nM |
| | native TTR-L55P | $3.3\ 10^4$ | $4.6\ 10^{-5}$ | 1.4 nM |

Example 11: Passive Immunization of Transgenic Mice for Human Val30Met TTR, Presenting Tissue TTR Deposition, with Chimeric Human-Mouse Recombinant Anti-TTR Antibody Results in Removal of Deposition Passive immunization was performed similar as described in international application WO 2010/030203, in particular Example 3, the disclosure content of which is incorporated herein by reference as well as of the references Kohno et al., Am. J. Pathol. (1997), 1497-1508 and Sousa et al., Am. J. Pathol. (2002), 1935-48, cited therein.

In brief, monoclonal antibody was administered intraperitonealy weekly for 12 weeks at a dose of 3 mg/kg to 7-month-old and 17-month-old FAP mice, which were transgenic for human Val30Met-TTR allele and knockout for the murine TTR gene (Kohno et al., (1997), supra). In the five days following the last dose, animals were sacrificed, and various tissues were collected and fixed in paraformaldehyde solution, and embedded in paraffin. 3-5 µm sections were cut and processed for immunohistochemistry using the commercial anti-TTR antibody described above. A standard immunofluorescence procedure was used, which was very similar to the one indicated in example 7 with only difference that a fluorescent secondary antibody was used for detection. The surface of tissue invaded with TTR deposit was quantified and expressed as percentage of total tissue area. Statistical analysis of treatment effect was performed with two-tailed, unpaired t-test.

This transgenic mouse line reproduce the key pathological mechanism common to TTR amyloid diseases which consists in TTR tetramer disassembly and misfolding of the TTR monomers into a toxic and insoluble amyloidogenic conformation. Like FAP patients, these transgenic mice typically present age-dependent TTR deposition. The evaluation of treatment efficacy was investigated in two groups of transgenic mice which were 7-month-old and 17-month-old at treatment onset; ages where TTR deposition is important and invading many gastrointestinal tissues. Remarkably, passive immunization with the exemplary antibody NI-301.37F1 was associated with statistically significant reduction in the tissue surface invaded with TTR deposition when treatment was started at 7 months of age, see FIG. 12A. Treatment had a similar effect in old mice, leading to almost significant reduction in TTR deposition, see FIG. 12B.

Example 12: Human-Derived, Recombinant Anti-TTR Antibodies Bind to Pathological TTR Deposits In Vivo To determine whether human-derived, recombinant anti-TTR antibodies are able to bind to pathological TTR deposits in vivo, adult FAP mice of 7 months of age were injected with the antibody NI-301.37F1 at 30 mg/kg i.p. or with PBS for comparison. After 48 hours, these mice were submitted to transcardiac perfusion and tissues were processed for histological analysis.

Pathological TTR deposits were detected using a rabbit polyclonal, anti-TTR antibody in combination with fluorescently labeled anti-rabbit IgG antibody, whereas the localization of the injected antibody NI-301.37F1 was detected with a fluorescently labeled anti-human IgG antibody. In particular, immunoprecipitation was performed as follows.

Immunoprecipitation of NI-301.37F1 and isotype control antibodies from mouse plasma samples was performed for 2 hours at RT, using protein A/G-coupled magnetic beads (Pierce #88803) loaded with anti-human IgG antibody (Jackson Immunoresearch #709-005-098). After 3 washes with PBS-T, samples were eluted from magnetic beads with a 0.2M glycine buffer (pH2.5), neutralized with 1M Tris HCl (pH8.0), mixed with LDS-loading buffer (Life technologies #NP0007) and heated 10 min at 90° C. Samples were then loaded on a 4-12% bis-tris gel (Life technologies #WG1403A) run for 40 min at 200 V in MOPS running buffer. After protein transfer on a nitrocellulose membrane, TTR protein was detected using either the conformation independent TTR antibody (Dako #A0002, 150 ng/ml) or the antibody NI-301.37F1 (20 nM), in combination with HRP-coupled protein A (Life technologies #10-1023, 1/10'000 dilution) and luminescent imaging.

The in vivo target engagement as described in FIG. 13A-13F was performed in adult FAP mice (7-months-old) which received a single injection of antibody NI-301.37F1 at 30 mg/kg i.p. or PBS. 48 hours later, mice were perfused with PBS and organs were collected and processed for histological analysis. Pathological TTR deposits were detected by immunofluorescence using a commercial rabbit polyclonal anti-TTR antibody (Dako #A0002, 4.8 µg/ml) in combination with a Cy5-conjugated anti-rabbit antibody (Jackson Immunoresearch #711-175-152, 1/200 dilution). Presence (or absence) of NI-301.37F1 was detected simultaneously using a Cy3-conjugated anti-human antibody (Jackson Immunoresearch #709-165-149, 1/200 dilution). The same scanning parameters were used for imaging NI-301.37F1-injected and PBS-injected tissues, and images received the same display adjustments.

As shown in FIG. 13A-13F, NI-301.37F1-dependent staining was highly colocalized with TTR staining in NI-301.37F1-injected mice, but was completely absent in PBS-injected mice, as expected. This result indicates that the anti-TTR antibody NI-301.37F1 is binding to pathological TTR deposits in vivo.

Example 13: Detection of Misfolded TTR Protein Deposits In Vivo does not Require Tissue Biopsies This diagnostic procedure replacing tissue biopsy and histological analysis in the diagnosis process of TTR amyloid diseases associated with aggregated, mutated, and/or misfolded TTR is exemplified herein below and illustrated in FIG. 14A-14B. In particular, the experiment was performed with 7-month-old FAP mice, as described above; see Example 11, supra. These mice reproduce the core pathophysiological mechanism of FAP and, like patients, present age-dependent TTR deposition in various tissues. Two FAP mice received a single intraperitoneal injection of the human-derived, recombinant anti-TTR monoclonal antibody NI-301.37F1 at a dose of 3 mg/kg. Prior antibody injection (t=0), and two days after injection (t=4 8h), small blood samples were collected and plasma were prepared for analysis. Plasma samples were submitted to immunoprecipitation with an anti-human IgG antibody (to retrieve the injected human anti-TTR antibody), with t=0 samples used as negative controls. The immunoprecipitation samples were then processed by western-blot to detect whether the anti-TTR antibody injected in mice had captured some misfolded TTR protein during the 48 hours where it circulated in vivo. Western-blots were performed using both conformation-specific and conformation-independent anti-TTR antibodies. A control experiment was performed with an isotype control antibody (not able to bind TTR protein) as negative control. An additional control consisted in incubating plasma samples from untreated FAP mice with the antibody NI-301.37F1 in vitro, and processing as described above.

The results presented in FIG. 14A-14B indicate that antibody NI-301.37F1 captured some misfolded TTR protein during the 48 hours incubation period in vivo. This was observed specifically for the antibody NI-301.37F1 and not for the isotype control antibody. Furthermore, the misfolded TTR protein captured by antibody NI-301.37F1 was not present in plasma samples collected from untreated mice. Altogether, these results indicate that the antibody NI-301.37F1 was able to remove misfolded TTR protein from insoluble TTR deposits in vivo, the presence of which could be detected without the need for tissue biopsies. One technical adjustment to use this diagnostic test in humans would consist in labeling the anti-TTR antibody allowing for its retrieval from human plasma sample with, for example, a biotin or histidine or streptavidin tag. Alternatively, the unmodified anti-TTR antibody could be retrieved from human plasma sample by means of an anti-idiotypic antibody.

TABLE IV

Mutations in the TTR gene

| Name (Protein Variant incl. 20-aa signal peptide) | Sequence Variant (mRNA) | Codon Change | Location | Reported Phenotype | Ethnic Group | References |
|---|---|---|---|---|---|---|
| Gly6Ser (p.Gly26Ser) | c.76G > A | GGT > AGT | Exon 2 | non-amyloidogenic | Caucasian | Jacobson (1994) Hum Mutat 3, 254 |
| Cys10Arg (p.Cys30Arg) | c.88T > C | TGT > CGT | Exon 2 | AN, E, H, PN | American (Hungarian) | Uemichi (1992) J Med Genet 29, 888 |
| Leu12Pro (p.Leu32Pro) | c.95T > C | CTG > CCG | Exon 2 | PN, AN, H, LM, L | British | Brett (1999) Brain 122, 183 |
| p.Met13Ile (p.Met33Ile) | c.99G > C | ATG > ATC | Exon 2 | non-amyloidogenic | German | Altland (1999) The 4th International Symposium on FAP and Other TTR Related Disorders. |

TABLE IV-continued

Mutations in the TTR gene

| Name (Protein Variant incl. 20-aa signal peptide) | Sequence Variant (mRNA) | Codon Change | Location | Reported Phenotype | Ethnic Group | References |
|---|---|---|---|---|---|---|
| Asp18Asn (p.Asp38Asn) | c.112G > A | GAT > AAT | Exon 2 | H | American | Connors (2003) Amyloid 10, 160 |
| Asp18Gly (p.Asp38Gly) | c.113A > G | GAT > GGT | Exon 2 | LM | Hungarian | Vidal (1996) Am J Pathol 148, 361 |
| Asp18Glu (p.Asp38Glu) | c.114T > A or G | GAT > GAA/G | Exon 2 | PN | South American | Connors (2004) Amyloid 11, 61 |
| Val20Ile (p.Val40Ile) | c.118G > A | GTC > ATC | Exon 2 | CTS, H | German, American | Jenne (1996) Proc Natl Acad Sci U S A 93, 6302 |
| Ser23Asn (p.Ser43Asn) | c.128G > A | AGT > AAT | Exon 2 | E, H, PN | Portuguese, American | Connors (1999) Amyloid 6, 114 |
| Pro24Ser (p.Pro44Ser) | c.130C > T | CCT > TCT | Exon 2 | CTS, H, PN | American | Uemichi (1995) J Med Genet 32, 279 |
| Ala25Ser (p.Ala45Ser) | c.133G > T | GCC > TCC | Exon 2 | H, PN | American | Yazatic (2002) Muscle Nerve 25, 244 |
| Ala25Thr (p.Ala45Thr) | c.133G > A | GCC > ACC | Exon 2 | CNS, PN | Japanese | Sekijima (2003) Lab Invest 83, 409 |
| Val28Met (p.Val48Met) | c.142G > A | GTG > ATG | Exon 2 | PN | Portuguese | Carvalho (2000) Muscle Nerve 23, 1016 |
| Val30Leu (p.Val50Leu) | c.148G > C | GTG > CTG | Exon 2 | AN, H, K, PN | Japanese, American | Murakami (1992) Biochem Biophys Res Commun 187, 397 |
| Val30Met (p.Val50Met) | c.148G > A | GTG > ATG | Exon 2 | AN, E, LM, PN | American Chinese, Japanese, European | Saraiva (1984) J Clin Invest 74, 104 |
| Val30Ala (p.Val50Ala) | c.149T > C | GTG > GCG | Exon 2 | AN, H | American (German) | Jones (1992) Clin Genet 41, 70 |
| Val30Gly (p.Val50Gly) | c.149T > G | GTG > GGG | Exon 2 | CNS, E, LM | American | Peterson (1997) Ann Neurol 41, 307 |
| Val32Ala (p.Val52Ala) | c.155T > C | GTG > GCG | Exon 2 | AN, H, PN | Chinese | Pica (2005) Muscle Nerve 32, 223 |
| Val32Gly (p.Val52Gly) | c.155T > G | GTG > GGG | Exon 2 | AN, PN | French | Plante-Bordeneuve (2003) J Med Genet 40, e120 |
| Phe33Ile (p.Phe53Ile) | c.157T > A | TTC > ATC | Exon 2 | E, PN | Jewish | Jacobson (1988) Biochem Biophys Res Commun 153(1):198 |
| Phe33Leu (p.Phe53Leu) | c.157T > C | TTC > CTC | Exon 2 | PN | American | Li (1991) Neurology 41, 893 |
| Phe33Val (p.Phe53Val) | c.157T > G | TTC > GTC | Exon 2 | PN | Chinese, British | Tachibana (1999) Amyloid 6(4):282 |
| Phe33Cys (p.Phe53Cys) | c.158T > G | TTC > TGC | Exon 2 | CTS, E, K,A H | American | Connors (2003) Amyloid 10, 160 |
| Arg34Gly (p.Arg54Gly) | c.160A > G | AGA > GGA | Exon 2 | E | Kosovo | Levy J, Hawkins PN, Rowczenio D, Godfrey T, Stawell R, Zamir E. The Ocular Immunology Clinic, Royal Victorian Eye and Ear Hospital, Melbourne, Australia. |
| Arg34Thr (p.Arg54Thr) | c.161G > C | AGA > ACA | Exon 2 | H, PN | Italian | Patrosso (1998) Am J Med Genet 77, 135 |
| Lys35Asn (p.Lys55Asn) | c.165G > C or T | AAG > AAC/T | Exon 2 | AN, H, PN | French | Reilly (1995) Brain 118, 849 |
| Ala36Pro (p.Ala56Pro) | c.166G > C | GCT > CCT | Exon 2 | CTS, E, PN | Greek, Italian, Jewish, American | Jones (1991) Am J Hum Genet 48, 979 |
| Asp38Ala (p.Asp58Ala) | c.173A > C | GAT > GCT | Exon 2 | AN, H, PN | Japanese | Yazaki (2000), Biochem Biophys Res Commun, 274(3): 702 |
| Asp38Val (p.Asp58Val) | c.173A > T | GAT > GTT | Exon 2 | H, PN | Guianese | Lachmann (2002) N Engl J Med 346, 1786 |
| Asp39Val (p.Asn59Val) | c.176A > T | GAC > GTC | Exon 2 | H | German | Eriksson (2009) Am J Surg Pathol 33 (1):58 |
| Trp41Leu (p.Trp61Leu) | c.182G > T | TGG > TTG | Exon 2 | E | American (Russian) | Yazaki (2002) Amyloid 9, 263 |
| Glu42Gly (p.Glu62Gly) | c.185A > G | GAG > GGG | Exon 2 | AN, H, PN | Japanese, Russian, American | Ueno (1990) Biochem Biophys Res Commun 169, 1117 |
| Glu42Asp (p.Glu62Asp) | c.186G > C or T | GAG > GAC/T | Exon 2 | H | French | Dupuy (1998) Amyloid 5, 285 |
| Phe44Tyr (p.Phe64Tyr) | c.191T > A | TTT > TAT | Exon 2 | AN, PN | French | Plante-Bordeneuve (2003) J Med Genet 40, e120 |
| Phe44Ser (p.Phe64Ser) | c.191T > C | TTT > TCT | Exon 2 | AN, H, PN | American | Klein (1998) Neurology 51, 1462 |
| Ala45Ser (p.Ala65Ser) | c.193G > T | GCC > TCC | Exon 2 | H | Swedish | Janunger (2000) Amyloid 7, 137 |
| Ala45Thr (p.Ala65Thr) | c.193G > A | GCC > ACC | Exon 2 | H | Irish, Italian, American | Saraiva (1992) Ain J Huin Genel 50, 1027 |
| Ala45Asp (p.Ala65Asp) | c.194C > A | GCC > GAC | Exon 2 | H, PN | Irish, American | Saraiva (1995) Hum Mutat 5, 191 |
| Gly47Arg (p.Gly67Arg) | c.199G > C | GGG > CGG | Exon 2 | AN, PN | Japanese | Murakami (1992) Biochem Biophys Res Commun 182, 520 |
| Gly47Arg (p.Gly67Arg) | c.199G > A | GGG > AGG | Exon 2 | H, PN | Italian | Ferlini (2000) Clin Genet 57, 284 |
| Gly47Ala (p.Gly67Ala) | c.200G > C | GGG > GCG | Exon 2 | AN, H, PN | German, Italian, French | Ferlini (1994) Hurn Mutat 4, 61 |
| Gly47Glu (p.Gly67Glu) | c.200G > A | GGG > GAG | Exon 2 | H, K, PN | German, Italian | Pelo (2002) Amyloid 9, 35 |
| Gly47Val (p.Gly67Val) | c.200G > T | GGG > GTG | Exon 2 | AN, CTS, H, PN | Sri Lankan | Booth (1993) Amyloid, 456 |
| Thr49Ala (p.Thr69Ala) | c.205A > G | ACC > GCC | Exon 3 | CTS, H, PN | Italian, French | Almeida (1992) Hum Mutat 1, 211 |

TABLE IV-continued

Mutations in the TTR gene

| Name (Protein Variant incl. 20-aa signal peptide) | Sequence Variant (mRNA) | Codon Change | Location | Reported Phenotype | Ethnic Group | References |
|---|---|---|---|---|---|---|
| Thr49Pro (p.Thr69Pro) | c.205A > C | ACC > CCC | Exon 3 | H, LM | American | Nakagawa (2008) J Neurol , 272 (1-2):186; Connors (2003) Amyloid 10, 160; |
| Thr49Ile (p.Thr69Ile) | c.206G > T | ACC > ATC | Exon 3 | H, PN | Japanese | Nakamura (1999) Hum Hered 49, 186 |
| Thr49Ser (p.Thr69Ser) | c.206G > G | ACC > AGC | Exon 3 | PN | Indian | Rowczenio (2010) XII International Symposium on Amyloidosis |
| Ser50Ile (p.Ser70Ile) | c.209G > T | AGT > ATT | Exon 3 | AN, H, PN | Japanese, Spanish | Saeki (1992) FEBS Lett 308, 35 |
| Ser50Arg (p.Ser70Arg) | c.210T > G | AGT > AGG | Exon 3 | AN, H, PN | Italian, French, Japanese | Ueno (1990) Biochem Biophys Res Commun 169, 1117 |
| Glu51Gly (p.Glu71Gly) | c.212A > G | GAG > GGG | Exon 3 | H | American | Connors (2003) Amyloid 10, 160 |
| Ser52Pro (p.Ser72Pro) | c.214T > C | TCT > CCT | Exon 3 | AN, H, K, PN | British | Stangou (1998) Transplantation 66(2):229 |
| Gly53Glu (p.Gly73Glu) | c.218G > A | GGA > GAA | Exon 3 | CNS, LM, N | French | Ellie (2001) Neurology 57, 135 |
| Gly53Ala (p.Gly73Ala) | c.218G > C | GGA > GCA | Exon 3 | AN, E, H, PN, LM | British | Douglass (2007) J Neurol Neurosurg Psychiatry 78, 193 |
| Glu54Leu (p.Glu74Leu) | c.220_221GA > TT | GAG > TTG | Exon 3 | H | Belgian | Rowczenio (2006) XI International Symposium on Amyloidosis |
| Glu54Lys (p.Glu74Lys) | c.220G > A | GAG > AAG | Exon 3 | AN, H, PN | Japanese | Togashi (1999) Neurology 53, 637 |
| Glu54Gly (p.Glu74Gly) | c.221A > G | GAG > GGG | Exon 3 | AN, E, PN | British | Reilly (1995) Brain 118, 849 |
| Glu54Asp (p.Glu74Asp) | c.222G > T | GAG > GAC | Exon 3 | Not listed | German | Eriksson (2009) Am J Surg Pathol 33 (1):58 |
| Glu54Gln (p.Glu74Gln) | c.220G > C | GAG > CAG | Exon 3 | H, PN | Romanian | Coriu D, XIII International Symposium on Amyloisosis |
| Leu55Gln (p.Leu75Gln) | c.224T > A | CTG > CAG | Exon 3 | AN, E, PN | American (Spanish) | Yazaki (2002) Amyloid 9, 268 |
| Leu55Arg (p.Leu75Arg) | c.224T > G | CTG > CGG | Exon 3 | LM, PN | German | Connors (2003) Amyloid 10, 160 |
| Leu55Pro (p.Leu75Pro) | c.224T > C | CTG > CCG | Exon 3 | AN, E, H, PN | Taiwanese, American (Dutch, German) | Jacobson (1992) Hum Genet 89, 353 |
| His56Arg (p.His76Arg) | c.227A > G | CAT > CGT | Exon 3 | H | American | Jacobson (1999) TTR Locus-specific database Unpublished |
| Leu58Arg (p.Leu78Arg) | c.233T > G | CTO > CGC | Exon 3 | AN, CTS, E, H | Japanese | Saeki (1991) Biochem Biophys Res Commun 180, 380 |
| Leu58His (p.Leu78His) | c.233T > A | CTC > CAC | Exon 3 | CTS, H | German, American (MD) | Nichols (1989) Genomics 5, 535 |
| Thr59Lys (p.Thr79Lys) | c.236G > A | ACA > AAA | Exon 3 | AN, H, PN | Italian, American (Asian) | Saraiva (1995) Hum Mutat 5, 191 |
| Thr60Ala (p.Thr80Ala) | c.238A > G | ACT > GCT | Exon 3 | CTS, H, PN | Australian, German, Irish, British, American | Wallace (1986) J Clin Invest 78, 6 |
| Glu61Lys (p.Glu81Lys) | c.241G > A | GAG > AAG | Exon 3 | PN | Japanese | Shiomi (1993) Biochem Biophys Res Commun 194, 1090 |
| Glu61Gly (p.Glu81Gly) | c.242A > G | GAG > GGG | Exon 3 | CTS, H, PN | American (English/Dutch) | Rosenzweig (2007) Amyloid 14, 65 |
| Glu62Lys (p.Glu82Lys) | c.243G > A | GAG > AAG | Exon 3 | H | Caucasian | Briani C, Cavallaro T', Ferrari S, Taioli F, Calamelli S, Verga L, Adami F, Fabrizi GM Sporadic transthyretin amyloidosis with a novel TTR gene mutation misdiagnosed as primary amyloidosis. J Neurol. 2012 Oct.; 259(10):2226-8. |
| Phe64Leu (p.Phe84Leu) | c.250T > C | TTT > CTT | Exon 3 | CTS, H, PN | Italian, American | Li (1991) Neurology 41, 893 |
| Phe64Ser (p.Phe84Ser) | c.251T > C | TTT > TCT | Exon 3 | E, LM, PN, CNS | Canadian (Italian), British | Uemichi (1999) Arch Neurol 56, 1152 |
| Gly67Glu (p.Gly87Glu) | c.260G > A | GGG > GAG | Exon 3 | H, PN | Chinese | Mak (2007) Amyloid, 14, 293 |
| Ile68Leu (p.Ile88Leu) | c.262A > T/C | ATA > C/TTA | Exon 3 | H | German, American | Almeida (1991) Basic Res Cardiol 86, 567 |
| Tyr69His (p.Tyr89His) | c.265T > C | TAC > CAC | Exon 3 | E | Scottish, American | Zeldenrust (1994) Amyloid, 1, 17 |
| Tyr69Ile (p.Tyr89Ile) | c.265-266TA > AT | TAC > ATC | Exon 3 | CTS, H | Japanese | Takei (2003) Amyloid 10, 25 |
| Lys70Asn (p.Lys90Asn) | c.270A > C/T | AAA > AAC/T | Exon 3 | CTS, E, PN | German, American | Izumoto (1992) Neurology 42, 2094 |
| Val71Ala (p.Val91Ala) | c.272T > C | GTG > GCG | Exon 3 | CTS, E, PN | French, Spanish | Almeida (1993) Hum Mutat 2, 420. |

TABLE IV-continued

Mutations in the TTR gene

| Name (Protein Variant incl. 20-aa signal peptide) | Sequence Variant (mRNA) | Codon Change | Location | Reported Phenotype | Ethnic Group | References |
|---|---|---|---|---|---|---|
| Ile73Val (p.Ile93Val) | c.277A > G | ATA > GTA | Exon 3 | AN, PN | Bangladeshi | Booth (1997) Hum Mutat 12, 135 |
| Asp74His (p.Asp94His) | c.280G > C | GAC > CAC | Exon 3 | non-amyloidogenic | German | Uemichi (1994) Amyloid, 1, 149 |
| Ser77Phe (p.Ser97Phe) | c.290C > T | TCT > TTT | Exon 3 | AN, PN | French | Plante-Bordeneuve (1998) Neurology 51, 700 |
| Ser77Tyr (p.Ser97Tyr) | c.290C > A | TCT > TAT | Exon 3 | H, K, PN | French, German, American (IL, TX) | Wallace (1988) J Clin Invest 81, 189 |
| Tyr78Phe (p.Tyr98Phe) | c.293A > T | TAC > TTC | Exon 3 | CTS, S, PN | French (Italian) | Magy (2003) Amyloid 10, 29 |
| Ala81Thr (p.Ala101Thr) | c.301G > A | GCA > ACA | Exon 3 | H | American | Connors (2003) Amyloid 10, 160 |
| Ala81Val (p.Ala101Val) | c.302C > T | GCA > GTA | Exon 3 | H | Russian, Polish | Rowczenio (2006) XI International Symposium on Amyloidosis |
| Gly83Arg (p. Gly103Arg) | c.307G > C | GGC > CGC | Exon 3 | E | Chinese | Xie Y, Zhao Y, Zhou JJ, Wang X. Identification of a TTR gene mutation in a family with hereditary vitreous amyloidosis Zhonghua Yi Xue Yi Chuan Xue Za Zhi. 2012 Feb.; 29(1):13-5. |
| Ile84Asn (p.Ile104Asn) | c.311T > A | ATC > AAC | Exon 3 | CTS, E, H | American | Skinner (1992) Ophthalmology 99, 503 |
| Ile84Ser (p.Ile104Ser) | c.311T > G | ATC > AGC | Exon 3 | CTS, E, H, L.M | Hungarian, Swiss, American | Dwulet (1986) J Clin Invest 78, 880 |
| Ile84Thr (p.Ile104Thr) | c.311T > C | ATC > ACC | Exon 3 | H, PN | German, British | Stangou (1998) Transplantation 66, 229 |
| Glu89Gln (p.Glu109Gln) | c.325G > C | GAG > CAG | Exon 3 | CTS, H, PN | Italy | Almeida (1992) Hum Mutat 1, 211 |
| Glu89Lys (p.Glu109Lys) | c.325G > A | GAG > AAG | Exon 3 | AN, H, PN | American | Nakamura (2000) Amyloid 7, 46 |
| His90Asn (p.His110Asn) | c.3280 > A | CAT > AAT | Exon 3 | non-amyloidogenic | German, Portuguese | Skare (1994) Clin Genet 45, 281 |
| His90Asp (p.His110Asp) | c.328C > G | CAT > GAT | Exon 3 | H | British | Rowczenio (2006) XI International Symposium on Amyloidosis |
| Ala91Ser (p.Ala111Ser) | c.331G > T | GCA > TCA | Exon 3 | AN, CTS, H, PN | French | Misrahi (1998) Hum Mutat 12, 71 |
| Gln92Lys (p.Gln112Lys) | c.334G > A | GAG > AAG | Exon 3 | H | Japanese | Saito (2001) Hum Pathol 32, 237 |
| Val93Met (p.Val113Met) | c.367G > A | GTG > ATG | Exon 4 | PN | Malian | Lozern (2008) The VIIth International Symposium on FAP and Other TTR Related Disorders. |
| Val94Ala (p.Val114Ala) | c.341T > C | GTA > GCA | Exon 4 | AN, H, PN | German, Greek (Cyprus) | Kristen (2007) Amyloid 14(4): 283 |
| Ala97Ser (p.Ala117Ser) | c.349G > T | GCC > TCC | Exon 4 | PN, H | Chinese, Taiwanese | Tachibana (1999) Amyloid 6, 282 |
| Ala97Gly (p.Ala117Gly) | c.350C > G | GCC > GGC | Exon 4 | H, PN | Japanese | Yasuda (1994) J Neurol Sci 121, 97 |
| Gly101Ser (p.Gly121Ser) | c.361G > A | GGC > AGC | Exon 4 | non-amyloid | Japanese | Kishikawa M et al (1988) Hum Mutat 12, 363 |
| Pro102Arg (p.Pro122Arg) | c.365C > G | CCC > CGC | Exon 4 | non-amyloid | German | Altland (1999) The 4th International Symposium on FAP and Other TTR Related Disorders. |
| Arg103Ser (p.Arg123Ser) | c.367C > A | CGC > AGC | Exon 4 | H | American | Connors (2003) Amyloid 10, 160 |
| Arg104Cys (p.Arg124Cys) | c.370C > T | CGC > TGC | Exon 4 | non-amyloid, | American | Torres (1996) Neuromuscular Disord Vol 6, S21, |
| Arg104His (p.Arg124His) | c.371G > A | CGC > CAC | Exon 4 | non-amyloid | Japanese, American | Terazaki (1999) Biochem Biophys Res Commun 264, 365 |
| Ile107Val (p.Ile127Val) | c.379A > G | ATT > GTT | Exon 4 | CTS, H, PN | German, American | Jacobson (1994) Hur Mutat 3, 399 |
| Ile107Phe (p.Ile127Phe) | c.379A > T | ATT > TTT | Exon 4 | AN, PN | British | Rowczenio (2006) XI International Symposium on Amyloidosis |
| Ile107Met (p.Ile127Met) | c.381T > G | ATT > ATG | Exon 4 | H, PN | German | Connors (2003) Amyloid 10, 160 |
| Ala108Ala (p.Ala128Ala) | c.384C > T | GCC > GCT | Exon 4 | non-amyloidogenic | Portuguese | Palha (1997) Amyloid 4,52 |
| Ala109Ser (p.Ala129Ser) | c.385G > T | GCC > TCC | Exon 4 | PN | Japanese | Date (1997) J Neurol Sci 150, 143 |
| Ala109Thr (p.Ala129Thr) | c.385G > A | GCC > ACC | Exon 4 | non-amyloidogenic | Portuguese | Moses (1990) J Clin Invest 86, 2025 |
| Ala109Val (p.Ala129Val) | c.386C > T | GCC > GTC | Exon 4 | non-amyloidogenic | American | Izumoto (1993) J Fhernatel 20 188 |
| Leu111Met (p.Leu131Met) | c.391C > A | CTG > ATG | Exon 4 | CTS, H | Danish | Nordlie (1988) Scand J Immunol 27, 119 |
| Ser112Ile (p.Ser132Ile) | c.395G > T | AGC > ATC | Exon 4 | H, PN | Italian | De Lucia (1993) Clin Neuropathol 12, S44 |
| Tyr114His (p.Tyr134His) | c.400T > C | TAC > CAC | Exon 4 | CTS | Japanese | Murakami (1994) Neurology44, 315 |
| Tyr114Cys (p.Tyr134Cys) | c.401A > G | TAC > TGC | Exon 4 | AN, E, H, LM, PN | Japanese | Ueno (1990) Biochem Biophys Res Commun 169, 143 |
| Tyr116Ser (p.Tyr136Ser) | c.407A > C | TAT > TCT | Exon 4 | AN, PN, CTS | French | Misrahi (1997) Hum Mutat 12, 71 |
| Thr119Met (p.Thr139Met) | c.416C > T | ACG > ATG | Exon 4 | non-amyloidogenic | Portuguese, American | Harrison (1991) Am J Med Genet 39, 442 |
| Ala120Ser (p.Ala140Ser) | c.418G > T | GCT > TCT | Exon 4 | AN, H, PN | Caribbean | Lachman (2002) N Engl J Med 346, 1786 |
| Val122del (p.Val142del) | c.424_426 | del GTC | Exon 4 | CNS, CTS, H, PN | American (Ecuador/Spain) | Uemichi (1997) Neurology 48 |

TABLE IV-continued

Mutations in the TTR gene

| Name (Protein Variant incl. 20-aa signal peptide) | Sequence Variant (mRNA) | Codon Change | Location | Reported Phenotype | Ethnic Group | References |
|---|---|---|---|---|---|---|
| Val122Ile (p.Val142Ile) | c.424G > A | GTC > ATC | Exon 4 | H | African, Portuguese, American | Jacobson (1990) Am J Hum Genet 47, 127 |
| Val122Ala (p.Val142Ala) | c.425T > C | GTC > GCC | Exon 4 | E, H, PN | Britsh, American | Theberge (1999) Amyloid 6, 54 |
| Pro125Ser (p.Pro145Ser) | c.433C > T | CCC > TCC | Exon 4 | non-amyloidogenic | Italian | Ferlini (1996)Neuromuscular Disord Vol 6, 823, |

Abbreviation Key:
AN = autonomic neuropathy;
CTS = carpal tunnel syndrom;
E = eye;
H = heart;
K = kidney;
L = liver;
LM = leptomeningeal;
N = neuropathy;
PN = polyneuropathy;
CNS = central nervous system

The invention claimed is:

1. A recombinant anti-transthyretin (TTR) antibody that binds mutated, misfolded, misassembled, and/or aggregated TTR species and/or fragments thereof and does not recognize physiological TTR species, wherein the antibody comprises a human fragment crystallizable (Fc) region of an IgG1 isotype and comprises complementarity determining regions (CDRs), wherein:
   (i) CDR-H1 comprises the amino acid sequence of SEQ ID NO: 104;
   (ii) CDR-H2 comprises the amino acid sequence of SEQ ID NO: 105;
   (iii) CDR-H3 comprises the amino acid sequence of SEQ ID NO: 106;
   (iv) CDR-L1 comprises the amino acid sequence of SEQ ID NO: 107;
   (v) CDR-L2 comprises the amino acid sequence of SEQ ID NO: 108; and
   (vi) CDR-L3 comprises the amino acid sequence of SEQ ID NO: 109.

2. The antibody of claim 1, wherein the antibody binds a TTR epitope comprising SEQ ID NO: 51.

3. The antibody of claim 2, wherein the antibody binds the TTR epitope comprising the amino acid sequence of SEQ ID NO: 51.

4. The antibody of claim 1, wherein the antibody:
   (i) comprises a detectable label, wherein the detectable label is selected from the group consisting of an enzyme, a radioisotope, a fluorophore and a heavy metal; and/or
   (ii) is attached to a drug.

5. A composition comprising the antibody of claim 1, wherein the composition is a pharmaceutical composition and further comprises a pharmaceutically acceptable carrier.

6. A kit comprising the antibody of claim 1 and instructions for use.

7. The antibody of claim 1, wherein the antibody comprises a heavy chain variable (VH) region comprising an amino acid sequence with at least 90% sequence identity to SEQ ID NO: 10 and a light chain variable region (VL) region comprising an amino acid sequence with at least 90% sequence identity to SEQ ID NO: 12.

8. The antibody of claim 1, wherein the antibody comprises a VH region comprising the amino acid sequence set forth in SEQ ID NO: 53.

9. The antibody of claim 1, wherein the antibody comprises a VH region comprising the amino acid sequence set forth in SEQ ID NO: 53 and a VL region comprising the amino acid sequence set forth in SEQ ID NO: 12.

10. A composition comprising the antibody of claim 1, wherein the composition is a diagnostic composition.

11. A kit comprising the composition of claim 5 and instructions for use.

12. A kit comprising the composition of claim 10 instructions for use.

13. The composition of claim 5, wherein the composition is a vaccine and/or comprises an additional agent for treating diseases associated with TTR amyloidosis.

* * * * *